US012767700B2

(12) United States Patent
Hubbell et al.

(10) Patent No.: US 12,767,700 B2
(45) Date of Patent: Oct. 20, 2026

(54) COMPOSITIONS AND METHODS COMPRISING PROTEASE-ACTIVATED THERAPEUTIC AGENTS

(71) Applicant: THE UNIVERSITY OF CHICAGO, Chicago, IL (US)

(72) Inventors: Jeffrey Hubbell, Chicago, IL (US); Jun Ishihara, Chicago, IL (US); Juan Mendoza, Chicago, IL (US); Aslan Mansurov, Chicago, IL (US)

(73) Assignee: THE UNIVERSITY OF CHICAGO, Chicago, IL (US)

(*) Notice: Subject to any disclaimer, the term of this patent is extended or adjusted under 35 U.S.C. 154(b) by 16 days.

(21) Appl. No.: 18/559,180

(22) PCT Filed: May 5, 2022

(86) PCT No.: PCT/US2022/072121
§ 371 (c)(1),
(2) Date: Nov. 6, 2023

(87) PCT Pub. No.: WO2022/236292
PCT Pub. Date: Nov. 10, 2022

(65) Prior Publication Data

US 2024/0228586 A1 Jul. 11, 2024

Related U.S. Application Data

(60) Provisional application No. 63/313,087, filed on Feb. 23, 2022, provisional application No. 63/185,941, filed on May 7, 2021.

(51) Int. Cl.

| | |
|---|---|
| ***C07K 14/715*** | (2006.01) |
| ***A61K 38/17*** | (2006.01) |
| ***A61K 38/20*** | (2006.01) |
| ***A61K 38/21*** | (2006.01) |
| ***A61K 39/395*** | (2006.01) |
| ***A61K 47/64*** | (2017.01) |
| ***A61K 47/68*** | (2017.01) |
| ***A61P 35/00*** | (2006.01) |
| ***C07K 14/47*** | (2006.01) |
| ***C07K 14/54*** | (2006.01) |
| ***C07K 14/55*** | (2006.01) |
| ***C07K 14/57*** | (2006.01) |

(52) U.S. Cl.
CPC ...... *C07K 14/7155* (2013.01); *A61K 38/1709* (2013.01); *A61K 38/1793* (2013.01); *A61K 38/2013* (2013.01); *A61K 38/208* (2013.01); *A61K 38/217* (2013.01); *A61K 39/395* (2013.01); *A61K 47/643* (2017.08); *A61K 47/6843* (2017.08); *A61P 35/00* (2018.01); *C07K 14/47* (2013.01); *C07K 14/5434* (2013.01); *C07K 14/55* (2013.01); *C07K 14/57* (2013.01); *C07K 14/7156* (2013.01); *C07K 2319/50* (2013.01)

(58) Field of Classification Search
CPC ................ C07K 14/7155; C07K 14/47; C07K 14/5434; C07K 14/55; C07K 14/57; C07K 14/7156; C07K 2319/50; C07K 2319/70; C07K 14/715; A61K 38/1709; A61K 38/1793; A61K 38/2013; A61K 38/208; A61K 38/217; A61K 39/395; A61K 47/643; A61K 47/6843; A61K 38/00; A61K 45/06; A61P 35/00
See application file for complete search history.

(56) References Cited

U.S. PATENT DOCUMENTS

| | | | |
|---|---|---|---|
| 6,358,524 | B1 | 3/2002 | Sedlacek et al. |
| 6,617,135 | B1 | 9/2003 | Gillies et al. |
| 7,018,626 | B2 | 3/2006 | Strom et al. |
| 7,081,354 | B2 | 7/2006 | Fleer et al. |
| 7,166,577 | B2 | 1/2007 | Otagiri et al. |
| 7,253,259 | B2 | 8/2007 | Otagiri et al. |

(Continued)

FOREIGN PATENT DOCUMENTS

| | | |
|---|---|---|
| CN | 1382158 | 11/2002 |
| CN | 107074967 | 8/2017 |

(Continued)

OTHER PUBLICATIONS

Spangler et al. (Annu Rev Immunol. 2015;33:139-67. PMID: 25493332) (Year: 2015).*
Poreba. (FEBS J. May 2020;287(10):1936-1969. PMID: 31991521) (Year: 2020).*
Gobin et al. (BMC Cancer. Jun. 14, 2019;19(1):581. PMID: 31200666) (Year: 2019).*
Puskas et al., (Immunology. Jun. 2011;133(2):206-20. PMID: 21426339) (Year: 2011).*
Bonati & Tang (Curr Opin Chem Biol. Jun. 2021;62:43-52. Epub Mar. 6, 2021. PMID: 33684633) (Year: 2021).*
Ishihara et al., (Sci Transi Med. Apr. 10, 2019;11(487}:eaan3259. PMID: 30971453) (Year: 2019).*

(Continued)

*Primary Examiner* — Misook Yu
(74) *Attorney, Agent, or Firm* — Norton Rose Fulbright US LLP

(57) ABSTRACT

The disclosure relates to the engineering of collagen-binding modification of masked therapeutic agents comprising one or more tumor-associated protease cleavage sites. Upon exposure to tumor-associated proteases in the tumor microenvironment, the polypeptide is cleaved, which unmasks the therapeutic agent, reducing off-target side effects and toxicity associated with systemic administration. Accordingly, aspects of the disclosure relate to a polypeptide comprising a therapeutic agent linked to a masking agent through a linker, wherein the linker comprises one or more tumor-associated protease cleavage sites, and wherein the masking agent blocks the association of the therapeutic agent to its therapeutic target, and further wherein the polypeptide is operatively linked to a collagen binding domain or a tumor-targeting agent.

15 Claims, 10 Drawing Sheets

Specification includes a Sequence Listing.

(56) References Cited

U.S. PATENT DOCUMENTS

| | | | |
|---|---|---|---|
| 7,556,816 | B2 | 7/2009 | Walker et al. |
| 7,867,491 | B2 | 1/2011 | Yang et al. |
| 7,927,596 | B2 | 4/2011 | Grant et al. |
| 7,939,056 | B2 | 5/2011 | Horwitz et al. |
| 8,246,960 | B2 | 8/2012 | Chang et al. |
| 8,558,048 | B2 | 10/2013 | Margolin et al. |
| 8,685,406 | B2 | 4/2014 | Walker et al. |
| 8,734,774 | B2 | 5/2014 | Frelinger et al. |
| 8,859,209 | B2 | 10/2014 | Larsen |
| 8,889,130 | B2 | 11/2014 | Kamath |
| 8,921,528 | B2 | 12/2014 | Holt et al. |
| 8,927,694 | B2 | 1/2015 | McDonagh et al. |
| 9,074,010 | B2 | 7/2015 | Sheffer et al. |
| 9,120,875 | B2 | 9/2015 | Gao et al. |
| 9,133,265 | B2 | 9/2015 | Sleep |
| 9,376,495 | B2 | 6/2016 | Bonvini et al. |
| 9,394,374 | B2 | 7/2016 | Hamblin et al. |
| 9,493,564 | B2 | 11/2016 | Thompson et al. |
| 9,675,672 | B2 | 6/2017 | Tagaya et al. |
| 9,714,281 | B2 | 7/2017 | Dasgupta et al. |
| 9,775,912 | B2 | 10/2017 | Steiner et al. |
| 9,879,077 | B2 | 1/2018 | Cha |
| 10,118,949 | B2 | 11/2018 | Abrahmsen et al. |
| 10,143,726 | B2 | 12/2018 | Oft |
| 10,233,228 | B2 | 3/2019 | Plumridge et al. |
| 10,245,298 | B2 | 4/2019 | Murali et al. |
| 10,293,043 | B2 | 5/2019 | Mumm et al. |
| 10,364,419 | B2 | 7/2019 | Buller et al. |
| 10,457,748 | B2 | 10/2019 | Dave et al. |
| 10,711,050 | B2 | 7/2020 | Schmidt et al. |
| 10,934,341 | B2 | 3/2021 | Cameron et al. |
| 10,934,572 | B2 | 3/2021 | Gosselin et al. |
| 11,028,166 | B2 | 6/2021 | Cini et al. |
| 11,046,767 | B2 | 6/2021 | Roobrouck et al. |
| 11,096,997 | B2 | 8/2021 | Mooney et al. |
| 2001/0056075 | A1 | 12/2001 | Gyuris et al. |
| 2002/0164719 | A1 | 11/2002 | Hall et al. |
| 2006/0025573 | A1 | 2/2006 | Gillies et al. |
| 2007/0041987 | A1 | 2/2007 | Carter |
| 2009/0325200 | A1 | 12/2009 | Beck |
| 2011/0014125 | A1 | 1/2011 | Bossmann et al. |
| 2013/0089516 | A1 | 4/2013 | Frelinger et al. |
| 2013/0123199 | A1 | 5/2013 | Lee |
| 2013/0288372 | A1 | 10/2013 | Dasgupta et al. |
| 2015/0038678 | A1 | 2/2015 | Eaton et al. |
| 2015/0283073 | A1 | 10/2015 | Tang |
| 2016/0068583 | A1 | 3/2016 | Van Vlasselaer et al. |
| 2016/0106858 | A1 | 4/2016 | Hall et al. |
| 2016/0186150 | A1* | 6/2016 | Deming et al. .......... C12N 9/16 |
| 2017/0096472 | A1 | 4/2017 | Rosen et al. |
| 2018/0000962 | A1 | 1/2018 | Eigenbrot, Jr. et al. |
| 2018/0009869 | A1 | 1/2018 | Lu et al. |
| 2018/0028679 | A1 | 2/2018 | Kratz et al. |
| 2018/0280524 | A1 | 10/2018 | Hubbell et al. |
| 2018/0326080 | A1 | 11/2018 | Deng |
| 2018/0333464 | A1 | 11/2018 | Mumm et al. |
| 2019/0070263 | A1 | 3/2019 | Azimi |
| 2019/0099485 | A1 | 4/2019 | Swartz et al. |
| 2019/0099487 | A1 | 4/2019 | Mumm et al. |
| 2019/0127489 | A1 | 5/2019 | Humphreys et al. |
| 2019/0144529 | A1 | 5/2019 | Adams et al. |
| 2019/0183992 | A1 | 6/2019 | Sands et al. |
| 2019/0184012 | A1 | 6/2019 | Qu et al. |
| 2019/0216898 | A1 | 7/2019 | Wang et al. |
| 2019/0282692 | A1 | 9/2019 | Bredehorst et al. |
| 2019/0290688 | A1 | 9/2019 | Bar-Sagi et al. |
| 2019/0307849 | A1 | 10/2019 | Oft |
| 2019/0352335 | A1 | 11/2019 | Jeong et al. |
| 2019/0365819 | A1 | 12/2019 | Jones et al. |
| 2019/0367576 | A1* | 12/2019 | Winston et al. ... C07K 14/5434 |
| 2019/0375799 | A1 | 12/2019 | Ekblad et al. |
| 2019/0375823 | A1 | 12/2019 | Dixit et al. |
| 2020/0048325 | A1 | 2/2020 | Zhan et al. |
| 2020/0055947 | A1 | 2/2020 | Khalil et al. |
| 2020/0069814 | A1 | 3/2020 | Zhao et al. |
| 2020/0079860 | A1 | 3/2020 | Khalil et al. |
| 2020/0102368 | A1 | 4/2020 | Andersen et al. |
| 2020/0102370 | A1 | 4/2020 | Wittrup et al. |
| 2020/0123228 | A1 | 4/2020 | Hubbell et al. |
| 2020/0148733 | A1 | 5/2020 | Hinner et al. |
| 2020/0172480 | A1 | 6/2020 | Zhao et al. |
| 2020/0179283 | A1 | 6/2020 | Fahmy et al. |
| 2020/0223901 | A1 | 7/2020 | Larson et al. |
| 2020/0230250 | A1 | 7/2020 | Park et al. |
| 2020/0255512 | A1 | 8/2020 | Fuh et al. |
| 2020/0268884 | A1 | 8/2020 | Markovic et al. |
| 2020/0276261 | A1 | 9/2020 | Zhao et al. |
| 2020/0281994 | A1 | 9/2020 | Irvine et al. |
| 2020/0317749 | A1 | 10/2020 | Dennis et al. |
| 2020/0339696 | A1 | 10/2020 | Gerstam et al. |
| 2020/0385442 | A1 | 12/2020 | Sleep et al. |
| 2020/0390861 | A1 | 12/2020 | Merchant |
| 2020/0392206 | A1 | 12/2020 | Finnis et al. |
| 2020/0405850 | A1 | 12/2020 | Irvine et al. |
| 2021/0009659 | A1 | 1/2021 | Dixit et al. |
| 2021/0017247 | A1 | 1/2021 | Jones et al. |
| 2021/0040179 | A1 | 2/2021 | Hubbell et al. |
| 2021/0046189 | A1 | 2/2021 | Jung et al. |
| 2021/0070839 | A1 | 3/2021 | Delahay et al. |
| 2021/0094995 | A1 | 4/2021 | Hubbell et al. |
| 2021/0115102 | A1 | 4/2021 | Winston et al. |
| 2021/0121533 | A1 | 4/2021 | Jones et al. |
| 2021/0139560 | A1 | 5/2021 | Larson et al. |
| 2021/0163565 | A1 | 6/2021 | Zhong et al. |
| 2021/0163599 | A1 | 6/2021 | Basran et al. |
| 2021/0171642 | A1 | 6/2021 | Hubbell et al. |
| 2021/0188963 | A1 | 6/2021 | Rommelaere et al. |
| 2021/0188967 | A1 | 6/2021 | Buyse |
| 2021/0230242 | A1 | 7/2021 | Zhong et al. |
| 2021/0230285 | A1 | 7/2021 | Cha |
| 2021/0244812 | A1 | 8/2021 | Hubbell et al. |
| 2022/0281936 | A1 | 9/2022 | Hubbell et al. |

FOREIGN PATENT DOCUMENTS

| | | |
|---|---|---|
| CN | 107531758 | 1/2018 |
| CN | 109553684 | 4/2019 |
| EP | 0638644 | 2/1995 |
| JP | 2010503396 | 2/2010 |
| JP | 5178513 | 4/2013 |
| JP | 2014506793 | 3/2014 |
| JP | 2015007086 | 1/2015 |
| JP | 2017537141 | 12/2017 |
| JP | 2019508476 | 3/2019 |
| JP | 2019123719 | 7/2019 |
| JP | 2019523653 | 8/2019 |
| JP | 2020515252 | 5/2020 |
| JP | 2020535264 | 12/2020 |
| JP | 2021006563 | 1/2021 |
| JP | 2021501221 | 1/2021 |
| JP | 6827411 | 2/2021 |
| JP | 2021073291 | 5/2021 |
| JP | 2021515599 | 6/2021 |
| KR | 101286721 | 7/2013 |
| WO | WO 2009/004339 | 1/2009 |
| WO | WO 2012/054929 | 4/2012 |
| WO | WO 2012/112690 | 8/2012 |
| WO | WO 2014/139468 | 9/2014 |
| WO | WO 2014/176284 | 10/2014 |
| WO | WO 2016/174575 | 11/2016 |
| WO | WO 2018/064190 | 4/2018 |
| WO | WO 2018/069467 | 4/2018 |
| WO | WO 2018/112394 | 6/2018 |
| WO | WO 2018/184003 | 10/2018 |
| WO | WO 2018/195386 | 10/2018 |
| WO | WO 2018/218231 | 11/2018 |
| WO | WO 2018/236701 | 12/2018 |
| WO | WO 2019/173289 | 9/2019 |
| WO | WO 2019/209965 | 10/2019 |
| WO | WO 2019/222294 | 11/2019 |
| WO | WO 2020/041758 | 2/2020 |
| WO | WO 2020/097325 | 5/2020 |
| WO | WO 2020/108426 | 6/2020 |
| WO | WO 2020/176478 | 9/2020 |

(56) References Cited

FOREIGN PATENT DOCUMENTS

| | | |
|---|---|---|
| WO | WO 2020/247973 | 12/2020 |
| WO | WO 2020/247974 | 12/2020 |
| WO | WO 2021/016640 | 1/2021 |
| WO | WO 2021/062406 | 4/2021 |
| WO | WO 2021/091986 | 5/2021 |
| WO | WO 2021/158938 | 8/2021 |

OTHER PUBLICATIONS

Addi et al., "Design and use of chimeric proteins containing a collagen-binding domain for wound healing and bone regeneration", Tissue Eng. Part B. Rev., 2017, 23:163-182.

Busher et al., "Clinical Methods: The History, Physical, and Labatory Examinations," 3rd edition, Boston: Buttersworths; 1990, Chapter 101. Available online from: www.ncbi.nlm.nih.gov/books/NBK204.

Castro et al., "Interferon-Gamma at the Crossroads of Tumor Immune Surveillance of Evasion", Front. Immunol., 9:847, 2018.

Chaudhury et al., "The major histocompatibility complex-related Fc receptor for IgG (FcRn) binds albumin and prolongs its lifespan", J. Exp. Med., 2003, 197:315-322.

Extended European Search Report issued in European Patent Application No. 22799803.6, dated Jul. 7, 2025.

Garamszegi et al. "Extracellular matrix-induced transforming growth factor-β receptor signaling dynamics", Oncogene, 2010, 29(16):2368-2380.

Gerspach et al, "Target-selective activation of a TNF prodrug by urokinase-type plasminogen activator (uPA) mediated proteolytic processing at the cell surface", Cancer Immunol Immunother,, 2006, 55:1590-1600.

Green et al., "Abraxane®, a novel Cremophor®-free, albumin-bound particle form of paclitaxel for the treatment of advanced non-small-cell lung cancer", Annals of Oncology, 2006, 17:1263-1268.

Hummel et al., "Synthetic Deletion of the Interleukin 23 Receptor (IL-23R) Stalk Region Led to Autonomous IL-23R Homodimerization and Activation", Molecular and Cellular Biology, 2017, 37(17), 1-19.

Ishihara et al., "Matrix-binding checkpoint immunotherapies enhance antitumor efficacy and reduce adverse events," Sci. Transl. Med., 9:eaan0401, pp. 1-14, 2017.

Ishihara et al., "Prolonged residence of an albumin-IL-4 fusion protein in secondary lymphoid organs ameliorates experimental autoimmune encephalomyelitis", Nat Biomed Eng, 2021, 5, 387-398.

Ishihara et al., "Targeted antibody and cytokine cancer immunotherapies through collagen affinity," Sci. Transl. Med., 11(487):eaau3259, pp. 1-12, 2019.

Katsumata et al., "Targeting inflammatory sites through collagen affinity enhances the therapeutic efficacy of anti-inflammatory antibodies", Sci. Adv., 2019, 5:eaay1971, 1-9.

Kratz et al., "Probing the cysteine-34 position of endogenous serum albumin with thiol-binding doxorubicin derivatives. Improved efficacy of an acid-sensitive doxorubicin derivative with specific albumin-binding properties compared to that of the parent compound.", J. Med. Chem., 2002, 45:5523-5533.

Kratz, F., "Albumin as a drug carrier: design of prodrugs, drug conjugates and nanoparticles", J. Control. Release, 2008, 132, 171-183.

Lasek et al., "Interleukin 12: still a promising candidate for tumor immunotherapy?", Cancer Immunol. Immunother., 63(5):419-35, 2014.

Mansurov et al., "Collagen-binding IL-12 enhances tumour inflammation and drives the complete remission of established 'immunologically cold' mouse tumours," Nat. Biomed. Eng., 4(5):531-543, 2020.

Mansurov, A., "Exploiting Tumor-intrinsic Cues to Engineer Interleukin-12 for Cancer Immunotherapy," The University of Chicago, Doctor of Philosophy Dissertation, pp. 1-137, 2021.

Partial Supplementary European Search Report issued in European Patent Application No. 22799803.6, dated Apr. 15, 2025.

PCT International Search Report and Written Opinion issued in International Application No. PCT/US2022/072121, dated Nov. 1, 2022.

PCT Invitation to Pay Additional Fees issued in International Application No. PCT/US2022/072121, dated Sep. 16, 2022.

Presky et al. "Analysis of the multiple interactions between IL-12 and the high affinity Il-12 receptor complex", The Journal of Immunology, 160(5):2174-2179, 1998.

Puskas et al., "Development of an attenuated interleukin-2 fusion protein that can be activated by tumour-expressed proteases", Immunology, 2011, 133(2), 206-220.

Sasaki et al., "Engineered collagen-binding serum albumin as a drug conjugate carrier for cancer therapy.", Sci. Adv., 2019, 5:eaaw6081, 12 pages.

Shan, "Il-12 family cytokines: hot molecules in tumor immunotherapy research," Chinese Journal of Cancer Biotherapy, 18(3):239-243, 2011. (English abstract only).

Skrombolas et al., "Development of an Interleukin-12 Fusion Protein That Is Activated by Cleavage with Matrix Metalloproteinase 9", Journal of Interferon and Cytokine Research, 2019, 39(4), 233-245.

Temming et al., "Evaluation of RGD-targeted albumin carriers for specific delivery of auristatin E to tumor blood vessels" Bioconjug. Chem., 2006, 17:1385-1394.

Villa et al., "A high-affinity human monoclonal antibody specific to the alternatively spliced EDA domain of fibronectin efficiently targets tumor neo-vasculature in vivo," Intl. J. Cancer, 122(11):2405-13, 2008.

Waldmann, A., "Cytokines in Cancer Immunotherapy," Cold Spring Harb. Perspect Biol., 10(12):a028472, pp. 1-25, 2018.

You et al. "The Extracellular Matrix and Remyelination Strategies in Multiple Sclerosis", eNeuro, 2018, 5(1), 1-4.

Yuba et al., "Suppression of Rheumatoid Arthritis by Enhanced Lymph Node Trafficking of Engineered Interleukin-10 in Murine Models" Arthritis and Rheumatology 2021, 73(5), 769-778.

Zheng et al., "Induction of apoptosis in mature T cells by tumour necrosis factor," Nature, 377(6547):348-51, 1995.

Zhong et al., "710 Development of IL-33 as a novel immunotherapy of cancer", Journal for Immuno Therapy of Cancer, 8(Suppl 3): A426, 2020.

Zorzi et al., "Non-covalent albumin-binding ligands for extending the circulating half-life of small biotherapeutics", Med. Chem. Commun., 10(7):1068-1081, 2019.

* cited by examiner

COMPOSITIONS AND METHODS COMPRISING PROTEASE-ACTIVATED THERAPEUTIC AGENTS

CROSS-REFERENCE FOR RELATED APPLICATIONS

This application is a national phase application under 35 U.S.C. § 371 of International Application No. PCT/US2022/072121, filed May 5, 2022, which claims the benefit of priority of U.S. Provisional Patent Application No. 63/185,941 filed May 7, 2021, and U.S. Provisional Patent Application No. 63/313,087 filed Feb. 23, 2022, each of which are hereby incorporated by reference in their entirety.

SEQUENCE LISTING

The instant application contains a Sequence Listing which has been submitted in ASCII format and is hereby incorporated by reference in its entirety. Said ASCII copy, created on Nov. 4, 2023, is named ARCDP0731US_ST25.txt and is 324,838 bytes.

BACKGROUND OF THE INVENTION

I. Field of the Invention

This invention relates to the field of treatment of disease and, in particular, to the treatment of cancer.

II. Background

Cytokine cancer immunotherapy using interleukin (IL)-12 has shown strong antitumor efficacy in both mouse and in human. However, due to its severe toxicity, some IL12 clinical trials have been terminated or unsuccessful. IL12 has not been approved to use in the clinic to date. Immunotherapies serve to activate immune responses, and as such, side-effects typically result from drug action in healthy organs. There is a need in the art for strategies to reduce the toxicity of therapeutic treatments.

SUMMARY OF INVENTION

The disclosure relates to the engineering of masked therapeutic agents comprising one or more tumor-associated protease cleavage sites. Upon exposure to tumor-associated proteases in the tumor microenvironment, the polypeptide is cleaved, which unmasks the therapeutic agent, reducing off-target side effects and toxicity associated with systemic administration. Accordingly, aspects of the disclosure relate to a polypeptide comprising a cytokine linked to a masking agent through a linker, wherein the linker comprises at least 2 protease cleavage sites of SEQ ID NO:138 and at least two protease cleavage sites of SEQ ID NO:134, and wherein the masking agent comprises a cytokine receptor polypeptide or fragment thereof that specifically binds to the cytokine. Further aspects relate to a polypeptide comprising a cytokine linked to a masking agent through a linker, wherein the linker comprises an amino acid sequence with at least 80% sequence identity to one of SEQ ID NOS:48, 103-108, or 219-246, and wherein the masking agent comprises a cytokine receptor polypeptide or fragment thereof that specifically binds to the cytokine. Also described is a polypeptide comprising a cytokine linked to a masking agent through a linker, wherein the linker comprises a glycine-serine linker; and wherein the masking agent comprises a cytokine receptor polypeptide or fragment thereof that specifically binds to the cytokine.

The linker may comprise an amino acid sequence having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to one of SEQ ID NOS:48, 103-108, or 219-246. In some aspects, the linker comprises or consists of the amino acid sequence of one of SEQ ID NOS:48, 103-108, or 219-246. In some aspects, the linker comprises SEQ ID NO:48.

Yet further aspects relate to a polypeptide comprising the amino acid sequence of one of SEQ ID NOS: 197-218, 247, or 248 or an amino acid sequence with at least 80% sequence identity to one of SEQ ID NOS: 197-218, 247, or 248. In some aspects, the polypeptide comprises or consists of an amino acid sequence having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to one of SEQ ID NOS: 197-218, 247-248.

Further aspects of the disclosure relate to a polypeptide comprising a cytokine linked to a masking agent through a linker, wherein the linker comprises one or more tumor-associated protease cleavage sites, and wherein the masking agent comprises a cytokine receptor polypeptide or fragment thereof that specifically binds to the cytokine. A masking agent refers to a molecule that blocks the association of a therapeutic agent with at least one binding partner. In some aspects, the therapeutic agent comprises an antibody, and the binding partner comprises an antigen. In some aspects, the therapeutic agent comprises a cytokine and the binding partner comprises a receptor polypeptide.

Further aspects relate to a composition comprising the polypeptides of the disclosure. Yet further aspects relate to nucleic acids encoding polypeptides of the disclosure and host cells comprising nucleic acids and/or polypeptides of the disclosure. Also provided are methods for making a polypeptide comprising expressing a nucleic acid of the disclosure in a host cell and isolating the expressed polypeptide. Further aspects relate to a method for treating cancer comprising administering a polypeptide or composition of the disclosure to a subject in need thereof, such as one that has cancer.

The cytokine may comprise interleukin-12 (IL12) and the masking agent may comprise interleukin 12 receptor (IL12R) polypeptide or an IL12-binding fragment thereof. In some aspects, the IL12 comprises one or both of the p35 and p40 subunits. In some aspects, the IL12 comprises the p35 and p40 subunits linked through a disulfide bond. In some aspects, the IL12 comprises the p35 and p40 subunits linked through a peptide linker. In some aspects, the IL12R polypeptide or fragment comprises interleukin 12 receptor beta 1 (IL12Rβ1), or a fragment thereof. The IL12 may comprise a polypeptide of SEQ ID NO:3 or a polypeptide having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO:3. The IL12R polypeptide or fragment may comprise interleukin 12 receptor beta 2 (IL12Rβ2), or a fragment thereof. The IL12Rβ1 polypeptide may comprise human FNI-II domain of IL-12Rβ1. In some aspects, the IL12Rβ1 polypeptide comprises a polypeptide of SEQ ID NO: 195 or a polypeptide having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO: 195. In some aspects, the polypeptide has or has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO: 195 and wherein the polypeptide binds to IL12. In some aspects, the polypeptide comprises SEQ ID NO:197 or a polypeptide having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO:197.

In some aspects, the masking agent is fused to the N-terminus of the p35 subunit of IL12, and wherein the linker comprising the tumor-associated protease cleavage site is between the masking agent and the p35 subunit of IL12. In some aspects, the masking agent is fused to the C-terminus of the p35 subunit of IL12, and wherein the linker comprising the tumor-associated protease cleavage site is between the masking agent and the p35 subunit of IL12. In some aspects, the masking agent is fused to the C-terminus of the p40 subunit of IL12, and wherein the linker is between the masking agent and the p40 subunit of IL12. In some aspects, the masking agent is fused to the N-terminus of the p40 subunit of IL12, and wherein the linker is between the masking agent and the p40 subunit of IL12. In some aspects, the cytokine comprises interleukin-2 (IL-2) and the masking agent comprises interleukin 2 receptor alpha subunit (IL-2Rα), interleukin 2 receptor beta subunit (IL-2Rβ), interleukin 2 receptor gamma subunit (IL-2Rγ), fragments, or combinations of fragments thereof. In some aspects, the cytokine comprises the amino acid sequence of SEQ ID NO:23 or an amino acid sequence having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO:23. In some aspects, the masking agent comprises the amino acid sequence of SEQ ID NO:27, 29, 31 or a fragment or combination of SEQ ID NO:27, 29, or 31. In some aspects, the masking agent comprises an amino acid sequence having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO:27, 29, and/or 31.

In some aspects, the cytokine comprises interferon-gamma (IFNγ) and the masking agent comprises interferon-gamma receptor 1 (IFNγR1), interferon-gamma receptor 2 (IFNγR2), fragments, or combinations of fragments thereof. In some aspects, the cytokine comprises the amino acid sequence of SEQ ID NO:26 or an amino acid sequence having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO:26. In some aspects, the masking agent comprises the amino acid sequence of SEQ ID NO:33, 35 or a fragment or combination of SEQ ID NO:33 and/or 35. In some aspects, the masking agent comprises an amino acid sequence having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO:33 and/or 35.

In some aspects, the polypeptide comprises at least four tumor-associated protease cleavage sites. In some aspects, the polypeptide comprises at least, at most, or exactly 4, 5, 6, 7, 8, 9, 10, 11, or 12 tumor-associated protease cleavage sites, or any range derivable therein. In some aspects, the linker further comprises at least one serine protease sensitive cleavage site. The serine protease sensitive cleavage site may comprise a cleavage site of SEQ ID NO:47 or SEQ ID NO:3. In some aspects, the linker comprises SEQ ID NO:219 or a polypeptide having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO:219. In some aspects, the linker comprises SEQ ID NO:220 or a polypeptide having or having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO:220.

In some aspects, the linker comprises or further comprises (GGGS)n, wherein n is 1-4. In some aspects, n is equal to 2.

In some aspects, the tumor-associated protease cleavage site comprises at least one tumor associated protease cleavage site described herein. In some aspects, the tumor-associated cleavage site comprises a cleavage site with an amino acid of one of SEQ ID NOS:13, 14, 49, 51, 55, 109-190. In some aspects, the polypeptide comprises at least two different tumor-associated protease cleavage site. In some aspects, the polypeptide comprises at least 2, 3, or 4 different tumor-associated protease cleavage sites, or any range derivable therein. In some aspects, the polypeptide comprises at least 2 of the same tumor-associated protease cleavage sites. In some aspects, the polypeptide comprises at least 2, 3, 4, 5, 6, 7, or 8 of the same protease cleavage sites, or any range derivable therein. In aspects which comprise more than one protease cleavage site, the protease cleavage sites may be adjacent or may have intervening amino acids. In some aspects, at least, at most, or exactly 0, 1, 2, 3, 4, 5, 6, 7, 8, 9, 10, 11, 12, 13, 14, 15, 16, 17, 18, 19, or 20 amino acids, or any range derivable therein, separate one tumor-associated protease cleavage site from another tumor-associated protease cleavage site.

In some aspects, the cytokine comprises an anti-inflammatory cytokine. In some aspects, the cytokine comprises a pro-inflammatory cytokine.

In some aspects, the polypeptide is conjugated to a tumor targeting agent. In some aspects, the tumor targeting agent comprises an antibody or an antigen-binding fragment thereof. In some aspects, the antibody or antigen-binding fragment comprises a stroma targeting antibody or stroma-binding fragment thereof. In some aspects, the antibody or binding fragment specifically binds to fibronectin, alternatively spliced domains of fibronectin, collagens, tenascins, periostins, syndecans, proteoglycans, or a tumor stroma cell-specific antigen. In some aspects, the antibody or binding fragment specifically binds toe extra domain A (EDA) or extra domain B (EDB) of fibronectin. In some aspects, the tumor targeting agent comprises a Fab that specifically binds to an alternatively spliced domain of fibronectin comprising extra domain A (EDA). In some aspects, the tumor targeting agent comprises an antibody or antigen binding fragment thereof that specifically binds to a tumor-associated antigen. Other tumor targeting agents include those recited in US20140294723A1, WO2001062298A2, WO1997045544A1, WO2006119897A2, WO2006050834A2, WO2008120101A2, WO2010078916A1, which are herein incorporated by reference.

In some aspects, the tumor targeting agent comprises a collagen binding domain. In some aspects, the polypeptide comprises at least two collagen binding domains. In some aspects, the polypeptide comprises at least 2, 3, 4, 5, or 6 collagen binding domains. In some aspects, the polypeptide comprises a collagen binding domain from decorin or von Willebrand factor (VWF). In some aspects, the collagen binding domain comprises a polypeptide comprising SEQ ID NO:1 or an amino acid sequence having or having at least 78, 79, 80, 81, 82, 83, 84, 85, 86, 87, 88, 89, 90, 91, 92, 93, 94, 95, 96, 97, 98, 99, or 100% sequence identity to SEQ ID NO:1.

In some aspects, the polypeptide further comprises a serum protein conjugated to the polypeptide. In some aspects, the serum protein is conjugated to the polypeptide through a peptide bond. In some aspects, the serum protein comprises albumin or a fragment thereof. In some aspects, the serum protein is at least 40, 45, 50, 55, 60, 65, 70, or 75 kDa (or any range derivable therein).

In some aspects, the polypeptide comprises a second linker. In some aspects, the second linker comprises glycine and serine amino acid residues. In some aspects, the polypeptide comprises a third, fourth, or fifth linker. In some aspects, the third, fourth, or fifth linker comprises glycine and serine amino acid residues. In some aspects, the linker comprises (GGGS)n, (SEQ ID NO:191) wherein n=1, 2, 3, 4, 5, 6, 7, or 8, or any range derivable therein, or GGGSGGGS (SEQ ID NO:47). In some aspects, the second linker comprises (GGGS)n (SEQ ID NO:191), wherein n=6. In some aspects, the polypeptide comprises a protein tag. In some aspects, the protein tag comprises a 6H tag (SEQ ID NO:87). In some aspects, the protein tag comprises a protein tag described herein. In some aspects, the polypeptide is not operatively linked to a particle, nanovesicle, or liposome. In some aspects, the composition does not comprise a liposome, particle, or nanovescicle.

The compositions may comprise or further comprise an additional polypeptide. In aspects of the disclosure, the methods may comprise or further comprise administration of an additional polypeptide. The additional polypeptide may be a polypeptide described herein. In some aspects, the composition comprises an additional polypeptide, wherein the polypeptide is an IL-12 p35 or p40 subunit. In some aspects, the additional polypeptide comprises a polypeptide of SEQ ID NO:3 or 4 or an amino acid sequence with at least 70% sequence identity to SEQ ID NO:3 or 4. In some aspects, the additional polypeptide comprises an amino acid sequence having or having at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to SEQ ID NO:3 or 4, or any derivable range therein.

In some aspects, the methods or the disclosure relate to the treatment of skin cancer, such as for the treatment of melanoma. In some aspects, the cancer comprises melanoma, colon, or breast cancer. In some aspects, the cancer comprises a solid tumor.

In some aspects, methods of the disclosure further comprise administration of one or more additional cancer therapies. In some aspects, the additional therapy is one described herein. In some aspects, the subject has or will receive an immunotherapy. In some aspects, the method further comprises administration of an immunotherapy. In a particular aspect, the immunotherapy comprises an immune checkpoint inhibitor. The immune checkpoint inhibitor may be an anti-PD-1 monoclonal antibody or an anti-CTLA-4 monoclonal antibody. Further exemplary immune checkpoint proteins that may be inhibited in aspects of the disclosure are described herein. In some aspects, the immune checkpoint inhibitor comprises one or more of nivolumab, pembrolizumab, pidilizumab, ipilimumab or tremelimumab. In some aspects, the immune checkpoint therapy is monotherapy. The term monotherapy, in the context of immune checkpoint therapy, refers to administration of one immune checkpoint inhibitor during the course of therapy. The monotherapy may be a therapy comprising of only one of a PD-1, PDL1, PDL2, CTLA-4, B7-1, or B7-2 inhibitor. In some aspects, the immune checkpoint inhibitor therapy comprises combination therapy. For example, the combination therapy may be a combination of (i) a PD-1, PDL1, or PDL2 inhibitor and (ii) a CTLA-4, B7-1, or B7-2 inhibitor. Particular combination therapies include those that comprise an anti-PD-1 antibody and an anti-CTLA-4 antibody. Further immunotherapies useful in the methods and compositions of the disclosure are described herein. In some aspects, the immunotherapy or additional therapy is administered before, after, or concurrent with the polypeptide. In some aspects, the polypeptide or composition is administered systemically. In some aspects, the polypeptide or composition is administered intratumorally. In some aspects, the polypeptide or composition is administered by a route of administration described herein. In some aspects, the polypeptide or composition is administered by intravenous injection. In some aspects, the subject has been previously treated with a cancer therapy. In some aspects, the subject has been determined to be non-responsive to the previous treatment or wherein the wherein the subject experienced non-specific toxicity to the previous treatment.

In some aspects, the toxicity of the treatment comprising the masked cytokine polypeptides of the disclosure is reduced compared to the toxicity of administration of the same dose of polypeptide that is unmasked. The reduction may be or may be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any derivable range therein.

In some aspects, the serum IFN-gamma level induced by the masked cytokine polypeptide of the disclosure is significantly less than the serum IFN-gamma level induced by the unmasked cytokine polypeptide. In some aspects, the serum IFN-gamma level induced by the masked cytokine polypeptide of the disclosure is or is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any derivable range therein, less than the serum IFN-gamma level induced by the unmasked cytokine polypeptide.

In some aspects, the tumor IFN-gamma level induced by the masked cytokine polypeptide of the disclosure is significantly less than the tumor IFN-gamma level induced by the unmasked cytokine polypeptide. In some aspects, the tumor IFN-gamma level induced by the masked cytokine polypeptide of the disclosure is or is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any derivable range therein, less than the tumor IFN-gamma level induced by the unmasked cytokine polypeptide.

In some aspects, the tumor volume is significantly decreased by the masked cytokine polypeptide of the disclosure. In some aspects, the tumor volume is decreased by or decreased by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any derivable range therein, after administration of the masked cytokine polypeptide of the disclosure. In some aspects, administration of the masked cytokine polypeptide cause a tumor volume decrease of or of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any derivable range therein, more than the decrease in tumor volume after administration of the unmasked cytokine polypeptide.

The term "cytokine polypeptide" as used herein refers to a polypeptide, which is cytokine or a receptor binding domain thereof and retains at a portion of cytokine activity. In certain aspects, the cytokine polypeptide is an active fragment of the cytokine.

The terms "protein", "polypeptide" and "peptide" are used interchangeably herein when referring to a gene product comprising a polymer of amino acids.

The terms "subject," "mammal," and "patient" are used interchangeably. In some aspects, the subject is a mammal. In some aspects, the subject is a human. In some aspects, the subject is a mouse, rat, rabbit, dog, donkey, or a laboratory test animal such as fruit fly, zebrafish, etc.

It is contemplated that the methods and compositions include exclusion of any of the embodiments described herein.

The use of the word "a" or "an" when used in conjunction with the term "comprising" may mean "one," but it is also consistent with the meaning of "one or more," "at least one," and "one or more than one."

The phrase "and/or" means "and" or "or". To illustrate, A, B, and/or C includes: A alone, B alone, C alone, a combination of A and B, a combination of A and C, a combination of B and C, or a combination of A, B, and C. In other words, "and/or" operates as an inclusive or.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. Compositions and methods "consisting essentially of" any of the ingredients or steps disclosed limits the scope of the claim to the specified materials or steps which do not materially affect the basic and novel characteristic of the claimed invention.

Any method in the context of a therapeutic, diagnostic, or physiologic purpose or effect may also be described in "use" claim language such as "Use of" any compound, composition, or agent discussed herein for achieving or implementing a described therapeutic, diagnostic, or physiologic purpose or effect.

Use of the one or more sequences or compositions may be employed based on any of the methods described herein. Other embodiments are discussed throughout this application. Any embodiment discussed with respect to one aspect of the disclosure applies to other aspects of the disclosure as well and vice versa.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
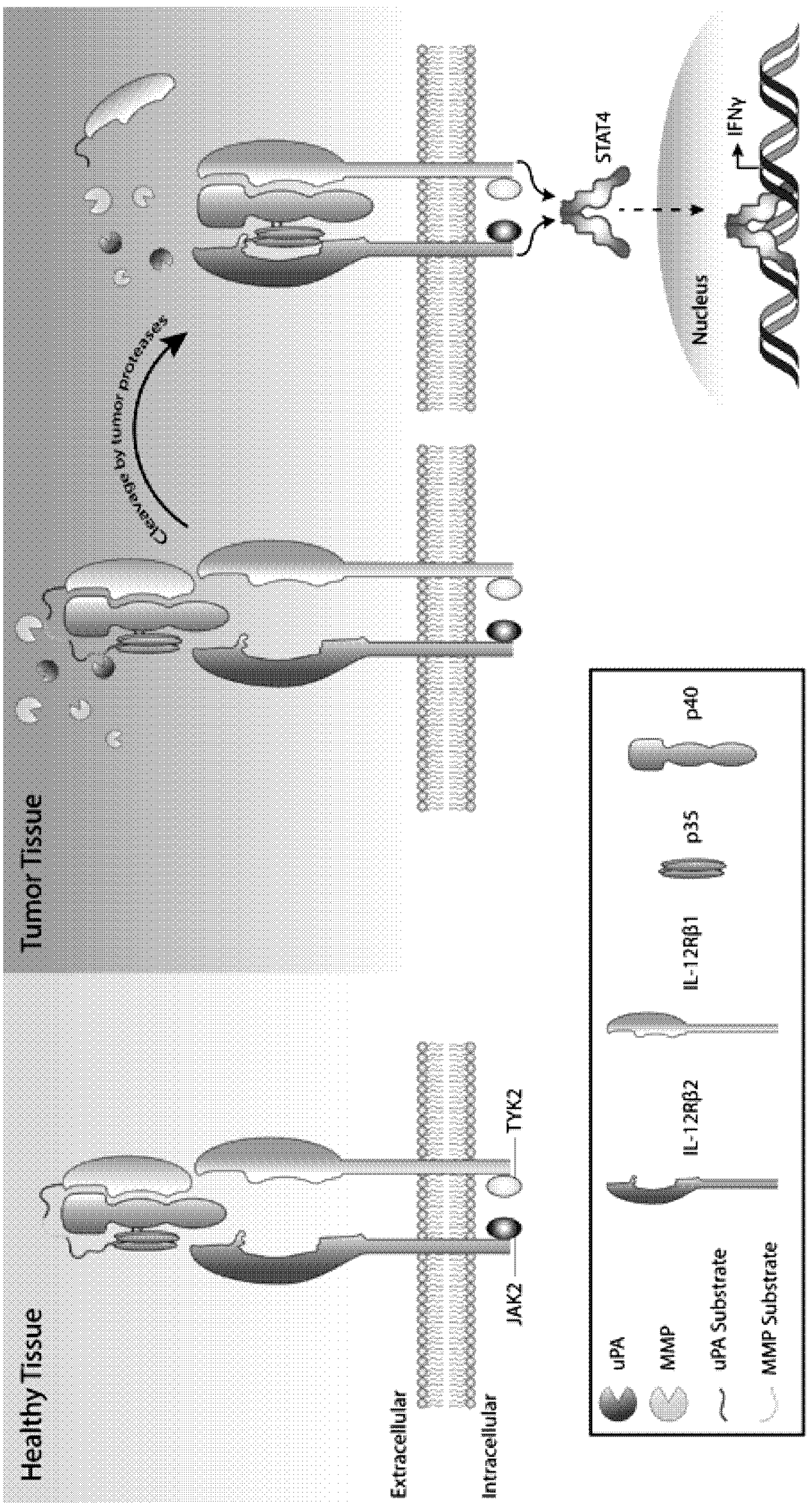
FIG. 1. Proposed mechanism of action of masked IL-12.

Cytokines are key factors for antitumor activities, but not many of them have been translated to the clinic to date. IL12 is one of the strongest antitumor cytokines, but due to its high toxicity, the clinical trial has been terminated or unsuccessful. Thus, decreasing its toxicity is an important strategy to translate it to the clinic. To improve CBD-IL12 therapy, a domain of the IL12 receptor IL12Rβ1 was fused to the IL12, to form IL12Rβ1-IL12. This fusion is inactive, but the inclusion of an MMP or thrombin cleavage site between the receptor making agent and the cytokine yields a pro-cytokine that can be activated in the tumor microenvironment. The inventors have demonstrated that the immunotoxicity of the IL12 is thus reduced, and that the IL12Rβ1-IL12 fusion with the protease-sensitive linker retains therapeutic utility. The inventors also found that introducing multi-cleavage sites in the linker (e.g. tandem MMP, tandem thrombin, and MMP-thrombin dyads and repeats) would increase the protease sensitivity and may increase the antitumor efficacy of IL12Rβ1-IL12 therapy. Furthermore, the use of a collagen binding domain fused to the masked therapeutic molecules of the disclosure is particularly useful, since the CBD increases the retention of the masked therapeutic agent in the tumor microenvironment, which prolongs the exposure of the masked therapeutic agent to the protease and increases the local concentration of the unmasked therapeutic agent. In conclusion, the inventors have developed a technology to reduce toxicity of therapeutic agents by fusing the cytokine receptor to the cytokine. Tumor specific proteases cleave the linker to activate the cytokine within the tumor.

I. POLYPEPTIDE ASPECTS

A. Therapeutic Agents and Masking Agents

Aspects of the disclosure relate to therapeutic agent and masking agents that bind to the therapeutic agent and prevent association of the therapeutic agent with its target to reduce toxicity associated with the therapeutic agent. The polypeptides of the disclosure comprise a tumor-associated protease cleavage site that unmasks the therapeutic agent when it encounters the relevant protease. Since the protease is one that is enriched in the tumor microenvironment, there is a reduction of the active therapeutic agent in normal tissues when administered systemically, compared to the systemic administration of the unmasked therapeutic agent.

1. Cytokines and Masking Polypeptides

In some aspects, the therapeutic agent comprises a cytokine or a therapeutic polypeptide from a cytokine. In certain aspects, the cytokine comprises a functionally active fragment of a cytokine. In some aspects, the functionally active cytokine fragment binds and activates the corresponding receptor. In some aspects, the cytokine comprises IL12. IL12 is a heterodimeric glycosylated cytokine comprised of disulfide-linked p35 (~35 kDa) and p40 (~40 kDa) subunits. The human IL12 p35 sequence is represented by the following: RNLPVATPDPGMFPCLHHSQNLL-RAVSNMLQKARQTLEFYPCTSEEIDHEDITKDKTST VEACLPLELTKNESCLNSRETSFITNGSCLAS-RKTSFMMALCLSSIYEDLKMYQVEFKTM NAKLL-MDPKRQIFLDQNMLAVIDELMQALNFN-SETVPQKSSLEEPDFYKTKIKLCILLHA FRIRAVTIDRVMSYLNAS (SEQ ID NO:3). The human IL12 p40 sequence is represented by the following: IWELKKDVYVVELDWYPDAPGEMVVLTCDTPEED-GITWTLDQSSEVLGSGKTLTIQVK EFGDAGQYTCHKGGEVLSHSLLLLHKKEDGIW-STDILKDQKEPKNKTFLRCEAKNYSGR FTCWWLT-TISTDLTFSVKSSRGSSDPQGVTCGAATL-SAERVRGDNKEYEYSVECQEDSA CPAAEESLPIEVMVDAVHKLKYENYTSSFFIR-DIIKPDPPKNLQLKPLKNSRQVEVSWEY PDTW-STPHSYFSLTFCVQVQGKSKREKKDRVFTDKTSATVI-CRKNASISVRAQDRYYSS SWSEWASVPCS (SEQ ID NO:4). The mouse IL12 p35 sequence is represented by the following: RVIPVSGPARCLSQSRNLLKTTDDMVK-TAREKLKHYSCTAEDIDHEDITRDQTSTLKTCL PLELHKNESCLATRETSSTTRGSCLPPQKT-SLMMTLCLGSIYEDLKMYQTEFQAINAALQ NHNHQQIILDKGMLVAIDELMQSLNHNGETLRQKP-PVGEADPYRVKMKLCILLHAFSTR VVTINRVMGYLSSA (SEQ ID NO:5). The mouse IL12 p40 sequence is represented by the following:

```
                                        (SEQ ID NO: 6)
MWELEKDVYVVEVDWTPDAPGETVNLTCDTPEEDDITWTSDQRHGVIGSG

KTLTITVKEFLDAGQYTCHKGGETLSHSHLLLHKKENGIWSTEILKNFKN

KTFLKCEAPNYSGRFTCSWLVQRNMDLKFNIKSSSSSPDSRAVTCGMASL

SAEKVTLDQRDYEKYSVSCQEDVTCPTAEETLPIELALEARQQNKYENYS

TSFFIRDIIKPDPPKNLQMKPLKNSQVEVSWEYPDSWSTPHSYFSLKFFV

RIQRKKEKMKETEEGCNQKGAFLVEKTSTEVQCKGGNVCVQAQDRYYNSS

CSKWACVPCRVRS
```

Suitable IL12 masking agents include polypeptides that bind to IL12 and prevent binding of IL12 to other molecules, such as IL12R. Exemplary polypeptides include polypeptides from IL12R, such as IL12Rβ1 and IL12Rβ2.

The mouse IL12Rβ1 is represented by a polypeptide with either of the following amino acid sequences:

(SEQ ID NO: 2)

QLGASGPGDGCCVEKTSFPEGASGSPLGPRNLSCYRVSKTDYECSWQYDG

PEDNVSHVLWCCFVPPNHTHTGQERCRYFSSGPDRTVQFWEQDGIPVLSK

VNFWVESRLGNRTMKSQKISQYLYNWTKTTPPLGHIKVSQSHRQLRMDWN

VSEEAGAEVQFRRRMPTTNWTLGDCGPQVNSGSGVLGDIRGSMSESCLCP

SENMAQEIQIRRRRRLSSGAPGGPWSDWSMPVCVPPEVLPQALVPRGS and (SEQ ID NO: 20)

QLGASGPGDGCCVEKTSFPEGASGSPLGPRNLSCYRVSKTDYECSWQYDG

PEDNVSHVLWCCFVPPNHTHTGQERCRYFSSGPDRTVQFWEQDGIPVLSK

VNFWVESRLGNRTMKSQKISQYLYNWTKTTPPLGHIKVSQSHRQLRMDWN

VSEEAGAEVQFRRRMPTTNWTLGDCGPQVNSGSGVLGDIRGSMSESCLCP

SENMAQEIQIRRRRRLSSGAPGGPWSDWSMPVCVPPEVLPQAKIKFLVEP

LNQGGRRRLTMQGQSPQLAVPEGCRGRPGAQVKKHLVLVRMLSCRCQAQT

SKTVPLGKKLNLSGATYDLNVLAKTRFGRSTIQKWHLPAQELTETRALNV

SVGGNMTSMQWAAQAPGTTYCLEWQPWFQHRNHTHCTLIVPEEEDPAKMV

THSWSSKPTLEQEECYRITVFASKNPKNPMLWATVLSSYYFGGNASRAGT

PRHVSVRNQTGDSVSVEWTASQLSTCPGVLTQYVVRCEAEDGAWESEWLV

PPTKTQVTLDGLRSRVMYKVQVRADTARLPGAWSHPQRFSFEVQISRLSI

IFASLGSFASVLLVGSLGYIGLNRAAWHLCPPLPTPCGSTAVEFPGSQGK

QAWQWCNPEDFPEVLYPRDALVVEMPGDRGDGTESPQAAPECALDTRRPL

ETQRQRQVQALSEARRLGLAREDCPRGDLAHVTLPLLLGGVTQGASVLDD

LWRTHKTAEPGPPTLGQEA.

The human IL12Rβ1 is represented by a polypeptide with the following amino acid sequence:

(SEQ ID NO: 19)

CRTSECCFQDPPYPDADSGSASGPRDLRCYRISSDRYECSWQYEGPTAGV

SHFLRCCLSSGRCCYFAAGSATRLQFSDQAGVSVLYTVTLWVESWARNQT

EKSPEVTLQLYNSVKYEPPLGDIKVSKLAGQLRMEWETPDNQVGAEVQFR

HRTPSSPWKLGDCGPQDDDTESCLCPLEMNVAQEFQLRRRQLGSQGSSWS

KWSSPVCVPPENPPQPQVRFSVEQLGQDGRRRLTLKEQPTQLELPEGCQG

LAPGTEVTYRLQLHMLSCPCKAKATRTLHLGKMPYLSGAAYNVAVISSNQ

FGPGLNQTWHIPADTHTEPVALNISVGTNGTTMYWPARAQSMTYCIEWQP

VGQDGGLATCSLTAPQDPDPAGMATYSWSRESGAMGQEKCYYITIFASAH

PEKLTLWSTVLSTYHFGGNASAAGTPHHVSVKNHSLDSVSVDWAPSLLST

CPGVLKEYVVRCRDEDSKQVSEHPVQPTETQVTLSGLRAGVAYTVQVRAD

TAWLRGVWSQPQRFSIEVQVSDWLIFFASLGSFLSILLVGVLGYLGLNRA

ARHLCPPLPTPCASSAIEFPGGKETWQWINPVDFQEEASLQEALVVEMSW

DKGERTEPLEKTELPEGAPELALDTELSLEDGDRCKAKM.

The human IL12Rβ2 is represented by a polypeptide with the following amino acid sequence:

(SEQ ID NO: 21)

KIDACKRGDVTVKPSHVILLGSTVNITCSLKPRQGCFHYSRRNKLILYK

FDRRINFHHGHSLNSQVTGLPLGTTLFVCKLACINSDEIQICGAEIFVG

VAPEQPQNLSCIQKGEQGTVACTWERGRDTHLYTEYTLQLSGPKNLTWQ

KQCKDIYCDYLDFGINLTPESPESNFTAKVTAVNSLGSSSSLPSTFTFL

DIVRPLPPWDIRIKFQKASVSRCTLYWRDEGLVLLNRLRYRPSNSRLWN

MVNVTKAKGRHDLLDLKPFTEYEFQISSKLHLYKGSWSDWSESLRAQTP

EEEPTGMLDVWYMKRHIDYSRQQISLFWKNLSVSEARGKILHYQVTLQE

LTGGKAMTQNITGHTSWTTVIPRTGNWAVAVSAANSKGSSLPTRINIMN

LCEAGLLAPRQVSANSEGMDNILVTWQPPRKDPSAVQEYVVEWRELHPG

GDTQVPLNWLRSRPYNVSALISENIKSYICYEIRVYALSGDQGGCSSIL

GNSKHKAPLSGPHINAITEEKGSILISWNSIPVQEQMGCLLHYRIYWKE

RDSNSQPQLCEIPYRVSQNSHPINSLQPRVTYVLWMTALTAAGESSHGN

EREFCLQGKANWMAFVAPSICIAIIMVGIFSTHYFQQKVFVLLAALRPQ

WCSREIPDPANSTCAKKYPIAEEKTQLPLDRLLIDWPTPEDPEPLVISE

VLHQVTPVFRHPPCSNWPQREKGIQGHQASEKDMMHSASSPPPPRALQA

ESRQLVDLYKVLESRGSDPKPENPACPWTVLPAGDLPTHDGYLPSNIDD

LPSHEAPLADSLEELEPQHISLSVFPSSSLHPLTFSCGDKLTLDQLKMR

CDSLML.

The mouse IL12Rβ2 is represented by a polypeptide with the following amino acid sequence:

(SEQ ID NO: 22)

NIDVCKLGTVTVQPAPVIPLGSAANISCSLNPKQGCSHYPSSNELILLKF

VNDVLVENLHGKKVHDHTGHSSTFQVTNLSLGMTLFVCKLNCSNSQKKPP

VPVCGVEISVGVAPEPPQNISCVQEGENGTVACSWNSGKVTYLKTNYTLQ

LSGPNNLTCQKQCFSDNRQNCNRLDLGINLSPDLAESRFIVRVTAINDLG

NSSSLPHTFTFLDIVIPLPPWDIRINFLNASGSRGTLQWEDEGQVVLNQL

RYQPLNSTSWNMVNATNAKGKYDLRDLRPFTEYEFQISSKLHLSGGSWSN

WSESLRTRTPEEEPVGILDIWYMKQDIDYDRQQISLFWKSLNPSEARGKI

LHYQVTLQEVTKKTTLQNTTRHTSWTRVIPRTGAWTASVSAANSKGASAP

THINIVDLCGTGLLAPHQVSAKSENMDNILVTWQPPKKADSAVREYIVEW

RALQPGSITKFPPHWLRIPPDNMSALISENIKPYICYEIRVHALSESQGG

CSSIRGDSKHKAPVSGPHITAITEKKERLFISWTHIPFPEQRGCILHYRI

YWKERDSTAQPELCEIQYRRSQNSHPISSLQPRVTYVLWMTAVTAAGESP

QGNEREFCPQGKANWKAFVISSICIAIITVGTFSIRYFRQKAFTLLSTLK

PQWYSRTIPDPANSTWVKKYPILEEKIQLPTDNLLMAWPTPEEPEPLIIH

EVLYHMIPVVRQPYYFKRGQGFQGYSTSKQDAMYIANPQATGTLTAETRQ

LVNLYKVLESRDPDSKLANLTSPLTVTPVNYLPSHEGYLPSNIEDLSPHE

ADPTDSFDLEHQHISLSIFASSSLRPLIFGGERLTLDRLKMGYDSLMSNE

A.

In some aspects, the cytokine comprises a polypeptide comprising an amino acid sequence of SEQ ID NO:3-6, or a polypeptide comprising an amino acid sequence of a fragment of the polypeptides represented by SEQ ID NO:3-6, or a polypeptide with at least 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide of SEQ ID NO:3-6 or a fragment thereof.

In some aspects, the cytokine comprises an IL12 polypeptide and the masking agent comprises an amino acid sequence of SEQ ID NO:2, or 19-22, or a polypeptide comprising an amino acid sequence of a fragment of the polypeptides represented by SEQ ID NO:2, or 19-22, or a polypeptide with at least 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide of SEQ ID NO:2, or 19-22 or a fragment thereof.

In some aspects, the cytokine comprises IL-2. The human IL-2 sequence comprises MAPTSSSTKKTQLQLEHLLLDLQMILNGINNYKNPKLTRMLTFKFYMPKKATELKHLQC LEEELKPLEEVLNLAQSKNFHLRPRDLISNINVIVLELKGSETTFMCEYADETATIVEFLN RWITFAQSIISTLT (SEQ ID NO:23). The mouse IL-2 sequence comprises PTSSSTSSSTAEAQQQQQQQQQQQQHLEQLLMDLQELLSRMENYRNLKLPRMLTFKFY LPKQATELKDLQCLEDELGPLRHVLDLTQSKSFQLEDAENFISNIRVTVVKLKGSDNTFE CQFDDESATVVDFLRRWIAFCQSIISTSPQ (SEQ ID NO:24).

In some aspects, the masking agent for IL-2 comprises an IL-2R polypeptide. In some aspects, the IL-2R polypeptide comprises a polypeptide from the IL-2Rbeta, IL-2Ralpha, or IL-2Rgamma subunit. Human Interleukin-2 receptor subunit beta comprises the following amino acid sequence: AVNGTSQFTCFYNSRANISCVWSQDGALQDTSCQVHAWPDRRRWNQTCELLPVSQAS WACNLILGAPDSQKLTTVDIVTLRVLCREGVRWRVMAIQDFKPFENLRLMAPISLQVVH VETHRCNISWEISQASHYFERHLEFEARTLSPGHTWEEAPLLTLKQKQEWICLETLTPDT QYEFQVRVKPLQGEFTTWSPWSQPLAFRTKPAALGKDT (SEQ ID NO:27). Mouse Interleukin-2 receptor subunit beta has the following amino acid sequence: AVKNCSHLECFYNSRANVSCMWSHEEALNVTTCHVHAKSNLRHWNKTCELTLVRQAS WACNLILGSFPESQSLTSVDLLDINVVCWEEKGWRRVKTCDFHPFDNLRLVAPHSLQVL HIDTQRCNISWKVSQVSHYIEPYLEFEARRRLLGHISWEDASVLSLKQRQQWLFLEMLIPS TSYEVQVRVKAQRNNTGTWSPWSQPLTFRTRPADPMKE (SEQ ID NO:28). Human Interleukin-2 receptor subunit alpha has the following amino acid sequence: ELCDDDPPEIPHATFKAMAYKEGTMLNCECKRGFRRIKSGSLYMLCTGNSSHSSWDNQ CQCTSSATRNTTKQVTPQPEEQKERKTTEMQSPMQPVDQASLPGHCREPPPWENEATER IYHFVVGQMVYYQCVQGYRALHRGPAESVCKMTHGKTRWTQPQLICTGEMETSQFPG EEKPQASPEGRPESETSCLVTTTDFQIQTEMAATMETSIFTTEYQ (SEQ ID NO:29). Mouse Interleukin-2 receptor subunit alpha has the following amino acid sequence: ELCLYDPPEVPNATFKALSYKNGTILNCECKRGFRRLKEL VYMRCLGNSWSSNCQCTSN SHDKSRKQVTAQLEHQKEQQTTTDMQKPTQSMHQENLTGHCREPPPWKHEDSKRIYHF VEGQSVHYECIPGYKALQRGPAISICKMKCGKTGWTQPQLTCVDEREHHRFLASEESQG SRNSSPESETSCPITTTDFPQPTETTAMTETFVLTMEYK (SEQ ID NO:30). Human Interleukin-2 receptor subunit gamma has the following amino acid sequence: LNTTILTPNGNEDTTADFFLTTMPTDSLSVSTLPLPEVQCFVFNVEYMNCTWNSSSEPQP TNLTLHYWYKNSDNDKVQKCSHYLFSEEITSGCQLQKKEIHLYQTFVVQLQDPREPRRQ ATQMLKLQNL VIPWAPENLTLHKLSESQLELNWNNRFLNHCLEHLVQYRTDWDHSWT EQSVDYRHKFSLPSVDGQKRYTFRVRSRFNPLCGSAQHWSEWSHPIHWGSNTSKENPFL FALEA (SEQ ID NO:31). Mouse Interleukin-2 receptor subunit gamma has the following amino acid sequence:

```
                                        (SEQ ID NO: 32)
WSSKVLMSSANEDIKADLILTSTAPEHLSAPTLPLPEVQCFVFNIEYMNC

TWNSSSEPQATNLTLHYRYKVSDNNTFQECSHYLFSKEITSGCQIQKEDI

QLYQTFVVQLQDPQKPQRRAVQKLNLQNLVIPRAPENLTLSNLSESQLEL

RWKSRHIKERCLQYLVQYRSNRDRSWTELIVNHEPRFSLPSVDELKRYTF

RVRSRYNPICGSSQQWSKWSQPVHWGSHTVEENPSLFALEA.
```

In some aspects, the cytokine comprises a polypeptide comprising an amino acid sequence of SEQ ID NO:23 or 24, or a polypeptide comprising an amino acid sequence of a fragment of the polypeptides represented by SEQ ID NO:23 and 24, or a polypeptide with at least 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide of SEQ ID NO:23 or 24 or a fragment thereof.

In some aspects, the cytokine comprises an IL-2 polypeptide and the masking agent comprises an amino acid sequence of SEQ ID NO:27-32, or a polypeptide comprising an amino acid sequence of a fragment of the polypeptides represented by SEQ ID NO:27-32, or a polypeptide with at least 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide of SEQ ID NO:27-32 or a fragment thereof.

In some aspects, the cytokine comprises IFNγ. The mouse IFNγ comprises the following sequence: HGTVIESLESLNNYFNSSGIDVEEKSLFLDIWRNWQKDGDMKILQSQIISFYLRLFEVLKD NQAISNNISVIESHLITTFFSNSKAKKDAFMSIAKFEVNNPQVQRQAFNELIRVVHQLLPE SSLRKRKRSRC (SEQ ID NO:25). The human IFNγ comprises the following sequence: QDPYVKEAENLKKYFNAGHSDVADNGTLFLGILKNWKEESDRKIMQSQIVSFYFKLFK NFKDDQSIQKSVETIKEDMNVKFFNSNKKKRDDFEKLTNYSVTDLNVQRKAIHELIQVM AELSPAAKTGKRKRSQMLFQGRRASQ (SEQ ID NO:26). It is also contemplated that IFNg of SEQ ID NO:25 and 26 comprise a methionine as the first amino acid. The IFNγ may be a functional fragment, such as one that is truncated at the C-terminus. For example, the IFNγ polypeptide may be one comprising at least 30, 31, 32, 33, 34, 35, 36, 37 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, or 132 contiguous amino acids of SEQ ID NO:25 or 26. In some aspects, the IFNγ polypeptide may be one comprising at least amino acids 1 to 30, 31, 32, 33, 34, 35, 36, 37 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, or 132 of SEQ ID NO:25 or 26 (or any range derivable therein).

In some aspects, the masking agent for a IFNγ polypeptide comprises a polypeptide from the IFNγ receptor 1 or IFNγ receptor 2. The human IFNγ receptor 1 comprises the following sequence:

```
                                    (SEQ ID NO: 33)
EMGTADLGPSSVPTPTNVTIESYNMNPIVYWEYQIMPQVPVFTVEVKNY

GVKNSEWIDACINISHHYCNISDHVGDPSNSLWVRVKARVGQKESAYAK

SEEFAVCRDGKIGPPKLDIRKEEKQIMIDIFHPSVFVNGDEQEVDYDPE

TTCYIRVYNVYVRMNGSEIQYKILTQKEDDCDEIQCQLAIPVSSLNSQY

CVSAEGVLHVWGVTTEKSKEVCITIFNSSIKG.
```

The mouse IFNγ receptor 1 comprises the following sequence: ALTSTEDPEPPSVPVPTNVLIKSYN-LNPVVCWEYQNMSQTPIFTVQVKVYSGSWTDSCT NISDHCCNIYEQIMYPDVSAWARVKAKVGQKESD-YARSKEFLMCLKGKVGPPGLEIRR KKE-EQLSVLVFHPEVVVNGESQGTMFGDGST-CYTFDYTVYVEHNRSGEILHTKHTVEK EECNETLCELNISVSTLDSRYCISVD-GISSFWQVRTEKSKDVCIPPFHDDRKDS (SEQ ID NO:34). The human IFNγ receptor 2 comprises the following sequence: SQLPAPQHPKIRLYNAEQVLSWEPVAL-SNSTRPVVYQVQFKYTDSKWFTADIMSIGVNC TQI-TATECDFTAASPSAGFPMDFNVTLRLRAELGALHS-AWVTMPWFQHYRNVTVGPPE NIEVTPGEGS-LIIRFSSPFDIADTSTAFFCYYVHYWEKGGIQQVKGP-FRSNSISLDNLKPSR VYCLQVQAQLLWNKSNI-FRVGHLSNISCYETMADASTELQQ (SEQ ID NO:35). The mouse IFNγ 2 comprises the following sequence: receptor

```
                                    (SEQ ID NO: 36)
ASSPDSFSQLAAPLNPRLHLYNDEQILTWEPSPSSNDPRPVVYQVEYSF

IDGSWHRLLEPNCTDITETKCDLTGGGRLKLFPHPFTVFLRVRAKRGNL

TSKWVGLEPFQHYENVTVGPPKNISVTPGKGSLVIHFSPPFDVFHGATF

QYLVHYWEKSETQQEQVEGPFKSNSIVLGNLKPYRVYCLQTEAQLILKN

KKIRPHGLLSNVSCHETTANASARLQQVILIPLGIFALLLGLTGACFTL

FLKYQSRVKYWFQAPPNIPEQIEEYLKDPDQFILEVLDKDGSPKEDSWD

SVSIISSPEKERDDVLQTP.
```

In some aspects, the cytokine comprises a polypeptide comprising an amino acid sequence of SEQ ID NO:25 or 26, or a polypeptide comprising an amino acid sequence of a fragment of the polypeptides represented by SEQ ID NO:25 and 26, or a polypeptide with at least 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide of SEQ ID NO:25 or 26 or a fragment thereof.

In some aspects, the cytokine comprises an IFNγ polypeptide and the masking agent comprises an amino acid sequence of SEQ ID NO:33-36, or a polypeptide comprising an amino acid sequence of a fragment of the polypeptides represented by SEQ ID NO:33-36, or a polypeptide with at least 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide of SEQ ID NO:33-36 or a fragment thereof.

In aspects of the disclosure, the masking agent made be a polypeptide or a functional fragment of a polypeptide described herein. In some aspects, the masking agent comprises a receptor polypeptide or a fragment thereof that binds to the cytokine.

2. Antibodies

In some aspects, the therapeutic agent comprises an antibody, such as a therapeutic antibody. In some aspects, the therapeutic antibody is modified by the site-specific substitution of an amino acid in either the heavy or light chain variable region with a cysteine (Cys). The sulfhydryl (SH) group in the side chain of the substituted-in Cys serves as a chemical handle for attaching a masking agent that interferes with the antibody's ability to bind to its antigen. The masking agent may be a group that sterically inhibits antibody-antigen binding, but otherwise does not specifically interact with either the antibody or the antigen.

Alternatively, the masking agent can interact with the antibody, for example by electrostatic or van der Waals forces. A tumor-associated protease cleavage site may be between or link the masking agent and the antibody.

In some aspects, the masking agent can have pharmacological activity of its own after its release by cleavage of the tumor-associated protease cleavage site. The Cys substitution sites are selected such that replacing the original amino acid with a Cys does not detrimentally affect the ability of the antibody to specifically and strongly bind to its antigen. Further, removal of the masking agent can leave behind a residual chemical group still covalently attached to the Cys. In one aspect, there is provided a prodrugged antibody according to formula (I):

$$(M\text{-}L)_m\text{-}Ab \qquad \text{I}$$

wherein Ab is an antibody having at least one amino acid in its heavy or light chain variable region replaced by a Cys, wherein the replaced amino acid (a) is in a framework region; (b) has a side chain exposure of at least 30% and (c) is within 10 A, preferably 5 A, of a CDR amino acid; M is a masking agent that inhibits binding of Ab to its antigen; each L is, independently, a linker moiety bonded to M and Ab, L comprising a tumor-associated cleavage site and being bonded to Ab at aforesaid Cys; and m is 1, 2, 3, or 4.

In some aspects, the at least one replaced amino in antibody Ab is at Kabat position 1, 3, 5, 19, 23, 25, 43, 46, 68, 72, 74, 75, 76, 82a, 82b, 83, 84, 85, or 105 of the heavy chain variable region or at Kabat position 1, 3, 5, 7, 8, 18, 20, 45, 57, 60, 63, 65, 66, 67, 69, 77, or 100 of the light chain variable region. In some aspects, the at least one replaced amino acid in antibody Ab is at Kabat position 23 of the heavy chain or Kabat position 67 of the light chain. In some aspects, there is provided an antibody having a Cys at Kabat position 67 of the light chain. The antibody can be an anti-CTLA4 antibody or an anti-CD137 antibody. In some aspects, there is provided an antibody having a Cys at Kabat position 23 of the heavy chain. The antibody can be an anti-CTLA4 antibody or an anti-CD137 antibody.

The masked therapeutic antibody of the disclosure can be polyclonal, monoclonal, mouse, human, humanized, or chimeric. Suitable amino acids in the heavy and light chain variable regions for substitution with a Cys are framework amino acids whose side chains are solvent exposed—preferably at least 30% exposed—so that the substituted-in Cys is accessible for attachment of the masking agent. It is also important that the substituted-out amino acid is near a CDR amino acid, so that the masking agent can effectively interfere with antibody-antigen binding. A distance of no more than 10 A is preferred, more preferably no more than 5 A. Preferred positions for Cys substitution include positions 23 in the heavy chain variable region and 67 in the light chain variable region, numbering per Kabat. Both positions are in the framework region of the respective variable regions. A Cys can be substituted into these positions by site-specific substitution techniques well known in the art. A substitution at the first site can be referred to, using a shorthand notation, as VL X67C, where X denotes the substituted-out amino acid. In native antibodies, this site is highly conserved and is often Ser. A substitution at the second site can be similarly referred to as VH X23C.

A masked antibody of this disclosure can have either a substitution in the VH region or in the VL region, or both. If the antibody has only one of these substitutions, the theoretical maximum number of blocking moiety-linker compounds that can be attached is two, although a masked antibody preparation may assay statistically for a lower number, reflecting chemical inefficiency in the attachment process. If the antibody has both substitutions, the theoretical maximum number is four.

In some aspects, the antibody is a bispecific antibody, which has two different pairs of heavy and light chains. Thus, a masked antibody of this disclosure can be a bispecific antibody in which only one heavy/light chain pair has been masked or one in which both heavy/light chain pairs have been masked. The substitution of an amino acid in a VH or VL region with a Cys, for the purpose of introducing a sulfhydryl side chain amenable to conjugation by maleimide addition chemistry to make an antibody-drug conjugate, is also known. See, for example, Eigenbrot et al. 2007 and Bhakta et a/. 2016).

Masking agents that can be used to interfere with or block activity of a masked antibody with its antigen include: polyethylene glycol (PEG), an albumin binding polypeptide, adnectin, a peptide, and a soluble globular protein such as albumin or fibrinogen. In some aspects, the blocking agent comprises PEG having a molecular weight of at least about 2 kDa, with 2 kDa corresponding to PEG with about 45 —(CH2CH2O)— repeating units, and preferably PEG with a molecular weight of at least about 5 kDa, with 5 kDa corresponding to PEG with about 115 —(CH2CH2O)— repeating units.

An antibody having a Cys as described herein can be conjugated to a masking agent having a maleimide terminal group by Michael addition of the Cys sulfhydryl (SH), as known in the art. The procedures for such conjugation are well known in the art; see, for example, Shepard et al, WO 2017/112624 A 1 (2017), which is herein incorporated by reference. Further examples of specific masking agents for therapeutic antibodies are disclose in WO2019036433, which is herein incorporated by reference.

In further aspects, the therapeutic agent may be an antibody in which variable regions are masked by linkage of the N-termini of variable regions chains to coiled-coil forming peptides. The coiled-coil forming peptides associate with one another to form coiled coils (i.e., the respective peptides each form coils and these coils are coiled around each other). The coiled coils may sterically inhibit binding of the antibody binding site to its target. In some aspects, the antibody comprises a bivalent antibody. Non-covalent associations between the coiled coil forming peptides are sufficient to form a stable coiled coils inhibiting binding of the antibody variable region; it is not for example necessary for the coiled-coil forming peptides to be further linked by a disulfide bridge between terminal cysteines of the respective peptides. The presence of non-naturally occurring cysteines is potentially disadvantageous because they can lead to misfolding or misconjugation problems. Masking of antibodies by this format can reduce binding affinities (and cytotoxic activities in the case of ADC's) by over a hundred fold. Antibodies can be masked in this format without significant impairment of expression, purification, conjugation, pharmacokinetics, or binding or other activity on unmasking.

In some aspects, the masking agent comprises a coiled coil. Coiled coil forming peptides are peptide pairs that can associate with one another to form coiled coils. "Coiled coils" is a term of art referring to bundles of alpha-helices wound into superhelical structures. Leucine zipper forming peptides are one example of peptides associating to form coiled coils. The coiled coils formed in the current disclosure typically are formed from two coiled coil forming peptides. Coiled coils can form with alpha helices on the peptides in parallel or opposite orientations. Coiled coils are further characterized by packing of amino acid side chains in the core of the bundle, called knobs-into-holes, in which a residue from one helix (knob) packs into a space surrounded by four side chains of the facing helix (hole). The residues engaged in knobs-into-holes interactions are usually hydrophobic, whereas the outer residues are hydrophilic, the sequence of coiled coils therefore shows a 'heptad' repeat in the chemical nature of side chains. Examples of consensus formulae for heptad repeats in coiled coils forming peptides are provided by WO2011034605, which is herein incorporated by reference.

In some aspects, the coiled coil comprises Formula II:

$$(XI, X2, X3, X4, X5, X6, X7)n \qquad \text{II}$$

wherein XI is a hydrophobic amino acid or asparagine; X2, X3 and X6 are any amino acid; X4 is a hydrophobic amino acid; and X5 and X7 are each a charged amino acid residue.

Examples of coiled coil comprise:

(SEQ ID NO: 58)
GASTSVDELQAEVDQLQDENYALKTKVAQLRKKVEKLSE;

(SEQ ID NO: 59)
GASTTVAQLRERVKTLRAQNYELESEVQRLREQVAQLA;

(SEQ ID NO: 60)
EACGASTSVDELQAEVDQLQDENYALKTKVAQLRKKVEKLSE;

-continued (SEQ ID NO: 61)
EACGASTTVAQLRERVKTLRAQNYELESEVQRLREQVAQLA;

(SEQ ID NO: 62)
LEIEAAFLERENTALETRVAELRQRVQRARNRVSQYRTRY;

(SEQ ID NO: 63)
LEIRAAFLRQRNTALRTEVAELEQEVQRLENEVSQYETRY;

(SEQ ID NO: 64)
EACGALEIEAAFLERENTALETRVAELRQRVQRARNRVSQYRTRY;

(SEQ ID NO: 65)
EACGALEIRAAFLRQRNTALRTEVAELEQEVQRLENEVSQYETRY;

(SEQ ID NO: 66)
LEIRAAFLRRRNTALRTRVAELRQRVQRLRNIVSQYETRY;

(SEQ ID NO: 67)
LEIEAAFLEQENTALETEVAELEQEVQRLENIVSQYETRY;

(SEQ ID NO: 68)
EACGALEIRAAFLRRRNTALRTRVAELRQRVQRLRNIVSQYETRY;

(SEQ ID NO: 69)
EACGALEIEAAFLEQENTALETEVAELEQEVQRLENIVSQYETRY;

(SEQ ID NO: 70)
QGASTSVDELQAEVDQLEDENYALKTKVAQLRKKVEKL;

(SEQ ID NO: 71)
QGASTTVAQLEEKVKTLRAENYELKSEVQRLEEQVAQL;

(SEQ ID NO: 72)
EACGASTSVDELQAEVDQLEDENYALKTKVAQLRKKVEKL;

(SEQ ID NO: 73)
EACGASTTVAQLEEKVKTLRAENYELKSEVQRLEEQVAQL;

(SEQ ID NO: 74)
AGLTDTLQAETDQLEDKKSALQTEIANLLKEKEKLEFILAAH;

(SEQ ID NO: 75)
AGRIARLEEKVKTLKAQNSELASTANMLREQVAQLKQKVMNY;

(SEQ ID NO: 76)
EACGAGLTDTLQAETDQLEDKKSALQTEIANLLKEKEKLEFILAAH;

(SEQ ID NO: 77)
EACGAGRIARLEEKVKTLKAQNSELASTANMLREQVAQLKQKVMNY;

(SEQ IDNO: 78)
GKIAALKQKIAALKYKNAALKKKIAALKQ;

(SEQ ID NO: 79)
GEIAALEQEIAALEKENAALEWEIAALEQ;

(SEQ ID NO: 80)
EACGAGKIAALKOKIAALKYKNAALKKKIAALKQ;
and (SEQ ID NO: 81)
EACGAGEIAALEQEIAALEKENAALEWEIAALEQ.

Coiled coils forming peptides are linked to the N-termini of antibody variable regions via a linker including a tumor-associated protease cleavage site. A typical antibody includes a heavy and light chain variable region, in which case a coiled-coil forming peptide is linked to the N-termini of each. A bivalent antibody has two binding sites, which may or may not be the same. In a normal monospecific antibody, the binding sites are the same and the antibody has two identical light and heavy chain pairs. In this case, each heavy chain is linked to the same coiled-coil forming peptide and each light chain to the same coiled-coil forming peptide (which may or may not be the same as the peptide linked to the heavy chain).

In a bispecific antibody, the binding sites are different and formed from two different heavy and light chain pairs. The binding sites can have specificity for different targets or different epitopes on the same target. If the binding sites have specificity for different targets, the targets can be on the same cell (e.g., two different surface antigens on a cancer cell) or two different cells (e.g., one surface antigen on a cancer cell and one on an immune cell such as a T-cell). For example, one binding site of a bispecific antibody can be directed against CD3 or 4-1BB.

In a bispecific antibody, the heavy and light chain variable region of one binding site can be respectively linked to coiled-coil forming peptides. The heavy and light chain variable regions of the other binding site may or may not be also linked to coiled coil peptides. If the heavy light pairs of both binding sites are both linked to coiled coil peptides, then typically both heavy chain variable regions are linked to the same type of coiled-coil forming peptide as are both light chain variable regions. Masking of both binding sites can be useful, for example, if both binding sites have specificity for surface antigens on the same tumor. Masking of one but not both binding sites can be useful for example, when one binding site is specific for a tumor surface antigen and the other has specificity for a surface antigen on an immune cell. Either the binding site with specificity for the tumor surface antigen or for the immune cell antigen can be masked. Some bispecific antibodies with specificities to both a tumor surface antigen and an immune cell have masking of both sites.

Coiled coils can be formed from the same peptide forming a homodimer or two different peptides forming a heterodimer. For formation of a homodimer, light and heavy antibody chains are linked to the same coiled coil forming peptide. For formation of a heterodimer, light and heavy antibody chains are linked to different coiled coils peptides. For some pairs of coiled coil forming peptides, it is preferred that one of the pair be linked to the heavy chain and the other to the light chain of an antibody although the reverse orientation is also possible.

Each antibody chain can be linked to a single coiled coil forming peptide or multiple such peptides in tandem (e.g., two, three, four or five copies of a peptide). If the latter, the peptides in tandem linkage are usually the same. Also if tandem linkage is employed, light and heavy chains are usually linked to the same number of peptides.

Linkage of antibody chains to coiled coil forming peptides can reduce the binding affinity of an antibody by, for example, at least 10, 50, 100, 200, 500, 1000, 1500, 2000, 4000, 5000 or 10,000-fold relative to the same antibody without such linkage or after cleavage of such linkage. In some such antibodies, binding affinity is reduced 50-10,000, 50-5000, 50-4000, 50-1000, 100-10,000, 100-5000, 100-4000, 200-10,000, 200-5000, 50-1500, 100-1500, 200-1500, 200-1000, 500-1500, 50-1000, 100-1000, 200-1000, 500-1000, 50-500, 100-500 fold.

Antibodies include non-human, humanized, human, chimeric, and veneered antibodies, nanobodies, dAbs, scFV's, Fabs, and the like. Some such antibodies include immuno specific for a cancer cell antigen, preferably one on the cell surface internalizable within a cell on antibody binding. Targets to which antibodies can be directed include receptors on cancer cells and their ligands or counter-receptors (e.g., CD3, CD19, CD20, CD22, CD30, CD33, CD34, CD40, CD44, CD52, CD70, CD79a, CD123, Her-2, EphA2, lymphocyte associated antigen 1, VEGF or VEGFR, CTLA-4, LIV-1, nectin-4, CD74, and SLTRK-6).

In some aspects, the antibody comprises brentuximab or brentuximab vedotin, anti-CD30, alemtuzumab, anti-CD52, rituximab, anti-CD20, trastuzumab Her/neu, nimotuzumab, cetuximab, anti-EGFR, bevacizumab, anti-VEGF, palivizumab, anti-RSV, abciximab, GpIIb/IIIa, infliximab, adalimumab, certolizumab, golimumab TNF-alpha, baciliximab, daclizumab, anti-IL-2, omalizumab, anti-IgE, gemtuzumab or vadastuximab, anti-CD33, natalizumab, anti-VLA-4, vedolizumab alpha4beta7, belimumab, anti-BAFF, otelixizumab, teplizumab, anti-CD3, ofatumumab, ocrelizumab, epratuzumab, anti-CD22, alemtuzumumab, eculizumab, canakimumab, mepolizumab, reslizumab, tocilizumab, ustekinumab, and briakinumab.

Further aspects are described in WO2018107125, which is herein incorporated by reference.

B. Collagen Binding Domain

Collagen is an extracellular matrix (ECM)-protein that regulates a variety of cellular biological functions, such as proliferation, differentiation, and adhesion in both normal and tumor tissue (Ricard-Blum, Cold Spring Harb Perspect Biol 3:a004978, 2011). Collagen is the most abundant protein in the mammalian body and exists in almost all tissues in one or more of 28 isoforms (Ricard-Blum, Cold Spring Harb Perspect Biol 3:a004978, 2011). The blood vessel sub-endothelial space is rich in collagen. Because of its insolubility under physiological conditions, collagen barely exists within the blood (Dubois et al., Blood 107: 3902-06, 2006; Bergmeier and Hynes, Cold Spring Harb Perspect Biol 4:a005132, 2012). Tumor vasculature is reported to be permeable due to an abnormal structure (Nagy et al., British journal of cancer 100:865, 2009). Thus, with its leaky vasculature, collagen is exposed in the tumor (Liang et al., Journal of controlled release 209:101-109, 2015; Liang et al., Sci Rep 6:18205, 2016; Yasunaga et al., Bioconjugate chemistry 22:1776-83, 2011; Xu et al. The Journal of cell biology 154:1069-80, 2001; Swartz and Lund, Nat Rev Cancer 12:210-19). Also, tumor tissue contains increased amounts of collagen compared to normal tissues (Zhou et al. J Cancer 8:1466-76, 2017; Provenzano et al. BMC Med 6:11, 2008).

von Willebrand factor (vWF) is a blood coagulation factor and binds to both type I and type III collagen, and the adhesion receptor GPIb on blood platelets (Lenting et al., Journal of thrombosis and haemostasis:JTH 10:2428-37, 2012; Shahidi Advances in experimental medicine and biology 906:285-306, 2017). When injured, collagen beneath endothelial cells is exposed to blood plasma, and vWF-collagen binding initiates the thrombosis cascade (Shahidi Advances in experimental medicine and biology 906:285-306, 2017; Wu et al. Blood 99:3623-28, 2002). The vWF A domain has the highest affinity against collagen among reported non-bacterial origin proteins/peptides (Addi et al., Tissue Engineering Part B: Reviews, 2016). Particularly within the A domain, the A3 domain of vWF has been reported as a collagen binding domain (CBD) (Ribba et al. Thrombosis and haemostasis 86:848-54, 2001). As described above, the inventors contemplated that a fusion protein with the vWF A3 CBD may achieve targeted cytokine immunotherapy even when injected systemically due to exposure of collagen via the leaky tumor vasculature.

In some aspects, the collagen binding domain comprises a polypeptide from decorin. Exemplary decorin polypeptides include human decorin, or a fragment thereof, which is represented by the following sequence: CGPFQQRGLFDFMLEDEASGIGPEVPDDRDFEPSLGPVCPFRCQCHLRVVQCSDLGLDK VPKDLPPDTTLLDLQNNKITEIKDGDFKNLKNLHALILVNNKISKVSPGAFTPLVKLERL YLSKNQLKELPEKMPKTLQELRAHENEITKVRKVTFNGLNQMIVIELGTNPLKSSGIENG AFQGMKKLSYIRIADTNITSIPQGLPPSLTELHLDGNKISRVDAASLKGLNNLAKLGLSFN SISAVDNGSLANTPHLRELHLDNNKLTRVPGGLAEHKYIQVVYLHNNNISVVGSSDFCPP GHNTKKASYSGVSLFSNPVQYWEIQPSTFRCVYVRSAIQLGNYK (SEQ ID NO:40), a peptide derived from human decorin: LRELHLDNNC (SEQ ID NO:41), and a peptide derived from bovine decorin: LRELHLNNNC (SEQ ID NO:44).

In some aspects, the CBD comprises a polypeptide fragment from vWF. In some aspects, the CBD comprises vWF A1 derived from human sequence, residues 1237-1458 (474-695 of mature VWF) or a fragment thereof, which is represented by the amino acid sequence:

```
                                         (SEQ ID NO: 39)
CQEPGGLVVPPTDAPVSPTTLYVEDISEPPLHDFYCSRLLDLVFLLDGS

SRLSEAEFEVLKAFVVDMMERLRISQKWVRVAVVEYHDGSHAYIGLKDR

KRPSELRRIASQVKYAGSQVASTSEVLKYTLFQIFSKIDRPEASRITLL

LMASQEPQRMSRNFVRYVQGLKKKKVIVIPVGIGPHANLKQIRLIEKQA

PENKAFVLSSVDELEQQRDEIVSYLC.
```

In some aspects, the CBP comprises all or a fragment of vWF A3, which is represented by the following amino acid sequences:

```
                                         (SEQ ID NO: 37)
CSQPLDVILLLDGSSSFPASYFDEMKSFAKAFISKANIGPRLTQVSVLQ

YGSITTIDVPWNVVPEKAHLLSLVDVMQREGGPSQIGDALGFAVRYLTS

EMHGARPGASKAVVILVTDVSVDSVDAAADAARSNRVTVFPIGIGDRYD

AAQLRILAGPAGDSNVVKLQRIEDLPTMVTLGNSFLHKLCSGFVRICTG
and

                                         (SEQ ID NO: 45)
CSQPLDVILLLDGSSSFPASYFDEMKSFAKAFISKANIGPRLTQVSVLQ

YGSITTIDVPWNVVPEKAHLLSLVDVMQREGGPSQIGDALGFAVRYLTS

EMHGARPGASKAVVILVTDVSVDSVDAAADAARSNRVTVFPIGIGDRYD

AAQLRILAGPAGDSNVVKLQRIEDLPTMVTLGNSFLHKLCSGFVRI.
```

In some aspects, the CBP comprises vWF A3 domain polypeptide with a 6H tag (SEQ ID NO:87) with the following amino acid sequence:

```
                                          (SEQ ID NO: 1)
CSQPLDVILLLDGSSSFPASYFDEMKSFAKAFISKANIGPRLTQVSVLQ

YGSITTIDVPWNVVPEKAHLLSLVDVMQREGGPSQIGDALGFAVRYLTS

EMHGARPGASKAVVILVTDVSVDSVDAAADAARSNRVTVFPIGIGDRYD

AAQLRILAGPAGDSNVVKLQRIEDLPTMVTLGNSFLHKLCSGFVRICTG

HHHHHH.
```

In some aspects, the CBP comprises a peptide or polypeptide from von Willebrand factor (vWF), such as a collagen binding peptide from vWF. The sequence of human vWF comprises the following:

(SEQ ID NO: 38)

MIPARFAGVLLALALILPGTLCAEGTRGRSSTARCSLFGSDFVNTFDGSMYSFAGYCSYL

LAGGCQKRSFSIIGDFQNGKRVSLSVYLGEFFDIHLFVNGTVTQGDQRVSMPYASKGLY

LETEAGYYKLSGEAYGFVARIDGSGNFQVLLSDRYFNKTCGLCGNFNIFAEDDFMTQEG

TLTSDPYDFANSWALSSGEQWCERASPPSSSCNISSGEMQKGLWEQCQLLKSTSVFARC

HPLVDPEPFVALCEKTLCECAGGLECACPALLEYARTCAQEGMVLYGWTDHSACSPVC

PAGMEYRQCVSPCARTCQSLHINEMCQERCVDGCSCPEGQLLDEGLCVESTECPCVHSG

KRYPPGTSLSRDCNTCICRNSQWICSNEECPGECLVTGQSHFKSFDNRYFTFSGICQYLLA

RDCQDHSFSIVIETVQCADDRDAVCTRSVTVRLPGLHNSLVKLKHGAGVAMDGQDVQL

PLLKGDLRIQHTVTASVRLSYGEDLQMDWDGRGRLLVKLSPVYAGKTCGLCGNYNGN

QGDDFLTPSGLAEPRVEDFGNAWKLHGDCQDLQKQHSDPCALNPRMTRFSEEACAVLT

SPTFEACHRAVSPLPYLRNCRYDVCSCSDGRECLCGALASYAAACAGRGVRVAWREPG

RCELNCPKGQVYLQCGTPCNLTCRSLSYPDEECNEACLEGCFCPPGLYMDERGDCVPK

AQCPCYYDGEIFQPEDIFSDHHTMCYCEDGFMHCTMSGVPGSLLPDAVLSSPLSHRSKR

SLSCRPPMVKLVCPADNLRAEGLECTKTCQNYDLECMSMGCVSGCLCPPGMVRHENR

CVALERCPCFHQGKEYAPGETVKIGCNTCVCRDRKWNCTDHVCDATCSTIGMAHYLTF

DGLKYLFPGECQYVLVQDYCGSNPGTFRILVGNKGCSHPSVKCKKRVTILVEGGEIELF

DGEVNVKRPMKDETHFEVVESGRYIILLLGKALSVVWDRHLSISVVLKQTYQEKVCGLC

GNFDGIQNNDLTSSNLQVEEDPVDFGNSWKVSSQCADTRKVPLDSSPATCHNNIMKQT

MVDSSCRILTSDVFQDCNKLVDPEPYLDVCIYDTCSCESIGDCACFCDTIAAYAHVCAQ

HGKVVTWRTATLCPQSCEERNLRENGYECEWRYNSCAPACQVTCQHPEPLACPVQCVE

GCHAHCPPGKILDELLQTCVDPEDCPVCEVAGRRFASGKKVTLNPSDPEHCQICHCDVV

NLTCEACQEPGGLVVPPTDAPVSPTTLYVEDISEPPLHDFYCSRLLDLVFLLDGSSRLSEA

EFEVLKAFVVDMMERLRISQKWVRVAVVEYHDGSHAYIGLKDRKRPSELRRIASQVKY

AGSQVASTSEVLKYTLFQIFSKIDRPEASRITLLLMASQEPQRMSRNFVRYVQGLKKKKV

IVIPVGIGPHANLKQIRLIEKQAPENKAFVLSSVDELEQQRDEIVSYLCDLAPEAPPPTLPP

DMAQVTVGPGLLGVSTLGPKRNSMVLDVAFVLEGSDKIGEADFNRSKEFMEEVIQRMD

VGQDSIHVTVLQYSYMVTVEYPFSEAQSKGDILQRVREIRYQGGNRTNTGLALRYLSDH

SFLVSQGDREQAPNLVYMVTGNPASDEIKRLPGDIQVVPIGVGPNANVQELERIGWPNA

PILIQDFETLPREAPDLVLQRCCSGEGLQIPTLSPAPDCSQPLDVILLLDGSSSFPASYFDE

MKSFAKAFISKANIGPRLTQVSVLQYGSITTIDVPWNVVPEKAHLLSLVDVMQREGGPS

QIGDALGFAVRYLTSEMHGARPGASKAVVILVTDVSVDSVDAAADAARSNRVTVFPIGI

GDRYDAAQLRILAGPAGDSNVVKLQRIEDLPTMVTLGNSFLHKLCSGFVRICMDEDGNE

KRPGDVWTLPDQCHTVTCQPDGQTLLKSHRVNCDRGLRPSCPNSQSPVKVEETCGCRW

TCPCVCTGSSTRHIVTFDGQNFKLTGSCSYVLFQNKEQDLEVILHNGACSPGARQGCMK

SIEVKHSALSVELHSDMEVTVNGRLVSVPYVGGNMEVNVYGAIMHEVRFNHLGHIFTF

TPQNNEFQLQLSPKTFASKTYGLCGICDENGANDFMLRDGTVTTDWKTLVQEWTVQRP

GQTCQPILEEQCLVPDSSHCQVLLLPLFAECHKVLAPATFYAICQQDSCHQEQVCEVIAS

YAHLCRTNGVCVDWRTPDFCAMSCPPSLVYNHCEHGCPRHCDGNVSSCGDHPSEGCFC

PPDKVMLEGSCVPEEACTQCIGEDGVQHQFLEAWVPDHQPCQICTCLSGRKVNCTTQPC

PTAKAPTCGLCEVARLRQNADQCCPEYECVCDPVSCDLPPVPHCERGLQPTLTNPGECR

-continued

PNFTCACRKEECKRVSPPSCPPHRLPTLRKTQCCDEYECACNCVNSTVSCPLGYLASTAT

NDCGCTTTTCLPDKVCVHRSTIYPVGQFWEEGCDVCTCTDMEDAVMGLRVAQCSQKP

CEDSCRSGFTYVLHEGECCGRCLPSACEVVTGSPRGDSQSSWKSVGSQWASPENPCLIN

ECVRVKEEVFIQQRNVSCPQLEVPVCPSGFQLSCKTSACCPSCRCERMEACMLNGTVIGP

GKTVMIDVCTTCRCMVQVGVISGFKLECRKTTCNPCPLGYKEENNTGECCGRCLPTACT

IQLRGGQIMTLKRDETLQDGCDTHFCKVNERGEYFWEKRVTGCPPFDEHKCLAEGGKI

MKIPGTCCDTCEEPECNDITARLQYVKVGSCKSEVEVDIHYCQGKCASKAMYSIDINDV

QDQCSCCSPTRTEPMQVALHCTNGSVVYHEVLNAMECKCSPRKCSK.

In some aspects, the peptide is from the vWF A3 domain and has the following amino acid sequence (or a fragment thereof):

(SEQ ID NO: 46)

CSGEGLQIPTLSPAPDCSQPLDVILLLDGSSSFPASYFDEMKSFAKAFI

SKANIGPRLTQVSVLQYGSITTIDVPWNVVPEKAHLLSLVDVMQREGGP

SQIGDALGFAVRYLTSEMHGARPGASKAVVILVTDVSVDSVDAAADAAR

SNRVTVFPIGIGDRYDAAQLRILAGPAGDSNVVKLQRIEDLPTMVTLGN

SFLHKLCSG.

The CBP peptide or polypeptide may be a peptide with 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a CBD peptide or fragment of the peptides described above, such as SEQ ID NOS:1, 37-41, and 44-46.

C. Linker

In some aspects, the polypeptides comprise or further comprise a linker. The linker may be between any two domains of the polypeptide. In some aspects, the polypeptide comprises a linker between the CBP and the cytokine. In some aspects, the polypeptide comprises a linker in between the CBP and the serum polypeptide. In some aspects, the polypeptide comprises a linker in between the masking agent and the cytokine. In some aspects, the polypeptide comprises a linker in between the albumin and the cytokine. In some aspects, the polypeptide comprises a linker in between the therapeutic agent and the masking agent. In some aspects, the polypeptide comprises a linker in between the therapeutic agent and the CBP. In some aspects, the linker comprises one or more tumor-associated protease cleavage sites. A tumor-associated protease cleavage site refers to a cleavage site that is recognized by a protease that is highly upregulated or enriched in the tumor microenvironment. While the tumor-associated protease cleavage site may not be tumor-specific, meaning that the protease is only expressed in the tumor, it is tumor-enriched, meaning that the protease is expressed at a level in the tumor microenvironment that is higher than normal tissues or most normal tissues. In some aspects, the tumor-associated protease cleavage site comprises an amino acid sequence that is recognized and cleaved by a matrix metalloproteinase. For example, the tumor-associated protease cleavage site may be one that is cleaved by MMP1, MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27, MMP28, or combinations thereof. In some aspects, the tumor-associated protease cleavage site comprises the MMP-response sequence of SEQ ID NO: 13: GLLSGRSDNH. In some aspects, the tumor-associated protease cleavage site may be one that is cleaved by thrombin. In some aspects, the thrombin-responsive sequence comprises SEQ ID NO:14: LVPRGS.

In some aspects, two polypeptides such as a two of a CBP, serum protein, therapeutic agent, masking agent, and cytokine may be linked through a bifunctional linker. Linkers, such as amino acid or peptidimimetic sequences may be inserted between the peptide and/or antibody sequence. In an aspect, a fynomer domain is joined to a Heavy (H) chain or Light (L) chain immediately after the last amino acid at the amino(NH2)-terminus or the carboxy(C)-terminus of the Heavy (H) chain or the Light (L) chain. Linkers may have one or more properties that include a flexible conformation, an inability to form an ordered secondary structure or a hydrophobic or charged character which could promote or interact with either domain. Examples of amino acids typically found in flexible protein regions may include Gly, Asn and Ser. For example, a suitable peptide linker may be GGGSGGGS (SEQ ID NO:47) or (GGGS—SEQ ID NO:191)n, wherein n=1, 2, 3, 4, 5, 6, 7, 8, 9, or 10 (or any range derivable therein). Other near neutral amino acids, such as Thr and Ala, may also be used in the linker sequence. The length of the linker sequence may vary without significantly affecting the function or activity of the fusion protein (see, e.g., U.S. Pat. No. 6,087,329). Examples of linkers may also include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST). Examples of linkers further comprise a linear carbon chain, such as CN (where N=1-100 carbon atoms, e.g. N=1, 2, 3, 4, 5, 6, 7, 8, 9, 10, 11, 12, 13, 14, or 15, or more). In some aspects, the linker can be a dipeptide linker, such as a valine-citrulline (val-cit), a phenylalanine-lysine (phe-lys) linker, or maleimidocapronic-valine-citruline-p-aminobenzyloxycarbonyl (vc) linker. In some aspects, the linker is sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its sulfo-NHS ester is reactive toward primary amines (as found in lysine and the protein or peptide N-terminus). Further, the linker may be maleimidocaproyl (mc).

In some aspects, the linker comprises one or more polypeptides that are cleavable by—i.e., are a substrate for—an enzyme (a protease) that is uniquely expressed or overexpressed in a cancer or tumor microenvironment, compared to healthy tissue or organ. Preferably, the enzyme is found in the extracellular environment of a tumor. Examples of such proteases include: aspartate proteases (e.g., renin), fibroblast activation protein (FAP), aspartic cathepsins (e.g., cathepsin D, caspase 1, caspase 2, etc.), cysteine cathepsins (e.g., cathepsin B), cysteine proteases (e.g., legumain), disintegrin/metalloproteinases (ADAMS, e.g., ADAM8, ADAM9), disintegrin/metalloproteinases with thrombospondin motifs (ADAMTS, e.g., ADAMTS1), integral membrane serine proteases (e.g., matriptase 2, MT-SP1/matriptase, TMPRSS2, TMPRSS3, TMPRSS4), kallikrein-related peptidases (KLKs, e.g. KLK4, KLK5), matrix metalloproteases (e.g., MMP-1, MMP-2, MMP-9), and serine proteases (e.g., cathepsin A, coagulation factor proteases such as elastase, plasmin, thrombin, PSA, uPA, Factor Vila, Factor Xa, and HCV NS3/4). Preferably, the protease is fibroblast activation protein (FAP), urokinase-type plasminogen activator (uPA, urokinase), MT-SP1/matriptase, legumain, or a matrix metalloprotease (especially MMP-1, MMP-2, and MMP-9). Those skilled in the art will appreciate that the choice of the enzyme and the corresponding cleavable peptide will depend on the disease to be treated and the protease(s) expressed by the affected tissue or organ.

Further examples of tumor-associated protease sites include LSGRSDNH (SEQ ID NO:49), cleaved by urokinase, matriptase, or legumain; VPLSLYS (SEQ ID NO:50), cleaved by MMP2 or MMP9; PLGLAG (SEQ ID NO:51), cleaved by MMP2; VLVPMAMMAS (SEQ ID NO:52), cleaved by MMP1; XXQARAX (SEQ ID NO:53), wherein X is alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, cleaved by Matriptase; and XXQARVX (SEQ ID NO:249), wherein X is alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, cleaved by Matriptase; AGPR (SEQ ID NO:54), cleaved by matriptase; AANL (SEQ ID NO:55) and PTNL (SEQ ID NO:56), cleaved by Legumain; and TSGRSANP (SEQ ID NO:57).

A linker sequence may be included in the polypeptides of the disclosures. For example, a linker having at least, at most, or exactly 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids (or any derivable range therein) may separate or be between any two of a CBP, serum protein, therapeutic agent, masking agent, and cytokine.

The linker may comprise a sequence of SEQ ID NO:13, 14, or 47-57 or a peptide with at least 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to SEQ ID NO:13, 14, or 47-57.

Further examples of tumor-associated protease sites include those in the table below:

| Substrate Sequence | SEQ ID NO | Protease | Substrate Sequence | SEQ ID NO | Protease |
|---|---|---|---|---|---|
| YLGRSYKV | 109 | C1s | RPLALWRS | 152 | MMP7 |
| FK | | Cathepsin B | NKSRLGLG | 153 | MMP7/Cathpsin B |
| TSQVNGLN | 110 | Elastase 2 | GPQGIAGQR | 154 | MMP9 |
| APPPVVLL | 111 | Matrilysin (MMP7) | PVGLIG | 155 | MMP2/9 |
| GGGGF | 112 | Cathepsin B | KPVSLSYR | 156 | MMP9 |
| TPEHVVPY | 113 | Endothelin-converting enzyme 1 | QPVGINTS | 157 | MMP3 (stromelysin-1) |
| PRSFFRLGK | 114 | Cathepsin D | PLGMTS | 158 | MMP9 |
| PQGRIVGG | 115 | Hepsin | PRALM | 159 | MMP9 |
| EVLLSWAV | 116 | Cathepsin G | GPLPLR | 160 | MT1-MMP |
| AANL | 55 | Legumain | KQLRVVNG | 161 | MT-SP1/ST14/uPA/Hepsin |
| PVSLSYRC | 117 | Cathepsin G | PLGLYA | 162 | Pan-MMP |
| LRELHLDN | 118 | Matrilysin (MMP7) | AFK | | Plasmin |
| AAPV | 119 | Elastase 2 | LVPRGS | 14 | Thrombin |
| IPENFFGV | 120 | Matrilysin (MMP7) | GGR | | Plasmin/TMPRSS2 |
| PRFKIIGG | 121 | Hepsin | HSSKLQL | 163 | PSA |
| MLEDEASG | 122 | Matrilysin (MMP7) | SSKYQ | 164 | PSA |
| KQSRKFVP | 123 | Matriptase(ST14) | GPLGVRGK | 165 | MMP2 |
| RQARVVGG | 124 | Matriptase2/Hepsin | GGGSGGGS | 47 | Control |
| GKAFRRL | 125 | Hk2 | PRGMAS | 166 | MMP9 |
| GPLGLWAQ | 126 | MMP (esp 2/9) | AAALGNVAP | 167 | MMP9 |

-continued

| Substrate Sequence | SEQ ID NO | Protease | Substrate Sequence | SEQ ID NO | Protease |
|---|---|---|---|---|---|
| SLGRKIQI | 127 | MASP2 | GGSGRSANA | 168 | uPA |
| PVSLR | 128 | MMP1 | PLGVRG | 169 | MMP2/9 |
| AAATSIAM | 129 | MMP11 (stromelysin-3) | SGRSANAK | 170 | uPA |
| AAGAMFLE | 130 | MMP11 (stromelysin-3) | GPLGLWAGG | 171 | MMP2 |
| EAAAATSI | 131 | MMP11 (stromelysin-3 | SGRSA | 172 | uPA |
| PRHLR | 132 | MMP14 | PLGLYL | 173 | MMP2/9 |
| PRGLRK | 133 | MMP14 | SRRRVNSL | 174 | uPA |
| VPLSLYSG | 134 | MMP (esp 2/9) | GSTFF | 175 | Cathepsin D |
| PRGLRP | 135 | MMP15/16/24/25 | CPGRVVGG | 176 | uPa/tPA |
| PRHLRN | 136 | MMP15/16/24/25 | GTQFF | 177 | Cathepsin D |
| PRWLRS | 137 | MMP15/16/24/25 | PQGLAG | 178 | MMP9 |
| HPVGLLAR | 138 | MMP2 | QVVAG | 179 | Cathepsin B |
| KGPLGVRG | 139 | MMP2 | TYSRSRYL | 180 | uPA |
| CGLDD | 140 | MMP2/9 | NSGRAVTY | 181 | uPA |
| STAVIVSA | 141 | MMP3 (stromelysin-1) | GPQGARGQ | 182 | MMP9 |
| PLGLAG | 51 | MMP2 | PSSRRRVN | 183 | uPA |
| GPLGIAGQ | 142 | MMP2/9 | PLGLYAL | 184 | MMP2/9 |
| PLGLWA | 143 | MMP2 | PMKRLTLG | 185 | Cathepsin B |
| GPLGMLSQ | 144 | MMP2/9 | DDDKIVGG | 186 | Cathepsin B |
| PLGVRGK | 145 | MMP2 | HLVEALYL | 187 | Cathepsin B |
| GPQGIWGQ | 146 | MMP2/9, MT1-MMP | EVDLLIGS | 188 | Cathepsin B |
| AIPVSLR | 147 | MMP2 | PRFKIIGG | 121 | Cathepsin B |
| GPLGLARK | 148 | MMP7 | AVRWLLTA | 189 | MMP9 |
| PQGIAMG | 149 | MMP2 | LSGRSDNH | 49 | uPA/matriptase/legumain |
| VASSSTAV | 150 | MMP3 (stromelysin-1) | GGGRR | 190 | uPA |
| PLGL | 151 | MMP2/9 | | | |

D. Serum Proteins

In some aspects, the polypeptides of the disclosure are further linked to a serum protein. Serum proteins include, for example, albumin, globulin, and fibrinogen. Globulins include alpha 1 globulins, alpha 2 globulins, beta globulins, and gamma globulins. The albumin may be mouse, human, bovine, or any other homologous albumin protein. In some aspects, the albumin comprises human serum albumin, which is encoded by the ALB gene, and exemplified by the following amino acid sequence:

(SEQ ID NO: 43)

KWVTFISLLFLFSSAYSRGVFRRDAHKSEVAHRFKDLGEENFKALVLIAFAQYLQQCPFE

DHVKLVNEVTEFAKTCVADESAENCDKSLHTLFGDKLCTVATLRETYGEMADCCAKQ

EPERNECFLQHKDDNPNLPRLVRPEVDVMCTAFHDNEETFLKKYLYEIARRHPYFYAPE

LLFFAKRYKAAFTECCQAADKAACLLPKLDELRDEGKASSAKQRLKCASLQKFGERAF

KAWAVARLSQRFPKAEFAEVSKLVTDLTKVHTECCHGDLLECADDRADLAKYICENQD

-continued

SISSKLKECCEKPLLEKSHCIAEVENDEMPADLPSLAADFVESKDVCKNYAEAKDVFLG

MFLYEYARRHPDYSVVLLLRLAKTYETTLEKCCAAADPHECYAKVFDEFKPLVEEPQN

LIKQNCELFEQLGEYKFQNALLVRYTKKVPQVSTPTLVEVSRNLGKVGSKCCKHPEAKR

MPCAEDYLSVVLNQLCVLHEKTPVSDRVTKCCTESLVNRRPCFSALEVDETYVPKEFNA

ETFTFHADICTLSEKERQIKKQTALVELVKHKPKATKEQLKAVMDDFAAFVEKCCKAD

DKETCFAEEGKKLVAASQAALGL.

In some aspects, the albumin comprises mouse albumin having the following sequence:

(SEQ ID NO: 42)

EAHKSEIAHRYNDLGEQHFKGLVLIAFSQYLQKCSYDEHAKLVQEVTDFAKTCVADES

AANCDKSLHTLFGDKLCAIPNLRENYGELADCCTKQEPERNECFLQHKDDNPSLPPFER

PEAEAMCTSFKENPTTFMGHYLHEVARRHPYFYAPELLYYAEQYNEILTQCCAEADKES

CLTPKLDGVKEKALVSSVRQRMKCSSMQKFGERAFKAWAVARLSQTFPNADFAEITKL

ATDLTKVNKECCHGDLLECADDRAELAKYMCENQATISSKLQTCCDKPLLKKAHCLSE

VEHDTMPADLPAIAADFVEDQEVCKNYAEAKDVFLGTFLYEYSRRHPDYSVSLLLRLA

KKYEATLEKCCAEANPPACYGTVLAEFQPLVEEPKNLVKTNCDLYEKLGEYGFQNAILV

RYTQKAPQVSTPTLVEAARNLGRVGTKCCTLPEDQRLPCVEDYLSAILNRVCLLHEKTP

VSEHVTKCCSGSLVERRPCFSALTVDETYVPKEFKAETFTFHSDICTLPEKEKQIKKQTAL

AELVKHKPKATAEQLKTVMDDFAQFLDTCCKAADKDTCFSTEGPNLVTRCKDALA.

In some aspects, the serum protein comprises a polypeptide of SEQ ID NO:42 or 43, or a fragment thereof, or a polypeptide with 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to SEQ ID NO:42, 43, or a fragment thereof.

E. Polypeptide Aspects

Specific polypeptide aspects are exemplified below:

| | |
|---|---|
| mIL12Rβ1<br>ThrombinlinkerIL12<br>p35 | QLGASGPGDGCCVEKTSFPEGASGSPLGPRNLSCYRVSKTDYECSW<br>QYDGPEDNVSHVLWCCFVPPNHTHTGQERCRYFSSGPDRTVQFWE<br>QDGIPVLSKVNFWVESRLGNRTMKSQKISQYLYNWTKTTPPLGHIK<br>VSQSHRQLRMDWNVSEEAGAEVQFRRRMPTTNWTLGDCGPQVNS<br>GSGVLGDIRGSMSESCLCPSENMAQEIQIRRRRRLSSGAPGGPWSD<br>WSMPVCVPPEVLPQALVPRGSGGGSGGGSRVIPVSGPARCLSQSRN<br>LLKTTDDMVKTAREKLKHYSCTAEDIDHEDITRDQTSTLKTCLPLE<br>LHKNESCLATRETSSTTRGSCLPPQKTSLMMTLCLGSIYEDLKMYQ<br>TEFQAINAALQNHNHQQIILDKGMLVAIDELMQSLNHNGETLRQKP<br>PVGEADPYRVKMKLCILLHAFSTRVVTINRVMGYLSSA (SEQ ID<br>NO: 7) |
| CBD-<br>mIL12Rβ1<br>mbinlinkerIL12<br>Throp40 | QLGASGPGDGCCVEKTSFPEGASGSPLGPRNLSCYRVSKTDYECSW<br>QYDGPEDNVSHVLWCCFVPPNHTHTGQERCRYFSSGPDRTVQFWE<br>QDGIPVLSKVNFWVESRLGNRTMKSQKISQYLYNWTKTTPPLGHIK<br>VSQSHRQLRMDWNVSEEAGAEVQFRRRMPTTNWTLGDCGPQVNS<br>GSGVLGDIRGSMSESCLCPSENMAQEIQIRRRRRLSSGAPGGPWSD<br>WSMPVCVPPEVLPQALVPRGSGGGSGGGSGGGSGGGSGGGSGGG<br>SMWELEKDVYVVEVDWTPDAPGETVNLTCDTPEEDDITWTSDQR<br>HGVIGSGKTLTITVKEFLDAGQYTCHKGGETLSHSHLLLHKKENGI<br>WSTEILKNFKNKTFLKCEAPNYSGRFTCSWLVQRNMDLKFNIKSSS<br>SSPDSRAVTCGMASLSAEKVTLDQRDYEKYSVSCQEDVTCPTAEE<br>TLPIELALEARQQNKYENYSTSFFIRDIIKPDPPKNLQMKPLKNSQV<br>EVSWEYPDSWSTPHSYFSLKFFVRIQRKKEKMKETEEGCNQKGAF<br>LVEKTSTEVQCKGGNVCVQAQDRYYNSSCSKWACVPCRVRS (SEQ<br>ID NO: 8) |
| mIL12Rβ1<br>MMPlinkerIL12p35 | QLGASGPGDGCCVEKTSFPEGASGSPLGPRNLSCYRVSKTDYECSW<br>QYDGPEDNVSHVLWCCFVPPNHTHTGQERCRYFSSGPDRTVQFWE |

-continued

| | |
|---|---|
| | QDGIPVLSKVNFWVESRLGNRTMKSQKISQYLYNWTKTTPPLGHIK<br>VSQSHRQLRMDWNVSEEAGAEVQFRRRMPTTNWTLGDCGPQVNS<br>GSGVLGDIRGSMSESCLCPSENMAQEIQIRRRRRLSSGAPGGPWSD<br>WSMPVCVPPEVLPQAGLLSGRSDNHGGGSGGGSRVIPVSGPARCLS<br>QSRNLLKTTDDMVKTAREKLKHYSCTAEDIDHEDITRDQTSTLKTC<br>LPLELHKNESCLATRETSSTTRGSCLPPQKTSLMMTLCLGSIYEDLK<br>MYQTEFQAINAALQNHNHQQIILDKGMLVAIDELMQSLNHNGETL<br>RQKPPVGEADPYRVKMKLCILLHAFSTRVVTINRVMGYLSSAHHH<br>HHH (SEQ ID NO: 9) |
| mIL12Rβ1-<br>MMPlinker-<br>IL12p40 | CCVEKTSFPEGASGSPLGPRNLSCYRVSKTDYECSWQYDGPEDNVS<br>HVLWCCFVPPNHTHTGQERCRYFSSGPDRTVQFWEQDGIPVLSKV<br>NFWVESRLGNRTMKSQKISQYLYNWTKTTPPLGHIKVSQSHRQLR<br>MDWNVSEEAGAEVQFRRRMPTTNWTLGDCGPQVNSGSGVLGDIR<br>GSMSESCLCPSENMAQEIQIRRRRRLSSGAPGGPWSDWSMPVCVPP<br>EVLPQAGLLSGRSDNHGGGSGGGSGGGSGGGSGGGSGGGSMWEL<br>EKDVYVVEVDWTPDAPGETVNLTCDTPEEDDITWTSDQRHGVIGS<br>GKTLTITVKEFLDAGQYTCHKGGETLSHSHLLLHKKENGIWSTEIL<br>KNFKNKTFLKCEAPNYSGRFTCSWLVQRNMDLKFNIKSSSSSPDSR<br>AVTCGMASLSAEKVTLDQRDYEKYSVSCQEDVTCPTAEETLPIELA<br>LEARQQNKYENYSTSFFIRDIIKPDPPKNLQMKPLKNSQVEVSWEY<br>PDSWSTPHSYFSLKFFVRIQRKKEKMKETEEGCNQKGAFLVEKTST<br>EVQCKGGNVCVQAQDRYYNSSCSKWACVPCRVRS (SEQ ID<br>NO: 10) |
| CBD-<br>mIL12Rβ1<br>Thrombinlinker-<br>IL12p40 | CSQPLDVILLLDGSSSFPASYFDEMKSFAKAFISKANIGPRLTQVSVL<br>QYGSITTIDVPWNVVPEKAHLLSLVDVMQREGGPSQIGDALGFAV<br>RYLTSEMHGARPGASKAVVILVTDVSVDSVDAAADAARSNRVTVF<br>PIGIGDRYDAAQLRILAGPAGDSNVVKLQRIEDLPTMVTLGNSFLH<br>KLCSGFVRIGGGSGGGSQLGASGPGDGCCVEKTSFPEGASGSPLGP<br>RNLSCYRVSKTDYECSWQYDGPEDNVSHVLWCCFVPPNHTHTGQ<br>ERCRYFSSGPDRTVQFWEQDGIPVLSKVNFWVESRLGNRTMKSQK<br>ISQYLYNWTKTTPPLGHIKVSQSHRQLRMDWNVSEEAGAEVQFRR<br>RMPTTNWTLGDCGPQVNSGSGVLGDIRGSMSESCLCPSENMAQEI<br>QIRRRRRLSSGAPGGPWSDWSMPVCVPPEVLPQALVPRGSGGGSG<br>GGSGGGSGGGSGGGSGGGSMWELEKDVYVVEVDWTPDAPGETV<br>NLTCDTPEEDDITWTSDQRHGVIGSGKTLTITVKEFLDAGQYTCHK<br>GGETLSHSHLLLHKKENGIWSTEILKNFKNKTFLKCEAPNYSGRFT<br>CSWLVQRNMDLKFNIKSSSSSPDSRAVTCGMASLSAEKVTLDQRD<br>YEKYSVSCQEDVTCPTAEETLPIELALEARQQNKYENYSTSFFIRDII<br>KPDPPKNLQMKPLKNSQVEVSWEYPDSWSTPHSYFSLKFFVRIQRK<br>KEKMKETEEGCNQKGAFLVEKTSTEVQCKGGNVCVQAQDRYYNS<br>SCSKWACVPCRVRS (SEQ ID NO: 11) |
| CBD-<br>mIL12Rβ1-<br>MMPlinker-<br>IL12p40 | CSQPLDVILLLDGSSSFPASYFDEMKSFAKAFISKANIGPRLTQVSVL<br>QYGSITTIDVPWNVVPEKAHLLSLVDVMQREGGPSQIGDALGFAV<br>RYLTSEMHGARPGASKAVVILVTDVSVDSVDAAADAARSNRVTVF<br>PIGIGDRYDAAQLRILAGPAGDSNVVKLQRIEDLPTMVTLGNSFLH<br>KLCSGFVRIGGGSGGGSQLGASGPGDGCCVEKTSFPEGASGSPLGP<br>RNLSCYRVSKTDYECSWQYDGPEDNVSHVLWCCFVPPNHTHTGQ<br>ERCRYFSSGPDRTVQFWEQDGIPVLSKVNFWVESRLGNRTMKSQK<br>ISQYLYNWTKTTPPLGHIKVSQSHRQLRMDWNVSEEAGAEVQFRR<br>RMPTTNWTLGDCGPQVNSGSGVLGDIRGSMSESCLCPSENMAQEI<br>QIRRRRRLSSGAPGGPWSDWSMPVCVPPEVLPQAGLLSGRSDNHG<br>GGSGGGSGGGSGGGSGGGSGGGSMWELEKDVYVVEVDWTPDAP<br>GETVNLTCDTPEEDDITWTSDQRHGVIGSGKTLTITVKEFLDAGQY<br>TCHKGGETLSHSHLLLHKKENGIWSTEILKNFKNKTFLKCEAPNYS<br>GRFTCSWLVQRNMDLKFNIKSSSSSPDSRAVTCGMASLSAEKVTLD<br>QRDYEKYSVSCQEDVTCPTAEETLPIELALEARQQNKYENYSTSFFI<br>RDIIKPDPPKNLQMKPLKNSQVEVSWEYPDSWSTPHSYFSLKFFVRI<br>QRKKEKMKETEEGCNQKGAFLVEKTSTEVQCKGGNVCVQAQDRY<br>YNSSCSKWACVPCRVRS (SEQ ID NO: 12) |
| mIL12Rβ1-<br>Thrombin-<br>MMP-<br>MMPlinker-<br>IL12p35 | QLGASGPGDGCCVEKTSFPEGASGSPLGPRNLSCYRVSKTDYECSW<br>QYDGPEDNVSHVLWCCFVPPNHTHTGQERCRYFSSGPDRTVQFWE<br>QDGIPVLSKVNFWVESRLGNRTMKSQKISQYLYNWTKTTPPLGHIK<br>VSQSHRQLRMDWNVSEEAGAEVQFRRRMPTTNWTLGDCGPQVNS<br>GSGVLGDIRGSMSESCLCPSENMAQEIQIRRRRRLSSGAPGGPWSD<br>WSMPVCVPPEVLPQALVPRGSGLLSGRSDNHGLLSGRSDNHGGGS<br>GGGSRVIPVSGPARCLSQSRNLLKTTDDMVKTAREKLKHYSCTAE<br>DIDHEDITRDQTSTLKTCLPLELHKNESCLATRETSSTTRGSCLPPQK<br>TSLMMTLCLGSIYEDLKMYQTEFQAINAALQNHNHQQIILDKGML<br>VAIDELMQSLNHNGETLRQKPPVGEADPYRVKMKLCILLHAFSTR<br>VVTINRVMGYLSSA (SEQ ID NO: 15) |
| mIL12Rβ1<br>MMPMMPMMP<br>linkerIL12p35 | CCVEKTSFPEGASGSPLGPRNLSCYRVSKTDYECSWQYDGPEDNVS<br>HVLWCCFVPPNHTHTGQERCRYFSSGPDRTVQFWEQDGIPVLSKV<br>NFWVESRLGNRTMKSQKISQYLYNWTKTTPPLGHIKVSQSHRQLR<br>MDWNVSEEAGAEVQFRRRMPTTNWTLGDCGPQVNSGSGVLGDIR |

-continued

| | |
|---|---|
| | GSMSESCLCPSENMAQEIQIRRRRRLSSGAPGGPWSDWSMPVCVPP<br>EVLPQAGLLSGRSDNHGLLSGRSDNHGLLSGRSDNHGGGSGGGSR<br>VIPVSGPARCLSQSRNLLKTTDDMVKTAREKLKHYSCTAEDIDHED<br>ITRDQTSTLKTCLPLELHKNESCLATRETSSTTRGSCLPPQKTSLMM<br>TLCLGSIYEDLKMYQTEFQAINAALQNHNHQQIILDKGMLVAIDEL<br>MQSLNHNGETLRQKPPVGEADPYRVKMKLCILLHAFSTRVVTINR<br>VMGYLSSA (SEQ ID NO: 16) |
| mIL12Rβ1-<br>Thrombin-<br>Thrombin-<br>Thrombin-<br>linker-IL12p35 | CCVEKTSFPEGASGSPLGPRNLSCYRVSKTDYECSWQYDGPEDNVS<br>HVLWCCFVPPNHTHTGQERCRYFSSGPDRTVQFWEQDGIPVLSKV<br>NFWVESRLGNRTMKSQKISQYLYNWTKTTPPLGHIKVSQSHRQLR<br>MDWNVSEEAGAEVQFRRRMPTTNWTLGDCGPQVNSGSGVLGDIR<br>GSMSESCLCPSENMAQEIQIRRRRRLSSGAPGGPWSDWSMPVCVPP<br>EVLPQALVPRGSLVPRGSLVPRGSGGGSGGGSRVIPVSGPARCLSQS<br>RNLLKTTDDMVKTAREKLKHYSCTAEDIDHEDITRDQTSTLKTCLP<br>LELHKNESCLATRETSSTTRGSCLPPQKTSLMMTLCLGSIYEDLKM<br>YQTEFQAINAALQNHNHQQIILDKGMLVAIDELMQSLNHNGETLR<br>QKPPVGEADPYRVKMKLCILLHAFSTRVVTINRVMGYLSSA (SEQ<br>ID NO: 17) |
| mIL12Rβ1-<br>Throm3-<br>MMP3-linker-<br>IL12p35 | CCVEKTSFPEGASGSPLGPRNLSCYRVSKTDYECSWQYDGPEDNVS<br>HVLWCCFVPPNHTHTGQERCRYFSSGPDRTVQFWEQDGIPVLSKV<br>NFWVESRLGNRTMKSQKISQYLYNWTKTTPPLGHIKVSQSHRQLR<br>MDWNVSEEAGAEVQFRRRMPTTNWTLGDCGPQVNSGSGVLGDIR<br>GSMSESCLCPSENMAQEIQIRRRRRLSSGAPGGPWSDWSMPVCVPP<br>EVLPQALVPRGSLVPRGSLVPRGSGLLSGRSDNHGLLSGRSDNHGL<br>LSGRSDNHGGGSGGGSRVIPVSGPARCLSQSRNLLKTTDDMVKTA<br>REKLKHYSCTAEDIDHEDITRDQTSTLKTCLPLELHKNESCLATRET<br>SSTTRGSCLPPQKTSLMMTLCLGSIYEDLKMYQTEFQAINAALQNH<br>NHQQIILDKGMLVAIDELMQSLNHNGETLRQKPPVGEADPYRVKM<br>KLCILLHAFSTRVVTINRVMGYLSSA (SEQ ID NO: 18) |
| VWF A3<br>domain protein | CSQPLDVILLLDGSSSFPASYFDEMKSFAKAFISKANIGPRLTQVSVL<br>QYGSITTIDVPWNVVPEKAHLLSLVDVMQREGGPSQIGDALGFAVR<br>YLTSEMHGARPGASKAVVILVTDVSVDSVDAAADAARSNRVTVFPI<br>GIGDRYDAAQLRILAGPAGDSNVVKLQRIEDLPTMVTLGNSFLHKL<br>CSGFVRICTGHHHHHH (SEQ ID NO: 1) |
| FN12mIL-<br>12Rβ1 | QLGASGPGDGCCVEKTSFPEGASGSPLGPRNLSCYRVSKTDYECSW<br>QYDGPEDNVSHVLWCCFVPPNHTHTGQERCRYFSSGPDRTVQFWE<br>QDGIPVLSKVNFWVESRLGNRTMKSQKISQYLYNWTKTTPPLGHIK<br>VSQSHRQLRMDWNVSEEAGAEVQFRRRMPTTNWTLGDCGPQVNS<br>GSGVLGDIRGSMSESCLCPSENMAQEIQIRRRRLSSGAPGGPWSD<br>WSMPVCVPPEVLPQALVPRGS (SEQ ID NO: 2) |
| Human IL-12 | p35 Subunit:<br>RNLPVATPDPGMFPCLHHSQNLLRAVSNMLQKARQTLEFYPCTSEEI<br>DHEDITKDKTSTVEACLPLELTKNESCLNSRETSFITNGSCLASRKTS<br>FMMALCLSSIYEDLKMYQVEFKTMNAKLLMDPKRQIFLDQNMLA<br>VIDELMQALNFNSETVPQKSSLEEPDFYKTKIKLCILLHAFRIRAVTI<br>DRVMSYLNAS (SEQ ID NO: 3)<br>p40 Subunit:<br>IWELKKDVYVVELDWYPDAPGEMVVLTCDTPEEDGITWTLDQSSE<br>VLGSGKTLTIQVKEFGDAGQYTCHKGGEVLSHSLLLLHKKEDGIWS<br>TDILKDQKEPKNKTFLRCEAKNYSGRFTCWWLTTISTDLTFSVKSSR<br>GSSDPQGVTCGAATLSAERVRGDNKEYEYSVECQEDSACPAAEESL<br>PIEVMVDAVHKLKYENYTSSFFIRDIIKPDPPKNLQLKPLKNSRQVE<br>VSWEYPDTWSTPHSYFSLTFCVQVQGKSKREKKDRVFTDKTSATVI<br>CRKNASISVRAQDRYYSSSWSEWASVPCS (SEQ ID NO: 4) |
| Mouse IL-12 | p35 Subunit:<br>RVIPVSGPARCLSQSRNLLKTTDDMVKTAREKLKHYSCTAEDIDHE<br>DITRDQTSTLKTCLPLELHKNESCLATRETSSTTRGSCLPPQKTSLM<br>MTLCLGSIYEDLKMYQTEFQAINAALQNHNHQQIILDKGMLVAIDE<br>LMQSLNHNGETLRQKPPVGEADPYRVKMKLCILLHAFSTRVVTINR<br>VMGYLSSA (SEQ ID NO: 5)<br>p40 Subunit:<br>MWELEKDVYVVEVDWTPDAPGETVNLTCDTPEEDDITWTSDQRH<br>GVIGSGKTLTITVKEFLDAGQYTCHKGGETLSHSHLLLHKKENGIW<br>STEILKNFKNKTFLKCEAPNYSGRFTCSWLVQRNMDLKFNIKSSSSS<br>PDSRAVTCGMASLSAEKVTLDQRDYEKYSVSCQEDVTCPTAEETLP<br>IELALEARQQNKYENYSTSFFIRDIIKPDPPKNLQMKPLKNSQVEVS<br>WEYPDSWSTPHSYFSLKFFVRIQRKKEKMKETEEGCNQKGAFLVE<br>KTSTEVQCKGGNVCVQAQDRYYNSSCSKWACVPCRVRS (SEQ ID<br>NO: 6) |

-continued

| | |
|---|---|
| uPA responsive sequence (LS) | GLLSGRSDNH (SEQ ID NO: 13) |
| MMP responsive sequence (HP) | HPVGLLAR (SEQ ID NO: 138) |
| MMP responsive sequence (VP) | VPLSLYSG (SEQ ID NO: 134) |
| MMP responsive sequence (PL) | PLGVRGK (SEQ ID NO: 145) |
| MMP responsive sequence (GER) | GERGPPGPQGAARGFPGTPGL (SEQ ID NO: 194) |
| Human IL-12Rβ1 | CRTSECCFQDPPYPDADSGSASGPRDLRCYRISSDRYECSWQYEGP<br>TAGVSHFLRCCLSSGRCCYFAAGSATRLQFSDQAGVSVLYTVTLWV<br>ESWARNQTEKSPEVTLQLYNSVKYEPPLGDIKVSKLAGQLRMEWE<br>TPDNQVGAEVQFRHRTPSSPWKLGDCGPQDDDTESCLCPLEMNVA<br>QEFQLRRRQLGSQGSSWSKWSSPVCVPPENPPQPQVRFSVEQLGQD<br>GRRRLTLKEQPTQLELPEGCQGLAPGTEVTYRLQLHMLSCPCKAK<br>ATRTLHLGKMPYLSGAAYNVAVISSNQFGPGLNQTWHIPADTHTEP<br>VALNISVGTNGTTMYWPARAQSMTYCIEWQPVGQDGGLATCSLTA<br>PQDPDPAGMATYSWSRESGAMGQEKCYYITIFASAHPEKLTLWSTV<br>LSTYHFGGNASAAGTPHHVSVKNHSLDSVSVDWAPSLLSTCPGVL<br>KEYVVRCRDEDSKQVSEHPVQPTETQVTLSGLRAGVAYTVQVRAD<br>TAWLRGVWSQPQRFSIEVQVSDWLIFFASLGSFLSILLVGVLGYLGL<br>NRAARHLCPPLPTPCASSAIEFPGGKETWQWINPVDFQEEASLQEA<br>LVVEMSWDKGERTEPLEKTELPEGAPELALDTELSLEDGDRCKAK<br>M (SEQ ID NO: 19) |
| Human FNI-II domain IL-12Rβ1 | CRTSECCFQDPPYPDADSGSASGPRDLRCYRISSDRYECSWQYEGP<br>TAGVSHFLRCCLSSGRCCYFAAGSATRLQFSDQAGVSVLYTVTLWV<br>ESWARNQTEKSPEVTLQLYNSVKYEPPLGDIKVSKLAGQLRMEWE<br>TPDNQVGAEVQFRHRTPSSPWKLGDCGPQDDDTESCLCPLEMNVA<br>QEFQLRRRQLGSQGSSWSKWSSPVCVPPE (SEQ ID NO: 195) |
| Mouse IL-12Rβ1 | QLGASGPGDGCCVEKTSFPEGASGSPLGPRNLSCYRVSKTDYECSW<br>QYDGPEDNVSHVLWCCFVPPNHTHTGQERCRYFSSGPDRTVQFWE<br>QDGIPVLSKVNFWVESRLGNRTMKSQKISQYLYNWTKTTPPLGHIK<br>VSQSHRQLRMDWNVSEEAGAEVQFRRRMPTTNWTLGDCGPQVNS<br>GSGVLGDIRGSMSESCLCPSENMAQEIQIRRRRRLSSGAPGGPWSD<br>WSMPVCVPPEVLPQAKIKFLVEPLNQGGRRRLTMQGQSPQLAVPEG<br>CRGRPGAQVKKHLVLVRMLSCRCQAQTSKTVPLGKKLNLSGATYD<br>LNVLAKTRFGRSTIQKWHLPAQELTETRALNVSVGGNMTSMQWA<br>AQAPGTTYCLEWQPWFQHRNHTHCTLIVPEEEDPAKMVTHSWSSK<br>PTLEQEECYRITVFASKNPKNPMLWATVLSSYYFGGNASRAGTPRH<br>VSVRNQTGDSVSVEWTASQLSTCPGVLTQYVVRCEAEDGAWESE<br>WLVPPTKTQVTLDGLRSRVMYKVQVRADTARLPGAWSHPQRFSFE<br>VQISRLSIIFASLGSFASVLLVGSLGYIGLNRAAWHLCPPLPTPCGSTA<br>VEFPGSQGKQAWQWCNPEDFPEVLYPRDALVVEMPGDRGDGTESP<br>QAAPECALDTRRPLETQRQRQVQALSEARRLGLAREDCPRGDLAH<br>VTLPLLLGGVTQGASVLDDLWRTHKTAEPGPPTLGQEA (SEQ ID<br>NO: 20) |
| Human IL-12Rβ2 | KIDACKRGDVTVKPSHVILLGSTVNITCSLKPRQGCFHYSRRNKLIL<br>YKFDRRINFHHGHSLNSQVTGLPLGTTLFVCKLACINSDEIQICGAEI<br>FVGVAPEQPQNLSCIQKGEQGTVACTWERGRDTHLYTEYTLQLSGP<br>KNLTWQKQCKDIYCDYLDFGINLTPESPESNFTAKVTAVNSLGSSSS<br>LPSTFTFLDIVRPLPPWDIRIKFQKASVSRCTLYWRDEGLVLLNRLR<br>YRPSNSRLWNMVNVTKAKGRHDLLDLKPFTEYEFQISSKLHLYKG<br>SWSDWSESLRAQTPEEEPTGMLDVWYMKRHIDYSRQQISLFWKNL<br>SVSEARGKILHYQVTLQELTGGKAMTQNITGHTSWTTVIPRTGNWA<br>VAVSAANSKGSSLPTRINIMNLCEAGLLAPRQVSANSEGMDNILVT<br>WQPPRKDPSAVQEYVVEWRELHPGGDTQVPLNWLRSRPYNVSALI<br>SENIKSYICYEIRVYALSGDQGGCSSILGNSKHKAPLSGPHINAITEE<br>KGSILISWNSIPVQEQMGCLLHYRIYWKERDSNSQPQLCEIPYRVSQ<br>NSHPINSLQPRVTYVLWMTALTAAGESSHGNEREFCLQGKANWMA<br>FVAPSICIAIIMVGIFSTHYFQQKVFVLLAALRPQWCSREIPDPANST<br>CAKKYPIAEEKTQLPLDRLLIDWPTPEDPEPLVISEVLHQVTPVFRHP<br>PCSNWPQREKGIQGHQASEKDMMHSASSPPPPRALQAESRQLVDL |

-continued

| | |
|---|---|
| | YKVLESRGSDPKPENPACPWTVLPAGDLPTHDGYLPSNIDDLPSHE APLADSLEELEPQHISLSVFPSSSLHPLTFSCGDKLTLDQLKMRCDSL ML (SEQ ID NO: 21) |
| Mouse IL-12Rβ2 | NIDVCKLGTVTVQPAPVIPLGSAANISCSLNPKQGCSHYPSSNELILL KFVNDVLVENLHGKKVHDHTGHSSTFQVTNLSLGMTLFVCKLNCS NSQKKPPVPVCGVEISVGVAPEPPQNISCVQEGENGTVACSWNSGK VTYLKTNYTLQLSGPNNLTCQKQCFSDNRQNCNRLDLGINLSPDLA ESRFIVRVTAINDLGNSSSLPHTFTFLDIVIPLPPWDIRINFLNASGSR GTLQWEDEGQVVLNQLRYQPLNSTSWNMVNATNAKGKYDLRDL RPFTEYEFQISSKLHLSGGSWSNWSESLRTRTPEEEPVGILDIWYMK QDIDYDRQQISLFWKSLNPSEARGKILHYQVTLQEVTKKTTLQNTT RHTSWTRVIPRTGAWTASVSAANSKGASAPTHINIVDLCGTGLLAP HQVSAKSENMDNILVTWQPPKKADSAVREYIVEWRALQPGSITKFP PHWLRIPPDNMSALISENIKPYICYEIRVHALSESQGGCSSIRGDSKH KAPVSGPHITAITEKKERLFISWTHIPFPEQRGCILHYRIYWKERDST AQPELCEIQYRRSQNSHPISSLQPRVTYVLWMTAVTAAGESPQGNER EFCPQGKANWKAFVISSICIAIITVGTFSIRYFRQKAFTLLSTLKPQW YSRTIPDPANSTWVKKYPILEEKIQLPTDNLLMAWPTPEEPEPLIIHE VLYHMIPVVRQPYYFKRGQGFQGYSTSKQDAMYIANPQATGTLTA ETRQLVNLYKVLESRDPDSKLANLTSPLTVTPVNYLPSHEGYLPSNI EDLSPHEADPTDSFDLEHQHISLSIFASSSLRPLIFGGERLTLDRLKM GYDSLMSNEA (SEQ ID NO: 22) |
| Human FNI-II domain IL-12Rβ1-Hu_p35 (GGGS) | CRTSECCFQDPPYPDADSGSASGPRDLRCYRISSDRYECSWQYEGP TAGVSHFLRCCLSSGRCCYFAAGSATRLQFSDQAGVSVLYTVTLWV ESWARNQTEKSPEVTLQLYNSVKYEPPLGDIKVSKLAGQLRMEWE TPDNQVGAEVQFRHRTPSSPWKLGDCGPQDDDTESCLCPLEMNVA QEFQLRRRQLGSQGSSWSKWSSPVCVPPEGGGSGGGSGGGSGGGS GGGSGGGSGGGSGGGSGGGSGGGSGGGSGRNLPVATPDPGMFPCL HHSQNLLRAVSNMLQKARQTLEFYPCTSEEIDHEDITKDKTSTVEA CLPLELTKNESCLNSRETSFITNGSCLASRKTSFMMALCLSSIYEDLK MYQVEFKTMNAKLLMDPKRQIFLDQNMLAVIDELMQALNFNSET VPQKSSLEEPDFYKTKIKLCILLHAFRIRAVTIDRVMSYLNAS (SEQ ID NO: 196) |
| Human FN12rb 1HPVP 2LS(51)_p35 | CRTSECCFQDPPYPDADSGSASGPRDLRCYRISSDRYECSWQYEGP TAGVSHFLRCCLSSGRCCYFAAGSATRLQFSDQAGVSVLYTVTLWV ESWARNQTEKSPEVTLQLYNSVKYEPPLGDIKVSKLAGQLRMEWE TPDNQVGAEVQFRHRTPSSPWKLGDCGPQDDDTESCLCPLEMNVA QEFQLRRRQLGSQGSSWSKWSSPVCVPPEHPVGLLARVPLSLYSGH PVGLLARVPLSLYSGSGLLSGRSDNHGGGSGGGSRNLPVATPDPGM FPCLHHSQNLLRAVSNMLQKARQTLEFYPCTSEEIDHEDITKDKTST VEACLPLELTKNESCLNSRETSFITNGSCLASRKTSFMMALCLSSIYE DLKMYQVEFKTMNAKLLMDPKRQIFLDQNMLAVIDELMQALNFN SETVPQKSSLEEPDFYKTKIKLCILLHAFRIRAVTIDRVMSYLNAS (SEQ ID NO: 197) |
| Linker | HPVGLLARVPLSLYSGHPVGLLARVPLSLYSGSGLLSGRSDNH (SEQ ID NO: 219) |
| Linker | HPVGLLARVPLSLYSGHPVGLLARVPLSLYSGSGLLSGRSDNHGGG SGGGS (SEQ ID NO: 220) |
| FN12mIL12rb1 HPVP2LSmIL12 p35 | QLGASGPGDCCVEKTSFPEGASGSPLGPRNLSCYRVSKTDYECSWQ YDGPEDNVSHVLWCCFVPPNHTHTGQERCRYFSSGPDRTVQFWEQ DGIPVLSKVNFWVESRLGNRTMKSQKISQYLYNWTKTTPPLGHIKV SQSHRQLRMDWNVSEEAGAEVQFRRRMPTTNWTLGDCGPQVNSG SGVLGDIRGSMSESCLCPSENMAQEIQIRRRRRLSSGAPGGPWSDW SMPVCVPPEVLPQAHPVGLLARVPLSYSGHPVGLLARVPLSYSGSG LLSGRSDNHGGGSGGGSRVIPVSGPARCLSQSRNLLKTTDDMVKTA REKLKHYSCTAEDIDHEDITRDQTSTLKTCLPLELHKNESCLATRET SSTTRGSCLPPQKTSLMMTLCLGSIYEDLKMYQTEFQAINAALQNH NHQQIILDKGMLVAIDELMQSLNHNGETLRQKPPVGEADPYRVKM KLCILLHAFSTRVVTINRVMGYLSSA (SEQ ID NO: 198) |
| Linker | HPVGLLARVPLSYSGHPVGLLARVPLSYSGSGLLSGRSDNH (SEQ ID NO: 103) |
| Linker | HPVGLLARVPLSYSGHPVGLLARVPLSYSGSGLLSGRSDNHGGGSG GGS (SEQ ID NO: 225) |
| FN12mIL12rb1 PL3mIL12p35 | QLGASGPGDCCVEKTSFPEGASGSPLGPRNLSCYRVSKTDYECSWQ YDGPEDNVSHVLWCCFVPPNHTHTGQERCRYFSSGPDRTVQFWEQ DGIPVLSKVNFWVESRLGNRTMKSQKISQYLYNWTKTTPPLGHIKV SQSHRQLRMDWNVSEEAGAEVQFRRRMPTTNWTLGDCGPQVNSG SGVLGDIRGSMSESCLCPSENMAQEIQIRRRRRLSSGAPGGPWSDW SMPVCVPPEVLPQAPLGVRGKPLGVRGKPLGVRGKGGGSGGGSRV IPVSGPARCLSQSRNLLKTTDDMVKTAREKLKHYSCTAEDIDHEDIT |

-continued

| | |
|---|---|
| | RDQTSTLKTCLPLELHKNESCLATRETSSTTRGSCLPPQKTSLMMTL CLGSIYEDLKMYQTEFQAINAALQNHNHQQIILDKGMLVAIDELMQ SLNHNGETLRQKPPVGEADPYRVKMKLCILLHAFSTRVVTINRVMG YLSSA (SEQ ID NO: 199) |
| Linker | PLGVRGKPLGVRGKPLGVRGK (SEQ ID NO: 104) |
| Linker | PLGVRGKPLGVRGKPLGVRGKGGGSGGGS (SEQ ID NO: 226) |
| FN12mIL12rb1 GER2mIL12p35 | QLGASGPGDCCVEKTSFPEGASGSPLGPRNLSCYRVSKTDYECSWQ YDGPEDNVSHVLWCCFVPPNHTHTGQERCRYFSSGPDRTVQFWEQ DGIPVLSKVNFWVESRLGNRTMKSQKISQYLYNWTKTTPPLGHIKV SQSHRQLRMDWNVSEEAGAEVQFRRRMPTTNWTLGDCGPQVNSG SGVLGDIRGSMSESCLCPSENMAQEIQIRRRRRLSSGAPGGPWSDW SMPVCVPPEVLPQAGERGPPGPQGAARGFPGTPGLGERGPPGPQGA ARGFPGTPGLGGGSGGGSRVIPVSGPARCLSQSRNLLKTTDDMVKT AREKLKHYSCTAEDIDHEDITRDQTSTLKTCLPLELHKNESCLATRE TSSTTRGSCLPPQKTSLMMTLCLGSIYEDLKMYQTEFQAINAALQN HNHQQIILDKGMLVAIDELMQSLNHNGETLRQKPPVGEADPYRVK MKLCILLHAFSTRVVTINRVMGYLSSA (SEQ ID NO: 200) |
| Linker | GERGPPGPQGAARGFPGTPGLGERGPPGPQGAARGFPGTPGL (SEQ ID NO: 105) |
| Linker | GERGPPGPQGAARGFPGTPGLGERGPPGPQGAARGFPGTPGLGGGS GGGS (SEQ ID NO: 227) |
| FN12mIL12rb1 PL3GER2mIL 12p35 | QLGASGPGDCCVEKTSFPEGASGSPLGPRNLSCYRVSKTDYECSWQ YDGPEDNVSHVLWCCFVPPNHTHTGQERCRYFSSGPDRTVQFWEQ DGIPVLSKVNFWVESRLGNRTMKSQKISQYLYNWTKTTPPLGHIKV SQSHRQLRMDWNVSEEAGAEVQFRRRMPTTNWTLGDCGPQVNSG SGVLGDIRGSMSESCLCPSENMAQEIQIRRRRRLSSGAPGGPWSDW SMPVCVPPEVLPQAPLGVRGKPLGVRGKPLGVRGKGERGPPGPQG AARGFPGTPGLGERGPPGPQGAARGFPGTPGLGGGSGGGSRVIPVS GPARCLSQSRNLLKTTDDMVKTAREKLKHYSCTAEDIDHEDITRDQ TSTLKTCLPLELHKNESCLATRETSSTTRGSCLPPQKTSLMMTLCLG SIYEDLKMYQTEFQAINAALQNHNHQQIILDKGMLVAIDELMQSLN HNGETLRQKPPVGEADPYRVKMKLCILLHAFSTRVVTINRVMGYLS SA (SEQ ID NO: 201) |
| Linker | PLGVRGKPLGVRGKPLGVRGKGERGPPGPQGAARGFPGTPGLGER GPPGPQGAARGFPGTPGL (SEQ ID NO: 106) |
| Linker | PLGVRGKPLGVRGKPLGVRGKGERGPPGPQGAARGFPGTPGLGER GPPGPQGAARGFPGTPGLGGGSGGGS (SEQ ID NO: 228) |
| FN12mIL12rb1 HPVPLSPL2m IL12p35 | QLGASGPGDCCVEKTSFPEGASGSPLGPRNLSCYRVSKTDYECSWQ YDGPEDNVSHVLWCCFVPPNHTHTGQERCRYFSSGPDRTVQFWEQ DGIPVLSKVNFWVESRLGNRTMKSQKISQYLYNWTKTTPPLGHIKV SQSHRQLRMDWNVSEEAGAEVQFRRRMPTTNWTLGDCGPQVNSG SGVLGDIRGSMSESCLCPSENMAQEIQIRRRRRLSSGAPGGPWSDW SMPVCVPPEVLPQAHPVGLLARVPLSYSGHPVGLLARVPLSYSGSG LLSGRSDNHPLGVRGKPLGVRGKGGGSGGGSRVIPVSGPARCLSQS RNLLKTTDDMVKTAREKLKHYSCTAEDIDHEDITRDQTSTLKTCLP LELHKNESCLATRETSSTTRGSCLPPQKTSLMMTLCLGSIYEDLKM YQTEFQAINAALQNHNHQQIILDKGMLVAIDELMQSLNHNGETLRQ KPPVGEADPYRVKMKLCILLHAFSTRVVTINRVMGYLSSA (SEQ ID NO: 202) |
| Linker | PLGVRGKPLGVRGK (SEQ ID NO: 107) |
| Linker | PLGVRGKPLGVRGKGGGSGGGS (SEQ ID NO: 229) |
| FN12mIL12rb1 HPVPLSPLGE R2IL12p35 | QLGASGPGDCCVEKTSFPEGASGSPLGPRNLSCYRVSKTDYECSWQ YDGPEDNVSHVLWCCFVPPNHTHTGQERCRYFSSGPDRTVQFWEQ DGIPVLSKVNFWVESRLGNRTMKSQKISQYLYNWTKTTPPLGHIKV SQSHRQLRMDWNVSEEAGAEVQFRRRMPTTNWTLGDCGPQVNSG SGVLGDIRGSMSESCLCPSENMAQEIQIRRRRRLSSGAPGGPWSDW SMPVCVPPEVLPQAHPVGLLARVPLSYSGHPVGLLARVPLSYSGSG LLSGRSDNHPLGVRGKPLGVRGKGERGPPGPQGAARGFPGTPGLG ERGPPGPQGAARGFPGTPGLGGGSGGGSRVIPVSGPARCLSQSRNLL KTTDDMVKTAREKLKHYSCTAEDIDHEDITRDQTSTLKTCLPLELH KNESCLATRETSSTTRGSCLPPQKTSLMMTLCLGSIYEDLKMYQTE FQAINAALQNHNHQQIILDKGMLVAIDELMQSLNHNGETLRQKPPV GEADPYRVKMKLCILLHAFSTRVVTINRVMGYLSSA (SEQ ID NO: 203) |

-continued

| | |
|---|---|
| Linker | HPVGLLARVPLSYSGHPVGLLARVPLSYSGSGLLSGRSDNHPLGVR GKPLGVRGKGERGPPGPQGAARGFPGTPGLGERGPPGPQGAARGF PGTPGL (SEQ ID NO: 108) |
| Linker | HPVGLLARVPLSYSGHPVGLLARVPLSYSGSGLLSGRSDNHPLGVR GKPLGVRGKGERGPPGPQGAARGFPGTPGLGERGPPGPQGAARGF PGTPGLGGGSGGGS (SEQ ID NO: 230) |
| CBD-FN12mIL12rb1 HPVPLSIL12p35 | CSQPLDVILLLDGSSSFPASYFDEMKSFAKAFISKANIGPRLTQVSVL QYGSITTIDVPWNVVPEKAHLLSLVDVMQREGGPSQIGDALGFAVR YLTSEMHGARPGASKAVVILVTDVSVDSVDAAADAARSNRVTVFPI GIGDRYDAAQLRILAGPAGDSNVVKLQRIEDLPTMVTLGNSFLHKL CSGFVRIGGGSGGGSCCVEKTSFPEGASGSPLGPRNLSCYRVSKTD YECSWQYDGPEDNVSHVLWCCFVPPNHTHTGQERCRYFSSGPDRT VQFWEQDGIPVLSKVNFWVESRLGNRTMKSQKISQYLYNWTKTTP PLGHIKVSQSHRQLRMDWNVSEEAGAEVQFRRRMPTTNWTLGDC GPQVNSGSGVLGDIRGSMSESCLCPSENMAQEIQIRRRRRLSSGAPG GPWSDWSMPVCVPPEVLPQAHPVGLLARVPLSYSGSGLLSGRSDN HGGGSGGGSRVIPVSGPARCLSQSRNLLKTTDDMVKTAREKLKHYS CTAEDIDHEDITRDQTSTLKTCLPLELHKNESCLATRETSSTTRGSCL PPQKTSLMMTLCLGSIYEDLKMYQTEFQAINAALQNHNHQQIILDK GMLVAIDELMQSLNHNGETLRQKPPVGEADPYRVKMKLCILLHAFS TRVVTINRVMGYLSSA (SEQ ID NO: 204) |
| Linker | HPVGLLARVPLSYSGSGLLSGRSDNH (SEQ ID NO: 221) |
| Linker | HPVGLLARVPLSYSGSGLLSGRSDNHGGGSGGGS (SEQ ID NO: 231) |
| CBDFN12mIL 12rb1HPVP2L SIL12p35 | CSQPLDVILLLDGSSSFPASYFDEMKSFAKAFISKANIGPRLTQVSVL QYGSITTIDVPWNVVPEKAHLLSLVDVMQREGGPSQIGDALGFAVR YLTSEMHGARPGASKAVVILVTDVSVDSVDAAADAARSNRVTVFPI GIGDRYDAAQLRILAGPAGDSNVVKLQRIEDLPTMVTLGNSFLHKL CSGFVRIGGGSGGGSCCVEKTSFPEGASGSPLGPRNLSCYRVSKTD YECSWQYDGPEDNVSHVLWCCFVPPNHTHTGQERCRYFSSGPDRT VQFWEQDGIPVLSKVNFWVESRLGNRTMKSQKISQYLYNWTKTTP PLGHIKVSQSHRQLRMDWNVSEEAGAEVQFRRRMPTTNWTLGDC GPQVNSGSGVLGDIRGSMSESCLCPSENMAQEIQIRRRRRLSSGAPG GPWSDWSMPVCVPPEVLPQAHPVGLLARVPLSYSGHPVGLLARVP LSYSGSGLLSGRSDNHGGGSGGGSRVIPVSGPARCLSQSRNLLKTTD DMVKTAREKLKHYSCTAEDIDHEDITRDQTSTLKTCLPLELHKNES CLATRETSSTTRGSCLPPQKTSLMMTLCLGSIYEDLKMYQTEFQAIN AALQNHNHQQIILDKGMLVAIDELMQSLNHNGETLRQKPPVGEAD PYRVKMKLCILLHAFSTRVVTINRVMGYLSSA (SEQ ID NO: 205) |
| Linker | HPVGLLARVPLSYSGHPVGLLARVPLSYSGSGLLSGRSDNH (SEQ ID NO: 103) |
| Linker | HPVGLLARVPLSYSGHPVGLLARVPLSYSGSGLLSGRSDNHGGGSG GGS (SEQ ID NO: 225) |
| FN12mIL12rb1 HPVP2LS3IL12 p35 | QLGASGPGDCCVEKTSFPEGASGSPLGPRNLSCYRVSKTDYECSWQ YDGPEDNVSHVLWCCFVPPNHTHTGQERCRYFSSGPDRTVQFWEQ DGIPVLSKVNFWVESRLGNRTMKSQKISQYLYNWTKTTPPLGHIKV SQSHRQLRMDWNVSEEAGAEVQFRRRMPTTNWTLGDCGPQVNSG SGVLGDIRGSMSESCLCPSENMAQEIQIRRRRRLSSGAPGGPWSDW SMPVCVPPEVLPQAHPVGLLARVPLSYSGHPVGLLARVPLSYSGSG LLSGRSDNHISSGLLSGRSDNHISSGLLSGRSDNHGGGSGGGSRVIP VSGPARCLSQSRNLLKTTDDMVKTAREKLKHYSCTAEDIDHEDITR DQTSTLKTCLPLELHKNESCLATRETSSTTRGSCLPPQKTSLMMTLC LGSIYEDLKMYQTEFQAINAALQNHNHQQIILDKGMLVAIDELMQS LNHNGETLRQKPPVGEADPYRVKMKLCILLHAFSTRVVTINRVMG YLSSA (SEQ ID NO: 206) |
| linker | HPVGLLARVPLSYSGHPVGLLARVPLSYSGSGLLSGRSDNHISSGLL SGRSDNHISSGLLSGRSDNH (SEQ ID NO: 222) |
| Linker | HPVGLLARVPLSYSGHPVGLLARVPLSYSGSGLLSGRSDNHISSGLL SGRSDNHISSGLLSGRSDNHGGGSGGGS (SEQ ID NO: 232) |
| FNIL12rb1PL1 p35 | QLGASGPGDGCCVEKTSFPEGASGSPLGPRNLSCYRVSKTDYECSW QYDGPEDNVSHVLWCCFVPPNHTHTGQERCRYFSSGPDRTVQFWE QDGIPVLSKVNFWVESRLGNRTMKSQKISQYLYNWTKTTPPLGHIK VSQSHRQLRMDWNVSEEAGAEVQFRRRMPTTNWTLGDCGPQVNS GSGVLGDIRGSMSESCLCPSENMAQEIQIRRRRRLSSGAPGGPWSD WSMPVCVPPEVLPQAGGGSGGGSGGGSGGGSPLGVRGKGGGSGG GSGGGSGGGSGGGSGGGSRVIPVSGPARCLSQSRNLLKTTDDMVK TAREKLKHYSCTAEDIDHEDITRDQTSTLKTCLPLELHKNESCLATR ETSSTTRGSCLPPQKTSLMMTLCLGSIYEDLKMYQTEFQAINAALQ |

-continued

| | |
|---|---|
| | NHNHQQIILDKGMLVAIDELMQSLNHNGETLRQKPPVGEADPYRV KMKLCILLHAFSTRVVTINRVMGYLSSA (SEQ ID NO: 207) |
| Linker | GGGSGGGSGGGSGGGSPLGVRGKGGGSGGGSGGGSGGGSGGGSG GGS (SEQ ID NO: 223) |
| FN12mIL12rb1 HP3(40)p35 | QLGASGPGDGCCVEKTSFPEGASGSPLGPRNLSCYRVSKTDYECSW QYDGPEDNVSHVLWCCFVPPNHTHTGQERCRYFSSGPDRTVQFWE QDGIPVLSKVNFWVESRLGNRTMKSQKISQYLYNWTKTTPPLGHIK VSQSHRQLRMDWNVSEEAGAEVQFRRRMPTTNWTLGDCGPQVNS GSGVLGDIRGSMSESCLCPSENMAQEIQIRRRRRLSSGAPGGPWSD WSMPVCVPPEVLPQAGGGSGGGSHPVGLLARHPVGLLARHPVGLL ARGGGSGGGSRVIPVSGPARCLSQSRNLLKTTDDMVKTAREKLKH YSCTAEDIDHEDITRDQTSTLKTCLPLELHKNESCLATRETSSTTRGS CLPPQKTSLMMTLCLGSIYEDLKMYQTEFQAINAALQNHNHQQIIL DKGMLVAIDELMQSLNHNGETLRQKPPVGEADPYRVKMKLCILLH AFSTRVVTINRVMGYLSSA (SEQ ID NO: 208) |
| Linker | HPVGLLARHPVGLLARHPVGLLAR (SEQ ID NO: 224) |
| Linker | GGGSGGGSHPVGLLARHPVGLLARHPVGLLARGGGSGGGS (SEQ ID NO: 233) |
| FN12mIL12rb1 LS3(49)p35 | QLGASGPGDGCCVEKTSFPEGASGSPLGPRNLSCYRVSKTDYECSW QYDGPEDNVSHVLWCCFVPPNHTHTGQERCRYFSSGPDRTVQFWE QDGIPVLSKVNFWVESRLGNRTMKSQKISQYLYNWTKTTPPLGHIK VSQSHRQLRMDWNVSEEAGAEVQFRRRMPTTNWTLGDCGPQVNS GSGVLGDIRGSMSESCLCPSENMAQEIQIRRRRRLSSGAPGGPWSD WSMPVCVPPEVLPQAGGGSGGGSSGLLSGRSDNHSGLLSGRSDNH SGLLSGRSDNHGGGSGGGSRVIPVSGPARCLSQSRNLLKTTDDMVK TAREKLKHYSCTAEDIDHEDITRDQTSTLKTCLPLELHKNESCLATR ETSSTTRGSCLPPQKTSLMMTLCLGSIYEDLKMYQTEFQAINAALQ NHNHQQIILDKGMLVAIDELMQSLNHNGETLRQKPPVGEADPYRV KMKLCILLHAFSTRVVTINRVMGYLSSA (SEQ ID NO: 209) |
| Linker | SGLLSGRSDNHSGLLSGRSDNHSGLLSGRSDNH (SEQ ID NO: 234) |
| Linker | GGGSGGGSSGLLSGRSDNHSGLLSGRSDNHSGLLSGRSDNHGGGS GGGS (SEQ ID NO: 235) |
| FN12mIL12rb1 HPVPLS(43)p35 | QLGASGPGDGCCVEKTSFPEGASGSPLGPRNLSCYRVSKTDYECSW QYDGPEDNVSHVLWCCFVPPNHTHTGQERCRYFSSGPDRTVQFWE QDGIPVLSKVNFWVESRLGNRTMKSQKISQYLYNWTKTTPPLGHIK VSQSHRQLRMDWNVSEEAGAEVQFRRRMPTTNWTLGDCGPQVNS GSGVLGDIRGSMSESCLCPSENMAQEIQIRRRRRLSSGAPGGPWSD WSMPVCVPPEVLPQAGGGSGGGSHPVGLLARVPLSLYSGSGLLSGR SDNHGGGSGGGSRVIPVSGPARCLSQSRNLLKTTDDMVKTAREKLK HYSCTAEDIDHEDITRDQTSTLKTCLPLELHKNESCLATRETSSTTRG SCLPPQKTSLMMTLCLGSIYEDLKMYQTEFQAINAALQNHNHQQII LDKGMLVAIDELMQSLNHNGETLRQKPPVGEADPYRVKMKLCILL HAFSTRVVTINRVMGYLSSA (SEQ ID NO: 210) |
| Linker | HPVGLLARVPLSLYSGSGLLSGRSDNH (SEQ ID NO: 236) |
| Linker | GGGSGGGSHPVGLLARVPLSLYSGSGLLSGRSDNHGGGSGGGS (SEQ ID NO: 237) |
| FN12mIL12rb1 HPVP2LS(51) p35 | QLGASGPGDGCCVEKTSFPEGASGSPLGPRNLSCYRVSKTDYECSW QYDGPEDNVSHVLWCCFVPPNHTHTGQERCRYFSSGPDRTVQFWE QDGIPVLSKVNFWVESRLGNRTMKSQKISQYLYNWTKTTPPLGHIK VSQSHRQLRMDWNVSEEAGAEVQFRRRMPTTNWTLGDCGPQVNS GSGVLGDIRGSMSESCLCPSENMAQEIQIRRRRRLSSGAPGGPWSD WSMPVCVPPEVLPQAHPVGLLARVPLSLYSGHPVGLLARVPLSLYS GSGLLSGRSDNHGGGSGGGSRVIPVSGPARCLSQSRNLLKTTDDMV KTAREKLKHYSCTAEDIDHEDITRDQTSTLKTCLPLELHKNESCLAT RETSSTTRGSCLPPQKTSLMMTLCLGSIYEDLKMYQTEFQAINAAL QNHNHQQIILDKGMLVAIDELMQSLNHNGETLRQKPPVGEADPYR VKMKLCILLHAFSTRVVTINRVMGYLSSA (SEQ ID NO: 211) |
| Linker | HPVGLLARVPLSLYSGHPVGLLARVPLSLYSGSGLLSGRSDNH (SEQ ID NO: 219) |
| Linker | HPVGLLARVPLSLYSGHPVGLLARVPLSLYSGSGLLSGRSDNHGGG SGGGS (SEQ ID NO: 220) |
| FN12mIL12rb1 VP3(44)p35 | QLGASGPGDGCCVEKTSFPEGASGSPLGPRNLSCYRVSKTDYECSW QYDGPEDNVSHVLWCCFVPPNHTHTGQERCRYFSSGPDRTVQFWE QDGIPVLSKVNFWVESRLGNRTMKSQKISQYLYNWTKTTPPLGHIK VSQSHRQLRMDWNVSEEAGAEVQFRRRMPTTNWTLGDCGPQVNS |

-continued

| | |
|---|---|
| | GSGVLGDIRGSMSESCLCPSENMAQEIQIRRRRRLSSGAPGGPWSD<br>WSMPVCVPPEVLPQAGGGSGGGSVPLSLYSGVPLSLYSGVPLSLYS<br>GGGGSGGGSGGGSRVIPVSGPARCLSQSRNLLKTTDDMVKTAREKL<br>KHYSCTAEDIDHEDITRDQTSTLKTCLPLELHKNESCLATRETSSTTR<br>GSCLPPQKTSLMMTLCLGSIYEDLKMYQTEFQAINAALQNHNHQQI<br>ILDKGMLVAIDELMQSLNHNGETLRQKPPVGEADPYRVKMKLCILL<br>HAFSTRVVTINRVMGYLSSA (SEQ ID NO: 212) |
| Linker | VPLSLYSGVPLSLYSGVPLSLYS (SEQ ID NO: 238) |
| Linker | GGGSGGGSVPLSLYSGVPLSLYSGVPLSLYSGGGGSGGGSGGGS<br>(SEQ ID NO: 239) |
| FN12mIL12rb1<br>VPuPA2(54)p35 | QLGASGPGDGCCVEKTSFPEGASGSPLGPRNLSCYRVSKTDYECSW<br>QYDGPEDNVSHVLWCCFVPPNHTHTGQERCRYFSSGPDRTVQFWE<br>QDGIPVLSKVNFWVESRLGNRTMKSQKISQYLYNWTKTTPPLGHIK<br>VSQSHRQLRMDWNVSEEAGAEVQFRRRMPTTNWTLGDCGPQVNS<br>GSGVLGDIRGSMSESCLCPSENMAQEIQIRRRRRLSSGAPGGPWSD<br>WSMPVCVPPEVLPQAGGGSGGGSVPLSLYSGGGGSGGGSLSGRSD<br>NHLSGRSDNHGGGSGGGSRVIPVSGPARCLSQSRNLLKTTDDMVK<br>TAREKLKHYSCTAEDIDHEDITRDQTSTLKTCLPLELHKNESCLATR<br>ETSSTTRGSCLPPQKTSLMMTLCLGSIYEDLKMYQTEFQAINAALQ<br>NHNHQQIILDKGMLVAIDELMQSLNHNGETLRQKPPVGEADPYRV<br>KMKLCILLHAFSTRVVTINRVMGYLSSA (SEQ ID NO: 213) |
| Linker | VPLSLYSGGGGSGGGSLSGRSDNHLSGRSDNH (SEQ ID NO: 240) |
| Linker | GGGSGGGSVPLSLYSGGGGSGGGSLSGRSDNHLSGRSDNHGGGSG<br>GGS (SEQ ID NO: 241) |
| Human FNI-II<br>domain IL-<br>12Rβ1-Hu_p35<br>VPuPA2(54) | CRTSECCFQDPPYPDADSGSASGPRDLRCYRISSDRYECSWQYEGP<br>TAGVSHFLRCCLSSGRCCYFAAGSATRLQFSDQAGVSVLYTVTLWV<br>ESWARNQTEKSPEVTLQLYNSVKYEPPLGDIKVSKLAGQLRMEWE<br>TPDNQVGAEVQFRHRTPSSPWKLGDCGPQDDDTESCLCPLEMNVA<br>QEFQLRRRQLGSQGSSWSKWSSPVCVPPEGGGSGGGSVPLSLYSGG<br>GGSGGGSLSGRSDNHLSGRSDNHGGGSGGGSGRNLPVATPDPGMF<br>PCLHHSQNLLRAVSNMLQKARQTLEFYPCTSEEIDHEDITKDKTST<br>VEACLPLELTKNESCLNSRETSFITNGSCLASRKTSFMMALCLSSIYE<br>DLKMYQVEFKTMNAKLLMDPKRQIFLDQNMLAVIDELMQALNFN<br>SETVPQKSSLEEPDFYKTKIKLCILLHAFRIRAVTIDRVMSYLNAS<br>(SEQ ID NO: 214) |
| linker | VPLSLYSGGGGSGGGSLSGRSDNHLSGRSDNH (SEQ ID NO: 240) |
| Linker | GGGSGGGSVPLSLYSGGGGSGGGSLSGRSDNHLSGRSDNHGGGSG<br>GGSG (SEQ ID NO: 242) |
| Human FNI-II<br>domain IL-<br>12Rβ1-Hu_p35<br>VP3(44) | CRTSECCFQDPPYPDADSGSASGPRDLRCYRISSDRYECSWQYEGP<br>TAGVSHFLRCCLSSGRCCYFAAGSATRLQFSDQAGVSVLYTVTLWV<br>ESWARNQTEKSPEVTLQLYNSVKYEPPLGDIKVSKLAGQLRMEWE<br>TPDNQVGAEVQFRHRTPSSPWKLGDCGPQDDDTESCLCPLEMNVA<br>QEFQLRRRQLGSQGSSWSKWSSPVCVPPEGGGSGGGSVPLSLYSGV<br>PLSLYSGVPLSLYSGGGGSGGGSGGGSRNLPVATPDPGMFPCLHHS<br>QNLLRAVSNMLQKARQTLEFYPCTSEEIDHEDITKDKTSTVEACLPL<br>ELTKNESCLNSRETSFITNGSCLASRKTSFMMALCLSSIYEDLKMYQ<br>VEFKTMNAKLLMDPKRQIFLDQNMLAVIDELMQALNFNSETVPQK<br>SSLEEPDFYKTKIKLCILLHAFRIRAVTIDRVMSYLNAS (SEQ ID<br>NO: 215) |
| linker | VPLSLYSGVPLSLYSGVPLSLYS (SEQ ID NO: 238) |
| Linker | GGGSGGGSVPLSLYSGVPLSLYSGVPLSLYSGGGGSGGGSGGGS<br>(SEQ ID NO: 239) |
| Human FNI-II<br>domain IL-<br>12Rβ1-Hu_p35<br>HPVPLS(43) | CRTSECCFQDPPYPDADSGSASGPRDLRCYRISSDRYECSWQYEGP<br>TAGVSHFLRCCLSSGRCCYFAAGSATRLQFSDQAGVSVLYTVTLWV<br>ESWARNQTEKSPEVTLQLYNSVKYEPPLGDIKVSKLAGQLRMEWE<br>TPDNQVGAEVQFRHRTPSSPWKLGDCGPQDDDTESCLCPLEMNVA<br>QEFQLRRRQLGSQGSSWSKWSSPVCVPPEGGGSGGGSHPVGLLAR<br>VPLSLYSGSGLLSGRSDNHGGGSGGGSRNLPVATPDPGMFPCLHHS<br>QNLLRAVSNMLQKARQTLEFYPCTSEEIDHEDITKDKTSTVEACLPL<br>ELTKNESCLNSRETSFITNGSCLASRKTSFMMALCLSSIYEDLKMYQ<br>VEFKTMNAKLLMDPKRQIFLDQNMLAVIDELMQALNFNSETVPQK<br>SSLEEPDFYKTKIKLCILLHAFRIRAVTIDRVMSYLNAS (SEQ ID<br>NO: 216) |

-continued

| | |
|---|---|
| linker | HPVGLLARVPLSLYSGSGLLSGRSDNH (SEQ ID NO: 236) |
| Linker | GGGSGGGSHPVGLLARVPLSLYSGSGLLSGRSDNHGGGSGGGS (SEQ ID NO: 237) |
| Human FNI-II domain IL-12Rβ1-Hu_p35 PLGER2 | CRTSECCFQDPPYPDADSGSASGPRDLRCYRISSDRYECSWQYEGP TAGVSHFLRCCLSSGRCCYFAAGSATRLQFSDQAGVSVLYTVTLWV ESWARNQTEKSPEVTLQLYNSVKYEPPLGDIKVSKLAGQLRMEWE TPDNQVGAEVQFRHRTPSSPWKLGDCGPQDDDTESCLCPLEMNVA QEFQLRRRQLGSQGSSWSKWSSPVCVPPEPLGVRGKPLGVRGKGE RGPPGPQGAARGFPGTPGLGERGPPGPQGAARGFPGTPGLGGGSG GGSRNLPVATPDPGMFPCLHHSQNLLRAVSNMLQKARQTLEFYPCT SEEIDHEDITKDKTSTVEACLPLELTKNESCLNSRETSFITNGSCLAS RKTSFMMALCLSSIYEDLKMYQVEFKTMNAKLLMDPKRQIFLDQN MLAVIDELMQALNFNSETVPQKSSLEEPDFYKTKIKLCILLHAFRIR AVTIDRVMSYLNAS (SEQ ID NO: 217) |
| linker | PLGVRGKPLGVRGKGERGPPGPQGAARGFPGTPGLGERGPPGPQG AARGFPGTPGL (SEQ ID NO: 243) |
| Linker | PLGVRGKPLGVRGKGERGPPGPQGAARGFPGTPGLGERGPPGPQG AARGFPGTPGLGGGSGGGS (SEQ ID NO: 244) |
| Human FNI-II domain IL-12Rβ1-Hu_p35 HPVPLSPL2 | CRTSECCFQDPPYPDADSGSASGPRDLRCYRISSDRYECSWQYEGP TAGVSHFLRCCLSSGRCCYFAAGSATRLQFSDQAGVSVLYTVTLWV ESWARNQTEKSPEVTLQLYNSVKYEPPLGDIKVSKLAGQLRMEWE TPDNQVGAEVQFRHRTPSSPWKLGDCGPQDDDTESCLCPLEMNVA QEFQLRRRQLGSQGSSWSKWSSPVCVPPEHPVGLLARVPLSYSGHP VGLLARVPLSYSGSGLLSGRSDNHPLGVRGKPLGVRGKGGGSGGG SRNLPVATPDPGMFPCLHHSQNLLRAVSNMLQKARQTLEFYPCTSE EIDHEDITKDKTSTVEACLPLELTKNESCLNSRETSFITNGSCLASRK TSFMMALCLSSIYEDLKMYQVEFKTMNAKLLMDPKRQIFLDQNML AVIDELMQALNFNSETVPQKSSLEEPDFYKTKIKLCILLHAFRIRAVT IDRVMSYLNAS (SEQ ID NO: 218) |
| Linker | HPVGLLARVPLSYSGHPVGLLARVPLSYSGSGLLSGRSDNHPLGVR GKPLGVRGK (SEQ ID NO: 245) |
| Linker | HPVGLLARVPLSYSGHPVGLLARVPLSYSGSGLLSGRSDNHPLGVR GKPLGVRGKGGGSGGGS (SEQ ID NO: 246) |
| Mouse M-$(G_3S)_{11}$-p35 | QLGASGPGDCCVEKTSFPEGASGSPLGPRNLSCYRVSKTDYECSWQ YDGPEDNVSHVLWCCFVPPNHTHTGQERCRYFSSGPDRTVQFWEQ DGIPVLSKVNFWVESRLGNRTMKSQKISQYLYNWTKTTPPLGHIKV SQSHRQLRMDWNVSEEAGAEVQFRRRMPTTNWTLGDCGPQVNSG SGVLGDIRGSMSESCLCPSENMAQEIQIRRRRRLSSGAPGGPWSDW SMPVCVPPEVLPQAGGGSGGGSGGGSGGGSGGGSGGGSGGGSGG GSGGGSGGGSGGGSRVIPVSGPARCLSQSRNLLKTTDDMVKTAREK LKHYSCTAEDIDHEDITRDQTSTLKTCLPLELHKNESCLATRETSSTT RGSCLPPQKTSLMMTLCLGSIYEDLKMYQTEFQAINAALQNHNHQ QIILDKGMLVAIDELMQSLNHNGETLRQKPPVGEADPYRVKMKLCI LLHAFSTRVVTINRVMGYLSSAHHHHHH (SEQ ID NO: 247) |
| IL-12 Mask | QLGASGPGDCCVEKTSFPEGASGSPLGPRNLSCYRVSKTDYECSWQ YDGPEDNVSHVLWCCFVPPNHTHTGQERCRYFSSGPDRTVQFWEQ DGIPVLSKVNFWVESRLGNRTMKSQKISQYLYNWTKTTPPLGHIKV SQSHRQLRMDWNVSEEAGAEVQFRRRMPTTNWTLGDCGPQVNSG SGVLGDIRGSMSESCLCPSENMAQEIQIRRRRRLSSGAPGGPWSDW SMPVCVPPEVLPQA (SEQ ID NO: 192) |
| linker | GGGSGGGSGGGSGGGSGGGSGGGSGGGSGGGSGGGSGGGSGGGS (SEQ ID NO: 48) |
| p35 | RVIPVSGPARCLSQSRNLLKTTDDMVKTAREKLKHYSCTAEDIDHE DITRDQTSTLKTCLPLELHKNESCLATRETSSTTRGSCLPPQKTSLM MTLCLGSIYEDLKMYQTEFQAINAALQNHNHQQIILDKGMLVAIDE LMQSLNHNGETLRQKPPVGEADPYRVKMKLCILLHAFSTRVVTINR VMGYLSSA (SEQ ID NO: 5) |
| Mouse p40 | MWELEKDVYVVEVDWTPDAPGETVNLTCDTPEEDDITWTSDQRH GVIGSGKTLTITVKEFLDAGQYTCHKGGETLSHSHLLLHKKENGIW STEILKNFKNKTFLKCEAPNYSGRFTCSWLVQRNMDLKFNIKSSSSS PDSRAVTCGMASLSAEKVTLDQRDYEKYSVSCQEDVTCPTAEETLP IELALEARQQNKYENYSTSFFIRDIIKPDPPKNLQMKPLKNSQVEVS WEYPDSWSTPHSYFSLKFFVRIQRKKEKMKETEEGCNQKGAFLVE KTSTEVQCKGGNVCVQAQDRYYNSSCSKWACVPCRVRS (SEQ ID NO: 6) |

-continued

| | |
|---|---|
| Human M-($G_3S$)$_{11}$-p35 | CRTSECCFQDPPYPDADSGSASGPRDLRCYRISSDRYECSWQYEGP<br>TAGVSHFLRCCLSSGRCCYFAAGSATRLQFSDQAGVSVLYTVTLWV<br>ESWARNQTEKSPEVTLQLYNSVKYEPPLGDIKVSKLAGQLRMEWE<br>TPDNQVGAEVQFRHRTPSSPWKLGDCGPQDDDTESCLCPLEMNVA<br>QEFQLRRRQLGSQGSSWSKWSSPVCVPPEGGGSGGGSGGGSGGGS<br>GGGSGGGSGGGSGGGSGGGSGGGSGGGSGRNLPVATPDPGMFPCL<br>HHSQNLLRAVSNMLQKARQTLEFYPCTSEEIDHEDITKDKTSTVEA<br>CLPLELTKNESCLNSRETSFITNGSCLASRKTSFMMALCLSSIYEDLK<br>MYQVEFKTMNAKLLMDPKRQIFLDQNMLAVIDELMQALNFNSET<br>VPQKSSLEEPDFYKTKIKLCILLHAFRIRAVTIDRVMSYLNASHHHH<br>HH (SEQ ID NO: 248) |
| IL-12 Mask | CRTSECCFQDPPYPDADSGSASGPRDLRCYRISSDRYECSWQYEGP<br>TAGVSHFLRCCLSSGRCCYFAAGSATRLQFSDQAGVSVLYTVTLWV<br>ESWARNQTEKSPEVTLQLYNSVKYEPPLGDIKVSKLAGQLRMEWE<br>TPDNQVGAEVQFRHRTPSSPWKLGDCGPQDDDTESCLCPLEMNVA<br>QEFQLRRRQLGSQGSSWSKWSSPVCVPPE (SEQ ID NO: 195) |
| Linker | GGGSGGGSGGGSGGGSGGGSGGGSGGGSGGGSGGGSGGGSGGGS<br>(SEQ ID NO: 48) |
| p35 | RNLPVATPDPGMFPCLHHSQNLLRAVSNMLQKARQTLEFYPCTSEEI<br>DHEDITKDKTSTVEACLPLELTKNESCLNSRETSFITNGSCLASRKTS<br>FMMALCLSSIYEDLKMYQVEFKTMNAKLLMDPKRQIFLDQNMLA<br>VIDELMQALNFNSETVPQKSSLEEPDFYKTKIKLCILLHAFRIRAVTI<br>DRVMSYLNAS (SEQ ID NO: 3) |
| Human p40 | IWELKKDVYVVELDWYPDAPGEMVVLTCDTPEEDGITWTLDQSSE<br>VLGSGKTLTIQVKEFGDAGQYTCHKGGEVLSHSLLLLHKKEDGIWS<br>TDILKDQKEPKNKTFLRCEAKNYSGRFTCWWLTTISTDLTFSVKSSR<br>GSSDPQGVTCGAATLSAERVRGDNKEYEYSVECQEDSACPAAEESL<br>PIEVMVDAVHKLKYENYTSSFFIRDIIKPDPPKNLQLKPLKNSRQVE<br>VSWEYPDTWSTPHSYFSLTFCVQVQGKSKREKKDRVFTDKTSATVI<br>CRKNASISVRAQDRYYSSSWSEWASVPCS (SEQ ID NO: 4) |

In some aspects, the polypeptide has at least 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a polypeptide of the disclosure, such as SEQ ID NOS:7-12, and 15-18, or fragments thereof.

F. Protein Tags

In some aspects, the polypeptide further comprises a protein tag. The protein tag can be used for protein purification and/or immunoassays, for example. Exemplary protein tags include AviTag, a peptide allowing biotinylation by the enzyme BirA and so the protein can be isolated by streptavidin (GLNDIFEAQKIEWHE (SEQ ID NO:82)), Calmodulin-tag, a peptide bound by the protein calmodulin (KRRWKKNFIAVSAANRFKKISSSGAL (SEQ ID NO:83)), polyglutamate tag, a peptide binding efficiently to anion-exchange resin such as Mono-Q (EEEEEE (SEQ ID NO:84)), E-tag, a peptide recognized by an antibody (GAPVPYPDPLEPR (SEQ ID NO:102)), FLAG-tag, a peptide recognized by an antibody (DYKDDDDK (SEQ ID NO:85)), HA-tag, a peptide from hemagglutinin recognized by an antibody (YPYDVPDYA (SEQ ID NO:86)), His-tag, 5-10 histidines (HHHHH—SEQ ID NO:193) bound by a nickel or cobalt chelate (HHHHHH (SEQ ID NO:87)), Myc-tag, a peptide derived from c-myc recognized by an antibody (EQKLISEEDL (SEQ ID NO:88)), NE-tag, a novel 18-amino-acid synthetic peptide (TKENPRSNQEESYDDNES (SEQ ID NO:89)) recognized by a monoclonal IgG1 antibody, which is useful in a wide spectrum of applications including Western blotting, ELISA, flow cytometry, immunocytochemistry, immunoprecipitation, and affinity purification of recombinant proteins, S-tag, a peptide derived from Ribonuclease A (KETAAAKFERQHMDS (SEQ ID NO:90)), SBP-tag, a peptide which binds to streptavidin (MDEKTTGWRGGHVVEGLAGELEQLRARLEHHPQGQREP (SEQ ID NO:91)), Softag 1, for mammalian expression (SLAELLNAGLGGS (SEQ ID NO:92)), Softag 3, for prokaryotic expression (TQDPSRVG (SEQ ID NO:93)), Strep-tag, a peptide which binds to streptavidin or the modified streptavidin called streptactin (Strep-tag II: WSHPQFEK (SEQ ID NO:94)), TC tag, a tetracysteine tag that is recognized by FLASH and ReAsH biarsenical compounds (CCPGCC (SEQ ID NO:95)), V5 tag, a peptide recognized by an antibody (GKPIPNPLLGLDST (SEQ ID NO:96)), VSV-tag, a peptide recognized by an antibody (YTDIEMNRLGK (SEQ ID NO:97)), Xpress tag (DLYDDDDK (SEQ ID NO:98)), Covalent peptide tags, Isopeptag, a peptide which binds covalently to pilin-C protein (TDKDMTITFTNKKDAE (SEQ ID NO:99)), SpyTag, a peptide which binds covalently to SpyCatcher protein (AHIVMVDAYKPTK (SEQ ID NO:100)), SnoopTag, a peptide which binds covalently to SnoopCatcher protein (KLGDIEFIKVNK (SEQ ID NO:101)), BCCP (Biotin Carboxyl Carrier Protein), a protein domain biotinylated by BirA enabling recognition by streptavidin, Glutathione-S-transferase-tag, a protein which binds to immobilized glutathione, Green fluorescent protein-tag, a protein which is spontaneously fluorescent and can be bound by nanobodies, HaloTag, a mutated bacterial haloalkane dehalogenase that covalently attaches to a reactive haloalkane substrate, this allows attachment to a wide variety of substrates. Maltose binding protein-tag, a protein which binds to amylose agarose, Nus-tag, Thioredoxin-tag, Fc-tag, derived from immunoglobulin Fc domain, allow dimerization and solubilization. Can be used for purification on Protein-A Sepharose, Designed Intrinsically Disordered tags containing disorder promoting amino acids (P,E,S,T,A, Q,G,), and Ty-tag. In some aspects, the polypeptide comprises a 6H tag of SEQ ID NO:87.

II. PROTEINACEOUS COMPOSITIONS

The polypeptides or polynucleotides of the disclosure, such as the CBD, serum protein, therapeutic agent, masking agent, linker, or cytokine polypeptide, may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more variant amino acids or nucleic acid substitutions or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% similar, identical, or homologous with at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids or nucleic acids, or any range derivable therein, of SEQ ID NOS: 1-249.

The polypeptides of the disclosure, such as the CBD, serum protein, therapeutic agent, masking agent, linker, or cytokine polypeptide, may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NOS: 1-249.

In some aspects, a polypeptide of the disclosure may comprise amino acids 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) of SEQ ID NOS: 1-249.

In some aspects, a polypeptide of the disclosure, such as the CBD, serum protein, therapeutic agent, masking agent, linker, or cytokine polypeptide, may comprise at least, at most, about, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) contiguous amino acids of SEQ ID NOS: 1-249.

In some aspects, the polypeptide, such as the CBD, serum protein, therapeutic agent, masking agent, linker, or cytokine polypeptide, may comprise at least, at most, about, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) contiguous amino acids of SEQ ID NOS:1-249 that are at least, at most, or about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% similar, identical, or homologous with one of SEQ ID NOS: 1-249.

A polypeptide of the disclosure, such as the CBD, serum protein, therapeutic agent, masking agent, linker, or cytokine polypeptide may be at least, at most, or about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range derivable therein) similar, identical, or homologous with one of SEQ ID NOS: 1-249.

The polypeptides and nucleic acids of the disclosure may include at least, at most, about, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 substitutions (or any range derivable therein).

The substitution may be at amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 of one of SEQ ID NOS: 1-249. One or more of these substitutions may be specifically excluded from an aspect.

Peptides, polypeptides, and proteins of the disclosure, such as the CBD, serum protein, therapeutic agent, masking agent, linker, or cytokine polypeptide, having at least, having at least, or having 70, 75, 80, 85, 90, 91, 92, 93, 94, 95, 96, 97, 98, 99, 100% identity to any one of SEQ ID NOS: 1-249 includes a fragment of segment starting at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 (or any range derivable therein) and ending at amino acid 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, or 205 (or any range derivable therein).

In some aspects, the amino acid at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 of the peptide or polypeptide of one of SEQ ID NOS:1-249 is substituted with an alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa. One or more of these substitutions may be specifically excluded from an aspect.

Proteins may be recombinant, or synthesized in vitro. Alternatively, a non-recombinant or recombinant protein may be isolated from bacteria. It is also contemplated that bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids.

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity. Structures such as, for example, an enzymatic catalytic domain or interaction components may have amino acid substituted to maintain such function. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In other aspects, alteration of the function of a polypeptide is intended by introducing one or more substitutions. For example, certain amino acids may be substituted for other amino acids in a protein structure with the intent to modify the interactive binding capacity of interaction components. Structures such as, for example, protein interaction domains, nucleic acid interaction domains, and catalytic sites may have amino acids substituted to alter such function. Since it is the interactive capacity and nature of a protein that defines that protein's biological functional activity, certain amino acid substitutions can be made in a protein sequence, and in its underlying DNA coding sequence, and nevertheless produce a protein with different properties. It is thus contemplated by the inventors that various changes may be made in the DNA sequences of genes with appreciable alteration of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

In specific aspects, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One aspect includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed.

The generation of recombinant expression vectors, and the elements included therein, are discussed herein. Alternatively, the protein to be produced may be an endogenous protein normally synthesized by the cell used for protein production.

III. NUCLEIC ACIDS

In certain aspects, the current disclosure concerns recombinant polynucleotides encoding the proteins, polypeptides, and peptides of the invention, such as the CBD, serum protein, therapeutic agent, masking agent, linker, or cytokine polypeptide, and/or other molecules. Therefore, certain aspects relate to nucleotides encoding for a CBD, serum protein, therapeutic agent, masking agent, linker, or cytokine polypeptide, and fragments thereof.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs (or any range derivable therein), including all values and ranges there between, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein.

In particular aspects, the invention concerns isolated nucleic acid segments and recombinant vectors incorporating nucleic acid sequences that encode a polypeptide or peptide of the disclosure. The term "recombinant" may be used in conjunction with a polynucleotide or polypeptide and generally refers to a polypeptide or polynucleotide produced and/or manipulated in vitro or that is a replication product of such a molecule.

In other aspects, the invention concerns isolated nucleic acid segments and recombinant vectors incorporating nucleic acid sequences that encode a polypeptide or peptide of the disclosure.

The nucleic acid segments used in the current disclosure can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain aspects, the current disclosure provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this disclosure using the methods described herein (e.g., BLAST analysis using standard parameters).

The disclosure also contemplates the use of polynucleotides which are complementary to all the above described polynucleotides.

A. Vectors

Polypeptides of the disclosure may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a polypeptide of the disclosure, the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

B. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain aspects may direct high level expression of the introduced DNA segment under specified conditions, such as large-scale production of recombinant proteins or peptides.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

C. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain aspects of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

D. Selectable and Screenable Markers

In certain aspects of the invention, cells containing a nucleic acid construct of the current disclosure may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

E. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

F. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

IV. ADDITIONAL THERAPIES

A. Immunotherapy

In some aspects, the methods comprise administration of a cancer immunotherapy. Cancer immunotherapy (sometimes called immuno-oncology, abbreviated IO) is the use of the immune system to treat cancer. Immunotherapies can be categorized as active, passive or hybrid (active and passive). These approaches exploit the fact that cancer cells often have molecules on their surface that can be detected by the immune system, known as tumor-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Immunotherapies useful in the methods of the disclosure are described below.

3. Checkpoint Inhibitors and Combination Treatment

Aspects of the disclosure may include administration of immune checkpoint inhibitors (also referred to as checkpoint inhibitor therapy), which are further described below.

b. PD-1, PD-L1, and PD-L2 inhibitors

PD-1 can act in the tumor microenvironment where T cells encounter an infection or tumor. Activated T cells upregulate PD-1 and continue to express it in the peripheral tissues. Cytokines such as IFN-gamma induce the expression of PD-L1 on epithelial cells and tumor cells. PD-L2 is expressed on macrophages and dendritic cells. The main role of PD-1 is to limit the activity of effector T cells in the periphery and prevent excessive damage to the tissues during an immune response. Inhibitors of the disclosure may block one or more functions of PD-1 and/or PD-L1 activity.

Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some aspects, PD-1, PD-L1, and PD-L2 are human PD-1, PD-L1 and PD-L2.

In some aspects, the PD-1 inhibitor is a molecule that inhibits the binding of PD-1 to its ligand binding partners. In a specific aspect, the PD-1 ligand binding partners are PD-L1 and/or PD-$L_2$. In another aspect, a PD-L1 inhibitor is a molecule that inhibits the binding of PD-L1 to its binding partners. In a specific aspect, PD-L1 binding partners are PD-1 and/or B7-1. In another aspect, the PD-L2 inhibitor is a molecule that inhibits the binding of PD-L2 to its binding partners. In a specific aspect, a PD-L2 binding partner is PD-1. The inhibitor may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 inhibitors for use in the methods and compositions provided herein are known in the art such as described in U.S. Patent Application Nos. US2014/0294898, US2014/022021, and US2011/0008369, all incorporated herein by reference.

In some aspects, the PD-1 inhibitor is an anti-PD-1 antibody (e.g., a human antibody, a humanized antibody, or a chimeric antibody). In some aspects, the anti-PD-1 antibody is selected from the group consisting of nivolumab, pembrolizumab, and pidilizumab. In some aspects, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some aspects, the PD-L1 inhibitor comprises AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. Pidilizumab, also known as CT-011, hBAT, or hBAT-1, is an anti-PD-1 antibody described in WO2009/101611. AMP-224, also known as B7-DCIg, is a PD-L2-Fc fusion soluble receptor described in WO2010/027827 and WO2011/066342. Additional PD-1 inhibitors include MEDI0680, also known as AMP-514, and REGN2810.

In some aspects, the immune checkpoint inhibitor is a PD-L1 inhibitor such as Durvalumab, also known as MEDI4736, atezolizumab, also known as MPDL3280A, avelumab, also known as MSB00010118C, MDX-1105, BMS-936559, or combinations thereof. In certain aspects, the immune checkpoint inhibitor is a PD-L2 inhibitor such as rHIgM12B7.

In some aspects, the inhibitor comprises the heavy and light chain CDRs or VRs of nivolumab, pembrolizumab, or pidilizumab. Accordingly, in one aspect, the inhibitor comprises the CDR1, CDR2, and CDR3 domains of the VH region of nivolumab, pembrolizumab, or pidilizumab, and the CDR1, CDR2 and CDR3 domains of the VL region of nivolumab, pembrolizumab, or pidilizumab. In another aspect, the antibody competes for binding with and/or binds to the same epitope on PD-1, PD-L1, or PD-L2 as the above-mentioned antibodies. In another aspect, the antibody has at least about 70, 75, 80, 85, 90, 95, 97, or 99% (or any derivable range therein) variable region amino acid sequence identity with the above-mentioned antibodies.

c. CTLA-4, B7-1, and B7-2

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to B7-1 (CD80) or B7-2 (CD86) on the surface of antigen-presenting cells. CTLA-4 is a member of the immunoglobulin superfamily that is expressed on the surface of Helper T cells and transmits an inhibitory signal to T cells. CTLA-4 is similar to the T-cell co-stimulatory protein, CD28, and both molecules bind to B7-1 and B7-2 on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules. Inhibitors of the disclosure may block one or more functions of CTLA-4, B7-1, and/or B7-2 activity. In some aspects, the inhibitor blocks the CTLA-4 and B7-1 interaction. In some aspects, the inhibitor blocks the CTLA-4 and B7-2 interaction.

In some aspects, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

A further anti-CTLA-4 antibody useful as a checkpoint inhibitor in the methods and compositions of the disclosure is ipilimumab (also known as 10D1, MDX-010, MDX-101, and Yervoy®) or antigen binding fragments and variants thereof (see, e.g., WO0 1/14424).

In some aspects, the inhibitor comprises the heavy and light chain CDRs or VRs of tremelimumab or ipilimumab. Accordingly, in one aspect, the inhibitor comprises the CDR1, CDR2, and CDR3 domains of the VH region of tremelimumab or ipilimumab, and the CDR1, CDR2 and CDR3 domains of the VL region of tremelimumab or ipilimumab. In another aspect, the antibody competes for binding with and/or binds to the same epitope on PD-1, B7-1, or B7-2 as the above-mentioned antibodies. In another aspect, the antibody has at least about 70, 75, 80, 85, 90, 95, 97, or 99% (or any derivable range therein) variable region amino acid sequence identity with the above-mentioned antibodies.

4. Inhibition of Co-Stimulatory Molecules

In some aspects, the immunotherapy comprises an inhibitor of a co-stimulatory molecule. In some aspects, the inhibitor comprises an inhibitor of B7-1 (CD80), B7-2 (CD86), CD28, ICOS, OX40 (TNFRSF4), 4-1BB (CD137; TNFRSF9), CD40L (CD40LG), GITR (TNFRSF18), and combinations thereof. Inhibitors include inhibitory antibodies, polypeptides, compounds, and nucleic acids.

5. Dendritic Cell Therapy

Dendritic cell therapy provokes anti-tumor responses by causing dendritic cells to present tumor antigens to lymphocytes, which activates them, priming them to kill other cells that present the antigen. Dendritic cells are antigen presenting cells (APCs) in the mammalian immune system. In cancer treatment, they aid cancer antigen targeting. One example of cellular cancer therapy based on dendritic cells is sipuleucel-T.

One method of inducing dendritic cells to present tumor antigens is by vaccination with autologous tumor lysates or short peptides (small parts of protein that correspond to the protein antigens on cancer cells). These peptides are often given in combination with adjuvants (highly immunogenic substances) to increase the immune and anti-tumor responses. Other adjuvants include proteins or other chemicals that attract and/or activate dendritic cells, such as granulocyte macrophage colony-stimulating factor (GM-CSF).

Dendritic cells can also be activated in vivo by making tumor cells express GM-CSF. This can be achieved by either genetically engineering tumor cells to produce GM-CSF or by infecting tumor cells with an oncolytic virus that expresses GM-CSF.

Another strategy is to remove dendritic cells from the blood of a patient and activate them outside the body. The dendritic cells are activated in the presence of tumor antigens, which may be a single tumor-specific peptide/protein or a tumor cell lysate (a solution of broken down tumor cells). These cells (with optional adjuvants) are infused and provoke an immune response.

Dendritic cell therapies include the use of antibodies that bind to receptors on the surface of dendritic cells. Antigens can be added to the antibody and can induce the dendritic cells to mature and provide immunity to the tumor.

6. CAR-T Cell Therapy

Chimeric antigen receptors (CARs, also known as chimeric immunoreceptors, chimeric T cell receptors or artificial T cell receptors) are engineered receptors that combine a new specificity with an immune cell to target cancer cells. Typically, these receptors graft the specificity of a monoclonal antibody onto a T cell. The receptors are called chimeric because they are fused of parts from different sources. CAR-T cell therapy refers to a treatment that uses such transformed cells for cancer therapy.

The basic principle of CAR-T cell design involves recombinant receptors that combine antigen-binding and T-cell activating functions. The general premise of CAR-T cells is to artificially generate T-cells targeted to markers found on cancer cells. Scientists can remove T-cells from a person, genetically alter them, and put them back into the patient for them to attack the cancer cells. Once the T cell has been engineered to become a CAR-T cell, it acts as a "living drug". CAR-T cells create a link between an extracellular ligand recognition domain to an intracellular signalling molecule which in turn activates T cells. The extracellular ligand recognition domain is usually a single-chain variable fragment (scFv). An important aspect of the safety of CAR-T cell therapy is how to ensure that only cancerous tumor cells are targeted, and not normal cells. The specificity of CAR-T cells is determined by the choice of molecule that is targeted.

Exemplary CAR-T therapies include Tisagenlecleucel (Kymriah) and Axicabtagene ciloleucel (Yescarta). In some aspects, the CAR-T therapy targets CD19.

7. Cytokine Therapy

Cytokines are proteins produced by many types of cells present within a tumor. They can modulate immune responses. The tumor often employs them to allow it to grow and reduce the immune response. These immune-modulating effects allow them to be used as drugs to provoke an immune response. Two commonly used cytokines are interferons and interleukins.

Interferons are produced by the immune system. They are usually involved in anti-viral response, but also have use for cancer. They fall in three groups: type I (IFN$\alpha$ and IFN$\beta$), type II (IFN$\gamma$) and type III (IFN$\lambda$).

Interleukins have an array of immune system effects. IL-2 is an exemplary interleukin cytokine therapy.

8. Adoptive T-Cell Therapy

Adoptive T cell therapy is a form of passive immunization by the transfusion of T-cells (adoptive cell transfer). They are found in blood and tissue and usually activate when they find foreign pathogens. Specifically, they activate when the T-cell's surface receptors encounter cells that display parts of foreign proteins on their surface antigens. These can be either infected cells, or antigen presenting cells (APCs). They are found in normal tissue and in tumor tissue, where they are known as tumor infiltrating lymphocytes (TILs). They are activated by the presence of APCs such as dendritic cells that present tumor antigens. Although these cells can attack the tumor, the environment within the tumor is highly immunosuppressive, preventing immune-mediated tumor death.

Multiple ways of producing and obtaining tumor targeted T-cells have been developed. T-cells specific to a tumor antigen can be removed from a tumor sample (TILs) or filtered from blood. Subsequent activation and culturing is performed ex vivo, with the results reinfused. Activation can take place through gene therapy, or by exposing the T cells to tumor antigens.

It is contemplated that a cancer treatment may exclude any of the cancer treatments described herein. Furthermore, aspects of the disclosure include patients that have been previously treated for a therapy described herein, are currently being treated for a therapy described herein, or have not been treated for a therapy described herein. In some aspects, the patient is one that has been determined to be resistant to a therapy described herein. In some aspects, the patient is one that has been determined to be sensitive to a therapy described herein.

B. Oncolytic Virus

In some aspects, the additional therapy comprises an oncolytic virus. An oncolytic virus is a virus that preferentially infects and kills cancer cells. As the infected cancer cells are destroyed by oncolysis, they release new infectious virus particles or virions to help destroy the remaining tumor. Oncolytic viruses are thought not only to cause direct destruction of the tumor cells, but also to stimulate host anti-tumor immune responses for long-term immunotherapy.

C. Polysaccharides

In some aspects, the additional therapy comprises polysaccharides. Certain compounds found in mushrooms, primarily polysaccharides, can up-regulate the immune system and may have anti-cancer properties. For example, beta-glucans such as lentinan have been shown in laboratory studies to stimulate macrophage, NK cells, T cells and immune system cytokines and have been investigated in clinical trials as immunologic adjuvants.

D. Neoantigens

In some aspects, the additional therapy comprises neoantigen administration. Many tumors express mutations. These mutations potentially create new targetable antigens (neoantigens) for use in T cell immunotherapy. The presence of CD8+ T cells in cancer lesions, as identified using RNA sequencing data, is higher in tumors with a high mutational burden. The level of transcripts associated with cytolytic activity of natural killer cells and T cells positively correlates with mutational load in many human tumors.

E. Chemotherapies

In some aspects, the additional therapy comprises a chemotherapy. Suitable classes of chemotherapeutic agents include (a) Alkylating Agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dicarbazine), (b) Antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) Natural Products, such as vinca alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) Miscellaneous Agents, such as platinum coordination complexes (e.g., cisplatin, carboplatin), substituted ureas (e.g., hydroxyurea), methylhydiazine derivatives (e.g., procarbazine), and adreocortical suppressants (e.g., taxol and mitotane). In some aspects, cisplatin is a particularly suitable chemotherapeutic agent.

Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes such as, for example, intravenous, subcutaneous, intratumoral or intraperitoneal injection. Cisplatin can be used alone or in combination with other agents, with efficacious doses used in clinical applications including about 15 mg/m2 to about 20 mg/m2 for 5 days every three weeks for a total of three courses being contemplated in certain aspects. In some aspects, the amount of cisplatin delivered to the cell and/or subject in conjunction with the construct comprising an Egr-1 promoter operatively linked to a polynucleotide encoding the therapeutic polypeptide is less than the amount that would be delivered when using cisplatin alone.

Other suitable chemotherapeutic agents include antimicrotubule agents, e.g., Paclitaxel ("Taxol") and doxorubicin hydrochloride ("doxorubicin"). The combination of an Egr-1 promoter/TNFα construct delivered via an adenoviral vector and doxorubicin was determined to be effective in overcoming resistance to chemotherapy and/or TNF-α, which suggests that combination treatment with the construct and doxorubicin overcomes resistance to both doxorubicin and TNF-α.

Doxorubicin is absorbed poorly and is preferably administered intravenously. In certain aspects, appropriate intravenous doses for an adult include about 60 mg/m2 to about 75 mg/m2 at about 21-day intervals or about 25 mg/m2 to about 30 mg/m2 on each of 2 or 3 successive days repeated at about 3 week to about 4 week intervals or about 20 mg/m2 once a week. The lowest dose should be used in elderly patients, when there is prior bone-marrow depression caused by prior chemotherapy or neoplastic marrow invasion, or when the drug is combined with other myelopoietic suppressant drugs.

Nitrogen mustards are another suitable chemotherapeutic agent useful in the methods of the disclosure. A nitrogen mustard may include, but is not limited to, mechlorethamine (HN2), cyclophosphamide and/or ifosfamide, melphalan (L-sarcolysin), and chlorambucil. Cyclophosphamide (CYTOXAN®) is available from Mead Johnson and NEOSTAR® is available from Adria), is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluouracil; 5-FU) and floxuridine (fluorode-oxyuridine; FudR). 5-FU may be administered to a subject in a dosage of anywhere between about 7.5 to about 1000 mg/m2. Further, 5-FU dosing schedules may be for a variety of time periods, for example up to six weeks, or as determined by one of ordinary skill in the art to which this disclosure pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present disclosure for these cancers as well.

The amount of the chemotherapeutic agent delivered to the patient may be variable. In one suitable aspect, the chemotherapeutic agent may be administered in an amount effective to cause arrest or regression of the cancer in a host, when the chemotherapy is administered with the construct. In other aspects, the chemotherapeutic agent may be administered in an amount that is anywhere between 2 to 10,000 fold less than the chemotherapeutic effective dose of the chemotherapeutic agent. For example, the chemotherapeutic agent may be administered in an amount that is about 20 fold less, about 500 fold less or even about 5000 fold less than the chemotherapeutic effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

F. Radiotherapy

In some aspects, the additional therapy or prior therapy comprises radiation, such as ionizing radiation. As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

In some aspects, the amount of ionizing radiation is greater than 20 Gy and is administered in one dose. In some aspects, the amount of ionizing radiation is 18 Gy and is administered in three doses. In some aspects, the amount of ionizing radiation is at least, at most, or exactly 2, 4, 6, 8, 10, 15, 16, 17, 18, 19, 20, 21, 22, 23, 24, 25, 26, 27, 18, 19, 30, 31, 32, 33, 34, 35, 36, 37, 38, 39, 40, 41, 42, 43, 44, 45, 46, 47, 48, 49, or 40 Gy (or any derivable range therein). In some aspects, the ionizing radiation is administered in at least, at most, or exactly 1, 2, 3, 4, 5, 6, 7, 8, 9, or 10 doses (or any derivable range therein). When more than one dose is administered, the does may be about 1, 4, 8, 12, or 24 hours or 1, 2, 3, 4, 5, 6, 7, or 8 days or 1, 2, 3, 4, 5, 6, 7, 8, 9, 10, 12, 14, or 16 weeks apart, or any derivable range therein.

In some aspects, the amount of IR may be presented as a total dose of IR, which is then administered in fractionated doses. For example, in some aspects, the total dose is 50 Gy administered in 10 fractionated doses of 5 Gy each. In some aspects, the total dose is 50-90 Gy, administered in 20-60 fractionated doses of 2-3 Gy each. In some aspects, the total dose of IR is at least, at most, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, or 150 (or any derivable range therein). In some aspects, the total dose is administered in fractionated doses of at least, at most, or about 1, 2, 3, 4, 5, 6, 7, 8, 9, 10, 12, 14, 15, 20, 25, 30, 35, 40, 45, or 50 Gy (or any derivable range therein. In some aspects, at least, at most, or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fractionated doses are administered (or any derivable range therein). In some aspects, at least, at most, or about 1, 2, 3, 4, 5, 6, 7, 8, 9, 10, 11, or 12 (or any derivable range therein) fractionated doses are administered per day. In some aspects, at least, at most, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) fractionated doses are administered per week.

G. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present aspects, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

H. Other Agents

It is contemplated that other agents may be used in combination with certain aspects of the present aspects to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other aspects, cytostatic or differentiation agents can be used in combination with certain aspects of the present aspects to improve the anti-hyperproliferative efficacy of the treatments. Inhibitors of cell adhesion are contemplated to improve the efficacy of the present aspects. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present aspects to improve the treatment efficacy.

V. COMBINATION THERAPY

The compositions and related methods of the present disclosure, particularly administration of the masked therapeutic agents of the disclosure may also be used in combination with the administration of additional therapies such as the additional therapeutics described herein or in combination with other traditional therapeutics known in the art for the treatment of cancer.

The therapeutic compositions and treatments disclosed herein may precede, be co-current with and/or follow another treatment or agent by intervals ranging from minutes to weeks. In aspects where agents are applied separately to a cell, tissue or organism, one would generally ensure that a significant period of time did not expire between the time of each delivery, such that the therapeutic agents would still be able to exert an advantageously combined effect on the cell, tissue or organism. For example, in such instances, it is contemplated that one may contact the cell, tissue or organism with two, three, four or more agents or treatments substantially simultaneously (i.e., within less than about a minute). In other aspects, one or more therapeutic agents or treatments may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering another therapeutic agent or treatment.

Various combination regimens of the therapeutic agents and treatments may be employed. Non-limiting examples of such combinations are shown below, wherein a therapeutic agent such as a composition disclosed herein is "A" and a second agent, such as an additional agent or therapy described herein or known in the art is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

In some aspects, more than one course of therapy may be employed. It is contemplated that multiple courses may be implemented.

VI. THERAPEUTIC METHODS

The current methods and compositions relate to methods for treating cancer. In some aspects, the cancer comprises a solid tumor. In some aspects, the cancer is non-lymphatic. In some aspects, the cancer is breast cancer or colon cancer.

The compositions of the disclosure may be used for in vivo, in vitro, or ex vivo administration. The route of administration of the composition may be, for example, intratumoral, intracutaneous, subcutaneous, intravenous, intralymphatic, and intraperitoneal administrations. In some aspects, the administration is intratumoral or intralymphatic or peri-tumoral. In some aspects, the compositions are administered directly into a cancer tissue or a lymph node.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The cancers amenable for treatment include, but are not limited to, tumors of all types, locations, sizes, and characteristics. The methods and compositions of the disclosure are suitable for treating, for example, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, specific breast cancers such as ductal carcinoma in situ, invasive ductal carcinoma, tubular carcinoma of the breast, medullary carcinoma of the breast, mucinous carcinoma of the breast, papillary carcinoma of the breast, cribriform carcinoma of the breast, invasive lobular carcinoma, inflammatory breast cancer, lobular carcinoma in situ, male breast cancer, paget's disease of the nipple, phyllodes tumors of the breast, recurrent and/or metastatic breast, cancer, luminal A or B breast cancer, triple-negative/basal-like breast cancer, and HER2-enriched breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

VII. PHARMACEUTICAL COMPOSITIONS AND METHODS

In some aspects, pharmaceutical compositions are administered to a subject. Different aspects involve administering an effective amount of a composition to a subject. In some aspects, a composition comprising an inhibitor may be administered to the subject or patient to treat cancer or reduce the size of a tumor. Additionally, such compounds can be administered in combination with an additional cancer therapy.

Compositions can be formulated for parenteral administration, e.g., formulated for injection via the intravenous, transcatheter injection, intraarterial injection, intramuscular, subcutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified. The preparation of such formulations will be known to those of skill in the art in light of the present disclosure. Other routes of administration include intratumoral, peri-tumoral, intralymphatic, injection into cancer tissue, and injection into lymph nodes. In some aspects, the administration is systemic.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. The pharmaceutically acceptable salts can be synthesized from the parent compound which contains a basic or acidic moiety by conventional chemical methods.

Some variation in dosage will necessarily occur depending on the condition of the subject. The person responsible for administration will, in any event, determine the appropriate dose for the individual subject. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the effects desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

In certain aspects, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or μg/kg or micrograms/kg/minute or mg/kg/min or micrograms/kg/hour or mg/kg/hour, or any range derivable therein.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of a condition. In some aspects, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of the condition have disappeared or been reduced or after 6, 12, 18, or 24 hours or 1, 2, 3, 4, or 5 days after symptoms of an infection have disappeared or been reduced.

VIII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Fusing Cytokine Receptor to Cytokine as a Mask of Cytokine Activity to Decrease its Toxicity and Increase its Tumor Specific Activation According to the National Cancer Institute, cancer is the second leading cause of death in the US. Cancer immunotherapy has revolutionized the way oncology is practiced clinically, thanks to checkpoint-blocking antibodies (for solid tumors) and adoptive T cell therapy (for liquid cancers). In patients with solid malignancies, checkpoint inhibitor (CPI) therapy induces durable responses in a subset (12.46% as of 2018) of patients (1). Much work has been and continues to be done to understand why only a fraction of patients respond to CPI therapy (2). These studies indicate that the success of CPI therapy depends on pre-existing intratumoral inflammation (3), particularly baseline evidence of activated T cells (4), IFNg-related gene expression signature (5,6) and expression of major histocompatibility complex (MHC) molecules (7). In order to further increase the response rates, novel treatment strategies that focus on inducing inflammation need to be brought to the clinic. Proinflammatory cytokines are powerful molecules capable of driving the differentiation of tumor-reactive CD8+ T cells, activating IFNg pathway and increasing the expression of MHC class I and II molecules. Despite this, their use in the clinic has been limited due to dose-limiting immune-related adverse events (irAEs) caused by these cytokines. Overcoming this challenge is an important step towards the successful translation of cytokines and their broad use in the clinic, as well as design of novel combination immunotherapy strategies.

IL-12 is a 60 kDa heterodimeric cytokine, composed of p35 and p40 subunits connected via a disulfide bond. It binds to the IL-12 receptor complex consisting of IL-12Rb1 and IL-12Rb2, induces phosphorylation of signal transducer and activator of transcription 4 (STAT4) and results in IFNg secretion by T and natural killer (NK) cells. IL-12 plays a crucial role in linking the innate and adaptive arms of immunity(8), as it activates CD4/8 T cells and drives T helper 1-(Th1)-biased response (9), acts as a growth factor for NK cells (10), and primes myeloid cells by augmenting MHC expression (11,12). IFNg itself can act directly on tumor cells, as IFNg receptor complex (IFNGR1 and IFNGR2) is expressed by cancer cells. IFNg exerts potent anti-angiogenic, anti-proliferative and pro-apoptotic effects on cancer cells (13). Most of antitumor activities of IL-12 are associated with IFNg (14), and so are the irAEs (15). In clinical trials, the main toxicities of IL-12 and IFNg therapies were "flu-like" symptoms (16,17) and elevations of liver enzymes (18). Thus, a successful IL-12 therapy must minimize levels of circulating IFNg, while maintaining its level in the tumor (19).

Type I IFNs (IFNa/b) were discovered as potent antiviral cytokines (20) and are now widely acknowledged as critical components of antitumor immunity as well (21). There are many type I IFN members and they all bind to a type I IFN-specific heterodimeric receptor complex, IFNAR1 and IFNAR2. Although IFNa/b and IFNg structurally resemble each other and elicit partially overlapping gene signature, responses stimulated by type I IFNs seem to be broader (22). Type I IFNs activate mainly STAT1, STAT2, but can also activate STAT3 and STAT5 (23-25), whereas IFNg primarily phosphorylates STAT1. IFNa can induce apoptosis of cancer cells, maturation of dendritic cells (DCs) and production of IL-15 by DCs (26). IFNa is approved for the treatment of hairy cell leukemia (27), Kaposi's sarcoma in patients with acquired immunodeficiency syndrome (28) and advanced melanoma (21), yet dose-limiting irAEs occur in 30-50% of the patients (29). In order to extend its serum half-life and decrease the number of doses, polyethylene glycol (PEG) was conjugated to IFNa-2b (PEG Intron) (30). Although this strategy provided a more serum-persistent form of IFNa, severe side effects were still reported, perhaps due to binding to IFNAR expressed on circulating cells and in healthy tissues (31). Engineering type I IFNs that can be activated specifically in the tumor would mitigate the irAEs and increase the fraction of patients benefiting from the therapy.

Here, the inventors sought to develop binding site masking methodology to IL-12 and IFNs, to improve its toxicity. They have used IL-12 receptor beta 1 (IL-12Rb1) fibronectin I and II domains, which are the cytokine binding domain of this receptor protein, as a mask for IL-12 binding site (FIG. 1). The inventors propose an innovative platform for engineering masked IL-12 and IFNs (type I and II), which stay latent during circulation and residence in healthy organs but become activated once in the tumor. They do so by exploiting a high affinity interaction between a cytokine and a subunit of its receptor. When fused together via a tumor protease-sensitive linker, the cytokine-receptor fusion protein acts as a prodrug, remaining inactive in the periphery. Unmasking occurs at the tumor site, either in the tumor extracellular matrix (ECM) or on the tumor cell surface by tumor-associated proteases. This approach will greatly reduce the incidence of irAEs associated with cytokine immunotherapy and enhance the intratumoral inflammation, and sensitizing tumors to CPI therapy, resulting in both increased treatment tolerability and efficacy.

B. Results

Figure 2:
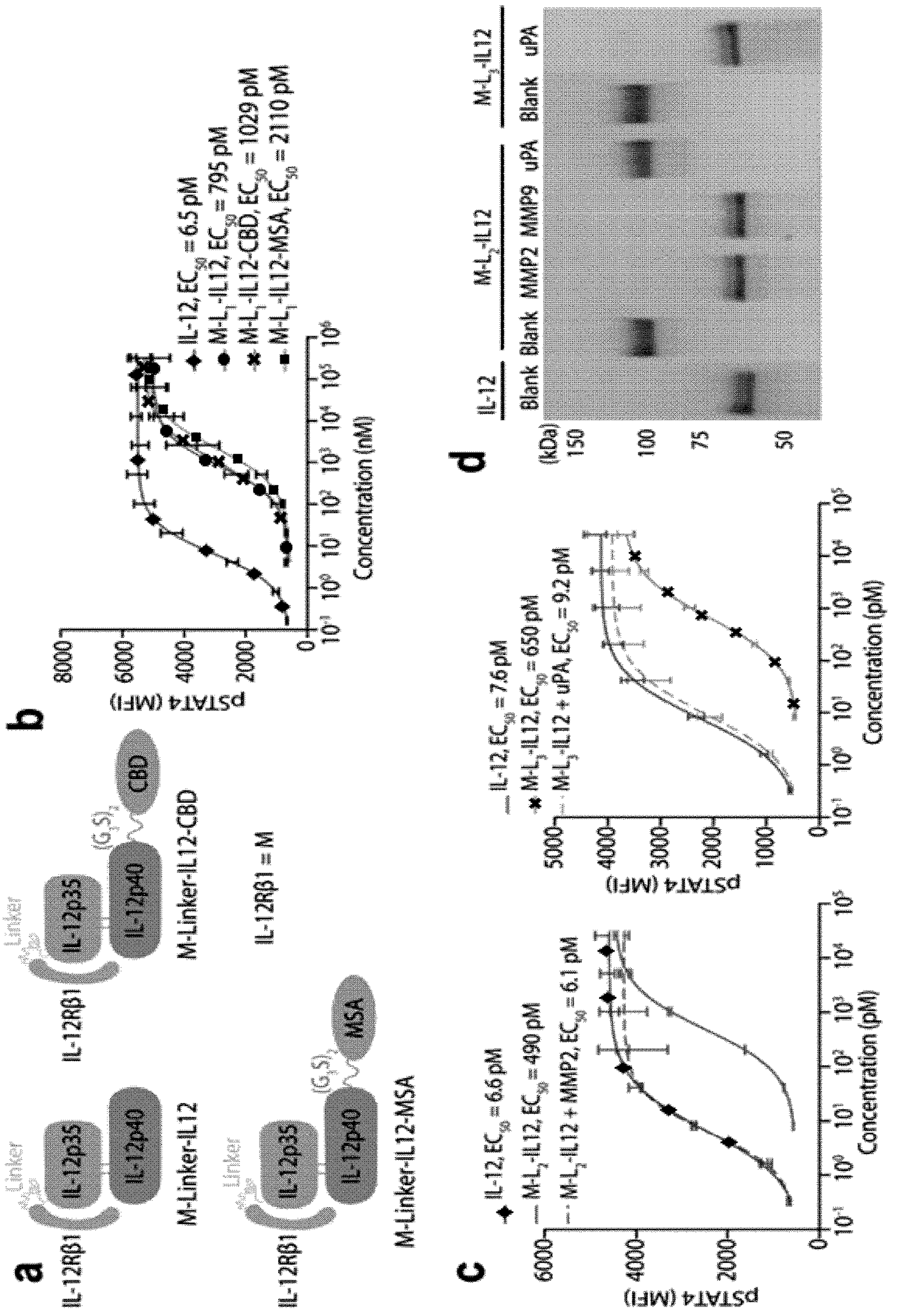
FIG. 2A-D. In vitro characterization of proIL12 constructs. a, Schematics illustrating designs of engineered proIL12 variants. b, Dose-response relationship of phosphorylated STAT4 with IL-12 and proIL12 variants in preactivated primary CD8$^+$ T cells. c, Activation of MMP-sensitive (left) or uPA-sensitive (right) proIL12 molecules with corresponding proteases. d, In vitro cleavage of IL12Rβ1-VP-IL12 and of IL12Rβ1-LS-IL12 by MMPs and uPA. IL-12, IL12Rβ1-VP-IL12 and IL12Rβ1-LS-IL12 were either treated with assay buffer only (Blank), MMP2, MMP9 or uPA for 30 min at 37° C. Decrease of molecular weight from ~105 kDa to ~60 kDa indicates proteolytic cleavage of IL12Rβ1-VP-IL12 and IL12Rβ1-LS-IL12.

Design of 'proIL12' molecules via fusion to IL-12Rb1: The inventors have designed the IL-12Rb1 fibronectin I and II domains recombinant fusion to IL-12 protein. Proteins were expressed by HEK293 cells and then purified by Histidine tag-affinity purification and size-exclusion column purification. Latency can be conferred to cytokines upon fusion of domains that inhibit cytokine-receptor interaction (49,50). It is hypothesized that fusion of part of the murine IL-12Rb1 (Q20-A261, will be referred as the Mask, "M") to IL-12 would render it inactive. This fragment is heavily glycosylated and has a molecular weight (MW) of 27 kDa. By exploiting the heterodimeric structure of IL-12, the inventors fused M to the N-terminus of mouse p35 subunit and co-transfected either with mouse p40, p40-CBD (to increase tumor retention) or p40-MSA (mouse serum albumin; to increase serum half-life) plasmids (FIG. 2A). The optimal linker length between the p35 subunit and IL-12Rb1 domain was determined by varying the number of repeats of (G3S)n and n=11 repeats yielded the purest and most stable fusion protein (M-L1-IL12, $L_1$ refers to (G3S)11 linker). Linkers shorter than that (n=2 and n=5) resulted in poorly folded proteins (data not shown). The inventors were also able to express M-L1-IL12-CBD and M-L1-IL12-MSA proteins. They then tested these constructs for their ability to phosphorylate STAT4 and compared the half-maximal effective concentration (EC50) to that of unmodified IL-12 (FIG. 2B). Masking of IL-12 provided a ~100-fold decrease in activity, supporting the choice of IL12Rb1 as a masking agent. We then expressed several cleavable variants of masked IL-12 by replacing (G3S)11 linker with reported substrates of MMPs and serine proteases. M-L2-IL12 contains 3 repeats of MMP2,9-sensitive VPLSLYSG (SEQ ID NO:134) (VP) substrate and M-L3-IL12 contains 3 repeats of uPA-, matriptase- and legumain-sensitive LSGRSDNH (SEQ ID NO:49) (LS) substrate. Upon incubation of protease-sensitive masked IL-12 variants with respective proteases, activity was fully restored (FIG. 2C). This was further visualized via SDS-polyacrylamide gel electrophoresis (SDS-PAGE) (FIG. 2D). Molecular weight of proIL12 decreases from ~100 kDa to MW of IL-12, indicating complete cleavage of the mask. These results suggest that proIL12 molecules have greatly decreased biological activity thanks to fusion with the portion of IL12Rb1 yet binding to the native IL12R complex is fully restored upon treatment of masked constructs with proteases, thus showing favorable masking and un-masking.

Figure 3:
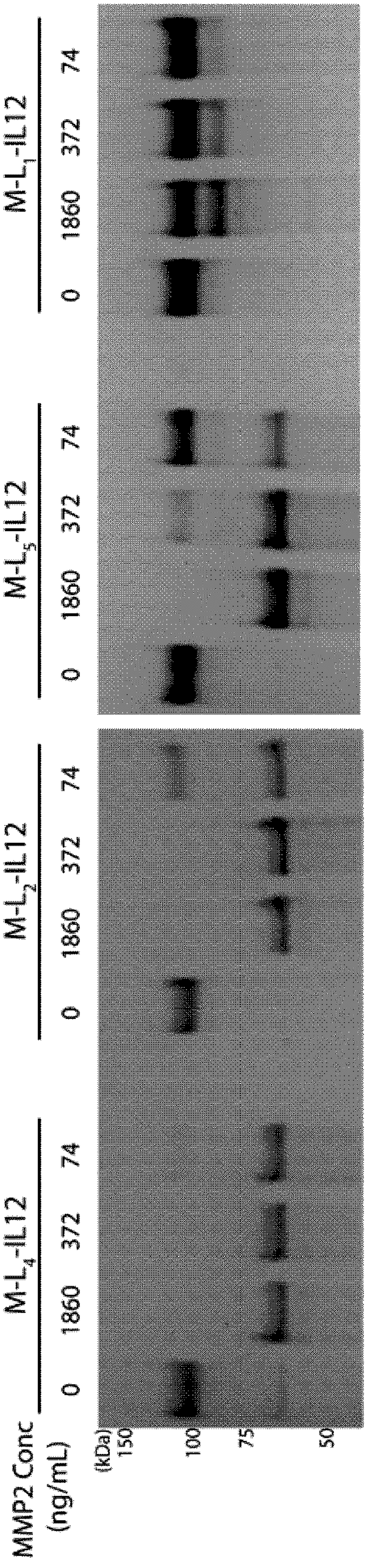
FIG. 3. Cleavage of different linkers by MMP2. ProIL12 molecules (all at the same concentration) containing indicated linker sequences were incubated with varying concentrations of MMP2 and cleavage was visualized via SDS-PAGE.
Figure 4:
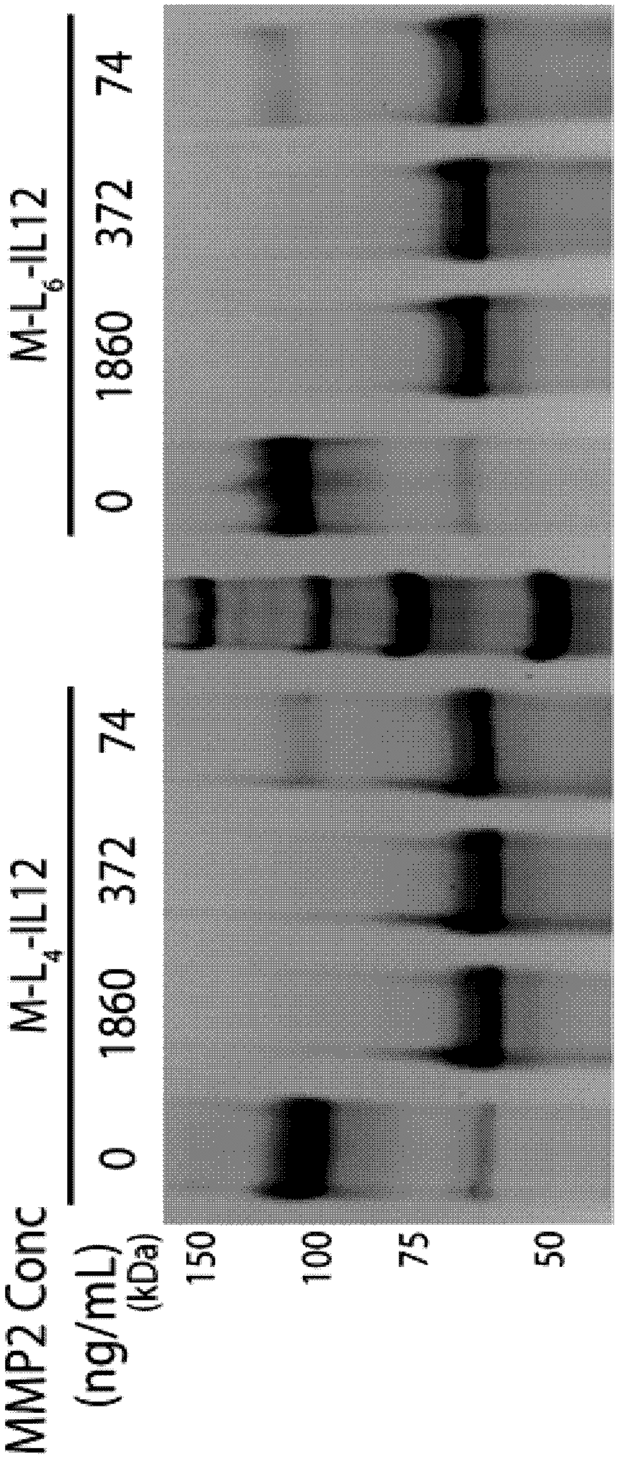
FIG. 4. Comparison of MMP2 sensitivity of $L_4$ and $L_6$.
Figure 6:
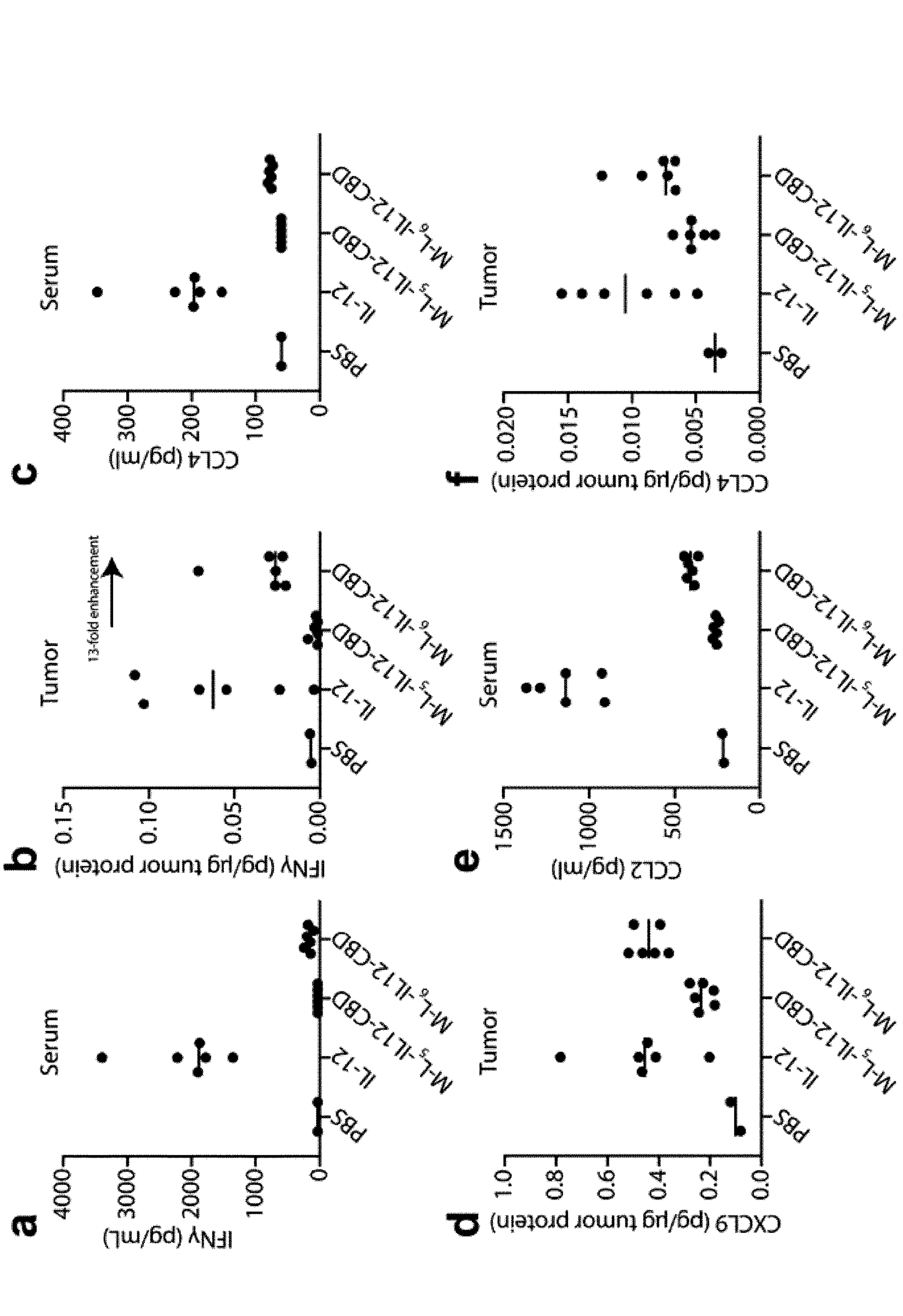
FIG. 6A-F. Quantification of circulating and intratumoral proinflammatory cytokines/chemokines. C57BL/6 mice were inoculated with B16F10 tumors on their back skin on day 0. On day 7, mice were treated i.v. with PBS, 5 mg IL-12, 15 mg M-$L_5$-IL12-CBD (on IL-12 basis) or 15 mg M-$L_6$-IL12-CBD (on IL-12 basis). On day 9, mice were bled, and sera were isolated. On day 10, mice were euthanized, and their tumors were harvested and homogenized. Serum IFNg (a), serum CCL4 (c), serum CCL2 (e), intratumoral IFNg (b), intratumoral CXCL9 (d), and intratumoral CCL4 (f) were measured via LEGENDPlex. Intratumoral cytokine/chemokine values were normalized by total protein concentration.

Linker Engineering: Given that many different linker designs are possible, the inventors explored whether it would be possible to increase linker efficiency in vitro against MMP2 (FIG. 3). Linker containing 3 repeats of HPVGLLAR (SEQ ID NO:138—"HP"), termed L4, was almost fully cleaved at the concentration of 74 ng/ml MMP2, whereas the L2 linker was only partially cleaved at that MMP2 concentration. Furthermore, the linker L5 (containing 1 repeat of VPLSLYSG—SEQ ID NO:134) was even less sensitive to MMP2 cleavage, indicating that increasing repeats of the substrate improves the cleavage kinetics. The inventors designed a linker with 2 repeats of each of HPVGLLAR (SEQ ID NO:138) and VPLSLYSG (SEQ ID NO:134) and added one serine protease sensitive LSGRSDNH (SEQ ID NO:49)-termed L6, to further diversify the repertoire of proteases. The resulting L6 linker, was as sensitive to MMP2 as the L4 linker (FIG. 4). To determine whether the improvement in sensitivity translates into improved antitumor efficacy without exacerbating toxicity, we treated B16F10 melanoma-bearing mice with PBS, IL-12, M-L5-IL12-CBD (low sensitivity linker) or M-L6-IL12-CBD (high sensitivity linker), and quantified serum and intratumoral inflammatory cytokine levels (FIG. 6). ProIL12 molecules induced very little serum IFNg, a key mediator of toxicity (FIG. 6A). However, the intratumoral levels of IFNg were 13-fold higher in mice receiving high sensitivity linker than in the ones receiving low sensitivity linker (FIG. 6B). Serum levels of other proinflammatory chemokines such as CCL2 and CCL4 were greatly diminished by proIL12 treatment when compared to IL-12 (FIGS.

6C,E). M-L6-IL12-CBD treatment induced similar level of CXCL9 as in IL-12-treated mice, a chemokine important for effector T cell recruitment (FIG. 6D). Cumulatively, these data demonstrate that proIL12 molecule bearing a high sensitivity linker is able to induce considerable intratumoral inflammation without causing toxicity. Furthermore, these studies point out that linker sensitivity is crucial for generating adequate intratumoral inflammation.

Figure 5:
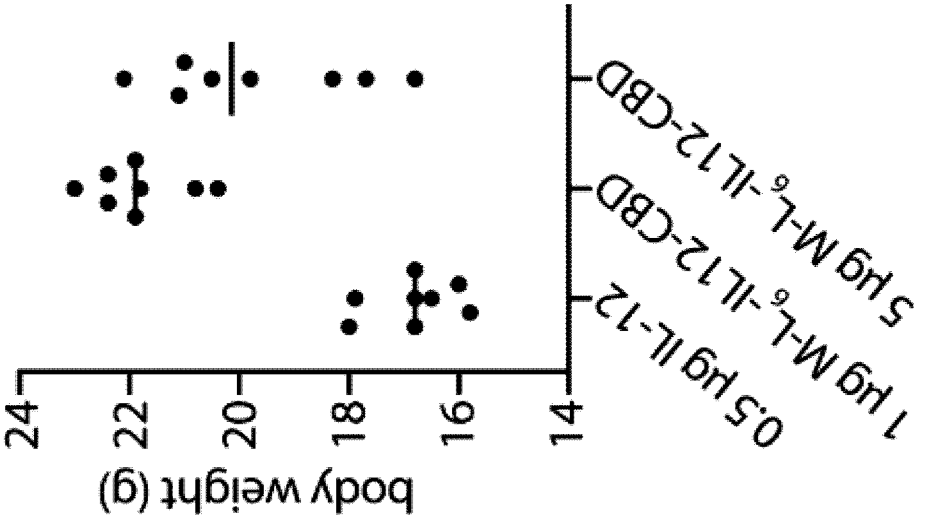
FIG. 5. Body weight of C3H/HeJ mice. 8-week-old female C3H/HeJ mice were dosed s.c. daily for 8 days with indicated amounts of IL-12 or proIL12 (all on IL-12 basis, n=8/group). Mice were weighed the day after the last injection.

Toxicity Assessment of proIL12 in healthy mice: Studies in B16F10-melanoma bearing mice indicated that fusion of a masking agent is able to drastically decrease circulating proinflammatory biomarkers. The inventors sought to investigate the effect of daily proIL12 treatment in healthy C3H/HeJ mice, which are hyperresponsive to low doses of IL-12 treatment (15,53). These mice exhibit physical changes, such as weight loss and lethargy upon daily administration of IL-12. We treated C3H/HeJ mice daily for 8 days with 0.5 mg IL-12, 1 mg M-L6-IL12-CBD or 5 mg M-L6-IL12-CBD (on IL-12 basis) and measured their weight the day after the last dose (FIG. 5). These results illustrate that, even when dosed at 10-fold molar excess, proIL12 is still less toxic than unmodified IL-12. It is also contemplated that the linkers of this example will provide for more favourable toxicological readouts such as systemic liver transaminase levels, pancreas damage levels and complete blood counts.

Figure 7:
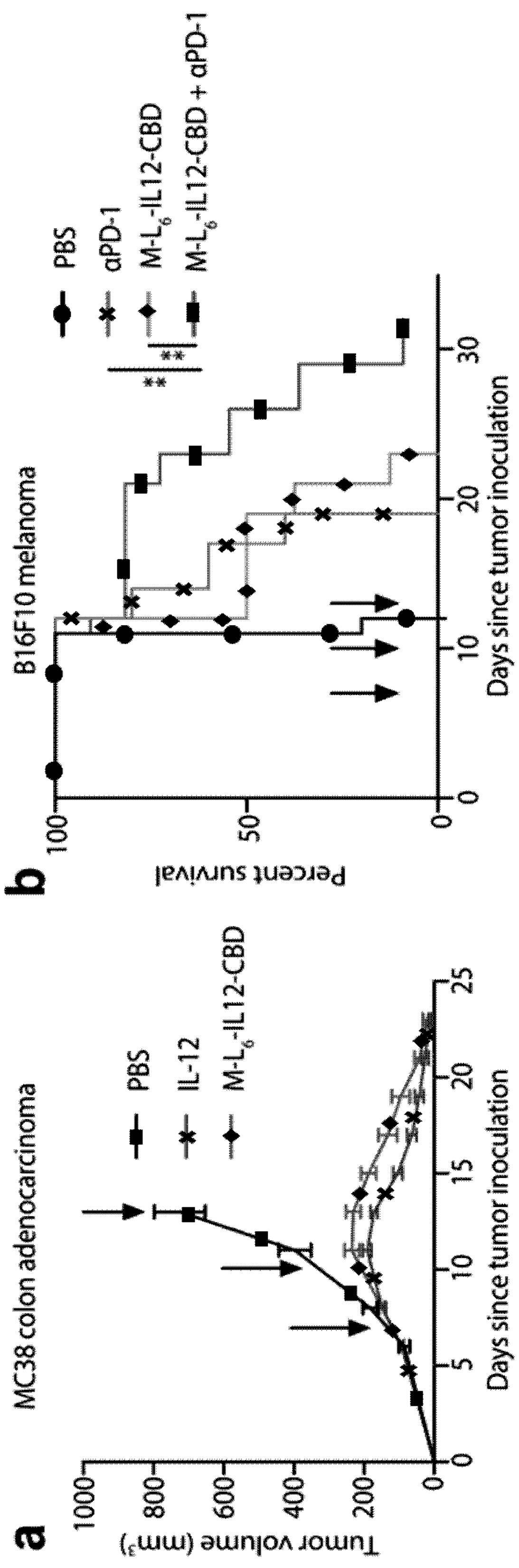
FIG. 7A-B. Antitumor Efficacy of proIL12 in syngeneic tumor models. a, C57BL/6 mice were inoculated with MC38 tumors on their back skin on day 0. On day 7, 10 and 13 mice were treated i.v. with PBS (n=7), 5 mg IL-12 (n=7), or 15 mg M-$L_6$-IL12-CBD (n=7; on IL-12 basis). b, C57BL/6 mice were inoculated with B16F10 tumors on their back skin on day 0. On day 7, 10 and 13 mice were treated i.v. with PBS (n=5), 15 mg M-$L_6$-IL12-CBD (n=8; on IL-12 basis), i.p. with 100 mg aPD-1 (n=5) or combination of M-$L_6$-IL12-CBD and aPD-1 (n=11).

Antitumor efficacy of proIL12 in syngeneic mouse models of cancer: In order to demonstrate that administration of proIL12 can lead to tumor regression or tumor control, the inventors tested the engineered molecules in a rapidly growing, MMP-expressing MC38 colon adenocarcinoma model (FIG. 7A). Mice bearing established tumors were treated with PBS, 5 mg IL-12 or 15 mg M-L6-IL12-CBD (3-fold molar excess) 3 times every 3 days starting on day 7 post-tumor inoculation. Both IL-12 and M-L6-IL12-CBD resulted in complete survival of all treated mice, whereas all PBS-treated mice died by day 13. These results confirmed that proIL12 is efficacious as a single-agent and its efficacy is similar to IL-12 in an immune-infiltrated tumor model. We also evaluated the antitumor effects of proIL12 in combination with a checkpoint-blocking antibody, aPD-1, in B16F10 melanoma model (FIG. 7B). Although both proIL12 and aPD-1 demonstrated some tumor control, combination of the two drugs significantly prolonged the survival of the mice. Together, these data demonstrate that proIL12 induces antitumor effects and can synergize with a checkpoint blocking antibody in syngeneic tumor models.

Figure 8:
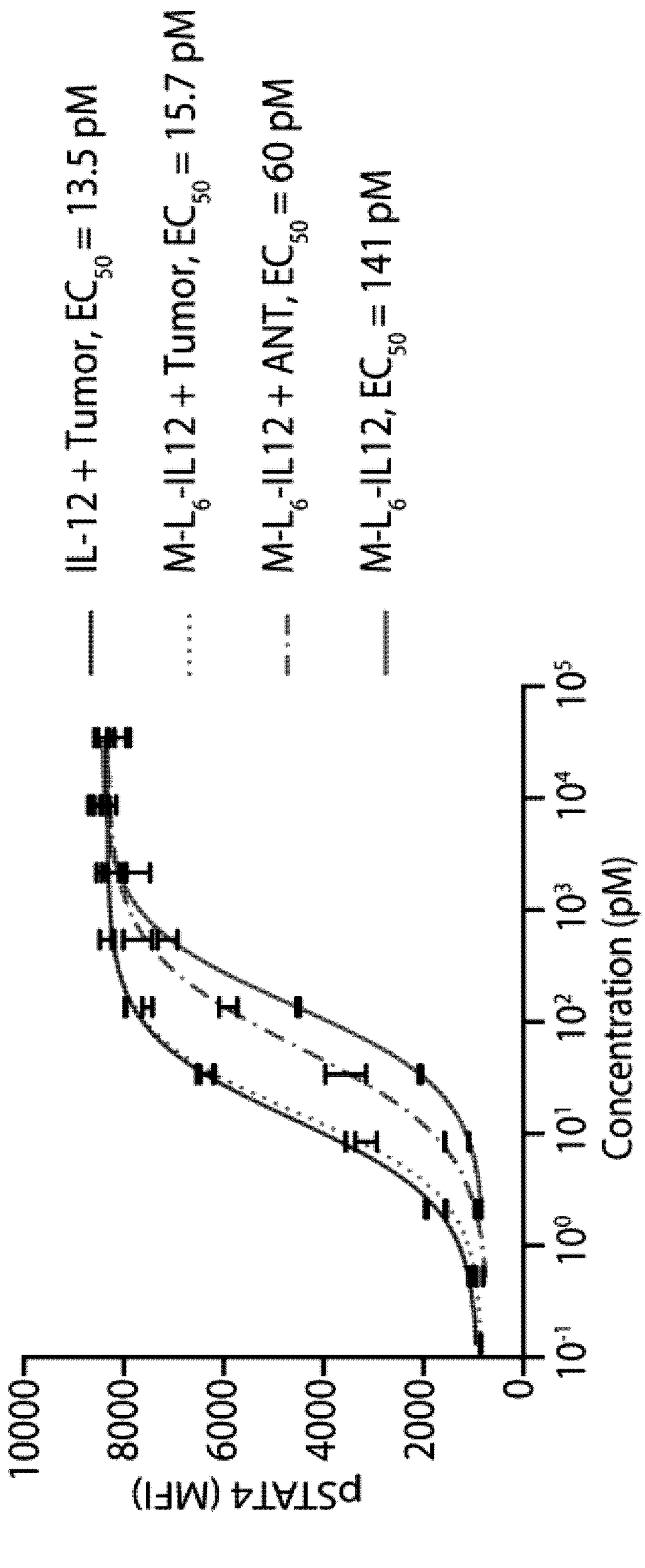
FIG. 8. Activation of proIL12 by human tumor homogenate. IL-12 and proIL12 were diluted to 50 mg/mL and incubated overnight at 37° C. with 2 mg/mL of either human tumor lysate or ANT lysate. As negative control, proIL12 was also incubated with buffer only. Reaction mixtures were further serially diluted in medium and applied to preactivated mouse $CD8^+$ T cells (n=2 per well) at indicated concentration.

Cleavage of proIL12 by human tumor homogenates: The inventors sought to investigate whether proIL12 can be cleaved by a tumor lysate, and whether the cleaved product can bind to IL12R complex and activate cell signaling. To test this, they obtained flash frozen human breast cancer biopsies, as well as a biopsy of the ANT (nonmalignant tissue) from the same patient. The tumor and the ANT were homogenized in an assay buffer commonly used for MMP activation assays and total protein concentration of the lysates was normalized. The inventors incubated proIL12 either with the tumor lysate, ANT lysate or assay buffer alone. We also incubated unmodified IL-12 with the tumor lysate (FIG. 8). Incubation of proIL12 with the human tumor lysate, but not ANT lysate, resulted in activation of proIL12 and induced phosphorylation of STAT4 in the same level as unmodified IL-12 did. Although incubation of proIL12 with ANT resulted in minor activation as compared to proIL12 incubated with buffer only, this is perhaps due to nonspecific degradation of the linker/mask by the intracellular proteases. Nevertheless, these results indicate that human tumor homogenates are able to cleave proIL12 and that activated product can agonize the IL12R complex.

Figure 9:
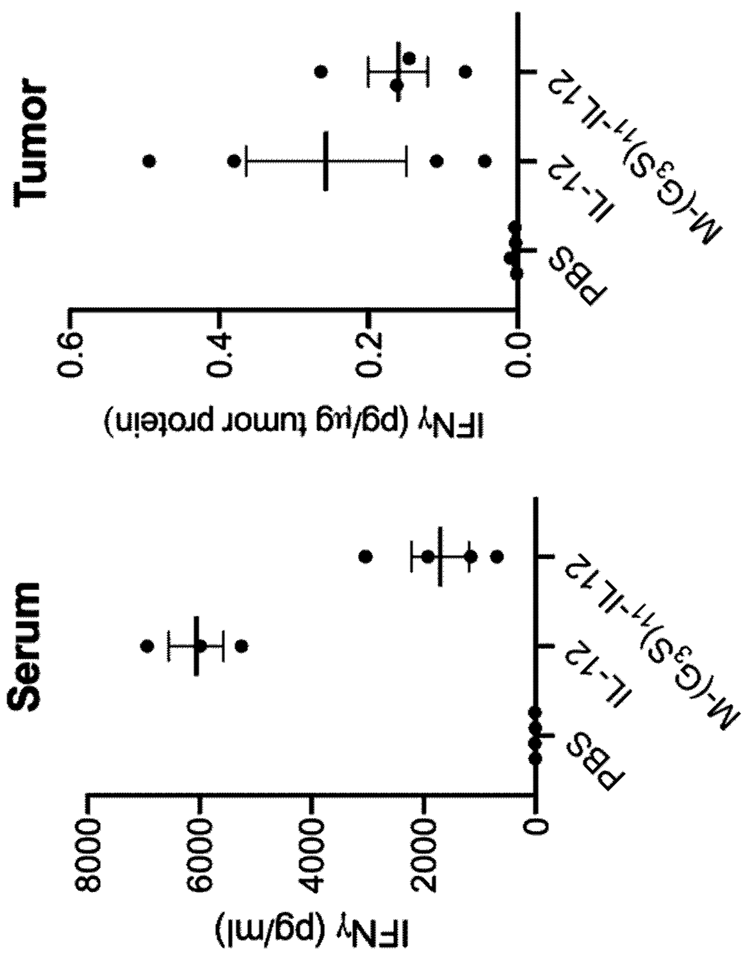
FIG. 9. Non-cleavable masked IL-12 minimizes systemic IFNγ production while maintaining intratumoral IFNγ. B16F10 melanoma-bearing mice were treated once intravenously with 5 μg IL-12 or 15 μg M-$(G_3S)_{11}$-IL12. Plasma and tumors were collected 2 and 3 days after cytokine treatment, respectively. Plasma IFNγ (left) and intratumoral IFNγ (right, normalized by total protein) were quantified using LEGENDPlex.

Engineered IFNg partial agonists decrease levels of STAT1 phosphorylation and bias towards the anti-cancer activity by upregulation of MHC-I without PD-L1: IFNγ is a highly pleiotropic cytokine that is a central coordinator of innate and adaptive immunity, through its actions on a wide range of immune cell types, including macrophages, DCs, and T cells (54). IFNγ is a homodimer (55), engaging two IFNγR1 receptors and two IFNγR2 receptors, which are constitutively expressed on all nucleated cells. Recent work from Prof. Mendoza describes the first complete structure of the hexameric IFNγ-receptor complex which provided a blueprint for breaking the pleiotropy of IFNγ (56). Structure-based designs of IFNγ variants alter the number and strength of binding to the receptors bound on a cell to tune down the strength of the cell signal. Reduction in the phospho-STAT1 signal by the partial agonists results in complete upregulation of the MHC-I necessary for antigen presentation on the tumor but limited expression of programmed death ligand 1 (PD-L1) which limits the activity of immune cells. Therefore, the partial agonists are biased towards the anti-cancer properties along the MHC-I:PD-L1 axis. These effects were demonstrated to work broadly on all cells tested which included seven cancer cell lines and three immune cell populations (FIG. 9). Because these findings were based on the human IFNγ protein, which does not cross-react with the mouse receptors, the inventors must first design a mouse version of the partial agonists. Design of the human analogs of the mouse partial agonists is a challenge because there are no structures of the mouse IFNγ ligand or receptors. Additionally, the sequence identity between the two species is low at 39%. Their first approach was to use a homology model from the human receptor complex where we predicted and screened 13 mouse variants. A mouse melanoma cell line, B16F10, was dosed with 2.5 or 62.5 nM of either wild-type or the mutants but no reduction in MHC-I or PD-L1 was detected by surface staining (data not shown). This experiment suggested engineering using a homology approach would be a challenge and new approaches should be employed.

C. Conclusion

In summary, these studies demonstrate the value of masked cytokines, achieved through fusion with structurally-selected domains of cytokine-specific receptors. Masked cytokines can be administered via i.v. infusion and become activated preferentially in the tumor. The CBD prolongs retention in the tumor. We show substantially reduced incidence of irAEs following administration of masked cytokines, while anti-cancer effects are maintained. This sets the stage for further detailed analysis of masked proinflammatory cytokines, converging with the end goal of treating tumors that are otherwise refractory to conventional immunotherapies. In conclusion, we have developed a technology to reduce cytokine toxicity by fusing cytokine receptor to cytokine. Tumor specific protease responsive site fusion activates the cytokine within tumor. To further improve CBD-IL-12 therapy, fused a domain of the IL-12 receptor IL-12Rb1 to the IL-12, to form IL-12Rb1-IL-12. This fusion is inactive, but inclusion of a MMP or uPA cleavage site between the receptor mask and the cytokine yields a pro-cytokine that can be activated in the tumor microenvironment. We have demonstrated that the immunotoxicity of the IL-12 is thus reduced, and that the IL-12Rb1-IL-12 fusion with the protease-sensitive linker retains therapeutic utility.

D. Materials and Methods

Production and purification of recombinant fusion protein of VWF A3 domain, IL-12Rb1 and IL-12: Protein production and purification were performed as described previously (57). The sequence encoding for the human VWF A3 domain residues Cys1670-Gly1874 (907-1111 of mature VWF), mouse/human IL-12, mouse/human IL-12Rb1 FNI-II domains, the fusion proteins were synthesized and subcloned into the mammalian expression vector pcDNA3.1(+) by Genscript. A sequence encoding for 6 His (SEQ ID NO:87) was added at the N-terminus for further purification of the recombinant protein. Suspension-adapted HEK-293F cells were routinely maintained in serum-free FreeStyle 293 Expression Medium (Gibco). On the day of transfection, cells were inoculated into fresh medium at a density of 1×106 cells/ml. 2 μg/ml plasmid DNA, 2 μg/ml linear 25 kDa polyethylenimine (Polysciences), and OptiPRO SFM media (4% final concentration, Thermo Fisher) were sequentially added. The culture flask was agitated by orbital shaking at 135 rpm at 37° C. in the presence of 5% CO2. 7 days after transfection, the cell culture medium was collected by centrifugation and filtered through a 0.22 μm filter. Culture media was loaded into a HisTrap HP 5 ml column (GE Healthcare), using an ÄKTA pure 25 (GE Healthcare). After washing of the column with wash buffer (20 mM imidazole, 20 mM NaH2PO4, 0.5 M NaCl, pH 7.4), protein was eluted with a gradient of 500 mM imidazole (in 20 mM NaH2PO4, 0.5 M NaCl, pH 7.4). The elusion solution was further purified with size exclusion chromatography using a HiLoad Superdex 200PG column (GE healthcare). All purification steps were carried out at 4° C. The expression of laminin LG domain was determined by western blotting using anti-His tag antibody (BioLegend) and the proteins were verified as >90% pure by SDS-PAGE.

Methods for in vitro cleavage: Recombinant mouse matrix metalloproteinase-2 (MMP2), MMP9 and recombinant human urokinase plasminogen activator (uPA) were purchased from R&D. Since MMP2 and MMP9 were supplied in their zymogen form, MMPs were first activated using 1 mM p-aminophenylmercuric acetate (APMA, Sigma) for 2 hr at 37° C. Following activation, MMPs and cytokines were diluted in an assay buffer containing 150 mM NaCl, 50 mM Tris, 10 mM CaCl2, 0.05% Brij-35 at pH=7.5. Final concentrations of MMP2, MMP9 and cytokine were 2 μg/mL, 5 μg/mL and 50 μg/mL, respectively. Cleavage conducted for 30 min at 37° C. Samples were then analyzed via gel electrophoresis. Cleavage using uPA was conducted according to manufacturer's protocol. Concentration of uPA was 10 g/mL.

Mice and cell lines: The mice and cell lines were prepared as described previously (58). C57BL/6 and C3H/HeJ age 8 to 12 weeks, were obtained from the Charles River laboratories. Experiments were performed with approval from the Institutional Animal Care and Use Committee of the University of Chicago. B16F10 cells were obtained from the American Type Culture Collection and cultured according to the instructions. All cell lines were checked for *mycoplasma* contamination by a pathogen test IMPACT I (IDEXX BioResearch).

Methods for pSTAT4 assessment: Mouse CD8+ T cells were purified from spleens of C57BL/6 mice using EasySep mouse CD8+ T cell isolation kit (Stem Cell). Purified CD8+ T cells (106 cells/mL) were activated in six-well plates precoated with 2 μg/mL α-CD3 (clone 17A2, Bioxcell) and supplemented with soluble 5 μg/mL α-CD28 (clone 37.51, BioLegend) and 30 ng/ml mouse IL-2 (Peprotech) for 3 days. Culture medium was IMDM (Gibco) containing 10% heat-inactivated FBS, 1% Penicillin/Streptomycin and 50 μM 2-mercaptoethanol (Sigma Aldrich). After 3 days of culture, activated CD8+ T cells were rested for 6 hrs in fresh culture medium and were transferred into 96-well plates (50,000 cells/well). Indicated amounts of IL-12 or proIL12 variants were applied to CD8+ T cells for 20 min at 37° C. to induce STAT4 phosphorylation. Cells were fixed immediately using BD Phosflow Lyse/Fix buffer for 10 min at 37° C. and then permeabilized with BD Phosflow Perm Buffer III for 30 min on ice. Cells were stained with Alexa Fluor (AF) 647-conjugated antibody against pSTAT4 (clone 38, BD) recognizing phosphorylation of Tyr693. Staining was performed for 1 hr at room temperature (RT) in the dark. Cells were acquired on BD LSR and data were analyzed using FlowJo (Treestar). Mean Fluorescence Intensity (MFI) of pSTAT4+ population was plotted against cytokine concentration. Dose-response curve was fitted using Prism (v8, GraphPad).

Plasma cytokine concentration analysis: The measurement is performed as described previously (58). 5×105 B16F10 melanoma cells were injected intradermally on left side of the back of each 8 week old C57BL/6 mouse. After 7 days, mice received indicated amounts of IL-12 and of proIL-12 variants. 2 days after IL-12 injection, blood samples were collected in heparinized tubes containing EDTA, followed centrifugation. Cytokine concentration in plasma was measured by LEGENDPLex Kit (BioLegend) according to the manufacture's protocol.

Anti-tumor efficacy of IL-12Rb1-IL-12 on B16F10 tumor: The measurement is performed as described previously (58). A total of 5×105 B16F10 cells re-suspended in 30 μL of PBS were inoculated intradermally on the left side of the back of each C57BL/6 mouse. After 7 days, mice were injected with IL-12 (5 μg), or IL-12Rb1-IL-12 (15 μg on IL-12 basis) i.v. Tumors were measured with a digital caliper starting 7 days after tumor inoculation, and volumes were calculated as ellipsoids, where V=4/3×3.14×depth/2×width/2×height/2. Mice were sacrificed at the point when either tumor volume had reached over 500 mm3.

Example 2—Addition of Serum Proteins for Prolonged Circulation

Pro-cytokine can be improved by CBD-fusion to yield prolonged residence in tumors and/or albumin fusion to yield prolonged circulation. Cytokines generally have a very short half-life in the blood (9). Because pro-cytokine technology is relying on the protease within the body (i.e. tumor), it is important to increase the retention time of injected pro-cytokine within tumor. The inventors employ two approaches to improve the CBD-cytokine platform. The first step is to fuse collagen binding domain to the pro-cytokines. As described in Example 1, CBD can target and retain the fused protein within the tumor due to the nature of the tumor vasculature. Thus, the activity of CBD-pro-cytokine is more specific within the tumor, resulting in enhanced efficacy and safety. This is a form of a dual tumor targeting system.

Another step is to extend the pro-cytokine blood half-life. Because extended blood half-life of injected cytokines will allow more chance to contact tumor tissues, it is hypothesized that the efficacy of CBD-pro-cytokines would be further enhanced. This can be achieved by fusing albumin to CBD-pro-cytokine or pro-cytokine. Thus, these additional aspects of a tumor targeted cytokine with extended blood half-life, which is active only within the tumor microenvironment, are further contemplated.

Example 3: Non-Cleavable Masked Cytokines

A. Background

Attenuation of cytokine bioactivity can provide leverage in terms of toxicity, thereby increasing the tolerability and the therapeutic index. Cytokine masking be achieved via fusion of domains that inhibit cytokine-receptor interaction. Our strategy employs the fusion of a receptor subunit domain (termed the mask, 'M') to the cytokine of interest to decrease the bioactivity. The masking domain and the cytokine are connected via a flexible linker (in our case, $(G_3S)_n$ where n can range from n=3 to n=15). In a previous invention, we taught the use of enzymatically-cleavable linkers; here, we make the surprising discovery that a non-cleavable, flexible linker can attenuate activity in a manner that leads to lower systemic toxicity yet still high intra-tumoral immune activation and anti-cancer effects.

B. Results

Figure 10:
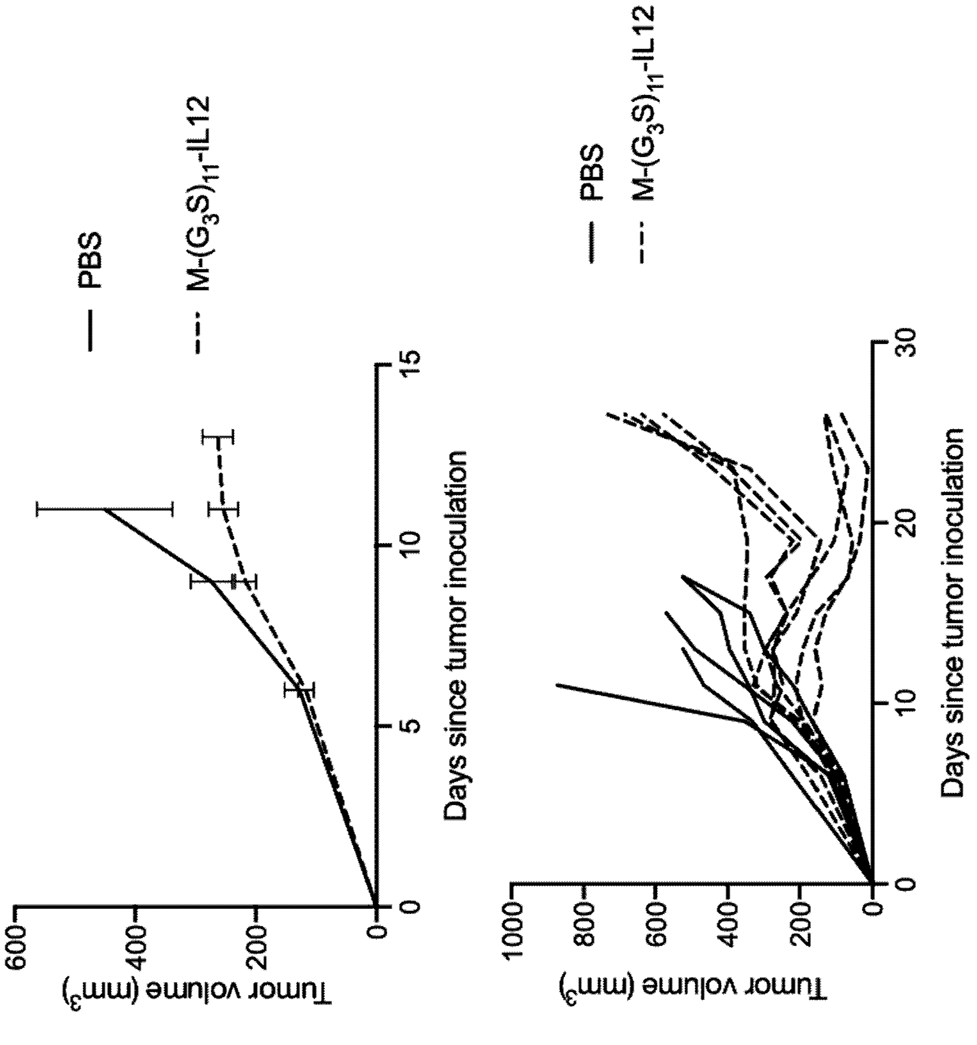
FIG. 10. Non-cleavable masked IL-12 exerts antitumor efficacy in MC38 colon cancer. On day 0, mice were inoculated with MC38 colon cancer cells subcutaneously and on days 7, 10 and 13 were treated intravenously either with saline or 15 μg M-$(G_3S)_{11}$-IL12. Average tumor sizes (top) and individual tumor curves (bottom) are shown.

To evaluate the decrease of systemic toxicity of the non-cleavable, attenuated masked IL-12, we treated B16F10 melanoma-bearing mice either with saline (PBS), 5 μg IL-12 (wild-type) or 15 μg M-$(G_3S)_{11}$-IL12 (non-cleavable masked IL-12). 2 days following treatment with cytokines, we bled the mice to measure serum IFNγ as a biomarker of systemic toxicity (FIG. 9, left). On the third day post-treatment, we collected the tumors and measured intratumoral IFNγ as an indicator of antitumor efficacy (FIG. 9, right). Attenuated, non-cleavable M-$(G_3S)_{11}$-IL12 significantly reduced plasma IFNγ yet still maintained intratumoral inflammation as compared to unmodified IL-12. We then evaluated whether M-$(GsS)_{11}$-IL12 is capable of driving an antitumor response in the MC38 colon adenocarcinoma model (FIG. 10). Non-cleavable M-$(G_3S)_{11}$-IL12 exerted a stronger antitumor immune response when compared to saline treatment.

| | |
|---|---|
| Mouse M-$(G_3S)_{11}$-p35 | QLGASGPGDCCVEKTSFPEGASGSPLGPRNLSCYRVSKTDYECSWQ<br>YDGPEDNVSHVLWCCFVPPNHTHTGQERCRYFSSGPDRTVQFWEQ<br>DGIPVLSKVNFWVESRLGNRTMKSQKISQYLYNWTKTTPPLGHIKV<br>SQSHRQLRMDWNVSEEAGAEVQFRRRMPTTNWTLGDCGPQVNSG<br>SGVLGDIRGSMSESCLCPSENMAQEIQIRRRRRLSSGAPGGPWSDWS<br>MPVCVPPEVLPQA**GGGSGGGSGGGSGGGSGGGSGGGSGGGSGG**<br>**GSGGGSGGGSGGGS**RVIPVSGPARCLSQSRNLLKTTDDMVKTARE<br>KLKHYSCTAEDIDHEDITRDQTSTLKTCLPLELHKNESCLATRETSS<br>TTRGSCLPPQKTSLMMTLCLGSIYEDLKMYQTEFQAINAALQNHNH<br>QQIILDKGMLVAIDELMQSLNHNGETLRQKPPVGEADPYRVKMKL<br>CILLHAFSTRVVTINRVMGYLSSAHHHHHH (SEQ ID NO: 247) |
| Mouse p40 | MWELEKDVYVVEVDWTPDAPGETVNLTCDTPEEDDITWTSDQRH<br>GVIGSGKTLTITVKEFLDAGQYTCHKGGETLSHSHLLLHKKENGIW<br>STEILKNFKNKTFLKCEAPNYSGRFTCSWLVQRNMDLKFNIKSSSSS<br>PDSRAVTCGMASLSAEKVTLDQRDYEKYSVSCQEDVTCPTAEETLP<br>IELALEARQQNKYENYSTSFFIRDIIKPDPPKNLQMKPLKNSQVEVS<br>WEYPDSWSTPHSYFSLKFFVRIQRKKEKMKETEEGCNQKGAFLVE<br>KTSTEVQCKGGNVCVQAQDRYYNSSCSKWACVPCRVRS (SEQ ID<br>NO: 6) |
| Human M-$(G_3S)_{11}$-p35 | CRTSECCFQDPPYPDADSGSASGPRDLRCYRISSDRYECSWQYEGPT<br>AGVSHFLRCCLSSGRCCYFAAGSATRLQFSDQAGVSVLYTVTLWV<br>ESWARNQTEKSPEVTLQLYNSVKYEPPLGDIKVSKLAGQLRMEWE<br>TPDNQVGAEVQFRHRTPSSPWKLGDCGPQDDDTESCLCPLEMNVA<br>QEFQLRRRQLGSQGSSWSKWSSPVCVPPE**GGGSGGGSGGGSGGG**<br>**SGGGSGGGSGGGSGGGSGGGSGGGSGGGS**GRNLPVATPDPGMF<br>PCLHHSQNLLRAVSNMLQKARQTLEFYPCTSEEIDHEDITKDKTSTV<br>EACLPLELTKNESCLNSRETSFITNGSCLASRKTSFMMALCLSSIYED<br>LKMYQVEFKTMNAKLLMDPKRQIFLDQNMLAVIDELMQALNFNSE<br>TVPQKSSLEEPDFYKTKIKLCILLHAFRIRAVTIDRVMSYLNASHHH<br>HHH (SEQ ID NO: 248) |
| Human p40 | IWELKKDVYVVELDWYPDAPGEMVVLTCDTPEEDGITWTLDQSSE<br>VLGSGKTLTIQVKEFGDAGQYTCHKGGEVLSHSLLLLHKKEDGIWS<br>TDILKDQKEPKNKTFLRCEAKNYSGRFTCWWLTTISTDLTFSVKSSR<br>GSSDPQGVTCGAATLSAERVRGDNKEYEYSVECQEDSACPAAEESL<br>PIEVMVDAVHKLKYENYTSSFFIRDIIKPDPPKNLQLKPLKNSRQVE<br>VSWEYPDTWSTPHSYFSLTFCVQVQGKSKREKKDRVFTDKTSATVI<br>CRKNASISVRAQDRYYSSSWSEWASVPCS (SEQ ID NO: 4) |

Amino acid sequences of mouse and human non-cleavable masked IL-12 variants. The functional IL-12 heterodimer is obtained via the co-transfection of the subunits encoding wild-type p35 (or masked p35) and p40.

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments. Any reference to a patent publication or other publication is a herein a specific incorporation by reference of the disclosure of that publication. The claims are not to be interpreted as including means-plus- or step-plus-function limitations, unless such a limitation is explicitly recited in a given claim using the phrase(s) "means for" or "step for," respectively.

REFERENCES

The following references and the publications referred to throughout the specification, to the extent that they provide exemplary procedural or other details supplementary to those set forth herein, are specifically incorporated herein by reference.

1. Haslam, A. & Prasad, V. Estimation of the Percentage of US Patients With Cancer Who Are Eligible for and Respond to Checkpoint Inhibitor Immunotherapy Drugs. JAMA Network Open 2, e192535-e192535 (2019).
2. Hodges, T. R., et al. Mutational burden, immune checkpoint expression, and mismatch repair in glioma: implications for immune checkpoint immunotherapy. Neuro-Oncology 19, 1047-1057 (2017).
3. Rodig, S. J., et al. MHC proteins confer differential sensitivity to CTLA-4 and PD-1 blockade in untreated metastatic melanoma. Sci Transl Med 10(2018).
4. Gide, T. N., et al. Distinct Immune Cell Populations Define Response to Anti-PD-1 Monotherapy and Anti-PD-1/Anti-CTLA-4 Combined Therapy. Cancer Cell 35, 238-255.e236 (2019).
5. Ayers, M., et al. IFN-γ-related mRNA profile predicts clinical response to PD-1 blockade. J Clin Invest 127, 2930-2940 (2017).
6. Gao, J., et al. Loss of IFN-γ Pathway Genes in Tumor Cells as a Mechanism of Resistance to Anti-CTLA-4 Therapy. Cell 167, 397-404.e399 (2016).
7. Liu, D., et al. Integrative molecular and clinical modeling of clinical outcomes to PD1 blockade in patients with metastatic melanoma. Nat Med 25, 1916-1927 (2019).
8. Langrish, C. L., et al. IL-12 and IL-23: master regulators of innate and adaptive immunity. Immunol Rev 202, 96-105 (2004).
9. Szabo, S. J., Dighe, A. S., Gubler, U. & Murphy, K. M. Regulation of the interleukin (IL)-12R beta 2 subunit expression in developing T helper 1 (Th1) and Th2 cells. J Exp Med 185, 817-824 (1997).
10. Kobayashi, M., et al. Identification and purification of natural killer cell stimulatory factor (NKSF), a cytokine with multiple biologic effects on human lymphocytes. J Exp Med 170, 827-845 (1989).
11. Grohmann, U., et al. IL-12 acts directly on DC to promote nuclear localization of NF-kappaB and primes DC for IL-12 production. Immunity 9, 315-323 (1998).
12. Nagayama, H., et al. IL-12 responsiveness and expression of IL-12 receptor in human peripheral blood monocyte-derived dendritic cells. J Immunol 165, 59-66 (2000).
13. Miller, C. H., Maher, S. G. & Young, H. A. Clinical Use of Interferon-gamma. Ann N Y Acad Sci 1182, 69-79 (2009).
14. Garris, C. S., et al. Successful Anti-PD-1 Cancer Immunotherapy Requires T Cell-Dendritic Cell Crosstalk Involving the Cytokines IFN-γ and IL-12. Immunity 49, 1148-1161.e1147 (2018).
15. Leonard, J. P., et al. Effects of single-dose interleukin-12 exposure on interleukin-12-associated toxicity and interferon-gamma production. Blood 90, 2541-2548 (1997).
16. Kurzrock, R., Quesada, J. R., Rosenblum, M. G., Sherwin, S. A. & Gutterman, J. U. Phase I study of i.v. administered recombinant gamma interferon in cancer patients. Cancer Treat Rep 70, 1357-1364 (1986).
17. Atkins, M. B., et al. Phase I evaluation of intravenous recombinant human interleukin 12 in patients with advanced malignancies. Clin Cancer Res 3, 409-417 (1997).
18. Garnick, M. B., et al. Phase I/II study of recombinant interferon gamma in advanced renal cell carcinoma. J Urol 139, 251-255 (1988).
19. Mansurov, A., et al. Collagen-binding IL-12 enhances tumour inflammation and drives the complete remission of established immunologically cold mouse tumours. Nat Biomed Eng 4, 531-543 (2020).
20. Sin, W. X., Li, P., Yeong, J. P. & Chin, K. C. Activation and regulation of interferon-β in immune responses. Immunol Res 53, 25-40 (2012).
21. Borden, E. C. Interferons α and β in cancer: therapeutic opportunities from new insights. Nat Rev Drug Discov 18, 219-234 (2019).
22. Platanias, L. C. Mechanisms of type-I- and type-II-interferon-mediated signalling. Nat Rev Immunol 5, 375-386 (2005).
23. Darnell, J. E., Jr., Kerr, I. M. & Stark, G. R. Jak-STAT pathways and transcriptional activation in response to IFNs and other extracellular signaling proteins. Science 264, 1415-1421 (1994).
24. Meinke, A., Barahmand-Pour, F., Wöhrl, S., Stoiber, D. & Decker, T. Activation of different Stat5 isoforms contributes to cell-type-restricted signaling in response to interferons. Mol Cell Biol 16, 6937-6944 (1996).
25. Stark, G. R., Kerr, I. M., Williams, B. R., Silverman, R. H. & Schreiber, R. D. How cells respond to interferons. Annu Rev Biochem 67, 227-264 (1998).
26. Mattei, F., Schiavoni, G., Belardelli, F. & Tough, D. F. IL-15 Is Expressed by Dendritic Cells in Response to Type I IFN, Double-Stranded RNA, or Lipopolysaccharide and Promotes Dendritic Cell Activation. The Journal of Immunology 167, 1179-1187 (2001).
27. Golomb, H. M., et al. Alpha-2 interferon therapy of hairy-cell leukemia: a multicenter study of 64 patients. J Clin Oncol 4, 900-905 (1986).
28. Groopman, J. E., et al. Recombinant alpha-2 interferon therapy for Kaposi's sarcoma associated with the acquired immunodeficiency syndrome. Ann Intern Med 100, 671-676 (1984).
29. Kantarjian, H. M., O'Brien, S., Anderlini, P. & Talpaz, M. Treatment of myelogenous leukemia: current status and investigational options. Blood 87, 3069-3081 (1996).
30. Wang, Y. S., et al. Identification of the major positional isomer of pegylated interferon alpha-2b. Biochemistry 39, 10634-10640 (2000).
31. Bukowski, R. M., et al. Treating cancer with PEG Intron: pharmacokinetic profile and dosing guidelines for an improved interferon-alpha-2b formulation. Cancer 95, 389-396 (2002).
32. Hollingsworth, R. E. & Jansen, K. Turning the corner on therapeutic cancer vaccines, npj Vaccines 4, 7 (2019).
33. Ishihara, J., et al. Targeted antibody and cytokine cancer immunotherapies through collagen affinity. Sci Transl Med 11(2019).
34. Fischer, A. Mechanism of the Proteolytic Activity of Malignant Tissue Cells. Nature 157, 442-442 (1946).

35. Kessenbrock, K., Plaks, V. & Werb, Z. Matrix metalloproteinases: regulators of the tumor microenvironment. Cell 141, 52-67 (2010).
36. Ulisse, S., Baldini, E., Sorrenti, S. & D'Armiento, M. The urokinase plasminogen activator system: a target for anti-cancer therapy. Curr Cancer Drug Targets 9, 32-71 (2009).
37. Uhland, K. Matriptase and its putative role in cancer. Cell Mol Life Sci 63, 2968-2978 (2006).
38. Ardi, V. C., Kupriyanova, T. A., Deryugina, E. I. & Quigley, J. P. Human neutrophils uniquely release TIMP-free MMP-9 to provide a potent catalytic stimulator of angiogenesis. Proc Natl Acad Sci USA 104, 20262-20267 (2007).
39. Nakamura, E. S., Koizumi, K., Kobayashi, M. & Saiki, I. Inhibition of lymphangiogenesis-related properties of murine lymphatic endothelial cells and lymph node metastasis of lung cancer by the matrix metalloproteinase inhibitor MMI270. Cancer Sci 95, 25-31 (2004).
40. Liu, S. C., et al. Relationships between the level of matrix metalloproteinase-2 and tumor size of breast cancer. Clin Chim Acta 371, 92-96 (2006).
41. Schmalfeldt, B., et al. Increased expression of matrix metalloproteinases (MMP)-2, MMP-9, and the urokinase-type plasminogen activator is associated with progression from benign to advanced ovarian cancer. Clin Cancer Res 7, 2396-2404 (2001).
42. Werle, B., et al. Cathepsin B, plasminogenactivator-inhibitor (PAI-1) and plasminogenactivator-receptor (uPAR) are prognostic factors for patients with non-small cell lung cancer. Anticancer Res 24, 4147-4161 (2004).
43. Remacle, A., Murphy, G. & Roghi, C. Membrane type I-matrix metalloproteinase (MT1-MMP) is internalised by two different pathways and is recycled to the cell surface. Journal of Cell Science 116, 3905-3916 (2003).
44. Cui, G., Cai, F., Ding, Z. & Gao, L. MMP14 predicts a poor prognosis in patients with colorectal cancer. Hum Pathol 83, 36-42 (2019).
45. Yao, Q., Kou, L., Tu, Y. & Zhu, L. MMP-Responsive 'Smart' Drug Delivery and Tumor Targeting. Trends Pharmacol Sci 39, 766-781 (2018).
46. Dai, Z., Yao, Q. & Zhu, L. MMP2-Sensitive PEG-Lipid Copolymers: A New Type of Tumor-Targeted P-Glycoprotein Inhibitor. ACS Appl Mater Interfaces 8, 12661-12673 (2016).
47. Desnoyers, L. R., et al. Tumor-Specific Activation of an EGFR-Targeting Probody Enhances Therapeutic Index. Science Translational Medicine 5, 207ra144-207ra144 (2013).
48. Trang, V. H., et al. A coiled-coil masking domain for selective activation of therapeutic antibodies. Nature Biotechnology 37, 761-765 (2019).
49. Adams, G., Vessillier, S., Dreja, H. & Chernajovsky, Y. Targeting cytokines to inflammation sites. Nat Biotechnol 21, 1314-1320 (2003).
50. Gerspach, J., et al. Restoration of membrane TNF-like activity by cell surface targeting and matrix metalloproteinase-mediated processing of a TNF prodrug. Cell Death Differ 13, 273-284 (2006).
51. Turk, B. E., Huang, L. L., Piro, E. T. & Cantley, L. C. Determination of protease cleavage site motifs using mixture-based oriented peptide libraries. Nat Biotechnol 19, 661-667 (2001).
52. Spranger, S., Dai, D., Horton, B. & Gajewski, T. F. Tumor-Residing Batf3 Dendritic Cells Are Required for Effector T Cell Trafficking and Adoptive T Cell Therapy. Cancer Cell 31, 711-723.e714 (2017).
53. Huber, V. C., et al. Delivery of IL-12 intranasally leads to reduced IL-12-mediated toxicity. Int Immunopharmacol 3, 801-809 (2003).
54. Ni, L. & Lu, J. Interferon gamma in cancer immunotherapy. Cancer Med 7, 4509-4516 (2018).
55. Yphantis, D. A. & Arakawa, T. Sedimentation equilibrium measurements of recombinant DNA derived human interferon gamma. Biochemistry 26, 5422-5427 (1987).
56. Mendoza, J. L., et al. Structure of the IFN gamma receptor complex guides design of biased agonists. Nature 567, 56-+(2019).
57. Martino, M. M., et al. Growth factors engineered for super-affinity to the extracellular matrix enhance tissue healing. Science 343, 885-888 (2014).
58. Ishihara, J., et al. Matrix-binding checkpoint immunotherapies enhance antitumor efficacy and reduce adverse events. Sci Transl Med 9(2017).

The invention claimed is:

1. A polypeptide comprising interleukin-12 (IL-12) linked to a masking agent through a linker, wherein the masking agent comprises IL-12R or an IL-12-binding fragment thereof, and wherein the linker comprises the amino acid sequence of SEQ ID NO: 13.

2. The polypeptide of claim 1, wherein the IL12 comprises the p35 and p40 subunits linked through a disulfide bond or through a peptide linker.

3. The polypeptide of claim 1, wherein the IL12R polypeptide or fragment comprises IL12Rβ1, or a fragment thereof and wherein the IL12Rβ1 polypeptide or fragment comprises human FNI-II domain of IL-12Rβ1.

4. The polypeptide of claim 1, wherein the masking agent is fused to the N-terminus of the p35 subunit of IL12, and wherein the linker is between the masking agent and the p35 subunit of IL12 or wherein the masking agent is fused to the C-terminus of the p40 subunit of IL12, and wherein the linker is between the masking agent and the p40 subunit of IL12.

5. The polypeptide of claim 1, wherein the linker comprises the amino acid sequence of SEQ ID NO:219 or SEQ ID NO:220 or an amino acid sequence that has at least 80% sequence identity to SEQ ID NO:219 or SEQ ID NO:220.

6. The polypeptide of claim 1, wherein the polypeptide is conjugated to a tumor targeting agent.

7. The polypeptide of claim 6, wherein the tumor-targeting agent comprises an antibody or antigen-binding fragment thereof, and wherein the antibody or antigen-binding fragment comprises a stroma targeting antibody or stroma-binding fragment thereof.

8. The polypeptide of claim 7, wherein the tumor targeting agent comprises a Fab that specifically binds to an alternatively spliced domain of fibronectin comprising extra domain A (EDA).

9. The polypeptide of claim 7, wherein the tumor targeting agent comprises an antibody or antigen binding fragment thereof that specifically binds to a tumor-associated antigen or wherein the tumor targeting agent comprises a collagen binding domain and wherein the collagen binding domain comprises a collagen binding domain from decorin or von Willebrand factor (vWF).

10. The polypeptide of claim 1, wherein the polypeptide further comprises a serum protein conjugated to the polypeptide.

11. A pharmaceutical composition comprising the polypeptide of claim 1.

12. A nucleic acid encoding for the polypeptide of claim 1.

13. A host cell comprising the nucleic acid of claim 12.

14. A method for making a polypeptide comprising expressing the nucleic acid of claim 12 in a cell and isolate the expressed polypeptide.

15. A method for treating cancer comprising administering the polypeptide of claim 1.

* * * * *

SEQUENCE LISTING

```
<160> NUMBER OF SEQ ID NOS: 249

<210> SEQ ID NO 1
<211> LENGTH: 202
<212> TYPE: PRT
<213> ORGANISM: Artificial Sequence
<220> FEATURE:
<223> OTHER INFORMATION: Synthetic Polypeptide

<400> SEQUENCE: 1

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60
```

Glu Lys Ala His Leu Leu Ser Leu Val Asp Val Met Gln Arg Glu Gly
65 70 75 80

Gly Pro Ser Gln Ile Gly Asp Ala Leu Gly Phe Ala Val Arg Tyr Leu
85 90 95

Thr Ser Glu Met His Gly Ala Arg Pro Gly Ala Ser Lys Ala Val Val
100 105 110

Ile Leu Val Thr Asp Val Ser Val Asp Ser Val Asp Ala Ala Ala Asp
115 120 125

Ala Ala Arg Ser Asn Arg Val Thr Val Phe Pro Ile Gly Ile Gly Asp
130 135 140

Arg Tyr Asp Ala Ala Gln Leu Arg Ile Leu Ala Gly Pro Ala Gly Asp
145 150 155 160

Ser Asn Val Val Lys Leu Gln Arg Ile Glu Asp Leu Pro Thr Met Val
165 170 175

Thr Leu Gly Asn Ser Phe Leu His Lys Leu Cys Ser Gly Phe Val Arg
180 185 190

Ile Cys Thr Gly His His His His His His
195 200

<210> SEQ ID NO 2
<211> LENGTH: 248
<212> TYPE: PRT
<213> ORGANISM: Mus musculus

<400> SEQUENCE: 2

Gln Leu Gly Ala Ser Gly Pro Gly Asp Gly Cys Cys Val Glu Lys Thr
1 5 10 15

Ser Phe Pro Glu Gly Ala Ser Gly Ser Pro Leu Gly Pro Arg Asn Leu
20 25 30

Ser Cys Tyr Arg Val Ser Lys Thr Asp Tyr Glu Cys Ser Trp Gln Tyr
35 40 45

Asp Gly Pro Glu Asp Asn Val Ser His Val Leu Trp Cys Cys Phe Val
50 55 60

Pro Pro Asn His Thr His Thr Gly Gln Glu Arg Cys Arg Tyr Phe Ser
65 70 75 80

Ser Gly Pro Asp Arg Thr Val Gln Phe Trp Glu Gln Asp Gly Ile Pro
85 90 95

Val Leu Ser Lys Val Asn Phe Trp Val Glu Ser Arg Leu Gly Asn Arg
100 105 110

Thr Met Lys Ser Gln Lys Ile Ser Gln Tyr Leu Tyr Asn Trp Thr Lys
115 120 125

Thr Thr Pro Pro Leu Gly His Ile Lys Val Ser Gln Ser His Arg Gln
130 135 140

Leu Arg Met Asp Trp Asn Val Ser Glu Glu Ala Gly Ala Glu Val Gln
145 150 155 160

Phe Arg Arg Arg Met Pro Thr Thr Asn Trp Thr Leu Gly Asp Cys Gly
165 170 175

Pro Gln Val Asn Ser Gly Ser Gly Val Leu Gly Asp Ile Arg Gly Ser
180 185 190

Met Ser Glu Ser Cys Leu Cys Pro Ser Glu Asn Met Ala Gln Glu Ile
195 200 205

Gln Ile Arg Arg Arg Arg Arg Leu Ser Ser Gly Ala Pro Gly Gly Pro
210 215 220

Trp Ser Asp Trp Ser Met Pro Val Cys Val Pro Pro Glu Val Leu Pro
225 230 235 240

Gln Ala Leu Val Pro Arg Gly Ser
245

<210> SEQ ID NO 3
<211> LENGTH: 197
<212> TYPE: PRT
<213> ORGANISM: Homo Sapiens

<400> SEQUENCE: 3

Arg Asn Leu Pro Val Ala Thr Pro Asp Pro Gly Met Phe Pro Cys Leu
1 5 10 15

His His Ser Gln Asn Leu Leu Arg Ala Val Ser Asn Met Leu Gln Lys
20 25 30

Ala Arg Gln Thr Leu Glu Phe Tyr Pro Cys Thr Ser Glu Glu Ile Asp
35 40 45

His Glu Asp Ile Thr Lys Asp Lys Thr Ser Thr Val Glu Ala Cys Leu
50 55 60

Pro Leu Glu Leu Thr Lys Asn Glu Ser Cys Leu Asn Ser Arg Glu Thr
65 70 75 80

Ser Phe Ile Thr Asn Gly Ser Cys Leu Ala Ser Arg Lys Thr Ser Phe
85 90 95

Met Met Ala Leu Cys Leu Ser Ser Ile Tyr Glu Asp Leu Lys Met Tyr
100 105 110

Gln Val Glu Phe Lys Thr Met Asn Ala Lys Leu Leu Met Asp Pro Lys
115 120 125

Arg Gln Ile Phe Leu Asp Gln Asn Met Leu Ala Val Ile Asp Glu Leu
130 135 140

Met Gln Ala Leu Asn Phe Asn Ser Glu Thr Val Pro Gln Lys Ser Ser
145 150 155 160

Leu Glu Glu Pro Asp Phe Tyr Lys Thr Lys Ile Lys Leu Cys Ile Leu
165 170 175

Leu His Ala Phe Arg Ile Arg Ala Val Thr Ile Asp Arg Val Met Ser
180 185 190

Tyr Leu Asn Ala Ser
195

<210> SEQ ID NO 4
<211> LENGTH: 306
<212> TYPE: PRT
<213> ORGANISM: Homo Sapiens

<400> SEQUENCE: 4

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Ser Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Val Leu Ser His Ser Leu Leu
65 70 75 80

Leu Leu His Lys Lys Glu Asp Gly Ile Trp Ser Thr Asp Ile Leu Lys
85 90 95

```
Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 5
<211> LENGTH: 193
<212> TYPE: PRT
<213> ORGANISM: Mus musculus

<400> SEQUENCE: 5

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
    130                 135                 140
```

Asn His Asn Gly Glu Thr Leu Arg Gln Lys Pro Pro Val Gly Glu Ala
145 150 155 160

Asp Pro Tyr Arg Val Lys Met Lys Leu Cys Ile Leu Leu His Ala Phe
165 170 175

Ser Thr Arg Val Val Thr Ile Asn Arg Val Met Gly Tyr Leu Ser Ser
180 185 190

Ala

<210> SEQ ID NO 6
<211> LENGTH: 313
<212> TYPE: PRT
<213> ORGANISM: Mus musculus

<400> SEQUENCE: 6

Met Trp Glu Leu Glu Lys Asp Val Tyr Val Val Glu Val Asp Trp Thr
1 5 10 15

Pro Asp Ala Pro Gly Glu Thr Val Asn Leu Thr Cys Asp Thr Pro Glu
20 25 30

Glu Asp Asp Ile Thr Trp Thr Ser Asp Gln Arg His Gly Val Ile Gly
35 40 45

Ser Gly Lys Thr Leu Thr Ile Thr Val Lys Glu Phe Leu Asp Ala Gly
50 55 60

Gln Tyr Thr Cys His Lys Gly Gly Glu Thr Leu Ser His Ser His Leu
65 70 75 80

Leu Leu His Lys Lys Glu Asn Gly Ile Trp Ser Thr Glu Ile Leu Lys
85 90 95

Asn Phe Lys Asn Lys Thr Phe Leu Lys Cys Glu Ala Pro Asn Tyr Ser
100 105 110

Gly Arg Phe Thr Cys Ser Trp Leu Val Gln Arg Asn Met Asp Leu Lys
115 120 125

Phe Asn Ile Lys Ser Ser Ser Ser Ser Pro Asp Ser Arg Ala Val Thr
130 135 140

Cys Gly Met Ala Ser Leu Ser Ala Glu Lys Val Thr Leu Asp Gln Arg
145 150 155 160

Asp Tyr Glu Lys Tyr Ser Val Ser Cys Gln Glu Asp Val Thr Cys Pro
165 170 175

Thr Ala Glu Glu Thr Leu Pro Ile Glu Leu Ala Leu Glu Ala Arg Gln
180 185 190

Gln Asn Lys Tyr Glu Asn Tyr Ser Thr Ser Phe Phe Ile Arg Asp Ile
195 200 205

Ile Lys Pro Asp Pro Pro Lys Asn Leu Gln Met Lys Pro Leu Lys Asn
210 215 220

Ser Gln Val Glu Val Ser Trp Glu Tyr Pro Asp Ser Trp Ser Thr Pro
225 230 235 240

His Ser Tyr Phe Ser Leu Lys Phe Phe Val Arg Ile Gln Arg Lys Lys
245 250 255

Glu Lys Met Lys Glu Thr Glu Glu Gly Cys Asn Gln Lys Gly Ala Phe
260 265 270

Leu Val Glu Lys Thr Ser Thr Glu Val Gln Cys Lys Gly Gly Asn Val
275 280 285

Cys Val Gln Ala Gln Asp Arg Tyr Tyr Asn Ser Ser Cys Ser Lys Trp
290 295 300

Ala Cys Val Pro Cys Arg Val Arg Ser
305 310

<210> SEQ ID NO 7
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 7

Gln Leu Gly Ala Ser Gly Pro Gly Asp Gly Cys Cys Val Glu Lys Thr
1 5 10 15

Ser Phe Pro Glu Gly Ala Ser Gly Ser Pro Leu Gly Pro Arg Asn Leu
20 25 30

Ser Cys Tyr Arg Val Ser Lys Thr Asp Tyr Glu Cys Ser Trp Gln Tyr
35 40 45

Asp Gly Pro Glu Asp Asn Val Ser His Val Leu Trp Cys Cys Phe Val
50 55 60

Pro Pro Asn His Thr His Thr Gly Gln Glu Arg Cys Arg Tyr Phe Ser
65 70 75 80

Ser Gly Pro Asp Arg Thr Val Gln Phe Trp Glu Gln Asp Gly Ile Pro
85 90 95

Val Leu Ser Lys Val Asn Phe Trp Val Glu Ser Arg Leu Gly Asn Arg
100 105 110

Thr Met Lys Ser Gln Lys Ile Ser Gln Tyr Leu Tyr Asn Trp Thr Lys
115 120 125

Thr Thr Pro Pro Leu Gly His Ile Lys Val Ser Gln Ser His Arg Gln
130 135 140

Leu Arg Met Asp Trp Asn Val Ser Glu Glu Ala Gly Ala Glu Val Gln
145 150 155 160

Phe Arg Arg Arg Met Pro Thr Thr Asn Trp Thr Leu Gly Asp Cys Gly
165 170 175

Pro Gln Val Asn Ser Gly Ser Gly Val Leu Gly Asp Ile Arg Gly Ser
180 185 190

Met Ser Glu Ser Cys Leu Cys Pro Ser Glu Asn Met Ala Gln Glu Ile
195 200 205

Gln Ile Arg Arg Arg Arg Arg Leu Ser Ser Gly Ala Pro Gly Gly Pro
210 215 220

Trp Ser Asp Trp Ser Met Pro Val Cys Val Pro Pro Glu Val Leu Pro
225 230 235 240

Gln Ala Leu Val Pro Arg Gly Ser Gly Gly Gly Ser Gly Gly Gly Ser
245 250 255

Arg Val Ile Pro Val Ser Gly Pro Ala Arg Cys Leu Ser Gln Ser Arg
260 265 270

Asn Leu Leu Lys Thr Thr Asp Asp Met Val Lys Thr Ala Arg Glu Lys
275 280 285

Leu Lys His Tyr Ser Cys Thr Ala Glu Asp Ile Asp His Glu Asp Ile
290 295 300

Thr Arg Asp Gln Thr Ser Thr Leu Lys Thr Cys Leu Pro Leu Glu Leu
305 310 315 320

His Lys Asn Glu Ser Cys Leu Ala Thr Arg Glu Thr Ser Ser Thr Thr
325 330 335

Arg Gly Ser Cys Leu Pro Pro Gln Lys Thr Ser Leu Met Met Thr Leu
340 345 350

Cys Leu Gly Ser Ile Tyr Glu Asp Leu Lys Met Tyr Gln Thr Glu Phe
355 360 365

```
Gln Ala Ile Asn Ala Ala Leu Gln Asn His Asn His Gln Gln Ile Ile
    370                 375                 380

Leu Asp Lys Gly Met Leu Val Ala Ile Asp Glu Leu Met Gln Ser Leu
385                 390                 395                 400

Asn His Asn Gly Glu Thr Leu Arg Gln Lys Pro Pro Val Gly Glu Ala
                405                 410                 415

Asp Pro Tyr Arg Val Lys Met Lys Leu Cys Ile Leu Leu His Ala Phe
            420                 425                 430

Ser Thr Arg Val Val Thr Ile Asn Arg Val Met Gly Tyr Leu Ser Ser
        435                 440                 445

Ala


<210> SEQ ID NO 8
<211> LENGTH: 585
<212> TYPE: PRT
<213> ORGANISM: Artificial Sequence
<220> FEATURE:
<223> OTHER INFORMATION: Synthetic Polypeptide

<400> SEQUENCE: 8

Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
            20                  25                  30

Ser Cys Tyr Arg Val Ser Lys Thr Asp Tyr Glu Cys Ser Trp Gln Tyr
        35                  40                  45

Asp Gly Pro Glu Asp Asn Val Ser His Val Leu Trp Cys Cys Phe Val
    50                  55                  60

Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95

Val Leu Ser Lys Val Asn Phe Trp Val Glu Ser Arg Leu Gly Asn Arg
            100                 105                 110

Thr Met Lys Ser Gln Lys Ile Ser Gln Tyr Leu Tyr Asn Trp Thr Lys
        115                 120                 125

Thr Thr Pro Pro Leu Gly His Ile Lys Val Ser Gln Ser His Arg Gln
    130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Leu Val Pro Arg Gly Ser Gly Gly Gly Ser Gly Gly Gly Ser
                245                 250                 255

Gly Gly Gly Ser Gly Gly Gly Ser Gly Gly Gly Ser Gly Gly Gly Ser
            260                 265                 270
```

```
Met Trp Glu Leu Glu Lys Asp Val Tyr Val Val Glu Val Asp Trp Thr
        275                 280                 285

Pro Asp Ala Pro Gly Glu Thr Val Asn Leu Thr Cys Asp Thr Pro Glu
    290                 295                 300

Glu Asp Asp Ile Thr Trp Thr Ser Asp Gln Arg His Gly Val Ile Gly
305                 310                 315                 320

Ser Gly Lys Thr Leu Thr Ile Thr Val Lys Glu Phe Leu Asp Ala Gly
                325                 330                 335

Gln Tyr Thr Cys His Lys Gly Gly Glu Thr Leu Ser His Ser His Leu
            340                 345                 350

Leu Leu His Lys Lys Glu Asn Gly Ile Trp Ser Thr Glu Ile Leu Lys
        355                 360                 365

Asn Phe Lys Asn Lys Thr Phe Leu Lys Cys Glu Ala Pro Asn Tyr Ser
    370                 375                 380

Gly Arg Phe Thr Cys Ser Trp Leu Val Gln Arg Asn Met Asp Leu Lys
385                 390                 395                 400

Phe Asn Ile Lys Ser Ser Ser Ser Ser Pro Asp Ser Arg Ala Val Thr
                405                 410                 415

Cys Gly Met Ala Ser Leu Ser Ala Glu Lys Val Thr Leu Asp Gln Arg
            420                 425                 430

Asp Tyr Glu Lys Tyr Ser Val Ser Cys Gln Glu Asp Val Thr Cys Pro
        435                 440                 445

Thr Ala Glu Glu Thr Leu Pro Ile Glu Leu Ala Leu Glu Ala Arg Gln
    450                 455                 460

Gln Asn Lys Tyr Glu Asn Tyr Ser Thr Ser Phe Phe Ile Arg Asp Ile
465                 470                 475                 480

Ile Lys Pro Asp Pro Pro Lys Asn Leu Gln Met Lys Pro Leu Lys Asn
                485                 490                 495

Ser Gln Val Glu Val Ser Trp Glu Tyr Pro Asp Ser Trp Ser Thr Pro
            500                 505                 510

His Ser Tyr Phe Ser Leu Lys Phe Phe Val Arg Ile Gln Arg Lys Lys
        515                 520                 525

Glu Lys Met Lys Glu Thr Glu Glu Gly Cys Asn Gln Lys Gly Ala Phe
    530                 535                 540

Leu Val Glu Lys Thr Ser Thr Glu Val Gln Cys Lys Gly Gly Asn Val
545                 550                 555                 560

Cys Val Gln Ala Gln Asp Arg Tyr Tyr Asn Ser Ser Cys Ser Lys Trp
                565                 570                 575

Ala Cys Val Pro Cys Arg Val Arg Ser
            580                 585
```

<210> SEQ ID NO 9
<211> LENGTH: 459
<212> TYPE: PRT
<213> ORGANISM: Artificial Sequence
<220> FEATURE:
<223> OTHER INFORMATION: Synthetic Polypeptide

<400> SEQUENCE: 9

```
Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
            20                  25                  30

Ser Cys Tyr Arg Val Ser Lys Thr Asp Tyr Glu Cys Ser Trp Gln Tyr
        35                  40                  45
```

-continued

```
Asp Gly Pro Glu Asp Asn Val Ser His Val Leu Trp Cys Cys Phe Val
    50                  55                  60

Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95

Val Leu Ser Lys Val Asn Phe Trp Val Glu Ser Arg Leu Gly Asn Arg
            100                 105                 110

Thr Met Lys Ser Gln Lys Ile Ser Gln Tyr Leu Tyr Asn Trp Thr Lys
        115                 120                 125

Thr Thr Pro Pro Leu Gly His Ile Lys Val Ser Gln Ser His Arg Gln
    130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Gly Leu Leu Ser Gly Arg Ser Asp Asn His Gly Gly Gly Ser
                245                 250                 255

Gly Gly Gly Ser Arg Val Ile Pro Val Ser Gly Pro Ala Arg Cys Leu
            260                 265                 270

Ser Gln Ser Arg Asn Leu Leu Lys Thr Thr Asp Asp Met Val Lys Thr
        275                 280                 285

Ala Arg Glu Lys Leu Lys His Tyr Ser Cys Thr Ala Glu Asp Ile Asp
    290                 295                 300

His Glu Asp Ile Thr Arg Asp Gln Thr Ser Thr Leu Lys Thr Cys Leu
305                 310                 315                 320

Pro Leu Glu Leu His Lys Asn Glu Ser Cys Leu Ala Thr Arg Glu Thr
                325                 330                 335

Ser Ser Thr Thr Arg Gly Ser Cys Leu Pro Pro Gln Lys Thr Ser Leu
            340                 345                 350

Met Met Thr Leu Cys Leu Gly Ser Ile Tyr Glu Asp Leu Lys Met Tyr
        355                 360                 365

Gln Thr Glu Phe Gln Ala Ile Asn Ala Ala Leu Gln Asn His Asn His
    370                 375                 380

Gln Gln Ile Ile Leu Asp Lys Gly Met Leu Val Ala Ile Asp Glu Leu
385                 390                 395                 400

Met Gln Ser Leu Asn His Asn Gly Glu Thr Leu Arg Gln Lys Pro Pro
                405                 410                 415

Val Gly Glu Ala Asp Pro Tyr Arg Val Lys Met Lys Leu Cys Ile Leu
            420                 425                 430

Leu His Ala Phe Ser Thr Arg Val Val Thr Ile Asn Arg Val Met Gly
        435                 440                 445

Tyr Leu Ser Ser Ala His His His His His His
    450                 455
```

<210> SEQ ID NO 10
<211> LENGTH: 579
<212> TYPE: PRT
<213> ORGANISM: Artificial Sequence
<220> FEATURE:
<223> OTHER INFORMATION: Synthetic Polypeptide

<400> SEQUENCE: 10

```
Cys Cys Val Glu Lys Thr Ser Phe Pro Glu Gly Ala Ser Gly Ser Pro
1               5                   10                  15

Leu Gly Pro Arg Asn Leu Ser Cys Tyr Arg Val Ser Lys Thr Asp Tyr
            20                  25                  30

Glu Cys Ser Trp Gln Tyr Asp Gly Pro Glu Asp Asn Val Ser His Val
        35                  40                  45

Leu Trp Cys Cys Phe Val Pro Pro Asn His Thr His Thr Gly Gln Glu
    50                  55                  60

Arg Cys Arg Tyr Phe Ser Ser Gly Pro Asp Arg Thr Val Gln Phe Trp
65                  70                  75                  80

Glu Gln Asp Gly Ile Pro Val Leu Ser Lys Val Asn Phe Trp Val Glu
                85                  90                  95

Ser Arg Leu Gly Asn Arg Thr Met Lys Ser Gln Lys Ile Ser Gln Tyr
            100                 105                 110

Leu Tyr Asn Trp Thr Lys Thr Thr Pro Pro Leu Gly His Ile Lys Val
        115                 120                 125

Ser Gln Ser His Arg Gln Leu Arg Met Asp Trp Asn Val Ser Glu Glu
    130                 135                 140

Ala Gly Ala Glu Val Gln Phe Arg Arg Arg Met Pro Thr Thr Asn Trp
145                 150                 155                 160

Thr Leu Gly Asp Cys Gly Pro Gln Val Asn Ser Gly Ser Gly Val Leu
                165                 170                 175

Gly Asp Ile Arg Gly Ser Met Ser Glu Ser Cys Leu Cys Pro Ser Glu
            180                 185                 190

Asn Met Ala Gln Glu Ile Gln Ile Arg Arg Arg Arg Arg Leu Ser Ser
        195                 200                 205

Gly Ala Pro Gly Gly Pro Trp Ser Asp Trp Ser Met Pro Val Cys Val
    210                 215                 220

Pro Pro Glu Val Leu Pro Gln Ala Gly Leu Leu Ser Gly Arg Ser Asp
225                 230                 235                 240

Asn His Gly Gly Gly Ser Gly Gly Gly Ser Gly Gly Gly Ser Gly Gly
                245                 250                 255

Gly Ser Gly Gly Gly Ser Gly Gly Gly Ser Met Trp Glu Leu Glu Lys
            260                 265                 270

Asp Val Tyr Val Val Glu Val Asp Trp Thr Pro Asp Ala Pro Gly Glu
        275                 280                 285

Thr Val Asn Leu Thr Cys Asp Thr Pro Glu Glu Asp Asp Ile Thr Trp
    290                 295                 300

Thr Ser Asp Gln Arg His Gly Val Ile Gly Ser Gly Lys Thr Leu Thr
305                 310                 315                 320

Ile Thr Val Lys Glu Phe Leu Asp Ala Gly Gln Tyr Thr Cys His Lys
                325                 330                 335

Gly Gly Glu Thr Leu Ser His Ser His Leu Leu Leu His Lys Lys Glu
            340                 345                 350

Asn Gly Ile Trp Ser Thr Glu Ile Leu Lys Asn Phe Lys Asn Lys Thr
        355                 360                 365
```

Phe Leu Lys Cys Glu Ala Pro Asn Tyr Ser Gly Arg Phe Thr Cys Ser
    370                 375                 380

Trp Leu Val Gln Arg Asn Met Asp Leu Lys Phe Asn Ile Lys Ser Ser
385                 390                 395                 400

Ser Ser Ser Pro Asp Ser Arg Ala Val Thr Cys Gly Met Ala Ser Leu
                405                 410                 415

Ser Ala Glu Lys Val Thr Leu Asp Gln Arg Asp Tyr Glu Lys Tyr Ser
            420                 425                 430

Val Ser Cys Gln Glu Asp Val Thr Cys Pro Thr Ala Glu Glu Thr Leu
        435                 440                 445

Pro Ile Glu Leu Ala Leu Glu Ala Arg Gln Gln Asn Lys Tyr Glu Asn
    450                 455                 460

Tyr Ser Thr Ser Phe Phe Ile Arg Asp Ile Ile Lys Pro Asp Pro Pro
465                 470                 475                 480

Lys Asn Leu Gln Met Lys Pro Leu Lys Asn Ser Gln Val Glu Val Ser
                485                 490                 495

Trp Glu Tyr Pro Asp Ser Trp Ser Thr Pro His Ser Tyr Phe Ser Leu
            500                 505                 510

Lys Phe Phe Val Arg Ile Gln Arg Lys Lys Glu Lys Met Lys Glu Thr
        515                 520                 525

Glu Glu Gly Cys Asn Gln Lys Gly Ala Phe Leu Val Glu Lys Thr Ser
    530                 535                 540

Thr Glu Val Gln Cys Lys Gly Gly Asn Val Cys Val Gln Ala Gln Asp
545                 550                 555                 560

Arg Tyr Tyr Asn Ser Ser Cys Ser Lys Trp Ala Cys Val Pro Cys Arg
                565                 570                 575

Val Arg Ser

<210> SEQ ID NO 11
<211> LENGTH: 786
<212> TYPE: PRT
<213> ORGANISM: Artificial Sequence
<220> FEATURE:
<223> OTHER INFORMATION: Synthetic Polypeptide

<400> SEQUENCE: 11

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

-continued

```
Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile Gly Gly Gly Ser Gly Gly Gly Ser Gln Leu Gly Ala Ser Gly Pro
        195                 200                 205

Gly Asp Gly Cys Cys Val Glu Lys Thr Ser Phe Pro Glu Gly Ala Ser
    210                 215                 220

Gly Ser Pro Leu Gly Pro Arg Asn Leu Ser Cys Tyr Arg Val Ser Lys
225                 230                 235                 240

Thr Asp Tyr Glu Cys Ser Trp Gln Tyr Asp Gly Pro Glu Asp Asn Val
                245                 250                 255

Ser His Val Leu Trp Cys Cys Phe Val Pro Pro Asn His Thr His Thr
            260                 265                 270

Gly Gln Glu Arg Cys Arg Tyr Phe Ser Ser Gly Pro Asp Arg Thr Val
        275                 280                 285

Gln Phe Trp Glu Gln Asp Gly Ile Pro Val Leu Ser Lys Val Asn Phe
    290                 295                 300

Trp Val Glu Ser Arg Leu Gly Asn Arg Thr Met Lys Ser Gln Lys Ile
305                 310                 315                 320

Ser Gln Tyr Leu Tyr Asn Trp Thr Lys Thr Thr Pro Pro Leu Gly His
                325                 330                 335

Ile Lys Val Ser Gln Ser His Arg Gln Leu Arg Met Asp Trp Asn Val
            340                 345                 350

Ser Glu Glu Ala Gly Ala Glu Val Gln Phe Arg Arg Arg Met Pro Thr
        355                 360                 365

Thr Asn Trp Thr Leu Gly Asp Cys Gly Pro Gln Val Asn Ser Gly Ser
    370                 375                 380

Gly Val Leu Gly Asp Ile Arg Gly Ser Met Ser Glu Ser Cys Leu Cys
385                 390                 395                 400

Pro Ser Glu Asn Met Ala Gln Glu Ile Gln Ile Arg Arg Arg Arg Arg
                405                 410                 415

Leu Ser Ser Gly Ala Pro Gly Gly Pro Trp Ser Asp Trp Ser Met Pro
            420                 425                 430

Val Cys Val Pro Pro Glu Val Leu Pro Gln Ala Leu Val Pro Arg Gly
        435                 440                 445

Ser Gly Gly Gly Ser Gly Gly Gly Ser Gly Gly Gly Ser Gly Gly Gly
    450                 455                 460

Ser Gly Gly Gly Ser Gly Gly Gly Ser Met Trp Glu Leu Glu Lys Asp
465                 470                 475                 480

Val Tyr Val Val Glu Val Asp Trp Thr Pro Asp Ala Pro Gly Glu Thr
                485                 490                 495

Val Asn Leu Thr Cys Asp Thr Pro Glu Glu Asp Asp Ile Thr Trp Thr
            500                 505                 510

Ser Asp Gln Arg His Gly Val Ile Gly Ser Gly Lys Thr Leu Thr Ile
        515                 520                 525

Thr Val Lys Glu Phe Leu Asp Ala Gly Gln Tyr Thr Cys His Lys Gly
    530                 535                 540

Gly Glu Thr Leu Ser His Ser His Leu Leu Leu His Lys Lys Glu Asn
545                 550                 555                 560
```

Gly Ile Trp Ser Thr Glu Ile Leu Lys Asn Phe Lys Asn Lys Thr Phe
565 570 575

Leu Lys Cys Glu Ala Pro Asn Tyr Ser Gly Arg Phe Thr Cys Ser Trp
580 585 590

Leu Val Gln Arg Asn Met Asp Leu Lys Phe Asn Ile Lys Ser Ser Ser
595 600 605

Ser Ser Pro Asp Ser Arg Ala Val Thr Cys Gly Met Ala Ser Leu Ser
610 615 620

Ala Glu Lys Val Thr Leu Asp Gln Arg Asp Tyr Glu Lys Tyr Ser Val
625 630 635 640

Ser Cys Gln Glu Asp Val Thr Cys Pro Thr Ala Glu Glu Thr Leu Pro
645 650 655

Ile Glu Leu Ala Leu Glu Ala Arg Gln Gln Asn Lys Tyr Glu Asn Tyr
660 665 670

Ser Thr Ser Phe Phe Ile Arg Asp Ile Ile Lys Pro Asp Pro Pro Lys
675 680 685

Asn Leu Gln Met Lys Pro Leu Lys Asn Ser Gln Val Glu Val Ser Trp
690 695 700

Glu Tyr Pro Asp Ser Trp Ser Thr Pro His Ser Tyr Phe Ser Leu Lys
705 710 715 720

Phe Phe Val Arg Ile Gln Arg Lys Lys Glu Lys Met Lys Glu Thr Glu
725 730 735

Glu Gly Cys Asn Gln Lys Gly Ala Phe Leu Val Glu Lys Thr Ser Thr
740 745 750

Glu Val Gln Cys Lys Gly Gly Asn Val Cys Val Gln Ala Gln Asp Arg
755 760 765

Tyr Tyr Asn Ser Ser Cys Ser Lys Trp Ala Cys Val Pro Cys Arg Val
770 775 780

Arg Ser
785

<210> SEQ ID NO 12
<211> LENGTH: 790
<212> TYPE: PRT
<213> ORGANISM: Artificial Sequence
<220> FEATURE:
<223> OTHER INFORMATION: Synthetic Polypeptide

<400> SEQUENCE: 12

Cys Ser Gln Pro Leu Asp Val Ile Leu Leu Leu Asp Gly Ser Ser Ser
1 5 10 15

Phe Pro Ala Ser Tyr Phe Asp Glu Met Lys Ser Phe Ala Lys Ala Phe
20 25 30

Ile Ser Lys Ala Asn Ile Gly Pro Arg Leu Thr Gln Val Ser Val Leu
35 40 45

Gln Tyr Gly Ser Ile Thr Thr Ile Asp Val Pro Trp Asn Val Val Pro
50 55 60

Glu Lys Ala His Leu Leu Ser Leu Val Asp Val Met Gln Arg Glu Gly
65 70 75 80

Gly Pro Ser Gln Ile Gly Asp Ala Leu Gly Phe Ala Val Arg Tyr Leu
85 90 95

Thr Ser Glu Met His Gly Ala Arg Pro Gly Ala Ser Lys Ala Val Val
100 105 110

Ile Leu Val Thr Asp Val Ser Val Asp Ser Val Asp Ala Ala Ala Asp
115 120 125

```
Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile Gly Gly Gly Ser Gly Gly Gly Ser Gln Leu Gly Ala Ser Gly Pro
        195                 200                 205

Gly Asp Gly Cys Cys Val Glu Lys Thr Ser Phe Pro Glu Gly Ala Ser
    210                 215                 220

Gly Ser Pro Leu Gly Pro Arg Asn Leu Ser Cys Tyr Arg Val Ser Lys
225                 230                 235                 240

Thr Asp Tyr Glu Cys Ser Trp Gln Tyr Asp Gly Pro Glu Asp Asn Val
                245                 250                 255

Ser His Val Leu Trp Cys Cys Phe Val Pro Pro Asn His Thr His Thr
            260                 265                 270

Gly Gln Glu Arg Cys Arg Tyr Phe Ser Ser Gly Pro Asp Arg Thr Val
        275                 280                 285

Gln Phe Trp Glu Gln Asp Gly Ile Pro Val Leu Ser Lys Val Asn Phe
    290                 295                 300

Trp Val Glu Ser Arg Leu Gly Asn Arg Thr Met Lys Ser Gln Lys Ile
305                 310                 315                 320

Ser Gln Tyr Leu Tyr Asn Trp Thr Lys Thr Thr Pro Pro Leu Gly His
                325                 330                 335

Ile Lys Val Ser Gln Ser His Arg Gln Leu Arg Met Asp Trp Asn Val
            340                 345                 350

Ser Glu Glu Ala Gly Ala Glu Val Gln Phe Arg Arg Arg Met Pro Thr
        355                 360                 365

Thr Asn Trp Thr Leu Gly Asp Cys Gly Pro Gln Val Asn Ser Gly Ser
    370                 375                 380

Gly Val Leu Gly Asp Ile Arg Gly Ser Met Ser Glu Ser Cys Leu Cys
385                 390                 395                 400

Pro Ser Glu Asn Met Ala Gln Glu Ile Gln Ile Arg Arg Arg Arg Arg
                405                 410                 415

Leu Ser Ser Gly Ala Pro Gly Gly Pro Trp Ser Asp Trp Ser Met Pro
            420                 425                 430

Val Cys Val Pro Pro Glu Val Leu Pro Gln Ala Gly Leu Leu Ser Gly
        435                 440                 445

Arg Ser Asp Asn His Gly Gly Gly Ser Gly Gly Gly Ser Gly Gly Gly
    450                 455                 460

Ser Gly Gly Gly Ser Gly Gly Gly Ser Gly Gly Gly Ser Met Trp Glu
465                 470                 475                 480

Leu Glu Lys Asp Val Tyr Val Val Glu Val Asp Trp Thr Pro Asp Ala
                485                 490                 495

Pro Gly Glu Thr Val Asn Leu Thr Cys Asp Thr Pro Glu Glu Asp Asp
            500                 505                 510

Ile Thr Trp Thr Ser Asp Gln Arg His Gly Val Ile Gly Ser Gly Lys
        515                 520                 525

Thr Leu Thr Ile Thr Val Lys Glu Phe Leu Asp Ala Gly Gln Tyr Thr
    530                 535                 540
```

Cys His Lys Gly Gly Glu Thr Leu Ser His Ser His Leu Leu Leu His
545 550 555 560

Lys Lys Glu Asn Gly Ile Trp Ser Thr Glu Ile Leu Lys Asn Phe Lys
565 570 575

Asn Lys Thr Phe Leu Lys Cys Glu Ala Pro Asn Tyr Ser Gly Arg Phe
580 585 590

Thr Cys Ser Trp Leu Val Gln Arg Asn Met Asp Leu Lys Phe Asn Ile
595 600 605

Lys Ser Ser Ser Ser Ser Pro Asp Ser Arg Ala Val Thr Cys Gly Met
610 615 620

Ala Ser Leu Ser Ala Glu Lys Val Thr Leu Asp Gln Arg Asp Tyr Glu
625 630 635 640

Lys Tyr Ser Val Ser Cys Gln Glu Asp Val Thr Cys Pro Thr Ala Glu
645 650 655

Glu Thr Leu Pro Ile Glu Leu Ala Leu Glu Ala Arg Gln Gln Asn Lys
660 665 670

Tyr Glu Asn Tyr Ser Thr Ser Phe Phe Ile Arg Asp Ile Ile Lys Pro
675 680 685

Asp Pro Pro Lys Asn Leu Gln Met Lys Pro Leu Lys Asn Ser Gln Val
690 695 700

Glu Val Ser Trp Glu Tyr Pro Asp Ser Trp Ser Thr Pro His Ser Tyr
705 710 715 720

Phe Ser Leu Lys Phe Phe Val Arg Ile Gln Arg Lys Lys Glu Lys Met
725 730 735

Lys Glu Thr Glu Glu Gly Cys Asn Gln Lys Gly Ala Phe Leu Val Glu
740 745 750

Lys Thr Ser Thr Glu Val Gln Cys Lys Gly Gly Asn Val Cys Val Gln
755 760 765

Ala Gln Asp Arg Tyr Tyr Asn Ser Ser Cys Ser Lys Trp Ala Cys Val
770 775 780

Pro Cys Arg Val Arg Ser
785 790

<210> SEQ ID NO 13
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 13

Gly Leu Leu Ser Gly Arg Ser Asp Asn His
1 5 10

<210> SEQ ID NO 14
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 14

Leu Val Pro Arg Gly Ser
1 5

<210> SEQ ID NO 15
<211> LENGTH: 469
<212> TYPE: PRT
<213> ORGANISM: Artificial Sequence
<220> FEATURE:
<223> OTHER INFORMATION: Synthetic Polypeptide

<400> SEQUENCE: 15

```
Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
            20                  25                  30

Ser Cys Tyr Arg Val Ser Lys Thr Asp Tyr Glu Cys Ser Trp Gln Tyr
        35                  40                  45

Asp Gly Pro Glu Asp Asn Val Ser His Val Leu Trp Cys Cys Phe Val
    50                  55                  60

Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95

Val Leu Ser Lys Val Asn Phe Trp Val Glu Ser Arg Leu Gly Asn Arg
            100                 105                 110

Thr Met Lys Ser Gln Lys Ile Ser Gln Tyr Leu Tyr Asn Trp Thr Lys
        115                 120                 125

Thr Thr Pro Pro Leu Gly His Ile Lys Val Ser Gln Ser His Arg Gln
    130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Leu Val Pro Arg Gly Ser Gly Leu Leu Ser Gly Arg Ser Asp
                245                 250                 255

Asn His Gly Leu Leu Ser Gly Arg Ser Asp Asn His Gly Gly Gly Ser
            260                 265                 270

Gly Gly Gly Ser Arg Val Ile Pro Val Ser Gly Pro Ala Arg Cys Leu
        275                 280                 285

Ser Gln Ser Arg Asn Leu Leu Lys Thr Thr Asp Asp Met Val Lys Thr
    290                 295                 300

Ala Arg Glu Lys Leu Lys His Tyr Ser Cys Thr Ala Glu Asp Ile Asp
305                 310                 315                 320

His Glu Asp Ile Thr Arg Asp Gln Thr Ser Thr Leu Lys Thr Cys Leu
                325                 330                 335

Pro Leu Glu Leu His Lys Asn Glu Ser Cys Leu Ala Thr Arg Glu Thr
            340                 345                 350

Ser Ser Thr Thr Arg Gly Ser Cys Leu Pro Pro Gln Lys Thr Ser Leu
        355                 360                 365

Met Met Thr Leu Cys Leu Gly Ser Ile Tyr Glu Asp Leu Lys Met Tyr
    370                 375                 380
```

Gln Thr Glu Phe Gln Ala Ile Asn Ala Ala Leu Gln Asn His Asn His
385 390 395 400

Gln Gln Ile Ile Leu Asp Lys Gly Met Leu Val Ala Ile Asp Glu Leu
405 410 415

Met Gln Ser Leu Asn His Asn Gly Glu Thr Leu Arg Gln Lys Pro Pro
420 425 430

Val Gly Glu Ala Asp Pro Tyr Arg Val Lys Met Lys Leu Cys Ile Leu
435 440 445

Leu His Ala Phe Ser Thr Arg Val Val Thr Ile Asn Arg Val Met Gly
450 455 460

Tyr Leu Ser Ser Ala
465

<210> SEQ ID NO 16
<211> LENGTH: 463
<212> TYPE: PRT
<213> ORGANISM: Artificial Sequence
<220> FEATURE:
<223> OTHER INFORMATION: Synthetic Polypeptide

<400> SEQUENCE: 16

Cys Cys Val Glu Lys Thr Ser Phe Pro Glu Gly Ala Ser Gly Ser Pro
1 5 10 15

Leu Gly Pro Arg Asn Leu Ser Cys Tyr Arg Val Ser Lys Thr Asp Tyr
20 25 30

Glu Cys Ser Trp Gln Tyr Asp Gly Pro Glu Asp Asn Val Ser His Val
35 40 45

Leu Trp Cys Cys Phe Val Pro Pro Asn His Thr His Thr Gly Gln Glu
50 55 60

Arg Cys Arg Tyr Phe Ser Ser Gly Pro Asp Arg Thr Val Gln Phe Trp
65 70 75 80

Glu Gln Asp Gly Ile Pro Val Leu Ser Lys Val Asn Phe Trp Val Glu
85 90 95

Ser Arg Leu Gly Asn Arg Thr Met Lys Ser Gln Lys Ile Ser Gln Tyr
100 105 110

Leu Tyr Asn Trp Thr Lys Thr Thr Pro Pro Leu Gly His Ile Lys Val
115 120 125

Ser Gln Ser His Arg Gln Leu Arg Met Asp Trp Asn Val Ser Glu Glu
130 135 140

Ala Gly Ala Glu Val Gln Phe Arg Arg Arg Met Pro Thr Thr Asn Trp
145 150 155 160

Thr Leu Gly Asp Cys Gly Pro Gln Val Asn Ser Gly Ser Gly Val Leu
165 170 175

Gly Asp Ile Arg Gly Ser Met Ser Glu Ser Cys Leu Cys Pro Ser Glu
180 185 190

Asn Met Ala Gln Glu Ile Gln Ile Arg Arg Arg Arg Arg Leu Ser Ser
195 200 205

Gly Ala Pro Gly Gly Pro Trp Ser Asp Trp Ser Met Pro Val Cys Val
210 215 220

Pro Pro Glu Val Leu Pro Gln Ala Gly Leu Leu Ser Gly Arg Ser Asp
225 230 235 240

Asn His Gly Leu Leu Ser Gly Arg Ser Asp Asn His Gly Leu Leu Ser
245 250 255

Gly Arg Ser Asp Asn His Gly Gly Gly Ser Gly Gly Gly Ser Arg Val
260 265 270

```
Ile Pro Val Ser Gly Pro Ala Arg Cys Leu Ser Gln Ser Arg Asn Leu
        275                 280                 285

Leu Lys Thr Thr Asp Asp Met Val Lys Thr Ala Arg Glu Lys Leu Lys
    290                 295                 300

His Tyr Ser Cys Thr Ala Glu Asp Ile Asp His Glu Asp Ile Thr Arg
305                 310                 315                 320

Asp Gln Thr Ser Thr Leu Lys Thr Cys Leu Pro Leu Glu Leu His Lys
                325                 330                 335

Asn Glu Ser Cys Leu Ala Thr Arg Glu Thr Ser Ser Thr Thr Arg Gly
            340                 345                 350

Ser Cys Leu Pro Pro Gln Lys Thr Ser Leu Met Met Thr Leu Cys Leu
        355                 360                 365

Gly Ser Ile Tyr Glu Asp Leu Lys Met Tyr Gln Thr Glu Phe Gln Ala
    370                 375                 380

Ile Asn Ala Ala Leu Gln Asn His Asn His Gln Gln Ile Ile Leu Asp
385                 390                 395                 400

Lys Gly Met Leu Val Ala Ile Asp Glu Leu Met Gln Ser Leu Asn His
                405                 410                 415

Asn Gly Glu Thr Leu Arg Gln Lys Pro Pro Val Gly Glu Ala Asp Pro
            420                 425                 430

Tyr Arg Val Lys Met Lys Leu Cys Ile Leu Leu His Ala Phe Ser Thr
        435                 440                 445

Arg Val Val Thr Ile Asn Arg Val Met Gly Tyr Leu Ser Ser Ala
    450                 455                 460


<210> SEQ ID NO 17
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 17

Cys Cys Val Glu Lys Thr Ser Phe Pro Glu Gly Ala Ser Gly Ser Pro
1               5                   10                  15

Leu Gly Pro Arg Asn Leu Ser Cys Tyr Arg Val Ser Lys Thr Asp Tyr
            20                  25                  30

Glu Cys Ser Trp Gln Tyr Asp Gly Pro Glu Asp Asn Val Ser His Val
        35                  40                  45

Leu Trp Cys Cys Phe Val Pro Pro Asn His Thr His Thr Gly Gln Glu
    50                  55                  60

Arg Cys Arg Tyr Phe Ser Ser Gly Pro Asp Arg Thr Val Gln Phe Trp
65                  70                  75                  80

Glu Gln Asp Gly Ile Pro Val Leu Ser Lys Val Asn Phe Trp Val Glu
                85                  90                  95

Ser Arg Leu Gly Asn Arg Thr Met Lys Ser Gln Lys Ile Ser Gln Tyr
            100                 105                 110

Leu Tyr Asn Trp Thr Lys Thr Thr Pro Pro Leu Gly His Ile Lys Val
        115                 120                 125

Ser Gln Ser His Arg Gln Leu Arg Met Asp Trp Asn Val Ser Glu Glu
    130                 135                 140

Ala Gly Ala Glu Val Gln Phe Arg Arg Arg Met Pro Thr Thr Asn Trp
145                 150                 155                 160

Thr Leu Gly Asp Cys Gly Pro Gln Val Asn Ser Gly Ser Gly Val Leu
                165                 170                 175
```

```
Gly Asp Ile Arg Gly Ser Met Ser Glu Ser Cys Leu Cys Pro Ser Glu
            180                 185                 190

Asn Met Ala Gln Glu Ile Gln Ile Arg Arg Arg Arg Arg Leu Ser Ser
        195                 200                 205

Gly Ala Pro Gly Gly Pro Trp Ser Asp Trp Ser Met Pro Val Cys Val
    210                 215                 220

Pro Pro Glu Val Leu Pro Gln Ala Leu Val Pro Arg Gly Ser Leu Val
225                 230                 235                 240

Pro Arg Gly Ser Leu Val Pro Arg Gly Ser Gly Gly Gly Ser Gly Gly
                245                 250                 255

Gly Ser Arg Val Ile Pro Val Ser Gly Pro Ala Arg Cys Leu Ser Gln
            260                 265                 270

Ser Arg Asn Leu Leu Lys Thr Thr Asp Asp Met Val Lys Thr Ala Arg
        275                 280                 285

Glu Lys Leu Lys His Tyr Ser Cys Thr Ala Glu Asp Ile Asp His Glu
    290                 295                 300

Asp Ile Thr Arg Asp Gln Thr Ser Thr Leu Lys Thr Cys Leu Pro Leu
305                 310                 315                 320

Glu Leu His Lys Asn Glu Ser Cys Leu Ala Thr Arg Glu Thr Ser Ser
                325                 330                 335

Thr Thr Arg Gly Ser Cys Leu Pro Pro Gln Lys Thr Ser Leu Met Met
            340                 345                 350

Thr Leu Cys Leu Gly Ser Ile Tyr Glu Asp Leu Lys Met Tyr Gln Thr
        355                 360                 365

Glu Phe Gln Ala Ile Asn Ala Ala Leu Gln Asn His Asn His Gln Gln
    370                 375                 380

Ile Ile Leu Asp Lys Gly Met Leu Val Ala Ile Asp Glu Leu Met Gln
385                 390                 395                 400

Ser Leu Asn His Asn Gly Glu Thr Leu Arg Gln Lys Pro Pro Val Gly
                405                 410                 415

Glu Ala Asp Pro Tyr Arg Val Lys Met Lys Leu Cys Ile Leu Leu His
            420                 425                 430

Ala Phe Ser Thr Arg Val Val Thr Ile Asn Arg Val Met Gly Tyr Leu
        435                 440                 445

Ser Ser Ala
    450


<210> SEQ ID NO 18
<211> LENGTH: 481
<212> TYPE: PRT
<213> ORGANISM: Artificial Sequence
<220> FEATURE:
<223> OTHER INFORMATION: Synthetic Polypeptide

<400> SEQUENCE: 18

Cys Cys Val Glu Lys Thr Ser Phe Pro Glu Gly Ala Ser Gly Ser Pro
1               5                   10                  15

Leu Gly Pro Arg Asn Leu Ser Cys Tyr Arg Val Ser Lys Thr Asp Tyr
            20                  25                  30

Glu Cys Ser Trp Gln Tyr Asp Gly Pro Glu Asp Asn Val Ser His Val
        35                  40                  45

Leu Trp Cys Cys Phe Val Pro Pro Asn His Thr His Thr Gly Gln Glu
    50                  55                  60

Arg Cys Arg Tyr Phe Ser Ser Gly Pro Asp Arg Thr Val Gln Phe Trp
65                  70                  75                  80
```

```
Glu Gln Asp Gly Ile Pro Val Leu Ser Lys Val Asn Phe Trp Val Glu
                85                  90                  95

Ser Arg Leu Gly Asn Arg Thr Met Lys Ser Gln Lys Ile Ser Gln Tyr
            100                 105                 110

Leu Tyr Asn Trp Thr Lys Thr Thr Pro Pro Leu Gly His Ile Lys Val
        115                 120                 125

Ser Gln Ser His Arg Gln Leu Arg Met Asp Trp Asn Val Ser Glu Glu
    130                 135                 140

Ala Gly Ala Glu Val Gln Phe Arg Arg Arg Met Pro Thr Thr Asn Trp
145                 150                 155                 160

Thr Leu Gly Asp Cys Gly Pro Gln Val Asn Ser Gly Ser Gly Val Leu
                165                 170                 175

Gly Asp Ile Arg Gly Ser Met Ser Glu Ser Cys Leu Cys Pro Ser Glu
            180                 185                 190

Asn Met Ala Gln Glu Ile Gln Ile Arg Arg Arg Arg Arg Leu Ser Ser
        195                 200                 205

Gly Ala Pro Gly Gly Pro Trp Ser Asp Trp Ser Met Pro Val Cys Val
    210                 215                 220

Pro Pro Glu Val Leu Pro Gln Ala Leu Val Pro Arg Gly Ser Leu Val
225                 230                 235                 240

Pro Arg Gly Ser Leu Val Pro Arg Gly Ser Gly Leu Leu Ser Gly Arg
                245                 250                 255

Ser Asp Asn His Gly Leu Leu Ser Gly Arg Ser Asp Asn His Gly Leu
            260                 265                 270

Leu Ser Gly Arg Ser Asp Asn His Gly Gly Gly Ser Gly Gly Gly Ser
        275                 280                 285

Arg Val Ile Pro Val Ser Gly Pro Ala Arg Cys Leu Ser Gln Ser Arg
    290                 295                 300

Asn Leu Leu Lys Thr Thr Asp Asp Met Val Lys Thr Ala Arg Glu Lys
305                 310                 315                 320

Leu Lys His Tyr Ser Cys Thr Ala Glu Asp Ile Asp His Glu Asp Ile
                325                 330                 335

Thr Arg Asp Gln Thr Ser Thr Leu Lys Thr Cys Leu Pro Leu Glu Leu
            340                 345                 350

His Lys Asn Glu Ser Cys Leu Ala Thr Arg Glu Thr Ser Ser Thr Thr
        355                 360                 365

Arg Gly Ser Cys Leu Pro Pro Gln Lys Thr Ser Leu Met Met Thr Leu
    370                 375                 380

Cys Leu Gly Ser Ile Tyr Glu Asp Leu Lys Met Tyr Gln Thr Glu Phe
385                 390                 395                 400

Gln Ala Ile Asn Ala Ala Leu Gln Asn His Asn His Gln Gln Ile Ile
                405                 410                 415

Leu Asp Lys Gly Met Leu Val Ala Ile Asp Glu Leu Met Gln Ser Leu
            420                 425                 430

Asn His Asn Gly Glu Thr Leu Arg Gln Lys Pro Pro Val Gly Glu Ala
        435                 440                 445

Asp Pro Tyr Arg Val Lys Met Lys Leu Cys Ile Leu Leu His Ala Phe
    450                 455                 460

Ser Thr Arg Val Val Thr Ile Asn Arg Val Met Gly Tyr Leu Ser Ser
465                 470                 475                 480

Ala
```

<210> SEQ ID NO 19
<211> LENGTH: 639
<212> TYPE: PRT
<213> ORGANISM: Homo Sapiens

<400> SEQUENCE: 19

```
Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
            100                 105                 110

Ser Val Lys Tyr Glu Pro Pro Leu Gly Asp Ile Lys Val Ser Lys Leu
        115                 120                 125

Ala Gly Gln Leu Arg Met Glu Trp Glu Thr Pro Asp Asn Gln Val Gly
    130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Asp Thr Glu Ser Cys Leu Cys Pro
                165                 170                 175

Leu Glu Met Asn Val Ala Gln Glu Phe Gln Leu Arg Arg Arg Gln Leu
            180                 185                 190

Gly Ser Gln Gly Ser Ser Trp Ser Lys Trp Ser Ser Pro Val Cys Val
        195                 200                 205

Pro Pro Glu Asn Pro Pro Gln Pro Gln Val Arg Phe Ser Val Glu Gln
    210                 215                 220

Leu Gly Gln Asp Gly Arg Arg Arg Leu Thr Leu Lys Glu Gln Pro Thr
225                 230                 235                 240

Gln Leu Glu Leu Pro Glu Gly Cys Gln Gly Leu Ala Pro Gly Thr Glu
                245                 250                 255

Val Thr Tyr Arg Leu Gln Leu His Met Leu Ser Cys Pro Cys Lys Ala
            260                 265                 270

Lys Ala Thr Arg Thr Leu His Leu Gly Lys Met Pro Tyr Leu Ser Gly
        275                 280                 285

Ala Ala Tyr Asn Val Ala Val Ile Ser Ser Asn Gln Phe Gly Pro Gly
    290                 295                 300

Leu Asn Gln Thr Trp His Ile Pro Ala Asp Thr His Thr Glu Pro Val
305                 310                 315                 320

Ala Leu Asn Ile Ser Val Gly Thr Asn Gly Thr Thr Met Tyr Trp Pro
                325                 330                 335

Ala Arg Ala Gln Ser Met Thr Tyr Cys Ile Glu Trp Gln Pro Val Gly
            340                 345                 350

Gln Asp Gly Gly Leu Ala Thr Cys Ser Leu Thr Ala Pro Gln Asp Pro
        355                 360                 365

Asp Pro Ala Gly Met Ala Thr Tyr Ser Trp Ser Arg Glu Ser Gly Ala
    370                 375                 380
```

Met Gly Gln Glu Lys Cys Tyr Tyr Ile Thr Ile Phe Ala Ser Ala His
385 390 395 400

Pro Glu Lys Leu Thr Leu Trp Ser Thr Val Leu Ser Thr Tyr His Phe
405 410 415

Gly Gly Asn Ala Ser Ala Ala Gly Thr Pro His His Val Ser Val Lys
420 425 430

Asn His Ser Leu Asp Ser Val Ser Val Asp Trp Ala Pro Ser Leu Leu
435 440 445

Ser Thr Cys Pro Gly Val Leu Lys Glu Tyr Val Val Arg Cys Arg Asp
450 455 460

Glu Asp Ser Lys Gln Val Ser Glu His Pro Val Gln Pro Thr Glu Thr
465 470 475 480

Gln Val Thr Leu Ser Gly Leu Arg Ala Gly Val Ala Tyr Thr Val Gln
485 490 495

Val Arg Ala Asp Thr Ala Trp Leu Arg Gly Val Trp Ser Gln Pro Gln
500 505 510

Arg Phe Ser Ile Glu Val Gln Val Ser Asp Trp Leu Ile Phe Phe Ala
515 520 525

Ser Leu Gly Ser Phe Leu Ser Ile Leu Leu Val Gly Val Leu Gly Tyr
530 535 540

Leu Gly Leu Asn Arg Ala Ala Arg His Leu Cys Pro Pro Leu Pro Thr
545 550 555 560

Pro Cys Ala Ser Ser Ala Ile Glu Phe Pro Gly Gly Lys Glu Thr Trp
565 570 575

Gln Trp Ile Asn Pro Val Asp Phe Gln Glu Glu Ala Ser Leu Gln Glu
580 585 590

Ala Leu Val Val Glu Met Ser Trp Asp Lys Gly Glu Arg Thr Glu Pro
595 600 605

Leu Glu Lys Thr Glu Leu Pro Glu Gly Ala Pro Glu Leu Ala Leu Asp
610 615 620

Thr Glu Leu Ser Leu Glu Asp Gly Asp Arg Cys Lys Ala Lys Met
625 630 635

<210> SEQ ID NO 20
<211> LENGTH: 719
<212> TYPE: PRT
<213> ORGANISM: Mus musculus

<400> SEQUENCE: 20

Gln Leu Gly Ala Ser Gly Pro Gly Asp Gly Cys Cys Val Glu Lys Thr
1 5 10 15

Ser Phe Pro Glu Gly Ala Ser Gly Ser Pro Leu Gly Pro Arg Asn Leu
20 25 30

Ser Cys Tyr Arg Val Ser Lys Thr Asp Tyr Glu Cys Ser Trp Gln Tyr
35 40 45

Asp Gly Pro Glu Asp Asn Val Ser His Val Leu Trp Cys Cys Phe Val
50 55 60

Pro Pro Asn His Thr His Thr Gly Gln Glu Arg Cys Arg Tyr Phe Ser
65 70 75 80

Ser Gly Pro Asp Arg Thr Val Gln Phe Trp Glu Gln Asp Gly Ile Pro
85 90 95

Val Leu Ser Lys Val Asn Phe Trp Val Glu Ser Arg Leu Gly Asn Arg
100 105 110

Thr Met Lys Ser Gln Lys Ile Ser Gln Tyr Leu Tyr Asn Trp Thr Lys
115 120 125

-continued

```
Thr Thr Pro Pro Leu Gly His Ile Lys Val Ser Gln Ser His Arg Gln
    130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Lys Ile Lys Phe Leu Val Glu Pro Leu Asn Gln Gly Gly Arg
                245                 250                 255

Arg Arg Leu Thr Met Gln Gly Gln Ser Pro Gln Leu Ala Val Pro Glu
            260                 265                 270

Gly Cys Arg Gly Arg Pro Gly Ala Gln Val Lys Lys His Leu Val Leu
        275                 280                 285

Val Arg Met Leu Ser Cys Arg Cys Gln Ala Gln Thr Ser Lys Thr Val
    290                 295                 300

Pro Leu Gly Lys Lys Leu Asn Leu Ser Gly Ala Thr Tyr Asp Leu Asn
305                 310                 315                 320

Val Leu Ala Lys Thr Arg Phe Gly Arg Ser Thr Ile Gln Lys Trp His
                325                 330                 335

Leu Pro Ala Gln Glu Leu Thr Glu Thr Arg Ala Leu Asn Val Ser Val
            340                 345                 350

Gly Gly Asn Met Thr Ser Met Gln Trp Ala Ala Gln Ala Pro Gly Thr
        355                 360                 365

Thr Tyr Cys Leu Glu Trp Gln Pro Trp Phe Gln His Arg Asn His Thr
    370                 375                 380

His Cys Thr Leu Ile Val Pro Glu Glu Glu Asp Pro Ala Lys Met Val
385                 390                 395                 400

Thr His Ser Trp Ser Ser Lys Pro Thr Leu Glu Gln Glu Glu Cys Tyr
                405                 410                 415

Arg Ile Thr Val Phe Ala Ser Lys Asn Pro Lys Asn Pro Met Leu Trp
            420                 425                 430

Ala Thr Val Leu Ser Ser Tyr Tyr Phe Gly Gly Asn Ala Ser Arg Ala
        435                 440                 445

Gly Thr Pro Arg His Val Ser Val Arg Asn Gln Thr Gly Asp Ser Val
    450                 455                 460

Ser Val Glu Trp Thr Ala Ser Gln Leu Ser Thr Cys Pro Gly Val Leu
465                 470                 475                 480

Thr Gln Tyr Val Val Arg Cys Glu Ala Glu Asp Gly Ala Trp Glu Ser
                485                 490                 495

Glu Trp Leu Val Pro Pro Thr Lys Thr Gln Val Thr Leu Asp Gly Leu
            500                 505                 510

Arg Ser Arg Val Met Tyr Lys Val Gln Val Arg Ala Asp Thr Ala Arg
        515                 520                 525

Leu Pro Gly Ala Trp Ser His Pro Gln Arg Phe Ser Phe Glu Val Gln
    530                 535                 540
```

-continued

```
Ile Ser Arg Leu Ser Ile Ile Phe Ala Ser Leu Gly Ser Phe Ala Ser
545                 550                 555                 560

Val Leu Leu Val Gly Ser Leu Gly Tyr Ile Gly Leu Asn Arg Ala Ala
                565                 570                 575

Trp His Leu Cys Pro Pro Leu Pro Thr Pro Cys Gly Ser Thr Ala Val
            580                 585                 590

Glu Phe Pro Gly Ser Gln Gly Lys Gln Ala Trp Gln Trp Cys Asn Pro
        595                 600                 605

Glu Asp Phe Pro Glu Val Leu Tyr Pro Arg Asp Ala Leu Val Val Glu
    610                 615                 620

Met Pro Gly Asp Arg Gly Asp Gly Thr Glu Ser Pro Gln Ala Ala Pro
625                 630                 635                 640

Glu Cys Ala Leu Asp Thr Arg Arg Pro Leu Glu Thr Gln Arg Gln Arg
                645                 650                 655

Gln Val Gln Ala Leu Ser Glu Ala Arg Arg Leu Gly Leu Ala Arg Glu
            660                 665                 670

Asp Cys Pro Arg Gly Asp Leu Ala His Val Thr Leu Pro Leu Leu Leu
        675                 680                 685

Gly Gly Val Thr Gln Gly Ala Ser Val Leu Asp Asp Leu Trp Arg Thr
    690                 695                 700

His Lys Thr Ala Glu Pro Gly Pro Pro Thr Leu Gly Gln Glu Ala
705                 710                 715


<210> SEQ ID NO 21
<211> LENGTH: 839
<212> TYPE: PRT
<213> ORGANISM: Homo Sapiens

<400> SEQUENCE: 21

Lys Ile Asp Ala Cys Lys Arg Gly Asp Val Thr Val Lys Pro Ser His
1               5                   10                  15

Val Ile Leu Leu Gly Ser Thr Val Asn Ile Thr Cys Ser Leu Lys Pro
            20                  25                  30

Arg Gln Gly Cys Phe His Tyr Ser Arg Arg Asn Lys Leu Ile Leu Tyr
        35                  40                  45

Lys Phe Asp Arg Arg Ile Asn Phe His His Gly His Ser Leu Asn Ser
    50                  55                  60

Gln Val Thr Gly Leu Pro Leu Gly Thr Thr Leu Phe Val Cys Lys Leu
65                  70                  75                  80

Ala Cys Ile Asn Ser Asp Glu Ile Gln Ile Cys Gly Ala Glu Ile Phe
                85                  90                  95

Val Gly Val Ala Pro Glu Gln Pro Gln Asn Leu Ser Cys Ile Gln Lys
            100                 105                 110

Gly Glu Gln Gly Thr Val Ala Cys Thr Trp Glu Arg Gly Arg Asp Thr
        115                 120                 125

His Leu Tyr Thr Glu Tyr Thr Leu Gln Leu Ser Gly Pro Lys Asn Leu
    130                 135                 140

Thr Trp Gln Lys Gln Cys Lys Asp Ile Tyr Cys Asp Tyr Leu Asp Phe
145                 150                 155                 160

Gly Ile Asn Leu Thr Pro Glu Ser Pro Glu Ser Asn Phe Thr Ala Lys
                165                 170                 175

Val Thr Ala Val Asn Ser Leu Gly Ser Ser Ser Ser Leu Pro Ser Thr
            180                 185                 190

Phe Thr Phe Leu Asp Ile Val Arg Pro Leu Pro Pro Trp Asp Ile Arg
        195                 200                 205
```

-continued

```
Ile Lys Phe Gln Lys Ala Ser Val Ser Arg Cys Thr Leu Tyr Trp Arg
    210                 215                 220

Asp Glu Gly Leu Val Leu Leu Asn Arg Leu Arg Tyr Arg Pro Ser Asn
225                 230                 235                 240

Ser Arg Leu Trp Asn Met Val Asn Val Thr Lys Ala Lys Gly Arg His
                245                 250                 255

Asp Leu Leu Asp Leu Lys Pro Phe Thr Glu Tyr Glu Phe Gln Ile Ser
            260                 265                 270

Ser Lys Leu His Leu Tyr Lys Gly Ser Trp Ser Asp Trp Ser Glu Ser
        275                 280                 285

Leu Arg Ala Gln Thr Pro Glu Glu Glu Pro Thr Gly Met Leu Asp Val
    290                 295                 300

Trp Tyr Met Lys Arg His Ile Asp Tyr Ser Arg Gln Gln Ile Ser Leu
305                 310                 315                 320

Phe Trp Lys Asn Leu Ser Val Ser Glu Ala Arg Gly Lys Ile Leu His
                325                 330                 335

Tyr Gln Val Thr Leu Gln Glu Leu Thr Gly Gly Lys Ala Met Thr Gln
            340                 345                 350

Asn Ile Thr Gly His Thr Ser Trp Thr Thr Val Ile Pro Arg Thr Gly
        355                 360                 365

Asn Trp Ala Val Ala Val Ser Ala Ala Asn Ser Lys Gly Ser Ser Leu
    370                 375                 380

Pro Thr Arg Ile Asn Ile Met Asn Leu Cys Glu Ala Gly Leu Leu Ala
385                 390                 395                 400

Pro Arg Gln Val Ser Ala Asn Ser Glu Gly Met Asp Asn Ile Leu Val
                405                 410                 415

Thr Trp Gln Pro Pro Arg Lys Asp Pro Ser Ala Val Gln Glu Tyr Val
            420                 425                 430

Val Glu Trp Arg Glu Leu His Pro Gly Gly Asp Thr Gln Val Pro Leu
        435                 440                 445

Asn Trp Leu Arg Ser Arg Pro Tyr Asn Val Ser Ala Leu Ile Ser Glu
    450                 455                 460

Asn Ile Lys Ser Tyr Ile Cys Tyr Glu Ile Arg Val Tyr Ala Leu Ser
465                 470                 475                 480

Gly Asp Gln Gly Gly Cys Ser Ser Ile Leu Gly Asn Ser Lys His Lys
                485                 490                 495

Ala Pro Leu Ser Gly Pro His Ile Asn Ala Ile Thr Glu Glu Lys Gly
            500                 505                 510

Ser Ile Leu Ile Ser Trp Asn Ser Ile Pro Val Gln Glu Gln Met Gly
        515                 520                 525

Cys Leu Leu His Tyr Arg Ile Tyr Trp Lys Glu Arg Asp Ser Asn Ser
    530                 535                 540

Gln Pro Gln Leu Cys Glu Ile Pro Tyr Arg Val Ser Gln Asn Ser His
545                 550                 555                 560

Pro Ile Asn Ser Leu Gln Pro Arg Val Thr Tyr Val Leu Trp Met Thr
                565                 570                 575

Ala Leu Thr Ala Ala Gly Glu Ser Ser His Gly Asn Glu Arg Glu Phe
            580                 585                 590

Cys Leu Gln Gly Lys Ala Asn Trp Met Ala Phe Val Ala Pro Ser Ile
        595                 600                 605

Cys Ile Ala Ile Ile Met Val Gly Ile Phe Ser Thr His Tyr Phe Gln
    610                 615                 620
```

-continued

```
Gln Lys Val Phe Val Leu Leu Ala Ala Leu Arg Pro Gln Trp Cys Ser
625                 630                 635                 640

Arg Glu Ile Pro Asp Pro Ala Asn Ser Thr Cys Ala Lys Lys Tyr Pro
                645                 650                 655

Ile Ala Glu Glu Lys Thr Gln Leu Pro Leu Asp Arg Leu Leu Ile Asp
            660                 665                 670

Trp Pro Thr Pro Glu Asp Pro Glu Pro Leu Val Ile Ser Glu Val Leu
        675                 680                 685

His Gln Val Thr Pro Val Phe Arg His Pro Pro Cys Ser Asn Trp Pro
    690                 695                 700

Gln Arg Glu Lys Gly Ile Gln Gly His Gln Ala Ser Glu Lys Asp Met
705                 710                 715                 720

Met His Ser Ala Ser Ser Pro Pro Pro Pro Arg Ala Leu Gln Ala Glu
                725                 730                 735

Ser Arg Gln Leu Val Asp Leu Tyr Lys Val Leu Glu Ser Arg Gly Ser
            740                 745                 750

Asp Pro Lys Pro Glu Asn Pro Ala Cys Pro Trp Thr Val Leu Pro Ala
        755                 760                 765

Gly Asp Leu Pro Thr His Asp Gly Tyr Leu Pro Ser Asn Ile Asp Asp
    770                 775                 780

Leu Pro Ser His Glu Ala Pro Leu Ala Asp Ser Leu Glu Glu Leu Glu
785                 790                 795                 800

Pro Gln His Ile Ser Leu Ser Val Phe Pro Ser Ser Ser Leu His Pro
                805                 810                 815

Leu Thr Phe Ser Cys Gly Asp Lys Leu Thr Leu Asp Gln Leu Lys Met
            820                 825                 830

Arg Cys Asp Ser Leu Met Leu
        835


<210> SEQ ID NO 22
<211> LENGTH: 851
<212> TYPE: PRT
<213> ORGANISM: Mus musculus

<400> SEQUENCE: 22

Asn Ile Asp Val Cys Lys Leu Gly Thr Val Thr Val Gln Pro Ala Pro
1               5                   10                  15

Val Ile Pro Leu Gly Ser Ala Ala Asn Ile Ser Cys Ser Leu Asn Pro
            20                  25                  30

Lys Gln Gly Cys Ser His Tyr Pro Ser Ser Asn Glu Leu Ile Leu Leu
        35                  40                  45

Lys Phe Val Asn Asp Val Leu Val Glu Asn Leu His Gly Lys Lys Val
    50                  55                  60

His Asp His Thr Gly His Ser Ser Thr Phe Gln Val Thr Asn Leu Ser
65                  70                  75                  80

Leu Gly Met Thr Leu Phe Val Cys Lys Leu Asn Cys Ser Asn Ser Gln
                85                  90                  95

Lys Lys Pro Pro Val Pro Val Cys Gly Val Glu Ile Ser Val Gly Val
            100                 105                 110

Ala Pro Glu Pro Pro Gln Asn Ile Ser Cys Val Gln Glu Gly Glu Asn
        115                 120                 125

Gly Thr Val Ala Cys Ser Trp Asn Ser Gly Lys Val Thr Tyr Leu Lys
    130                 135                 140

Thr Asn Tyr Thr Leu Gln Leu Ser Gly Pro Asn Asn Leu Thr Cys Gln
145                 150                 155                 160
```

-continued

```
Lys Gln Cys Phe Ser Asp Asn Arg Gln Asn Cys Asn Arg Leu Asp Leu
                165                 170                 175

Gly Ile Asn Leu Ser Pro Asp Leu Ala Glu Ser Arg Phe Ile Val Arg
            180                 185                 190

Val Thr Ala Ile Asn Asp Leu Gly Asn Ser Ser Ser Leu Pro His Thr
        195                 200                 205

Phe Thr Phe Leu Asp Ile Val Ile Pro Leu Pro Pro Trp Asp Ile Arg
    210                 215                 220

Ile Asn Phe Leu Asn Ala Ser Gly Ser Arg Gly Thr Leu Gln Trp Glu
225                 230                 235                 240

Asp Glu Gly Gln Val Val Leu Asn Gln Leu Arg Tyr Gln Pro Leu Asn
                245                 250                 255

Ser Thr Ser Trp Asn Met Val Asn Ala Thr Asn Ala Lys Gly Lys Tyr
            260                 265                 270

Asp Leu Arg Asp Leu Arg Pro Phe Thr Glu Tyr Glu Phe Gln Ile Ser
        275                 280                 285

Ser Lys Leu His Leu Ser Gly Gly Ser Trp Ser Asn Trp Ser Glu Ser
    290                 295                 300

Leu Arg Thr Arg Thr Pro Glu Glu Glu Pro Val Gly Ile Leu Asp Ile
305                 310                 315                 320

Trp Tyr Met Lys Gln Asp Ile Asp Tyr Asp Arg Gln Gln Ile Ser Leu
                325                 330                 335

Phe Trp Lys Ser Leu Asn Pro Ser Glu Ala Arg Gly Lys Ile Leu His
            340                 345                 350

Tyr Gln Val Thr Leu Gln Glu Val Thr Lys Lys Thr Thr Leu Gln Asn
        355                 360                 365

Thr Thr Arg His Thr Ser Trp Thr Arg Val Ile Pro Arg Thr Gly Ala
    370                 375                 380

Trp Thr Ala Ser Val Ser Ala Ala Asn Ser Lys Gly Ala Ser Ala Pro
385                 390                 395                 400

Thr His Ile Asn Ile Val Asp Leu Cys Gly Thr Gly Leu Leu Ala Pro
                405                 410                 415

His Gln Val Ser Ala Lys Ser Glu Asn Met Asp Asn Ile Leu Val Thr
            420                 425                 430

Trp Gln Pro Pro Lys Lys Ala Asp Ser Ala Val Arg Glu Tyr Ile Val
        435                 440                 445

Glu Trp Arg Ala Leu Gln Pro Gly Ser Ile Thr Lys Phe Pro Pro His
    450                 455                 460

Trp Leu Arg Ile Pro Pro Asp Asn Met Ser Ala Leu Ile Ser Glu Asn
465                 470                 475                 480

Ile Lys Pro Tyr Ile Cys Tyr Glu Ile Arg Val His Ala Leu Ser Glu
                485                 490                 495

Ser Gln Gly Gly Cys Ser Ser Ile Arg Gly Asp Ser Lys His Lys Ala
            500                 505                 510

Pro Val Ser Gly Pro His Ile Thr Ala Ile Thr Glu Lys Lys Glu Arg
        515                 520                 525

Leu Phe Ile Ser Trp Thr His Ile Pro Phe Pro Glu Gln Arg Gly Cys
    530                 535                 540

Ile Leu His Tyr Arg Ile Tyr Trp Lys Glu Arg Asp Ser Thr Ala Gln
545                 550                 555                 560

Pro Glu Leu Cys Glu Ile Gln Tyr Arg Arg Ser Gln Asn Ser His Pro
                565                 570                 575
```

```
Ile Ser Ser Leu Gln Pro Arg Val Thr Tyr Val Leu Trp Met Thr Ala
            580                 585                 590

Val Thr Ala Ala Gly Glu Ser Pro Gln Gly Asn Glu Arg Glu Phe Cys
        595                 600                 605

Pro Gln Gly Lys Ala Asn Trp Lys Ala Phe Val Ile Ser Ser Ile Cys
    610                 615                 620

Ile Ala Ile Ile Thr Val Gly Thr Phe Ser Ile Arg Tyr Phe Arg Gln
625                 630                 635                 640

Lys Ala Phe Thr Leu Leu Ser Thr Leu Lys Pro Gln Trp Tyr Ser Arg
                645                 650                 655

Thr Ile Pro Asp Pro Ala Asn Ser Thr Trp Val Lys Lys Tyr Pro Ile
            660                 665                 670

Leu Glu Glu Lys Ile Gln Leu Pro Thr Asp Asn Leu Leu Met Ala Trp
        675                 680                 685

Pro Thr Pro Glu Glu Pro Glu Pro Leu Ile Ile His Glu Val Leu Tyr
    690                 695                 700

His Met Ile Pro Val Val Arg Gln Pro Tyr Tyr Phe Lys Arg Gly Gln
705                 710                 715                 720

Gly Phe Gln Gly Tyr Ser Thr Ser Lys Gln Asp Ala Met Tyr Ile Ala
                725                 730                 735

Asn Pro Gln Ala Thr Gly Thr Leu Thr Ala Glu Thr Arg Gln Leu Val
            740                 745                 750

Asn Leu Tyr Lys Val Leu Glu Ser Arg Asp Pro Asp Ser Lys Leu Ala
        755                 760                 765

Asn Leu Thr Ser Pro Leu Thr Val Thr Pro Val Asn Tyr Leu Pro Ser
    770                 775                 780

His Glu Gly Tyr Leu Pro Ser Asn Ile Glu Asp Leu Ser Pro His Glu
785                 790                 795                 800

Ala Asp Pro Thr Asp Ser Phe Asp Leu Glu His Gln His Ile Ser Leu
                805                 810                 815

Ser Ile Phe Ala Ser Ser Ser Leu Arg Pro Leu Ile Phe Gly Gly Glu
            820                 825                 830

Arg Leu Thr Leu Asp Arg Leu Lys Met Gly Tyr Asp Ser Leu Met Ser
        835                 840                 845

Asn Glu Ala
    850


<210> SEQ ID NO 23
<211> LENGTH: 134
<212> TYPE: PRT
<213> ORGANISM: Homo Sapiens

<400> SEQUENCE: 23

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95
```

```
Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130
```

<210> SEQ ID NO 24
<211> LENGTH: 148
<212> TYPE: PRT
<213> ORGANISM: Mus musculus

<400> SEQUENCE: 24

```
Pro Thr Ser Ser Ser Thr Ser Ser Ser Thr Ala Glu Ala Gln Gln Gln
1               5                   10                  15

Gln Gln Gln Gln Gln Gln Gln Gln Gln His Leu Glu Gln Leu Leu Met
            20                  25                  30

Asp Leu Gln Glu Leu Leu Ser Arg Met Glu Asn Tyr Arg Asn Leu Lys
        35                  40                  45

Leu Pro Arg Met Leu Thr Phe Lys Phe Tyr Leu Pro Lys Gln Ala Thr
    50                  55                  60

Glu Leu Lys Asp Leu Gln Cys Leu Glu Asp Glu Leu Gly Pro Leu Arg
65                  70                  75                  80

His Val Leu Asp Leu Thr Gln Ser Lys Ser Phe Gln Leu Glu Asp Ala
                85                  90                  95

Glu Asn Phe Ile Ser Asn Ile Arg Val Thr Val Val Lys Leu Lys Gly
            100                 105                 110

Ser Asp Asn Thr Phe Glu Cys Gln Phe Asp Asp Glu Ser Ala Thr Val
        115                 120                 125

Val Asp Phe Leu Arg Arg Trp Ile Ala Phe Cys Gln Ser Ile Ile Ser
    130                 135                 140

Thr Ser Pro Gln
145
```

<210> SEQ ID NO 25
<211> LENGTH: 133
<212> TYPE: PRT
<213> ORGANISM: Mus musculus

<400> SEQUENCE: 25

```
His Gly Thr Val Ile Glu Ser Leu Glu Ser Leu Asn Asn Tyr Phe Asn
1               5                   10                  15

Ser Ser Gly Ile Asp Val Glu Glu Lys Ser Leu Phe Leu Asp Ile Trp
            20                  25                  30

Arg Asn Trp Gln Lys Asp Gly Asp Met Lys Ile Leu Gln Ser Gln Ile
        35                  40                  45

Ile Ser Phe Tyr Leu Arg Leu Phe Glu Val Leu Lys Asp Asn Gln Ala
    50                  55                  60

Ile Ser Asn Asn Ile Ser Val Ile Glu Ser His Leu Ile Thr Thr Phe
65                  70                  75                  80

Phe Ser Asn Ser Lys Ala Lys Lys Asp Ala Phe Met Ser Ile Ala Lys
                85                  90                  95

Phe Glu Val Asn Asn Pro Gln Val Gln Arg Gln Ala Phe Asn Glu Leu
            100                 105                 110

Ile Arg Val Val His Gln Leu Leu Pro Glu Ser Ser Leu Arg Lys Arg
        115                 120                 125
```

Lys Arg Ser Arg Cys
    130

<210> SEQ ID NO 26
<211> LENGTH: 143
<212> TYPE: PRT
<213> ORGANISM: Homo Sapiens

<400> SEQUENCE: 26

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Gln Gly Arg Arg Ala Ser Gln
    130                 135                 140
```

<210> SEQ ID NO 27
<211> LENGTH: 214
<212> TYPE: PRT
<213> ORGANISM: Homo Sapiens

<400> SEQUENCE: 27

```
Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175
```

Gln Tyr Glu Phe Gln Val Arg Val Lys Pro Leu Gln Gly Glu Phe Thr
180 185 190

Thr Trp Ser Pro Trp Ser Gln Pro Leu Ala Phe Arg Thr Lys Pro Ala
195 200 205

Ala Leu Gly Lys Asp Thr
210

<210> SEQ ID NO 28
<211> LENGTH: 214
<212> TYPE: PRT
<213> ORGANISM: Mus musculus

<400> SEQUENCE: 28

Ala Val Lys Asn Cys Ser His Leu Glu Cys Phe Tyr Asn Ser Arg Ala
1 5 10 15

Asn Val Ser Cys Met Trp Ser His Glu Glu Ala Leu Asn Val Thr Thr
20 25 30

Cys His Val His Ala Lys Ser Asn Leu Arg His Trp Asn Lys Thr Cys
35 40 45

Glu Leu Thr Leu Val Arg Gln Ala Ser Trp Ala Cys Asn Leu Ile Leu
50 55 60

Gly Ser Phe Pro Glu Ser Gln Ser Leu Thr Ser Val Asp Leu Leu Asp
65 70 75 80

Ile Asn Val Val Cys Trp Glu Glu Lys Gly Trp Arg Arg Val Lys Thr
85 90 95

Cys Asp Phe His Pro Phe Asp Asn Leu Arg Leu Val Ala Pro His Ser
100 105 110

Leu Gln Val Leu His Ile Asp Thr Gln Arg Cys Asn Ile Ser Trp Lys
115 120 125

Val Ser Gln Val Ser His Tyr Ile Glu Pro Tyr Leu Glu Phe Glu Ala
130 135 140

Arg Arg Arg Leu Leu Gly His Ser Trp Glu Asp Ala Ser Val Leu Ser
145 150 155 160

Leu Lys Gln Arg Gln Gln Trp Leu Phe Leu Glu Met Leu Ile Pro Ser
165 170 175

Thr Ser Tyr Glu Val Gln Val Arg Val Lys Ala Gln Arg Asn Asn Thr
180 185 190

Gly Thr Trp Ser Pro Trp Ser Gln Pro Leu Thr Phe Arg Thr Arg Pro
195 200 205

Ala Asp Pro Met Lys Glu
210

<210> SEQ ID NO 29
<211> LENGTH: 219
<212> TYPE: PRT
<213> ORGANISM: Homo Sapiens

<400> SEQUENCE: 29

Glu Leu Cys Asp Asp Asp Pro Pro Glu Ile Pro His Ala Thr Phe Lys
1 5 10 15

Ala Met Ala Tyr Lys Glu Gly Thr Met Leu Asn Cys Glu Cys Lys Arg
20 25 30

Gly Phe Arg Arg Ile Lys Ser Gly Ser Leu Tyr Met Leu Cys Thr Gly
35 40 45

Asn Ser Ser His Ser Ser Trp Asp Asn Gln Cys Gln Cys Thr Ser Ser
50 55 60

```
Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln
    210                 215


<210> SEQ ID NO 30
<211> LENGTH: 215
<212> TYPE: PRT
<213> ORGANISM: Mus musculus

<400> SEQUENCE: 30

Glu Leu Cys Leu Tyr Asp Pro Pro Glu Val Pro Asn Ala Thr Phe Lys
1               5                   10                  15

Ala Leu Ser Tyr Lys Asn Gly Thr Ile Leu Asn Cys Glu Cys Lys Arg
            20                  25                  30

Gly Phe Arg Arg Leu Lys Glu Leu Val Tyr Met Arg Cys Leu Gly Asn
        35                  40                  45

Ser Trp Ser Ser Asn Cys Gln Cys Thr Ser Asn Ser His Asp Lys Ser
    50                  55                  60

Arg Lys Gln Val Thr Ala Gln Leu Glu His Gln Lys Glu Gln Gln Thr
65                  70                  75                  80

Thr Thr Asp Met Gln Lys Pro Thr Gln Ser Met His Gln Glu Asn Leu
                85                  90                  95

Thr Gly His Cys Arg Glu Pro Pro Pro Trp Lys His Glu Asp Ser Lys
            100                 105                 110

Arg Ile Tyr His Phe Val Glu Gly Gln Ser Val His Tyr Glu Cys Ile
        115                 120                 125

Pro Gly Tyr Lys Ala Leu Gln Arg Gly Pro Ala Ile Ser Ile Cys Lys
    130                 135                 140

Met Lys Cys Gly Lys Thr Gly Trp Thr Gln Pro Gln Leu Thr Cys Val
145                 150                 155                 160

Asp Glu Arg Glu His His Arg Phe Leu Ala Ser Glu Glu Ser Gln Gly
                165                 170                 175

Ser Arg Asn Ser Ser Pro Glu Ser Glu Thr Ser Cys Pro Ile Thr Thr
            180                 185                 190

Thr Asp Phe Pro Gln Pro Thr Glu Thr Thr Ala Met Thr Glu Thr Phe
        195                 200                 205
```

Val Leu Thr Met Glu Tyr Lys
    210                 215

<210> SEQ ID NO 31
<211> LENGTH: 240
<212> TYPE: PRT
<213> ORGANISM: Homo Sapiens

<400> SEQUENCE: 31

```
Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240
```

<210> SEQ ID NO 32
<211> LENGTH: 241
<212> TYPE: PRT
<213> ORGANISM: Mus musculus

<400> SEQUENCE: 32

```
Trp Ser Ser Lys Val Leu Met Ser Ser Ala Asn Glu Asp Ile Lys Ala
1               5                   10                  15

Asp Leu Ile Leu Thr Ser Thr Ala Pro Glu His Leu Ser Ala Pro Thr
            20                  25                  30

Leu Pro Leu Pro Glu Val Gln Cys Phe Val Phe Asn Ile Glu Tyr Met
        35                  40                  45

Asn Cys Thr Trp Asn Ser Ser Ser Glu Pro Gln Ala Thr Asn Leu Thr
    50                  55                  60

Leu His Tyr Arg Tyr Lys Val Ser Asp Asn Asn Thr Phe Gln Glu Cys
65                  70                  75                  80
```

```
Ser His Tyr Leu Phe Ser Lys Glu Ile Thr Ser Gly Cys Gln Ile Gln
                85                  90                  95

Lys Glu Asp Ile Gln Leu Tyr Gln Thr Phe Val Val Gln Leu Gln Asp
            100                 105                 110

Pro Gln Lys Pro Gln Arg Arg Ala Val Gln Lys Leu Asn Leu Gln Asn
        115                 120                 125

Leu Val Ile Pro Arg Ala Pro Glu Asn Leu Thr Leu Ser Asn Leu Ser
    130                 135                 140

Glu Ser Gln Leu Glu Leu Arg Trp Lys Ser Arg His Ile Lys Glu Arg
145                 150                 155                 160

Cys Leu Gln Tyr Leu Val Gln Tyr Arg Ser Asn Arg Asp Arg Ser Trp
                165                 170                 175

Thr Glu Leu Ile Val Asn His Glu Pro Arg Phe Ser Leu Pro Ser Val
            180                 185                 190

Asp Glu Leu Lys Arg Tyr Thr Phe Arg Val Arg Ser Arg Tyr Asn Pro
        195                 200                 205

Ile Cys Gly Ser Ser Gln Gln Trp Ser Lys Trp Ser Gln Pro Val His
    210                 215                 220

Trp Gly Ser His Thr Val Glu Glu Asn Pro Ser Leu Phe Ala Leu Glu
225                 230                 235                 240

Ala


<210> SEQ ID NO 33
<211> LENGTH: 228
<212> TYPE: PRT
<213> ORGANISM: Homo Sapiens

<400> SEQUENCE: 33

Glu Met Gly Thr Ala Asp Leu Gly Pro Ser Ser Val Pro Thr Pro Thr
1               5                   10                  15

Asn Val Thr Ile Glu Ser Tyr Asn Met Asn Pro Ile Val Tyr Trp Glu
            20                  25                  30

Tyr Gln Ile Met Pro Gln Val Pro Val Phe Thr Val Glu Val Lys Asn
        35                  40                  45

Tyr Gly Val Lys Asn Ser Glu Trp Ile Asp Ala Cys Ile Asn Ile Ser
    50                  55                  60

His His Tyr Cys Asn Ile Ser Asp His Val Gly Asp Pro Ser Asn Ser
65                  70                  75                  80

Leu Trp Val Arg Val Lys Ala Arg Val Gly Gln Lys Glu Ser Ala Tyr
                85                  90                  95

Ala Lys Ser Glu Glu Phe Ala Val Cys Arg Asp Gly Lys Ile Gly Pro
            100                 105                 110

Pro Lys Leu Asp Ile Arg Lys Glu Glu Lys Gln Ile Met Ile Asp Ile
        115                 120                 125

Phe His Pro Ser Val Phe Val Asn Gly Asp Glu Gln Glu Val Asp Tyr
    130                 135                 140

Asp Pro Glu Thr Thr Cys Tyr Ile Arg Val Tyr Asn Val Tyr Val Arg
145                 150                 155                 160

Met Asn Gly Ser Glu Ile Gln Tyr Lys Ile Leu Thr Gln Lys Glu Asp
                165                 170                 175

Asp Cys Asp Glu Ile Gln Cys Gln Leu Ala Ile Pro Val Ser Ser Leu
            180                 185                 190

Asn Ser Gln Tyr Cys Val Ser Ala Glu Gly Val Leu His Val Trp Gly
        195                 200                 205
```

Val Thr Thr Glu Lys Ser Lys Glu Val Cys Ile Thr Ile Phe Asn Ser
    210                 215                 220

Ser Ile Lys Gly
225

<210> SEQ ID NO 34
<211> LENGTH: 229
<212> TYPE: PRT
<213> ORGANISM: Mus musculus

<400> SEQUENCE: 34

Ala Leu Thr Ser Thr Glu Asp Pro Glu Pro Pro Ser Val Pro Val Pro
1               5                   10                  15

Thr Asn Val Leu Ile Lys Ser Tyr Asn Leu Asn Pro Val Val Cys Trp
            20                  25                  30

Glu Tyr Gln Asn Met Ser Gln Thr Pro Ile Phe Thr Val Gln Val Lys
        35                  40                  45

Val Tyr Ser Gly Ser Trp Thr Asp Ser Cys Thr Asn Ile Ser Asp His
    50                  55                  60

Cys Cys Asn Ile Tyr Glu Gln Ile Met Tyr Pro Asp Val Ser Ala Trp
65                  70                  75                  80

Ala Arg Val Lys Ala Lys Val Gly Gln Lys Glu Ser Asp Tyr Ala Arg
                85                  90                  95

Ser Lys Glu Phe Leu Met Cys Leu Lys Gly Lys Val Gly Pro Pro Gly
            100                 105                 110

Leu Glu Ile Arg Arg Lys Lys Glu Glu Gln Leu Ser Val Leu Val Phe
        115                 120                 125

His Pro Glu Val Val Val Asn Gly Glu Ser Gln Gly Thr Met Phe Gly
    130                 135                 140

Asp Gly Ser Thr Cys Tyr Thr Phe Asp Tyr Thr Val Tyr Val Glu His
145                 150                 155                 160

Asn Arg Ser Gly Glu Ile Leu His Thr Lys His Thr Val Glu Lys Glu
                165                 170                 175

Glu Cys Asn Glu Thr Leu Cys Glu Leu Asn Ile Ser Val Ser Thr Leu
            180                 185                 190

Asp Ser Arg Tyr Cys Ile Ser Val Asp Gly Ile Ser Ser Phe Trp Gln
        195                 200                 205

Val Arg Thr Glu Lys Ser Lys Asp Val Cys Ile Pro Pro Phe His Asp
    210                 215                 220

Asp Arg Lys Asp Ser
225

<210> SEQ ID NO 35
<211> LENGTH: 220
<212> TYPE: PRT
<213> ORGANISM: Homo Sapiens

<400> SEQUENCE: 35

Ser Gln Leu Pro Ala Pro Gln His Pro Lys Ile Arg Leu Tyr Asn Ala
1               5                   10                  15

Glu Gln Val Leu Ser Trp Glu Pro Val Ala Leu Ser Asn Ser Thr Arg
            20                  25                  30

Pro Val Val Tyr Gln Val Gln Phe Lys Tyr Thr Asp Ser Lys Trp Phe
        35                  40                  45

Thr Ala Asp Ile Met Ser Ile Gly Val Asn Cys Thr Gln Ile Thr Ala
    50                  55                  60

Thr Glu Cys Asp Phe Thr Ala Ala Ser Pro Ser Ala Gly Phe Pro Met
65 70 75 80

Asp Phe Asn Val Thr Leu Arg Leu Arg Ala Glu Leu Gly Ala Leu His
85 90 95

Ser Ala Trp Val Thr Met Pro Trp Phe Gln His Tyr Arg Asn Val Thr
100 105 110

Val Gly Pro Pro Glu Asn Ile Glu Val Thr Pro Gly Glu Gly Ser Leu
115 120 125

Ile Ile Arg Phe Ser Ser Pro Phe Asp Ile Ala Asp Thr Ser Thr Ala
130 135 140

Phe Phe Cys Tyr Tyr Val His Tyr Trp Glu Lys Gly Gly Ile Gln Gln
145 150 155 160

Val Lys Gly Pro Phe Arg Ser Asn Ser Ile Ser Leu Asp Asn Leu Lys
165 170 175

Pro Ser Arg Val Tyr Cys Leu Gln Val Gln Ala Gln Leu Leu Trp Asn
180 185 190

Lys Ser Asn Ile Phe Arg Val Gly His Leu Ser Asn Ile Ser Cys Tyr
195 200 205

Glu Thr Met Ala Asp Ala Ser Thr Glu Leu Gln Gln
210 215 220

<210> SEQ ID NO 36
<211> LENGTH: 313
<212> TYPE: PRT
<213> ORGANISM: Mus musculus

<400> SEQUENCE: 36

Ala Ser Ser Pro Asp Ser Phe Ser Gln Leu Ala Ala Pro Leu Asn Pro
1 5 10 15

Arg Leu His Leu Tyr Asn Asp Glu Gln Ile Leu Thr Trp Glu Pro Ser
20 25 30

Pro Ser Ser Asn Asp Pro Arg Pro Val Val Tyr Gln Val Glu Tyr Ser
35 40 45

Phe Ile Asp Gly Ser Trp His Arg Leu Leu Glu Pro Asn Cys Thr Asp
50 55 60

Ile Thr Glu Thr Lys Cys Asp Leu Thr Gly Gly Gly Arg Leu Lys Leu
65 70 75 80

Phe Pro His Pro Phe Thr Val Phe Leu Arg Val Arg Ala Lys Arg Gly
85 90 95

Asn Leu Thr Ser Lys Trp Val Gly Leu Glu Pro Phe Gln His Tyr Glu
100 105 110

Asn Val Thr Val Gly Pro Pro Lys Asn Ile Ser Val Thr Pro Gly Lys
115 120 125

Gly Ser Leu Val Ile His Phe Ser Pro Pro Phe Asp Val Phe His Gly
130 135 140

Ala Thr Phe Gln Tyr Leu Val His Tyr Trp Glu Lys Ser Glu Thr Gln
145 150 155 160

Gln Glu Gln Val Glu Gly Pro Phe Lys Ser Asn Ser Ile Val Leu Gly
165 170 175

Asn Leu Lys Pro Tyr Arg Val Tyr Cys Leu Gln Thr Glu Ala Gln Leu
180 185 190

Ile Leu Lys Asn Lys Lys Ile Arg Pro His Gly Leu Leu Ser Asn Val
195 200 205

```
Ser Cys His Glu Thr Thr Ala Asn Ala Ser Ala Arg Leu Gln Gln Val
    210                 215                 220

Ile Leu Ile Pro Leu Gly Ile Phe Ala Leu Leu Leu Gly Leu Thr Gly
225                 230                 235                 240

Ala Cys Phe Thr Leu Phe Leu Lys Tyr Gln Ser Arg Val Lys Tyr Trp
                245                 250                 255

Phe Gln Ala Pro Pro Asn Ile Pro Glu Gln Ile Glu Glu Tyr Leu Lys
            260                 265                 270

Asp Pro Asp Gln Phe Ile Leu Glu Val Leu Asp Lys Asp Gly Ser Pro
        275                 280                 285

Lys Glu Asp Ser Trp Asp Ser Val Ser Ile Ile Ser Ser Pro Glu Lys
    290                 295                 300

Glu Arg Asp Asp Val Leu Gln Thr Pro
305                 310
```

<210> SEQ ID NO 37
<211> LENGTH: 196
<212> TYPE: PRT
<213> ORGANISM: Artificial Sequence
<220> FEATURE:
<223> OTHER INFORMATION: Synthetic Polypeptide

<400> SEQUENCE: 37

```
Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile Cys Thr Gly
        195
```

<210> SEQ ID NO 38
<211> LENGTH: 2813
<212> TYPE: PRT
<213> ORGANISM: Artificial Sequence
<220> FEATURE:
<223> OTHER INFORMATION: Synthetic Polypeptide

<400> SEQUENCE: 38

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415
```

-continued

```
Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830
```

-continued

```
Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                 1015                 1020

Ser Trp  Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
    1115                 1120                 1125

Ser Cys  Glu Glu Arg Asn Leu  Arg Glu Asn Gly Tyr  Glu Cys Glu
    1130                 1135                 1140

Trp Arg  Tyr Asn Ser Cys Ala  Pro Ala Cys Gln Val  Thr Cys Gln
    1145                 1150                 1155

His Pro  Glu Pro Leu Ala Cys  Pro Val Gln Cys Val  Glu Gly Cys
    1160                 1165                 1170

His Ala  His Cys Pro Pro Gly  Lys Ile Leu Asp Glu  Leu Leu Gln
    1175                 1180                 1185

Thr Cys  Val Asp Pro Glu Asp  Cys Pro Val Cys Glu  Val Ala Gly
    1190                 1195                 1200

Arg Arg  Phe Ala Ser Gly Lys  Lys Val Thr Leu Asn  Pro Ser Asp
    1205                 1210                 1215

Pro Glu  His Cys Gln Ile Cys  His Cys Asp Val Val  Asn Leu Thr
    1220                 1225                 1230
```

```
Cys Glu  Ala Cys Gln Glu Pro  Gly Gly Leu Val Val  Pro Pro Thr
    1235                 1240                 1245

Asp Ala  Pro Val Ser Pro Thr  Thr Leu Tyr Val Glu  Asp Ile Ser
    1250                 1255                 1260

Glu Pro  Pro Leu His Asp Phe  Tyr Cys Ser Arg Leu  Leu Asp Leu
    1265                 1270                 1275

Val Phe  Leu Leu Asp Gly Ser  Ser Arg Leu Ser Glu  Ala Glu Phe
    1280                 1285                 1290

Glu Val  Leu Lys Ala Phe Val  Val Asp Met Met Glu  Arg Leu Arg
    1295                 1300                 1305

Ile Ser  Gln Lys Trp Val Arg  Val Ala Val Val Glu  Tyr His Asp
    1310                 1315                 1320

Gly Ser  His Ala Tyr Ile Gly  Leu Lys Asp Arg Lys  Arg Pro Ser
    1325                 1330                 1335

Glu Leu  Arg Arg Ile Ala Ser  Gln Val Lys Tyr Ala  Gly Ser Gln
    1340                 1345                 1350

Val Ala  Ser Thr Ser Glu Val  Leu Lys Tyr Thr Leu  Phe Gln Ile
    1355                 1360                 1365

Phe Ser  Lys Ile Asp Arg Pro  Glu Ala Ser Arg Ile  Thr Leu Leu
    1370                 1375                 1380

Leu Met  Ala Ser Gln Glu Pro  Gln Arg Met Ser Arg  Asn Phe Val
    1385                 1390                 1395

Arg Tyr  Val Gln Gly Leu Lys  Lys Lys Lys Val Ile  Val Ile Pro
    1400                 1405                 1410

Val Gly  Ile Gly Pro His Ala  Asn Leu Lys Gln Ile  Arg Leu Ile
    1415                 1420                 1425

Glu Lys  Gln Ala Pro Glu Asn  Lys Ala Phe Val Leu  Ser Ser Val
    1430                 1435                 1440

Asp Glu  Leu Glu Gln Gln Arg  Asp Glu Ile Val Ser  Tyr Leu Cys
    1445                 1450                 1455

Asp Leu  Ala Pro Glu Ala Pro  Pro Pro Thr Leu Pro  Pro Asp Met
    1460                 1465                 1470

Ala Gln  Val Thr Val Gly Pro  Gly Leu Leu Gly Val  Ser Thr Leu
    1475                 1480                 1485

Gly Pro  Lys Arg Asn Ser Met  Val Leu Asp Val Ala  Phe Val Leu
    1490                 1495                 1500

Glu Gly  Ser Asp Lys Ile Gly  Glu Ala Asp Phe Asn  Arg Ser Lys
    1505                 1510                 1515

Glu Phe  Met Glu Glu Val Ile  Gln Arg Met Asp Val  Gly Gln Asp
    1520                 1525                 1530

Ser Ile  His Val Thr Val Leu  Gln Tyr Ser Tyr Met  Val Thr Val
    1535                 1540                 1545

Glu Tyr  Pro Phe Ser Glu Ala  Gln Ser Lys Gly Asp  Ile Leu Gln
    1550                 1555                 1560

Arg Val  Arg Glu Ile Arg Tyr  Gln Gly Gly Asn Arg  Thr Asn Thr
    1565                 1570                 1575

Gly Leu  Ala Leu Arg Tyr Leu  Ser Asp His Ser Phe  Leu Val Ser
    1580                 1585                 1590

Gln Gly  Asp Arg Glu Gln Ala  Pro Asn Leu Val Tyr  Met Val Thr
    1595                 1600                 1605

Gly Asn  Pro Ala Ser Asp Glu  Ile Lys Arg Leu Pro  Gly Asp Ile
    1610                 1615                 1620
```

-continued

```
Gln Val  Val Pro Ile Gly Val  Gly Pro Asn Ala Asn  Val Gln Glu
    1625                 1630                 1635

Leu Glu  Arg Ile Gly Trp Pro  Asn Ala Pro Ile Leu  Ile Gln Asp
    1640                 1645                 1650

Phe Glu  Thr Leu Pro Arg Glu  Ala Pro Asp Leu Val  Leu Gln Arg
    1655                 1660                 1665

Cys Cys  Ser Gly Glu Gly Leu  Gln Ile Pro Thr Leu  Ser Pro Ala
    1670                 1675                 1680

Pro Asp  Cys Ser Gln Pro Leu  Asp Val Ile Leu Leu  Leu Asp Gly
    1685                 1690                 1695

Ser Ser  Ser Phe Pro Ala Ser  Tyr Phe Asp Glu Met  Lys Ser Phe
    1700                 1705                 1710

Ala Lys  Ala Phe Ile Ser Lys  Ala Asn Ile Gly Pro  Arg Leu Thr
    1715                 1720                 1725

Gln Val  Ser Val Leu Gln Tyr  Gly Ser Ile Thr Thr  Ile Asp Val
    1730                 1735                 1740

Pro Trp  Asn Val Val Pro Glu  Lys Ala His Leu Leu  Ser Leu Val
    1745                 1750                 1755

Asp Val  Met Gln Arg Glu Gly  Gly Pro Ser Gln Ile  Gly Asp Ala
    1760                 1765                 1770

Leu Gly  Phe Ala Val Arg Tyr  Leu Thr Ser Glu Met  His Gly Ala
    1775                 1780                 1785

Arg Pro  Gly Ala Ser Lys Ala  Val Val Ile Leu Val  Thr Asp Val
    1790                 1795                 1800

Ser Val  Asp Ser Val Asp Ala  Ala Ala Asp Ala Ala  Arg Ser Asn
    1805                 1810                 1815

Arg Val  Thr Val Phe Pro Ile  Gly Ile Gly Asp Arg  Tyr Asp Ala
    1820                 1825                 1830

Ala Gln  Leu Arg Ile Leu Ala  Gly Pro Ala Gly Asp  Ser Asn Val
    1835                 1840                 1845

Val Lys  Leu Gln Arg Ile Glu  Asp Leu Pro Thr Met  Val Thr Leu
    1850                 1855                 1860

Gly Asn  Ser Phe Leu His Lys  Leu Cys Ser Gly Phe  Val Arg Ile
    1865                 1870                 1875

Cys Met  Asp Glu Asp Gly Asn  Glu Lys Arg Pro Gly  Asp Val Trp
    1880                 1885                 1890

Thr Leu  Pro Asp Gln Cys His  Thr Val Thr Cys Gln  Pro Asp Gly
    1895                 1900                 1905

Gln Thr  Leu Leu Lys Ser His  Arg Val Asn Cys Asp  Arg Gly Leu
    1910                 1915                 1920

Arg Pro  Ser Cys Pro Asn Ser  Gln Ser Pro Val Lys  Val Glu Glu
    1925                 1930                 1935

Thr Cys  Gly Cys Arg Trp Thr  Cys Pro Cys Val Cys  Thr Gly Ser
    1940                 1945                 1950

Ser Thr  Arg His Ile Val Thr  Phe Asp Gly Gln Asn  Phe Lys Leu
    1955                 1960                 1965

Thr Gly  Ser Cys Ser Tyr Val  Leu Phe Gln Asn Lys  Glu Gln Asp
    1970                 1975                 1980

Leu Glu  Val Ile Leu His Asn  Gly Ala Cys Ser Pro  Gly Ala Arg
    1985                 1990                 1995

Gln Gly  Cys Met Lys Ser Ile  Glu Val Lys His Ser  Ala Leu Ser
    2000                 2005                 2010
```

-continued

```
Val Glu  Leu His Ser Asp Met  Glu Val Thr Val Asn  Gly Arg Leu
    2015                 2020                 2025

Val Ser  Val Pro Tyr Val Gly  Gly Asn Met Glu Val  Asn Val Tyr
    2030                 2035                 2040

Gly Ala  Ile Met His Glu Val  Arg Phe Asn His Leu  Gly His Ile
    2045                 2050                 2055

Phe Thr  Phe Thr Pro Gln Asn  Asn Glu Phe Gln Leu  Gln Leu Ser
    2060                 2065                 2070

Pro Lys  Thr Phe Ala Ser Lys  Thr Tyr Gly Leu Cys  Gly Ile Cys
    2075                 2080                 2085

Asp Glu  Asn Gly Ala Asn Asp  Phe Met Leu Arg Asp  Gly Thr Val
    2090                 2095                 2100

Thr Thr  Asp Trp Lys Thr Leu  Val Gln Glu Trp Thr  Val Gln Arg
    2105                 2110                 2115

Pro Gly  Gln Thr Cys Gln Pro  Ile Leu Glu Glu Gln  Cys Leu Val
    2120                 2125                 2130

Pro Asp  Ser Ser His Cys Gln  Val Leu Leu Leu Pro  Leu Phe Ala
    2135                 2140                 2145

Glu Cys  His Lys Val Leu Ala  Pro Ala Thr Phe Tyr  Ala Ile Cys
    2150                 2155                 2160

Gln Gln  Asp Ser Cys His Gln  Glu Gln Val Cys Glu  Val Ile Ala
    2165                 2170                 2175

Ser Tyr  Ala His Leu Cys Arg  Thr Asn Gly Val Cys  Val Asp Trp
    2180                 2185                 2190

Arg Thr  Pro Asp Phe Cys Ala  Met Ser Cys Pro Pro  Ser Leu Val
    2195                 2200                 2205

Tyr Asn  His Cys Glu His Gly  Cys Pro Arg His Cys  Asp Gly Asn
    2210                 2215                 2220

Val Ser  Ser Cys Gly Asp His  Pro Ser Glu Gly Cys  Phe Cys Pro
    2225                 2230                 2235

Pro Asp  Lys Val Met Leu Glu  Gly Ser Cys Val Pro  Glu Glu Ala
    2240                 2245                 2250

Cys Thr  Gln Cys Ile Gly Glu  Asp Gly Val Gln His  Gln Phe Leu
    2255                 2260                 2265

Glu Ala  Trp Val Pro Asp His  Gln Pro Cys Gln Ile  Cys Thr Cys
    2270                 2275                 2280

Leu Ser  Gly Arg Lys Val Asn  Cys Thr Thr Gln Pro  Cys Pro Thr
    2285                 2290                 2295

Ala Lys  Ala Pro Thr Cys Gly  Leu Cys Glu Val Ala  Arg Leu Arg
    2300                 2305                 2310

Gln Asn  Ala Asp Gln Cys Cys  Pro Glu Tyr Glu Cys  Val Cys Asp
    2315                 2320                 2325

Pro Val  Ser Cys Asp Leu Pro  Pro Val Pro His Cys  Glu Arg Gly
    2330                 2335                 2340

Leu Gln  Pro Thr Leu Thr Asn  Pro Gly Glu Cys Arg  Pro Asn Phe
    2345                 2350                 2355

Thr Cys  Ala Cys Arg Lys Glu  Glu Cys Lys Arg Val  Ser Pro Pro
    2360                 2365                 2370

Ser Cys  Pro Pro His Arg Leu  Pro Thr Leu Arg Lys  Thr Gln Cys
    2375                 2380                 2385

Cys Asp  Glu Tyr Glu Cys Ala  Cys Asn Cys Val Asn  Ser Thr Val
    2390                 2395                 2400
```

-continued

```
Ser Cys  Pro Leu Gly Tyr Leu  Ala Ser Thr Ala Thr  Asn Asp Cys
    2405                 2410                 2415

Gly Cys  Thr Thr Thr Thr Cys  Leu Pro Asp Lys Val  Cys Val His
    2420                 2425                 2430

Arg Ser  Thr Ile Tyr Pro Val  Gly Gln Phe Trp Glu  Glu Gly Cys
    2435                 2440                 2445

Asp Val  Cys Thr Cys Thr Asp  Met Glu Asp Ala Val  Met Gly Leu
    2450                 2455                 2460

Arg Val  Ala Gln Cys Ser Gln  Lys Pro Cys Glu Asp  Ser Cys Arg
    2465                 2470                 2475

Ser Gly  Phe Thr Tyr Val Leu  His Glu Gly Glu Cys  Cys Gly Arg
    2480                 2485                 2490

Cys Leu  Pro Ser Ala Cys Glu  Val Val Thr Gly Ser  Pro Arg Gly
    2495                 2500                 2505

Asp Ser  Gln Ser Ser Trp Lys  Ser Val Gly Ser Gln  Trp Ala Ser
    2510                 2515                 2520

Pro Glu  Asn Pro Cys Leu Ile  Asn Glu Cys Val Arg  Val Lys Glu
    2525                 2530                 2535

Glu Val  Phe Ile Gln Gln Arg  Asn Val Ser Cys Pro  Gln Leu Glu
    2540                 2545                 2550

Val Pro  Val Cys Pro Ser Gly  Phe Gln Leu Ser Cys  Lys Thr Ser
    2555                 2560                 2565

Ala Cys  Cys Pro Ser Cys Arg  Cys Glu Arg Met Glu  Ala Cys Met
    2570                 2575                 2580

Leu Asn  Gly Thr Val Ile Gly  Pro Gly Lys Thr Val  Met Ile Asp
    2585                 2590                 2595

Val Cys  Thr Thr Cys Arg Cys  Met Val Gln Val Gly  Val Ile Ser
    2600                 2605                 2610

Gly Phe  Lys Leu Glu Cys Arg  Lys Thr Thr Cys Asn  Pro Cys Pro
    2615                 2620                 2625

Leu Gly  Tyr Lys Glu Glu Asn  Asn Thr Gly Glu Cys  Cys Gly Arg
    2630                 2635                 2640

Cys Leu  Pro Thr Ala Cys Thr  Ile Gln Leu Arg Gly  Gly Gln Ile
    2645                 2650                 2655

Met Thr  Leu Lys Arg Asp Glu  Thr Leu Gln Asp Gly  Cys Asp Thr
    2660                 2665                 2670

His Phe  Cys Lys Val Asn Glu  Arg Gly Glu Tyr Phe  Trp Glu Lys
    2675                 2680                 2685

Arg Val  Thr Gly Cys Pro Pro  Phe Asp Glu His Lys  Cys Leu Ala
    2690                 2695                 2700

Glu Gly  Gly Lys Ile Met Lys  Ile Pro Gly Thr Cys  Cys Asp Thr
    2705                 2710                 2715

Cys Glu  Glu Pro Glu Cys Asn  Asp Ile Thr Ala Arg  Leu Gln Tyr
    2720                 2725                 2730

Val Lys  Val Gly Ser Cys Lys  Ser Glu Val Glu Val  Asp Ile His
    2735                 2740                 2745

Tyr Cys  Gln Gly Lys Cys Ala  Ser Lys Ala Met Tyr  Ser Ile Asp
    2750                 2755                 2760

Ile Asn  Asp Val Gln Asp Gln  Cys Ser Cys Cys Ser  Pro Thr Arg
    2765                 2770                 2775

Thr Glu  Pro Met Gln Val Ala  Leu His Cys Thr Asn  Gly Ser Val
    2780                 2785                 2790
```

Val Tyr His Glu Val Leu Asn Ala Met Glu Cys Lys Cys Ser Pro
2795 2800 2805

Arg Lys Cys Ser Lys
2810

<210> SEQ ID NO 39
<211> LENGTH: 222
<212> TYPE: PRT
<213> ORGANISM: Artificial Sequence
<220> FEATURE:
<223> OTHER INFORMATION: Synthetic Polypeptide

<400> SEQUENCE: 39

Cys Gln Glu Pro Gly Gly Leu Val Val Pro Pro Thr Asp Ala Pro Val
1 5 10 15

Ser Pro Thr Thr Leu Tyr Val Glu Asp Ile Ser Glu Pro Pro Leu His
20 25 30

Asp Phe Tyr Cys Ser Arg Leu Leu Asp Leu Val Phe Leu Leu Asp Gly
35 40 45

Ser Ser Arg Leu Ser Glu Ala Glu Phe Glu Val Leu Lys Ala Phe Val
50 55 60

Val Asp Met Met Glu Arg Leu Arg Ile Ser Gln Lys Trp Val Arg Val
65 70 75 80

Ala Val Val Glu Tyr His Asp Gly Ser His Ala Tyr Ile Gly Leu Lys
85 90 95

Asp Arg Lys Arg Pro Ser Glu Leu Arg Arg Ile Ala Ser Gln Val Lys
100 105 110

Tyr Ala Gly Ser Gln Val Ala Ser Thr Ser Glu Val Leu Lys Tyr Thr
115 120 125

Leu Phe Gln Ile Phe Ser Lys Ile Asp Arg Pro Glu Ala Ser Arg Ile
130 135 140

Thr Leu Leu Leu Met Ala Ser Gln Glu Pro Gln Arg Met Ser Arg Asn
145 150 155 160

Phe Val Arg Tyr Val Gln Gly Leu Lys Lys Lys Lys Val Ile Val Ile
165 170 175

Pro Val Gly Ile Gly Pro His Ala Asn Leu Lys Gln Ile Arg Leu Ile
180 185 190

Glu Lys Gln Ala Pro Glu Asn Lys Ala Phe Val Leu Ser Ser Val Asp
195 200 205

Glu Leu Glu Gln Gln Arg Asp Glu Ile Val Ser Tyr Leu Cys
210 215 220

<210> SEQ ID NO 40
<211> LENGTH: 344
<212> TYPE: PRT
<213> ORGANISM: Artificial Sequence
<220> FEATURE:
<223> OTHER INFORMATION: Synthetic Polypeptide

<400> SEQUENCE: 40

Cys Gly Pro Phe Gln Gln Arg Gly Leu Phe Asp Phe Met Leu Glu Asp
1 5 10 15

Glu Ala Ser Gly Ile Gly Pro Glu Val Pro Asp Asp Arg Asp Phe Glu
20 25 30

Pro Ser Leu Gly Pro Val Cys Pro Phe Arg Cys Gln Cys His Leu Arg
35 40 45

Val Val Gln Cys Ser Asp Leu Gly Leu Asp Lys Val Pro Lys Asp Leu
50 55 60

Pro Pro Asp Thr Thr Leu Leu Asp Leu Gln Asn Asn Lys Ile Thr Glu
65 70 75 80

Ile Lys Asp Gly Asp Phe Lys Asn Leu Lys Asn Leu His Ala Leu Ile
85 90 95

Leu Val Asn Asn Lys Ile Ser Lys Val Ser Pro Gly Ala Phe Thr Pro
100 105 110

Leu Val Lys Leu Glu Arg Leu Tyr Leu Ser Lys Asn Gln Leu Lys Glu
115 120 125

Leu Pro Glu Lys Met Pro Lys Thr Leu Gln Glu Leu Arg Ala His Glu
130 135 140

Asn Glu Ile Thr Lys Val Arg Lys Val Thr Phe Asn Gly Leu Asn Gln
145 150 155 160

Met Ile Val Ile Glu Leu Gly Thr Asn Pro Leu Lys Ser Ser Gly Ile
165 170 175

Glu Asn Gly Ala Phe Gln Gly Met Lys Lys Leu Ser Tyr Ile Arg Ile
180 185 190

Ala Asp Thr Asn Ile Thr Ser Ile Pro Gln Gly Leu Pro Pro Ser Leu
195 200 205

Thr Glu Leu His Leu Asp Gly Asn Lys Ile Ser Arg Val Asp Ala Ala
210 215 220

Ser Leu Lys Gly Leu Asn Asn Leu Ala Lys Leu Gly Leu Ser Phe Asn
225 230 235 240

Ser Ile Ser Ala Val Asp Asn Gly Ser Leu Ala Asn Thr Pro His Leu
245 250 255

Arg Glu Leu His Leu Asp Asn Asn Lys Leu Thr Arg Val Pro Gly Gly
260 265 270

Leu Ala Glu His Lys Tyr Ile Gln Val Val Tyr Leu His Asn Asn Asn
275 280 285

Ile Ser Val Val Gly Ser Ser Asp Phe Cys Pro Pro Gly His Asn Thr
290 295 300

Lys Lys Ala Ser Tyr Ser Gly Val Ser Leu Phe Ser Asn Pro Val Gln
305 310 315 320

Tyr Trp Glu Ile Gln Pro Ser Thr Phe Arg Cys Val Tyr Val Arg Ser
325 330 335

Ala Ile Gln Leu Gly Asn Tyr Lys
340

<210> SEQ ID NO 41
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 41

Leu Arg Glu Leu His Leu Asp Asn Asn Cys
1 5 10

<210> SEQ ID NO 42
<211> LENGTH: 584
<212> TYPE: PRT
<213> ORGANISM: Mus musculus

<400> SEQUENCE: 42

```
Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380

Lys Asn Leu Val Lys Thr Asn Cys Asp Leu Tyr Glu Lys Leu Gly Glu
385                 390                 395                 400
```

Tyr Gly Phe Gln Asn Ala Ile Leu Val Arg Tyr Thr Gln Lys Ala Pro
405 410 415

Gln Val Ser Thr Pro Thr Leu Val Glu Ala Ala Arg Asn Leu Gly Arg
420 425 430

Val Gly Thr Lys Cys Cys Thr Leu Pro Glu Asp Gln Arg Leu Pro Cys
435 440 445

Val Glu Asp Tyr Leu Ser Ala Ile Leu Asn Arg Val Cys Leu Leu His
450 455 460

Glu Lys Thr Pro Val Ser Glu His Val Thr Lys Cys Cys Ser Gly Ser
465 470 475 480

Leu Val Glu Arg Arg Pro Cys Phe Ser Ala Leu Thr Val Asp Glu Thr
485 490 495

Tyr Val Pro Lys Glu Phe Lys Ala Glu Thr Phe Thr Phe His Ser Asp
500 505 510

Ile Cys Thr Leu Pro Glu Lys Glu Lys Gln Ile Lys Lys Gln Thr Ala
515 520 525

Leu Ala Glu Leu Val Lys His Lys Pro Lys Ala Thr Ala Glu Gln Leu
530 535 540

Lys Thr Val Met Asp Asp Phe Ala Gln Phe Leu Asp Thr Cys Cys Lys
545 550 555 560

Ala Ala Asp Lys Asp Thr Cys Phe Ser Thr Glu Gly Pro Asn Leu Val
565 570 575

Thr Arg Cys Lys Asp Ala Leu Ala
580

<210> SEQ ID NO 43
<211> LENGTH: 608
<212> TYPE: PRT
<213> ORGANISM: Homo Sapiens

<400> SEQUENCE: 43

Lys Trp Val Thr Phe Ile Ser Leu Leu Phe Leu Phe Ser Ser Ala Tyr
1 5 10 15

Ser Arg Gly Val Phe Arg Arg Asp Ala His Lys Ser Glu Val Ala His
20 25 30

Arg Phe Lys Asp Leu Gly Glu Glu Asn Phe Lys Ala Leu Val Leu Ile
35 40 45

Ala Phe Ala Gln Tyr Leu Gln Gln Cys Pro Phe Glu Asp His Val Lys
50 55 60

Leu Val Asn Glu Val Thr Glu Phe Ala Lys Thr Cys Val Ala Asp Glu
65 70 75 80

Ser Ala Glu Asn Cys Asp Lys Ser Leu His Thr Leu Phe Gly Asp Lys
85 90 95

Leu Cys Thr Val Ala Thr Leu Arg Glu Thr Tyr Gly Glu Met Ala Asp
100 105 110

Cys Cys Ala Lys Gln Glu Pro Glu Arg Asn Glu Cys Phe Leu Gln His
115 120 125

Lys Asp Asp Asn Pro Asn Leu Pro Arg Leu Val Arg Pro Glu Val Asp
130 135 140

Val Met Cys Thr Ala Phe His Asp Asn Glu Glu Thr Phe Leu Lys Lys
145 150 155 160

Tyr Leu Tyr Glu Ile Ala Arg Arg His Pro Tyr Phe Tyr Ala Pro Glu
165 170 175

-continued

```
Leu Leu Phe Phe Ala Lys Arg Tyr Lys Ala Ala Phe Thr Glu Cys Cys
            180                 185                 190

Gln Ala Ala Asp Lys Ala Ala Cys Leu Leu Pro Lys Leu Asp Glu Leu
        195                 200                 205

Arg Asp Glu Gly Lys Ala Ser Ser Ala Lys Gln Arg Leu Lys Cys Ala
    210                 215                 220

Ser Leu Gln Lys Phe Gly Glu Arg Ala Phe Lys Ala Trp Ala Val Ala
225                 230                 235                 240

Arg Leu Ser Gln Arg Phe Pro Lys Ala Glu Phe Ala Glu Val Ser Lys
                245                 250                 255

Leu Val Thr Asp Leu Thr Lys Val His Thr Glu Cys Cys His Gly Asp
            260                 265                 270

Leu Leu Glu Cys Ala Asp Asp Arg Ala Asp Leu Ala Lys Tyr Ile Cys
        275                 280                 285

Glu Asn Gln Asp Ser Ile Ser Ser Lys Leu Lys Glu Cys Cys Glu Lys
    290                 295                 300

Pro Leu Leu Glu Lys Ser His Cys Ile Ala Glu Val Glu Asn Asp Glu
305                 310                 315                 320

Met Pro Ala Asp Leu Pro Ser Leu Ala Ala Asp Phe Val Glu Ser Lys
                325                 330                 335

Asp Val Cys Lys Asn Tyr Ala Glu Ala Lys Asp Val Phe Leu Gly Met
            340                 345                 350

Phe Leu Tyr Glu Tyr Ala Arg Arg His Pro Asp Tyr Ser Val Val Leu
        355                 360                 365

Leu Leu Arg Leu Ala Lys Thr Tyr Glu Thr Thr Leu Glu Lys Cys Cys
    370                 375                 380

Ala Ala Ala Asp Pro His Glu Cys Tyr Ala Lys Val Phe Asp Glu Phe
385                 390                 395                 400

Lys Pro Leu Val Glu Glu Pro Gln Asn Leu Ile Lys Gln Asn Cys Glu
                405                 410                 415

Leu Phe Glu Gln Leu Gly Glu Tyr Lys Phe Gln Asn Ala Leu Leu Val
            420                 425                 430

Arg Tyr Thr Lys Lys Val Pro Gln Val Ser Thr Pro Thr Leu Val Glu
        435                 440                 445

Val Ser Arg Asn Leu Gly Lys Val Gly Ser Lys Cys Cys Lys His Pro
    450                 455                 460

Glu Ala Lys Arg Met Pro Cys Ala Glu Asp Tyr Leu Ser Val Val Leu
465                 470                 475                 480

Asn Gln Leu Cys Val Leu His Glu Lys Thr Pro Val Ser Asp Arg Val
                485                 490                 495

Thr Lys Cys Cys Thr Glu Ser Leu Val Asn Arg Arg Pro Cys Phe Ser
            500                 505                 510

Ala Leu Glu Val Asp Glu Thr Tyr Val Pro Lys Glu Phe Asn Ala Glu
        515                 520                 525

Thr Phe Thr Phe His Ala Asp Ile Cys Thr Leu Ser Glu Lys Glu Arg
    530                 535                 540

Gln Ile Lys Lys Gln Thr Ala Leu Val Glu Leu Val Lys His Lys Pro
545                 550                 555                 560

Lys Ala Thr Lys Glu Gln Leu Lys Ala Val Met Asp Asp Phe Ala Ala
                565                 570                 575

Phe Val Glu Lys Cys Cys Lys Ala Asp Asp Lys Glu Thr Cys Phe Ala
            580                 585                 590
```

Glu Glu Gly Lys Lys Leu Val Ala Ala Ser Gln Ala Ala Leu Gly Leu
595 600 605

<210> SEQ ID NO 44
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 44

Leu Arg Glu Leu His Leu Asn Asn Asn Cys
1 5 10

<210> SEQ ID NO 45
<211> LENGTH: 193
<212> TYPE: PRT
<213> ORGANISM: Artificial Sequence
<220> FEATURE:
<223> OTHER INFORMATION: Synthetic Polypeptide

<400> SEQUENCE: 45

Cys Ser Gln Pro Leu Asp Val Ile Leu Leu Leu Asp Gly Ser Ser Ser
1 5 10 15

Phe Pro Ala Ser Tyr Phe Asp Glu Met Lys Ser Phe Ala Lys Ala Phe
20 25 30

Ile Ser Lys Ala Asn Ile Gly Pro Arg Leu Thr Gln Val Ser Val Leu
35 40 45

Gln Tyr Gly Ser Ile Thr Thr Ile Asp Val Pro Trp Asn Val Val Pro
50 55 60

Glu Lys Ala His Leu Leu Ser Leu Val Asp Val Met Gln Arg Glu Gly
65 70 75 80

Gly Pro Ser Gln Ile Gly Asp Ala Leu Gly Phe Ala Val Arg Tyr Leu
85 90 95

Thr Ser Glu Met His Gly Ala Arg Pro Gly Ala Ser Lys Ala Val Val
100 105 110

Ile Leu Val Thr Asp Val Ser Val Asp Ser Val Asp Ala Ala Ala Asp
115 120 125

Ala Ala Arg Ser Asn Arg Val Thr Val Phe Pro Ile Gly Ile Gly Asp
130 135 140

Arg Tyr Asp Ala Ala Gln Leu Arg Ile Leu Ala Gly Pro Ala Gly Asp
145 150 155 160

Ser Asn Val Val Lys Leu Gln Arg Ile Glu Asp Leu Pro Thr Met Val
165 170 175

Thr Leu Gly Asn Ser Phe Leu His Lys Leu Cys Ser Gly Phe Val Arg
180 185 190

Ile

<210> SEQ ID NO 46
<211> LENGTH: 205
<212> TYPE: PRT
<213> ORGANISM: Artificial Sequence
<220> FEATURE:
<223> OTHER INFORMATION: Synthetic Polypeptide

<400> SEQUENCE: 46

Cys Ser Gly Glu Gly Leu Gln Ile Pro Thr Leu Ser Pro Ala Pro Asp
1 5 10 15

Cys Ser Gln Pro Leu Asp Val Ile Leu Leu Leu Asp Gly Ser Ser Ser
20 25 30

Phe Pro Ala Ser Tyr Phe Asp Glu Met Lys Ser Phe Ala Lys Ala Phe
35 40 45

Ile Ser Lys Ala Asn Ile Gly Pro Arg Leu Thr Gln Val Ser Val Leu
50 55 60

Gln Tyr Gly Ser Ile Thr Thr Ile Asp Val Pro Trp Asn Val Val Pro
65 70 75 80

Glu Lys Ala His Leu Leu Ser Leu Val Asp Val Met Gln Arg Glu Gly
85 90 95

Gly Pro Ser Gln Ile Gly Asp Ala Leu Gly Phe Ala Val Arg Tyr Leu
100 105 110

Thr Ser Glu Met His Gly Ala Arg Pro Gly Ala Ser Lys Ala Val Val
115 120 125

Ile Leu Val Thr Asp Val Ser Val Asp Ser Val Asp Ala Ala Ala Asp
130 135 140

Ala Ala Arg Ser Asn Arg Val Thr Val Phe Pro Ile Gly Ile Gly Asp
145 150 155 160

Arg Tyr Asp Ala Ala Gln Leu Arg Ile Leu Ala Gly Pro Ala Gly Asp
165 170 175

Ser Asn Val Val Lys Leu Gln Arg Ile Glu Asp Leu Pro Thr Met Val
180 185 190

Thr Leu Gly Asn Ser Phe Leu His Lys Leu Cys Ser Gly
195 200 205

<210> SEQ ID NO 47
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 47

Gly Gly Gly Ser Gly Gly Gly Ser
1 5

<210> SEQ ID NO 48
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 48

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser Gly Gly Gly Ser
20 25 30

Gly Gly Gly Ser Gly Gly Gly Ser Gly Gly Gly Ser
35 40

<210> SEQ ID NO 49
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 49

Leu Ser Gly Arg Ser Asp Asn His
1 5

<210> SEQ ID NO 50
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 50

Val Pro Leu Ser Leu Tyr Ser
1 5

<210> SEQ ID NO 51
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 51

Pro Leu Gly Leu Ala Gly
1 5

<210> SEQ ID NO 52
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 52

Val Leu Val Pro Met Ala Met Met Ala Ser
1 5 10

<210> SEQ ID NO 53
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: X is alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine
<220> FEATURE:
<221> NAME/KEY: MISC_FEATURE
<222> LOCATION: (2)..(2)
<223> OTHER INFORMATION: X is alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine
<220> FEATURE:
<221> NAME/KEY: MISC_FEATURE
<222> LOCATION: (7)..(7)
<223> OTHER INFORMATION: X is alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine

<400> SEQUENCE: 53

Xaa Xaa Gln Ala Arg Ala Xaa
1 5

<210> SEQ ID NO 54
<211> LENGTH: 4
<212> TYPE: PRT
<213> ORGANISM: Artificial Sequence
<220> FEATURE:

<223> OTHER INFORMATION: Synthetic Polypeptide

<400> SEQUENCE: 54

Ala Gly Pro Arg
1

<210> SEQ ID NO 55
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 55

Ala Ala Asn Leu
1

<210> SEQ ID NO 56
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 56

Pro Thr Asn Leu
1

<210> SEQ ID NO 57
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 57

```
Thr Ser Gly Arg Ser Ala Asn Pro
1               5
```

<210> SEQ ID NO 58
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 58

```
Gly Ala Ser Thr Ser Val Asp Glu Leu Gln Ala Glu Val Asp Gln Leu
1               5                   10                  15

Gln Asp Glu Asn Tyr Ala Leu Lys Thr Lys Val Ala Gln Leu Arg Lys
            20                  25                  30

Lys Val Glu Lys Leu Ser Glu
        35
```

<210> SEQ ID NO 59
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 59

```
Gly Ala Ser Thr Thr Val Ala Gln Leu Arg Glu Arg Val Lys Thr Leu
1               5                   10                  15
```

```
Arg Ala Gln Asn Tyr Glu Leu Glu Ser Glu Val Gln Arg Leu Arg Glu
            20                  25                  30

Gln Val Ala Gln Leu Ala
        35
```

```
<210> SEQ ID NO 60
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 60

Glu Ala Cys Gly Ala Ser Thr Ser Val Asp Glu Leu Gln Ala Glu Val
1               5                   10                  15

Asp Gln Leu Gln Asp Glu Asn Tyr Ala Leu Lys Thr Lys Val Ala Gln
            20                  25                  30

Leu Arg Lys Lys Val Glu Lys Leu Ser Glu
        35                  40
```

```
<210> SEQ ID NO 61
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 61

Glu Ala Cys Gly Ala Ser Thr Thr Val Ala Gln Leu Arg Glu Arg Val
1               5                   10                  15

Lys Thr Leu Arg Ala Gln Asn Tyr Glu Leu Glu Ser Glu Val Gln Arg
            20                  25                  30

Leu Arg Glu Gln Val Ala Gln Leu Ala
        35                  40
```

```
<210> SEQ ID NO 62
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 62

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Ala Arg Asn Arg
            20                  25                  30

Val Ser Gln Tyr Arg Thr Arg Tyr
        35                  40
```

```
<210> SEQ ID NO 63
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 63

Leu Glu Ile Arg Ala Ala Phe Leu Arg Gln Arg Asn Thr Ala Leu Arg
1               5                   10                  15

Thr Glu Val Ala Glu Leu Glu Gln Glu Val Gln Arg Leu Glu Asn Glu
            20                  25                  30
```

```
Val Ser Gln Tyr Glu Thr Arg Tyr
        35                  40


<210> SEQ ID NO 64
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 64

Glu Ala Cys Gly Ala Leu Glu Ile Glu Ala Ala Phe Leu Glu Arg Glu
1               5                   10                  15

Asn Thr Ala Leu Glu Thr Arg Val Ala Glu Leu Arg Gln Arg Val Gln
            20                  25                  30

Arg Ala Arg Asn Arg Val Ser Gln Tyr Arg Thr Arg Tyr
        35                  40                  45


<210> SEQ ID NO 65
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 65

Glu Ala Cys Gly Ala Leu Glu Ile Arg Ala Ala Phe Leu Arg Gln Arg
1               5                   10                  15

Asn Thr Ala Leu Arg Thr Glu Val Ala Glu Leu Glu Gln Glu Val Gln
            20                  25                  30

Arg Leu Glu Asn Glu Val Ser Gln Tyr Glu Thr Arg Tyr
        35                  40                  45


<210> SEQ ID NO 66
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 66

Leu Glu Ile Arg Ala Ala Phe Leu Arg Arg Arg Asn Thr Ala Leu Arg
1               5                   10                  15

Thr Arg Val Ala Glu Leu Arg Gln Arg Val Gln Arg Leu Arg Asn Ile
            20                  25                  30

Val Ser Gln Tyr Glu Thr Arg Tyr
        35                  40


<210> SEQ ID NO 67
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 67

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Ile
            20                  25                  30

Val Ser Gln Tyr Glu Thr Arg Tyr
        35                  40
```

<210> SEQ ID NO 68
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 68

```
Glu Ala Cys Gly Ala Leu Glu Ile Arg Ala Ala Phe Leu Arg Arg Arg
1               5                   10                  15

Asn Thr Ala Leu Arg Thr Arg Val Ala Glu Leu Arg Gln Arg Val Gln
            20                  25                  30

Arg Leu Arg Asn Ile Val Ser Gln Tyr Glu Thr Arg Tyr
        35                  40                  45
```

<210> SEQ ID NO 69
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 69

```
Glu Ala Cys Gly Ala Leu Glu Ile Glu Ala Ala Phe Leu Glu Gln Glu
1               5                   10                  15

Asn Thr Ala Leu Glu Thr Glu Val Ala Glu Leu Glu Gln Glu Val Gln
            20                  25                  30

Arg Leu Glu Asn Ile Val Ser Gln Tyr Glu Thr Arg Tyr
        35                  40                  45
```

<210> SEQ ID NO 70
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 70

```
Gln Gly Ala Ser Thr Ser Val Asp Glu Leu Gln Ala Glu Val Asp Gln
1               5                   10                  15

Leu Glu Asp Glu Asn Tyr Ala Leu Lys Thr Lys Val Ala Gln Leu Arg
            20                  25                  30

Lys Lys Val Glu Lys Leu
        35
```

<210> SEQ ID NO 71
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 71

```
Gln Gly Ala Ser Thr Thr Val Ala Gln Leu Glu Glu Lys Val Lys Thr
1               5                   10                  15

Leu Arg Ala Glu Asn Tyr Glu Leu Lys Ser Glu Val Gln Arg Leu Glu
            20                  25                  30

Glu Gln Val Ala Gln Leu
        35
```

<210> SEQ ID NO 72

<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 72

```
Glu Ala Cys Gly Ala Ser Thr Ser Val Asp Glu Leu Gln Ala Glu Val
1               5                   10                  15

Asp Gln Leu Glu Asp Glu Asn Tyr Ala Leu Lys Thr Lys Val Ala Gln
            20                  25                  30

Leu Arg Lys Lys Val Glu Lys Leu
        35                  40
```

<210> SEQ ID NO 73
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 73

```
Glu Ala Cys Gly Ala Ser Thr Thr Val Ala Gln Leu Glu Glu Lys Val
1               5                   10                  15

Lys Thr Leu Arg Ala Glu Asn Tyr Glu Leu Lys Ser Glu Val Gln Arg
            20                  25                  30

Leu Glu Glu Gln Val Ala Gln Leu
        35                  40
```

<210> SEQ ID NO 74
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 74

```
Ala Gly Leu Thr Asp Thr Leu Gln Ala Glu Thr Asp Gln Leu Glu Asp
1               5                   10                  15

Lys Lys Ser Ala Leu Gln Thr Glu Ile Ala Asn Leu Leu Lys Glu Lys
            20                  25                  30

Glu Lys Leu Glu Phe Ile Leu Ala Ala His
        35                  40
```

<210> SEQ ID NO 75
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 75

```
Ala Gly Arg Ile Ala Arg Leu Glu Glu Lys Val Lys Thr Leu Lys Ala
1               5                   10                  15

Gln Asn Ser Glu Leu Ala Ser Thr Ala Asn Met Leu Arg Glu Gln Val
            20                  25                  30

Ala Gln Leu Lys Gln Lys Val Met Asn Tyr
        35                  40
```

<210> SEQ ID NO 76
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 76

Glu Ala Cys Gly Ala Gly Leu Thr Asp Thr Leu Gln Ala Glu Thr Asp
1 5 10 15

Gln Leu Glu Asp Lys Lys Ser Ala Leu Gln Thr Glu Ile Ala Asn Leu
20 25 30

Leu Lys Glu Lys Glu Lys Leu Glu Phe Ile Leu Ala Ala His
35 40 45

<210> SEQ ID NO 77
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 77

Glu Ala Cys Gly Ala Gly Arg Ile Ala Arg Leu Glu Glu Lys Val Lys
1 5 10 15

Thr Leu Lys Ala Gln Asn Ser Glu Leu Ala Ser Thr Ala Asn Met Leu
20 25 30

Arg Glu Gln Val Ala Gln Leu Lys Gln Lys Val Met Asn Tyr
35 40 45

<210> SEQ ID NO 78
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 78

Gly Lys Ile Ala Ala Leu Lys Gln Lys Ile Ala Ala Leu Lys Tyr Lys
1 5 10 15

Asn Ala Ala Leu Lys Lys Lys Ile Ala Ala Leu Lys Gln
20 25

<210> SEQ ID NO 79
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 79

Gly Glu Ile Ala Ala Leu Glu Gln Glu Ile Ala Ala Leu Glu Lys Glu
1 5 10 15

Asn Ala Ala Leu Glu Trp Glu Ile Ala Ala Leu Glu Gln
20 25

<210> SEQ ID NO 80
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 80

Glu Ala Cys Gly Ala Gly Lys Ile Ala Ala Leu Lys Gln Lys Ile Ala
1 5 10 15

Ala Leu Lys Tyr Lys Asn Ala Ala Leu Lys Lys Lys Ile Ala Ala Leu
20 25 30

Lys Gln

<210> SEQ ID NO 81
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 81

Glu Ala Cys Gly Ala Gly Glu Ile Ala Ala Leu Glu Gln Glu Ile Ala
1 5 10 15

Ala Leu Glu Lys Glu Asn Ala Ala Leu Glu Trp Glu Ile Ala Ala Leu
20 25 30

Glu Gln

<210> SEQ ID NO 82
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 82

Gly Leu Asn Asp Ile Phe Glu Ala Gln Lys Ile Glu Trp His Glu
1 5 10 15

<210> SEQ ID NO 83
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 83

Lys Arg Arg Trp Lys Lys Asn Phe Ile Ala Val Ser Ala Ala Asn Arg
1 5 10 15

Phe Lys Lys Ile Ser Ser Ser Gly Ala Leu
20 25

<210> SEQ ID NO 84
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 84

Glu Glu Glu Glu Glu Glu
1 5

<210> SEQ ID NO 85
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 85

Asp Tyr Lys Asp Asp Asp Asp Lys
1 5

<210> SEQ ID NO 86
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 86

Tyr Pro Tyr Asp Val Pro Asp Tyr Ala
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 87

His His His His His His
1               5

<210> SEQ ID NO 88
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 88

Glu Gln Lys Leu Ile Ser Glu Glu Asp Leu
1               5                   10

<210> SEQ ID NO 89
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 89

Thr Lys Glu Asn Pro Arg Ser Asn Gln Glu Glu Ser Tyr Asp Asp Asn
1               5                   10                  15

Glu Ser

<210> SEQ ID NO 90
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 90

Lys Glu Thr Ala Ala Ala Lys Phe Glu Arg Gln His Met Asp Ser
1               5                   10                  15

<210> SEQ ID NO 91
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 91

Met Asp Glu Lys Thr Thr Gly Trp Arg Gly Gly His Val Val Glu Gly
1               5                   10                  15

```
Leu Ala Gly Glu Leu Glu Gln Leu Arg Ala Arg Leu Glu His His Pro
            20                  25                  30

Gln Gly Gln Arg Glu Pro
        35


<210> SEQ ID NO 92
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 92

Ser Leu Ala Glu Leu Leu Asn Ala Gly Leu Gly Gly Ser
1               5                   10


<210> SEQ ID NO 93
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 93

Thr Gln Asp Pro Ser Arg Val Gly
1               5


<210> SEQ ID NO 94
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 94

Trp Ser His Pro Gln Phe Glu Lys
1               5


<210> SEQ ID NO 95
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 95

Cys Cys Pro Gly Cys Cys
1               5


<210> SEQ ID NO 96
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 96

Gly Lys Pro Ile Pro Asn Pro Leu Leu Gly Leu Asp Ser Thr
1               5                   10


<210> SEQ ID NO 97
<211> LENGTH: 11
<212> TYPE: PRT
<213> ORGANISM: Artificial Sequence
<220> FEATURE:
<223> OTHER INFORMATION: Synthetic Polypeptide
```

<400> SEQUENCE: 97

Tyr Thr Asp Ile Glu Met Asn Arg Leu Gly Lys
1 5 10

<210> SEQ ID NO 98
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 98

Asp Leu Tyr Asp Asp Asp Asp Lys
1 5

<210> SEQ ID NO 99
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 99

Thr Asp Lys Asp Met Thr Ile Thr Phe Thr Asn Lys Lys Asp Ala Glu
1 5 10 15

<210> SEQ ID NO 100
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 100

Ala His Ile Val Met Val Asp Ala Tyr Lys Pro Thr Lys
1 5 10

<210> SEQ ID NO 101
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 101

Lys Leu Gly Asp Ile Glu Phe Ile Lys Val Asn Lys
1 5 10

<210> SEQ ID NO 102
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 102

Gly Ala Pro Val Pro Tyr Pro Asp Pro Leu Glu Pro Arg
1 5 10

<210> SEQ ID NO 103
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 103

His Pro Val Gly Leu Leu Ala Arg Val Pro Leu Ser Tyr Ser Gly His
1 5 10 15

Pro Val Gly Leu Leu Ala Arg Val Pro Leu Ser Tyr Ser Gly Ser Gly
20 25 30

Leu Leu Ser Gly Arg Ser Asp Asn His
35 40

<210> SEQ ID NO 104
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 104

Pro Leu Gly Val Arg Gly Lys Pro Leu Gly Val Arg Gly Lys Pro Leu
1 5 10 15

Gly Val Arg Gly Lys
20

<210> SEQ ID NO 105
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 105

Gly Glu Arg Gly Pro Pro Gly Pro Gln Gly Ala Ala Arg Gly Phe Pro
1 5 10 15

Gly Thr Pro Gly Leu Gly Glu Arg Gly Pro Pro Gly Pro Gln Gly Ala
20 25 30

Ala Arg Gly Phe Pro Gly Thr Pro Gly Leu
35 40

<210> SEQ ID NO 106
<211> LENGTH: 63
<212> TYPE: PRT
<213> ORGANISM: Artificial Sequence
<220> FEATURE:
<223> OTHER INFORMATION: Synthetic Polypeptide

<400> SEQUENCE: 106

Pro Leu Gly Val Arg Gly Lys Pro Leu Gly Val Arg Gly Lys Pro Leu
1 5 10 15

Gly Val Arg Gly Lys Gly Glu Arg Gly Pro Pro Gly Pro Gln Gly Ala
20 25 30

Ala Arg Gly Phe Pro Gly Thr Pro Gly Leu Gly Glu Arg Gly Pro Pro
35 40 45

Gly Pro Gln Gly Ala Ala Arg Gly Phe Pro Gly Thr Pro Gly Leu
50 55 60

<210> SEQ ID NO 107
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 107

Pro Leu Gly Val Arg Gly Lys Pro Leu Gly Val Arg Gly Lys
1 5 10

<210> SEQ ID NO 108
<211> LENGTH: 97
<212> TYPE: PRT
<213> ORGANISM: Artificial Sequence
<220> FEATURE:
<223> OTHER INFORMATION: Synthetic Polypeptide

<400> SEQUENCE: 108

His Pro Val Gly Leu Leu Ala Arg Val Pro Leu Ser Tyr Ser Gly His
1 5 10 15

Pro Val Gly Leu Leu Ala Arg Val Pro Leu Ser Tyr Ser Gly Ser Gly
20 25 30

Leu Leu Ser Gly Arg Ser Asp Asn His Pro Leu Gly Val Arg Gly Lys
35 40 45

Pro Leu Gly Val Arg Gly Lys Gly Glu Arg Gly Pro Pro Gly Pro Gln
50 55 60

Gly Ala Ala Arg Gly Phe Pro Gly Thr Pro Gly Leu Gly Glu Arg Gly
65 70 75 80

Pro Pro Gly Pro Gln Gly Ala Ala Arg Gly Phe Pro Gly Thr Pro Gly
85 90 95

Leu

<210> SEQ ID NO 109
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 109

Tyr Leu Gly Arg Ser Tyr Lys Val
1 5

<210> SEQ ID NO 110
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 110

Thr Ser Gln Val Asn Gly Leu Asn
1 5

<210> SEQ ID NO 111
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 111

Ala Pro Pro Pro Val Val Leu Leu
1 5

<210> SEQ ID NO 112
<211> LENGTH: 5
<212> TYPE: PRT

<213> ORGANISM: Artificial Sequence
<220> FEATURE:
<223> OTHER INFORMATION: Synthetic Polypeptide

<400> SEQUENCE: 112

Gly Gly Gly Gly Phe
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 113

Thr Pro Glu His Val Val Pro Tyr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 114

Pro Arg Ser Phe Phe Arg Leu Gly Lys
1               5

<210> SEQ ID NO 115
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 115

Pro Gln Gly Arg Ile Val Gly Gly
1               5

<210> SEQ ID NO 116
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 116

Glu Val Leu Leu Ser Trp Ala Val
1               5

<210> SEQ ID NO 117
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 117

Pro Val Ser Leu Ser Tyr Arg Cys
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 118

Leu Arg Glu Leu His Leu Asp Asn
1               5

<210> SEQ ID NO 119
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 119

Ala Ala Pro Val
1

<210> SEQ ID NO 120
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 120

Ile Pro Glu Asn Phe Phe Gly Val
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 121

Pro Arg Phe Lys Ile Ile Gly Gly
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 122

Met Leu Glu Asp Glu Ala Ser Gly
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 123

Lys Gln Ser Arg Lys Phe Val Pro
1               5

<210> SEQ ID NO 124
<211> LENGTH: 8
<212> TYPE: PRT
<213> ORGANISM: Artificial Sequence
<220> FEATURE:

<223> OTHER INFORMATION: Synthetic Polypeptide

<400> SEQUENCE: 124

Arg Gln Ala Arg Val Val Gly Gly
1 5

<210> SEQ ID NO 125
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 125

Gly Lys Ala Phe Arg Arg Leu
1 5

<210> SEQ ID NO 126
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 126

Gly Pro Leu Gly Leu Trp Ala Gln
1 5

<210> SEQ ID NO 127
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 127

Ser Leu Gly Arg Lys Ile Gln Ile
1 5

<210> SEQ ID NO 128
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 128

Pro Val Ser Leu Arg
1 5

<210> SEQ ID NO 129
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 129

Ala Ala Ala Thr Ser Ile Ala Met
1 5

<210> SEQ ID NO 130
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 130

Ala Ala Gly Ala Met Phe Leu Glu
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 131

Glu Ala Ala Ala Ala Thr Ser Ile
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 132

Pro Arg His Leu Arg
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 133

Pro Arg Gly Leu Arg Lys
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 134

Val Pro Leu Ser Leu Tyr Ser Gly
1               5

<210> SEQ ID NO 135
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 135

Pro Arg Gly Leu Arg Pro
1               5

<210> SEQ ID NO 136
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 136

Pro Arg His Leu Arg Asn
1 5

<210> SEQ ID NO 137
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 137

Pro Arg Trp Leu Arg Ser
1 5

<210> SEQ ID NO 138
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 138

His Pro Val Gly Leu Leu Ala Arg
1 5

<210> SEQ ID NO 139
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 139

Lys Gly Pro Leu Gly Val Arg Gly
1 5

<210> SEQ ID NO 140
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 140

Cys Gly Leu Asp Asp
1 5

<210> SEQ ID NO 141
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 141

Ser Thr Ala Val Ile Val Ser Ala
1 5

<210> SEQ ID NO 142
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 142

Gly Pro Leu Gly Ile Ala Gly Gln
1               5

<210> SEQ ID NO 143
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 143

Pro Leu Gly Leu Trp Ala
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 144

Gly Pro Leu Gly Met Leu Ser Gln
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 145

Pro Leu Gly Val Arg Gly Lys
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 146

Gly Pro Gln Gly Ile Trp Gly Gln
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 147

Ala Ile Pro Val Ser Leu Arg
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 148

Gly Pro Leu Gly Leu Ala Arg Lys
1 5

<210> SEQ ID NO 149
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 149

Pro Gln Gly Ile Ala Met Gly
1 5

<210> SEQ ID NO 150
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 150

Val Ala Ser Ser Ser Thr Ala Val
1 5

<210> SEQ ID NO 151
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 151

Pro Leu Gly Leu
1

<210> SEQ ID NO 152
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 152

Arg Pro Leu Ala Leu Trp Arg Ser
1 5

<210> SEQ ID NO 153
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 153

Asn Lys Ser Arg Leu Gly Leu Gly
1 5

<210> SEQ ID NO 154
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 154

Gly Pro Gln Gly Ile Ala Gly Gln Arg
1 5

<210> SEQ ID NO 155
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 155

Pro Val Gly Leu Ile Gly
1 5

<210> SEQ ID NO 156
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 156

Lys Pro Val Ser Leu Ser Tyr Arg
1 5

<210> SEQ ID NO 157
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 157

Gln Pro Val Gly Ile Asn Thr Ser
1 5

<210> SEQ ID NO 158
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 158

Pro Leu Gly Met Thr Ser
1 5

<210> SEQ ID NO 159
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 159

Pro Arg Ala Leu Met
1 5

<210> SEQ ID NO 160
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 160

Gly Pro Leu Pro Leu Arg
1 5

<210> SEQ ID NO 161
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 161

Lys Gln Leu Arg Val Val Asn Gly
1 5

<210> SEQ ID NO 162
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 162

Pro Leu Gly Leu Tyr Ala
1 5

<210> SEQ ID NO 163
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 163

His Ser Ser Lys Leu Gln Leu
1 5

<210> SEQ ID NO 164
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 164

Ser Ser Lys Tyr Gln
1 5

<210> SEQ ID NO 165
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 165

Gly Pro Leu Gly Val Arg Gly Lys
1 5

<210> SEQ ID NO 166
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 166

Pro Arg Gly Met Ala Ser
1 5

<210> SEQ ID NO 167
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 167

Ala Ala Ala Leu Gly Asn Val Ala Pro
1 5

<210> SEQ ID NO 168
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 168

Gly Gly Ser Gly Arg Ser Ala Asn Ala
1 5

<210> SEQ ID NO 169
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 169

Pro Leu Gly Val Arg Gly
1 5

<210> SEQ ID NO 170
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 170

Ser Gly Arg Ser Ala Asn Ala Lys
1 5

<210> SEQ ID NO 171
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 171

Gly Pro Leu Gly Leu Trp Ala Gly Gly
1 5

<210> SEQ ID NO 172
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 172

Ser Gly Arg Ser Ala
1 5

<210> SEQ ID NO 173
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 173

Pro Leu Gly Leu Tyr Leu
1 5

<210> SEQ ID NO 174
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 174

Ser Arg Arg Arg Val Asn Ser Leu
1 5

<210> SEQ ID NO 175
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 175

Gly Ser Thr Phe Phe
1 5

<210> SEQ ID NO 176
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 176

Cys Pro Gly Arg Val Val Gly Gly
1 5

<210> SEQ ID NO 177
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 177

Gly Thr Gln Phe Phe
1 5

<210> SEQ ID NO 178
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 178

Pro Gln Gly Leu Ala Gly
1 5

<210> SEQ ID NO 179
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 179

Gln Val Val Ala Gly
1 5

<210> SEQ ID NO 180
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 180

Thr Tyr Ser Arg Ser Arg Tyr Leu
1 5

<210> SEQ ID NO 181
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 181

Asn Ser Gly Arg Ala Val Thr Tyr
1 5

<210> SEQ ID NO 182
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 182

Gly Pro Gln Gly Ala Arg Gly Gln
1 5

<210> SEQ ID NO 183
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 183

Pro Ser Ser Arg Arg Arg Val Asn
1 5

<210> SEQ ID NO 184
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 184

Pro Leu Gly Leu Tyr Ala Leu
1 5

<210> SEQ ID NO 185
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 185

Pro Met Lys Arg Leu Thr Leu Gly
1 5

<210> SEQ ID NO 186
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 186

Asp Asp Asp Lys Ile Val Gly Gly
1 5

<210> SEQ ID NO 187
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 187

His Leu Val Glu Ala Leu Tyr Leu
1 5

<210> SEQ ID NO 188
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 188

Glu Val Asp Leu Leu Ile Gly Ser
1 5

<210> SEQ ID NO 189
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 189

Ala Val Arg Trp Leu Leu Thr Ala
1 5

<210> SEQ ID NO 190
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 190

Gly Gly Gly Arg Arg
1 5

<210> SEQ ID NO 191
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 191

Gly Gly Gly Ser
1

<210> SEQ ID NO 192
<211> LENGTH: 241
<212> TYPE: PRT
<213> ORGANISM: Artificial Sequence
<220> FEATURE:
<223> OTHER INFORMATION: Synthetic Polypeptide

<400> SEQUENCE: 192

Gln Leu Gly Ala Ser Gly Pro Gly Asp Cys Cys Val Glu Lys Thr Ser
1 5 10 15

Phe Pro Glu Gly Ala Ser Gly Ser Pro Leu Gly Pro Arg Asn Leu Ser
20 25 30

Cys Tyr Arg Val Ser Lys Thr Asp Tyr Glu Cys Ser Trp Gln Tyr Asp
35 40 45

Gly Pro Glu Asp Asn Val Ser His Val Leu Trp Cys Cys Phe Val Pro
50 55 60

Pro Asn His Thr His Thr Gly Gln Glu Arg Cys Arg Tyr Phe Ser Ser
65 70 75 80

Gly Pro Asp Arg Thr Val Gln Phe Trp Glu Gln Asp Gly Ile Pro Val
85 90 95

Leu Ser Lys Val Asn Phe Trp Val Glu Ser Arg Leu Gly Asn Arg Thr
100 105 110

Met Lys Ser Gln Lys Ile Ser Gln Tyr Leu Tyr Asn Trp Thr Lys Thr
115 120 125

Thr Pro Pro Leu Gly His Ile Lys Val Ser Gln Ser His Arg Gln Leu
130 135 140

Arg Met Asp Trp Asn Val Ser Glu Glu Ala Gly Ala Glu Val Gln Phe
145 150 155 160

Arg Arg Arg Met Pro Thr Thr Asn Trp Thr Leu Gly Asp Cys Gly Pro
165 170 175

Gln Val Asn Ser Gly Ser Gly Val Leu Gly Asp Ile Arg Gly Ser Met
180 185 190

Ser Glu Ser Cys Leu Cys Pro Ser Glu Asn Met Ala Gln Glu Ile Gln
195 200 205

Ile Arg Arg Arg Arg Arg Leu Ser Ser Gly Ala Pro Gly Gly Pro Trp
210 215 220

Ser Asp Trp Ser Met Pro Val Cys Val Pro Pro Glu Val Leu Pro Gln
225 230 235 240

Ala

<210> SEQ ID NO 193
<211> LENGTH: 5

```
<212> TYPE: PRT
<213> ORGANISM: Artificial Sequence
<220> FEATURE:
<223> OTHER INFORMATION: Synthetic Polypeptide

<400> SEQUENCE: 193

His His His His His
1               5


<210> SEQ ID NO 194
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 194

Gly Glu Arg Gly Pro Pro Gly Pro Gln Gly Ala Ala Arg Gly Phe Pro
1               5                   10                  15

Gly Thr Pro Gly Leu
            20


<210> SEQ ID NO 195
<211> LENGTH: 211
<212> TYPE: PRT
<213> ORGANISM: Homo Sapiens

<400> SEQUENCE: 195

Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
            100                 105                 110

Ser Val Lys Tyr Glu Pro Pro Leu Gly Asp Ile Lys Val Ser Lys Leu
        115                 120                 125

Ala Gly Gln Leu Arg Met Glu Trp Glu Thr Pro Asp Asn Gln Val Gly
    130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Asp Thr Glu Ser Cys Leu Cys Pro
                165                 170                 175

Leu Glu Met Asn Val Ala Gln Glu Phe Gln Leu Arg Arg Arg Gln Leu
            180                 185                 190

Gly Ser Gln Gly Ser Ser Trp Ser Lys Trp Ser Ser Pro Val Cys Val
        195                 200                 205

Pro Pro Glu
    210


<210> SEQ ID NO 196
<211> LENGTH: 453
```

<212> TYPE: PRT
<213> ORGANISM: Homo Sapiens

<400> SEQUENCE: 196

```
Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
            100                 105                 110

Ser Val Lys Tyr Glu Pro Pro Leu Gly Asp Ile Lys Val Ser Lys Leu
        115                 120                 125

Ala Gly Gln Leu Arg Met Glu Trp Glu Thr Pro Asp Asn Gln Val Gly
    130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Asp Thr Glu Ser Cys Leu Cys Pro
                165                 170                 175

Leu Glu Met Asn Val Ala Gln Glu Phe Gln Leu Arg Arg Arg Gln Leu
            180                 185                 190

Gly Ser Gln Gly Ser Ser Trp Ser Lys Trp Ser Ser Pro Val Cys Val
        195                 200                 205

Pro Pro Glu Gly Gly Gly Ser Gly Gly Gly Ser Gly Gly Gly Ser Gly
    210                 215                 220

Gly Gly Ser Gly Gly Gly Ser Gly Gly Gly Ser Gly Gly Gly Ser Gly
225                 230                 235                 240

Gly Gly Ser Gly Gly Gly Ser Gly Gly Gly Ser Gly Gly Gly Ser Gly
                245                 250                 255

Arg Asn Leu Pro Val Ala Thr Pro Asp Pro Gly Met Phe Pro Cys Leu
            260                 265                 270

His His Ser Gln Asn Leu Leu Arg Ala Val Ser Asn Met Leu Gln Lys
        275                 280                 285

Ala Arg Gln Thr Leu Glu Phe Tyr Pro Cys Thr Ser Glu Glu Ile Asp
    290                 295                 300

His Glu Asp Ile Thr Lys Asp Lys Thr Ser Thr Val Glu Ala Cys Leu
305                 310                 315                 320

Pro Leu Glu Leu Thr Lys Asn Glu Ser Cys Leu Asn Ser Arg Glu Thr
                325                 330                 335

Ser Phe Ile Thr Asn Gly Ser Cys Leu Ala Ser Arg Lys Thr Ser Phe
            340                 345                 350

Met Met Ala Leu Cys Leu Ser Ser Ile Tyr Glu Asp Leu Lys Met Tyr
        355                 360                 365

Gln Val Glu Phe Lys Thr Met Asn Ala Lys Leu Leu Met Asp Pro Lys
    370                 375                 380

Arg Gln Ile Phe Leu Asp Gln Asn Met Leu Ala Val Ile Asp Glu Leu
385                 390                 395                 400
```

```
Met Gln Ala Leu Asn Phe Asn Ser Glu Thr Val Pro Gln Lys Ser Ser
                405                 410                 415

Leu Glu Glu Pro Asp Phe Tyr Lys Thr Lys Ile Lys Leu Cys Ile Leu
            420                 425                 430

Leu His Ala Phe Arg Ile Arg Ala Val Thr Ile Asp Arg Val Met Ser
        435                 440                 445

Tyr Leu Asn Ala Ser
    450


<210> SEQ ID NO 197
<211> LENGTH: 459
<212> TYPE: PRT
<213> ORGANISM: Homo Sapiens

<400> SEQUENCE: 197

Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
            100                 105                 110

Ser Val Lys Tyr Glu Pro Pro Leu Gly Asp Ile Lys Val Ser Lys Leu
        115                 120                 125

Ala Gly Gln Leu Arg Met Glu Trp Glu Thr Pro Asp Asn Gln Val Gly
    130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Asp Thr Glu Ser Cys Leu Cys Pro
                165                 170                 175

Leu Glu Met Asn Val Ala Gln Glu Phe Gln Leu Arg Arg Arg Gln Leu
            180                 185                 190

Gly Ser Gln Gly Ser Ser Trp Ser Lys Trp Ser Ser Pro Val Cys Val
        195                 200                 205

Pro Pro Glu His Pro Val Gly Leu Leu Ala Arg Val Pro Leu Ser Leu
    210                 215                 220

Tyr Ser Gly His Pro Val Gly Leu Leu Ala Arg Val Pro Leu Ser Leu
225                 230                 235                 240

Tyr Ser Gly Ser Gly Leu Leu Ser Gly Arg Ser Asp Asn His Gly Gly
                245                 250                 255

Gly Ser Gly Gly Gly Ser Arg Asn Leu Pro Val Ala Thr Pro Asp Pro
            260                 265                 270

Gly Met Phe Pro Cys Leu His His Ser Gln Asn Leu Leu Arg Ala Val
        275                 280                 285

Ser Asn Met Leu Gln Lys Ala Arg Gln Thr Leu Glu Phe Tyr Pro Cys
    290                 295                 300
```

Thr Ser Glu Glu Ile Asp His Glu Asp Ile Thr Lys Asp Lys Thr Ser
305 310 315 320

Thr Val Glu Ala Cys Leu Pro Leu Glu Leu Thr Lys Asn Glu Ser Cys
325 330 335

Leu Asn Ser Arg Glu Thr Ser Phe Ile Thr Asn Gly Ser Cys Leu Ala
340 345 350

Ser Arg Lys Thr Ser Phe Met Met Ala Leu Cys Leu Ser Ser Ile Tyr
355 360 365

Glu Asp Leu Lys Met Tyr Gln Val Glu Phe Lys Thr Met Asn Ala Lys
370 375 380

Leu Leu Met Asp Pro Lys Arg Gln Ile Phe Leu Asp Gln Asn Met Leu
385 390 395 400

Ala Val Ile Asp Glu Leu Met Gln Ala Leu Asn Phe Asn Ser Glu Thr
405 410 415

Val Pro Gln Lys Ser Ser Leu Glu Glu Pro Asp Phe Tyr Lys Thr Lys
420 425 430

Ile Lys Leu Cys Ile Leu Leu His Ala Phe Arg Ile Arg Ala Val Thr
435 440 445

Ile Asp Arg Val Met Ser Tyr Leu Asn Ala Ser
450 455

<210> SEQ ID NO 198
<211> LENGTH: 483
<212> TYPE: PRT
<213> ORGANISM: Artificial Sequence
<220> FEATURE:
<223> OTHER INFORMATION: Synthetic Polypeptide

<400> SEQUENCE: 198

Gln Leu Gly Ala Ser Gly Pro Gly Asp Cys Cys Val Glu Lys Thr Ser
1 5 10 15

Phe Pro Glu Gly Ala Ser Gly Ser Pro Leu Gly Pro Arg Asn Leu Ser
20 25 30

Cys Tyr Arg Val Ser Lys Thr Asp Tyr Glu Cys Ser Trp Gln Tyr Asp
35 40 45

Gly Pro Glu Asp Asn Val Ser His Val Leu Trp Cys Cys Phe Val Pro
50 55 60

Pro Asn His Thr His Thr Gly Gln Glu Arg Cys Arg Tyr Phe Ser Ser
65 70 75 80

Gly Pro Asp Arg Thr Val Gln Phe Trp Glu Gln Asp Gly Ile Pro Val
85 90 95

Leu Ser Lys Val Asn Phe Trp Val Glu Ser Arg Leu Gly Asn Arg Thr
100 105 110

Met Lys Ser Gln Lys Ile Ser Gln Tyr Leu Tyr Asn Trp Thr Lys Thr
115 120 125

Thr Pro Pro Leu Gly His Ile Lys Val Ser Gln Ser His Arg Gln Leu
130 135 140

Arg Met Asp Trp Asn Val Ser Glu Glu Ala Gly Ala Glu Val Gln Phe
145 150 155 160

Arg Arg Arg Met Pro Thr Thr Asn Trp Thr Leu Gly Asp Cys Gly Pro
165 170 175

Gln Val Asn Ser Gly Ser Gly Val Leu Gly Asp Ile Arg Gly Ser Met
180 185 190

Ser Glu Ser Cys Leu Cys Pro Ser Glu Asn Met Ala Gln Glu Ile Gln
195 200 205

Ile Arg Arg Arg Arg Arg Leu Ser Ser Gly Ala Pro Gly Gly Pro Trp
    210                 215                 220

Ser Asp Trp Ser Met Pro Val Cys Val Pro Pro Glu Val Leu Pro Gln
225                 230                 235                 240

Ala His Pro Val Gly Leu Leu Ala Arg Val Pro Leu Ser Tyr Ser Gly
                245                 250                 255

His Pro Val Gly Leu Leu Ala Arg Val Pro Leu Ser Tyr Ser Gly Ser
            260                 265                 270

Gly Leu Leu Ser Gly Arg Ser Asp Asn His Gly Gly Gly Ser Gly Gly
        275                 280                 285

Gly Ser Arg Val Ile Pro Val Ser Gly Pro Ala Arg Cys Leu Ser Gln
    290                 295                 300

Ser Arg Asn Leu Leu Lys Thr Thr Asp Asp Met Val Lys Thr Ala Arg
305                 310                 315                 320

Glu Lys Leu Lys His Tyr Ser Cys Thr Ala Glu Asp Ile Asp His Glu
                325                 330                 335

Asp Ile Thr Arg Asp Gln Thr Ser Thr Leu Lys Thr Cys Leu Pro Leu
            340                 345                 350

Glu Leu His Lys Asn Glu Ser Cys Leu Ala Thr Arg Glu Thr Ser Ser
        355                 360                 365

Thr Thr Arg Gly Ser Cys Leu Pro Pro Gln Lys Thr Ser Leu Met Met
    370                 375                 380

Thr Leu Cys Leu Gly Ser Ile Tyr Glu Asp Leu Lys Met Tyr Gln Thr
385                 390                 395                 400

Glu Phe Gln Ala Ile Asn Ala Ala Leu Gln Asn His Asn His Gln Gln
                405                 410                 415

Ile Ile Leu Asp Lys Gly Met Leu Val Ala Ile Asp Glu Leu Met Gln
            420                 425                 430

Ser Leu Asn His Asn Gly Glu Thr Leu Arg Gln Lys Pro Pro Val Gly
        435                 440                 445

Glu Ala Asp Pro Tyr Arg Val Lys Met Lys Leu Cys Ile Leu Leu His
    450                 455                 460

Ala Phe Ser Thr Arg Val Val Thr Ile Asn Arg Val Met Gly Tyr Leu
465                 470                 475                 480

Ser Ser Ala

<210> SEQ ID NO 199
<211> LENGTH: 463
<212> TYPE: PRT
<213> ORGANISM: Artificial Sequence
<220> FEATURE:
<223> OTHER INFORMATION: Synthetic Polypeptide

<400> SEQUENCE: 199

Gln Leu Gly Ala Ser Gly Pro Gly Asp Cys Cys Val Glu Lys Thr Ser
1               5                   10                  15

Phe Pro Glu Gly Ala Ser Gly Ser Pro Leu Gly Pro Arg Asn Leu Ser
            20                  25                  30

Cys Tyr Arg Val Ser Lys Thr Asp Tyr Glu Cys Ser Trp Gln Tyr Asp
        35                  40                  45

Gly Pro Glu Asp Asn Val Ser His Val Leu Trp Cys Cys Phe Val Pro
    50                  55                  60

Pro Asn His Thr His Thr Gly Gln Glu Arg Cys Arg Tyr Phe Ser Ser
65                  70                  75                  80

```
Gly Pro Asp Arg Thr Val Gln Phe Trp Glu Gln Asp Gly Ile Pro Val
                85                  90                  95

Leu Ser Lys Val Asn Phe Trp Val Glu Ser Arg Leu Gly Asn Arg Thr
            100                 105                 110

Met Lys Ser Gln Lys Ile Ser Gln Tyr Leu Tyr Asn Trp Thr Lys Thr
        115                 120                 125

Thr Pro Pro Leu Gly His Ile Lys Val Ser Gln Ser His Arg Gln Leu
    130                 135                 140

Arg Met Asp Trp Asn Val Ser Glu Glu Ala Gly Ala Glu Val Gln Phe
145                 150                 155                 160

Arg Arg Arg Met Pro Thr Thr Asn Trp Thr Leu Gly Asp Cys Gly Pro
                165                 170                 175

Gln Val Asn Ser Gly Ser Gly Val Leu Gly Asp Ile Arg Gly Ser Met
            180                 185                 190

Ser Glu Ser Cys Leu Cys Pro Ser Glu Asn Met Ala Gln Glu Ile Gln
        195                 200                 205

Ile Arg Arg Arg Arg Arg Leu Ser Ser Gly Ala Pro Gly Gly Pro Trp
    210                 215                 220

Ser Asp Trp Ser Met Pro Val Cys Val Pro Pro Glu Val Leu Pro Gln
225                 230                 235                 240

Ala Pro Leu Gly Val Arg Gly Lys Pro Leu Gly Val Arg Gly Lys Pro
                245                 250                 255

Leu Gly Val Arg Gly Lys Gly Gly Gly Ser Gly Gly Gly Ser Arg Val
            260                 265                 270

Ile Pro Val Ser Gly Pro Ala Arg Cys Leu Ser Gln Ser Arg Asn Leu
        275                 280                 285

Leu Lys Thr Thr Asp Asp Met Val Lys Thr Ala Arg Glu Lys Leu Lys
    290                 295                 300

His Tyr Ser Cys Thr Ala Glu Asp Ile Asp His Glu Asp Ile Thr Arg
305                 310                 315                 320

Asp Gln Thr Ser Thr Leu Lys Thr Cys Leu Pro Leu Glu Leu His Lys
                325                 330                 335

Asn Glu Ser Cys Leu Ala Thr Arg Glu Thr Ser Ser Thr Thr Arg Gly
            340                 345                 350

Ser Cys Leu Pro Pro Gln Lys Thr Ser Leu Met Met Thr Leu Cys Leu
        355                 360                 365

Gly Ser Ile Tyr Glu Asp Leu Lys Met Tyr Gln Thr Glu Phe Gln Ala
    370                 375                 380

Ile Asn Ala Ala Leu Gln Asn His Asn His Gln Gln Ile Ile Leu Asp
385                 390                 395                 400

Lys Gly Met Leu Val Ala Ile Asp Glu Leu Met Gln Ser Leu Asn His
                405                 410                 415

Asn Gly Glu Thr Leu Arg Gln Lys Pro Pro Val Gly Glu Ala Asp Pro
            420                 425                 430

Tyr Arg Val Lys Met Lys Leu Cys Ile Leu Leu His Ala Phe Ser Thr
        435                 440                 445

Arg Val Val Thr Ile Asn Arg Val Met Gly Tyr Leu Ser Ser Ala
    450                 455                 460
```

<210> SEQ ID NO 200
<211> LENGTH: 484
<212> TYPE: PRT
<213> ORGANISM: Artificial Sequence
<220> FEATURE:
<223> OTHER INFORMATION: Synthetic Polypeptide

<400> SEQUENCE: 200

Gln Leu Gly Ala Ser Gly Pro Gly Asp Cys Cys Val Glu Lys Thr Ser
1               5                   10                  15

Phe Pro Glu Gly Ala Ser Gly Ser Pro Leu Gly Pro Arg Asn Leu Ser
            20                  25                  30

Cys Tyr Arg Val Ser Lys Thr Asp Tyr Glu Cys Ser Trp Gln Tyr Asp
        35                  40                  45

Gly Pro Glu Asp Asn Val Ser His Val Leu Trp Cys Cys Phe Val Pro
    50                  55                  60

Pro Asn His Thr His Thr Gly Gln Glu Arg Cys Arg Tyr Phe Ser Ser
65                  70                  75                  80

Gly Pro Asp Arg Thr Val Gln Phe Trp Glu Gln Asp Gly Ile Pro Val
                85                  90                  95

Leu Ser Lys Val Asn Phe Trp Val Glu Ser Arg Leu Gly Asn Arg Thr
            100                 105                 110

Met Lys Ser Gln Lys Ile Ser Gln Tyr Leu Tyr Asn Trp Thr Lys Thr
        115                 120                 125

Thr Pro Pro Leu Gly His Ile Lys Val Ser Gln Ser His Arg Gln Leu
    130                 135                 140

Arg Met Asp Trp Asn Val Ser Glu Glu Ala Gly Ala Glu Val Gln Phe
145                 150                 155                 160

Arg Arg Arg Met Pro Thr Thr Asn Trp Thr Leu Gly Asp Cys Gly Pro
                165                 170                 175

Gln Val Asn Ser Gly Ser Gly Val Leu Gly Asp Ile Arg Gly Ser Met
            180                 185                 190

Ser Glu Ser Cys Leu Cys Pro Ser Glu Asn Met Ala Gln Glu Ile Gln
        195                 200                 205

Ile Arg Arg Arg Arg Arg Leu Ser Ser Gly Ala Pro Gly Gly Pro Trp
    210                 215                 220

Ser Asp Trp Ser Met Pro Val Cys Val Pro Pro Glu Val Leu Pro Gln
225                 230                 235                 240

Ala Gly Glu Arg Gly Pro Pro Gly Pro Gln Gly Ala Ala Arg Gly Phe
                245                 250                 255

Pro Gly Thr Pro Gly Leu Gly Glu Arg Gly Pro Pro Gly Pro Gln Gly
            260                 265                 270

Ala Ala Arg Gly Phe Pro Gly Thr Pro Gly Leu Gly Gly Ser Gly
        275                 280                 285

Gly Gly Ser Arg Val Ile Pro Val Ser Gly Pro Ala Arg Cys Leu Ser
    290                 295                 300

Gln Ser Arg Asn Leu Leu Lys Thr Thr Asp Asp Met Val Lys Thr Ala
305                 310                 315                 320

Arg Glu Lys Leu Lys His Tyr Ser Cys Thr Ala Glu Asp Ile Asp His
                325                 330                 335

Glu Asp Ile Thr Arg Asp Gln Thr Ser Thr Leu Lys Thr Cys Leu Pro
            340                 345                 350

Leu Glu Leu His Lys Asn Glu Ser Cys Leu Ala Thr Arg Glu Thr Ser
        355                 360                 365

Ser Thr Thr Arg Gly Ser Cys Leu Pro Pro Gln Lys Thr Ser Leu Met
    370                 375                 380

Met Thr Leu Cys Leu Gly Ser Ile Tyr Glu Asp Leu Lys Met Tyr Gln
385                 390                 395                 400

```
Thr Glu Phe Gln Ala Ile Asn Ala Ala Leu Gln Asn His Asn His Gln
                405                 410                 415

Gln Ile Ile Leu Asp Lys Gly Met Leu Val Ala Ile Asp Glu Leu Met
            420                 425                 430

Gln Ser Leu Asn His Asn Gly Glu Thr Leu Arg Gln Lys Pro Pro Val
        435                 440                 445

Gly Glu Ala Asp Pro Tyr Arg Val Lys Met Lys Leu Cys Ile Leu Leu
    450                 455                 460

His Ala Phe Ser Thr Arg Val Val Thr Ile Asn Arg Val Met Gly Tyr
465                 470                 475                 480

Leu Ser Ser Ala


<210> SEQ ID NO 201
<211> LENGTH: 505
<212> TYPE: PRT
<213> ORGANISM: Artificial Sequence
<220> FEATURE:
<223> OTHER INFORMATION: Synthetic Polypeptide

<400> SEQUENCE: 201

Gln Leu Gly Ala Ser Gly Pro Gly Asp Cys Cys Val Glu Lys Thr Ser
1               5                   10                  15

Phe Pro Glu Gly Ala Ser Gly Ser Pro Leu Gly Pro Arg Asn Leu Ser
            20                  25                  30

Cys Tyr Arg Val Ser Lys Thr Asp Tyr Glu Cys Ser Trp Gln Tyr Asp
        35                  40                  45

Gly Pro Glu Asp Asn Val Ser His Val Leu Trp Cys Cys Phe Val Pro
    50                  55                  60

Pro Asn His Thr His Thr Gly Gln Glu Arg Cys Arg Tyr Phe Ser Ser
65                  70                  75                  80

Gly Pro Asp Arg Thr Val Gln Phe Trp Glu Gln Asp Gly Ile Pro Val
                85                  90                  95

Leu Ser Lys Val Asn Phe Trp Val Glu Ser Arg Leu Gly Asn Arg Thr
            100                 105                 110

Met Lys Ser Gln Lys Ile Ser Gln Tyr Leu Tyr Asn Trp Thr Lys Thr
        115                 120                 125

Thr Pro Pro Leu Gly His Ile Lys Val Ser Gln Ser His Arg Gln Leu
    130                 135                 140

Arg Met Asp Trp Asn Val Ser Glu Glu Ala Gly Ala Glu Val Gln Phe
145                 150                 155                 160

Arg Arg Arg Met Pro Thr Thr Asn Trp Thr Leu Gly Asp Cys Gly Pro
                165                 170                 175

Gln Val Asn Ser Gly Ser Gly Val Leu Gly Asp Ile Arg Gly Ser Met
            180                 185                 190

Ser Glu Ser Cys Leu Cys Pro Ser Glu Asn Met Ala Gln Glu Ile Gln
        195                 200                 205

Ile Arg Arg Arg Arg Arg Leu Ser Ser Gly Ala Pro Gly Gly Pro Trp
    210                 215                 220

Ser Asp Trp Ser Met Pro Val Cys Val Pro Pro Glu Val Leu Pro Gln
225                 230                 235                 240

Ala Pro Leu Gly Val Arg Gly Lys Pro Leu Gly Val Arg Gly Lys Pro
                245                 250                 255

Leu Gly Val Arg Gly Lys Gly Glu Arg Gly Pro Pro Gly Pro Gln Gly
            260                 265                 270
```

```
Ala Ala Arg Gly Phe Pro Gly Thr Pro Gly Leu Gly Glu Arg Gly Pro
        275                 280                 285

Pro Gly Pro Gln Gly Ala Ala Arg Gly Phe Pro Gly Thr Pro Gly Leu
    290                 295                 300

Gly Gly Gly Ser Gly Gly Gly Ser Arg Val Ile Pro Val Ser Gly Pro
305                 310                 315                 320

Ala Arg Cys Leu Ser Gln Ser Arg Asn Leu Leu Lys Thr Thr Asp Asp
                325                 330                 335

Met Val Lys Thr Ala Arg Glu Lys Leu Lys His Tyr Ser Cys Thr Ala
            340                 345                 350

Glu Asp Ile Asp His Glu Asp Ile Thr Arg Asp Gln Thr Ser Thr Leu
        355                 360                 365

Lys Thr Cys Leu Pro Leu Glu Leu His Lys Asn Glu Ser Cys Leu Ala
    370                 375                 380

Thr Arg Glu Thr Ser Ser Thr Thr Arg Gly Ser Cys Leu Pro Pro Gln
385                 390                 395                 400

Lys Thr Ser Leu Met Met Thr Leu Cys Leu Gly Ser Ile Tyr Glu Asp
                405                 410                 415

Leu Lys Met Tyr Gln Thr Glu Phe Gln Ala Ile Asn Ala Ala Leu Gln
            420                 425                 430

Asn His Asn His Gln Gln Ile Ile Leu Asp Lys Gly Met Leu Val Ala
        435                 440                 445

Ile Asp Glu Leu Met Gln Ser Leu Asn His Asn Gly Glu Thr Leu Arg
    450                 455                 460

Gln Lys Pro Pro Val Gly Glu Ala Asp Pro Tyr Arg Val Lys Met Lys
465                 470                 475                 480

Leu Cys Ile Leu Leu His Ala Phe Ser Thr Arg Val Val Thr Ile Asn
                485                 490                 495

Arg Val Met Gly Tyr Leu Ser Ser Ala
            500                 505
```

<210> SEQ ID NO 202
<211> LENGTH: 497
<212> TYPE: PRT
<213> ORGANISM: Artificial Sequence
<220> FEATURE:
<223> OTHER INFORMATION: Synthetic Polypeptide

<400> SEQUENCE: 202

```
Gln Leu Gly Ala Ser Gly Pro Gly Asp Cys Cys Val Glu Lys Thr Ser
1               5                   10                  15

Phe Pro Glu Gly Ala Ser Gly Ser Pro Leu Gly Pro Arg Asn Leu Ser
            20                  25                  30

Cys Tyr Arg Val Ser Lys Thr Asp Tyr Glu Cys Ser Trp Gln Tyr Asp
        35                  40                  45

Gly Pro Glu Asp Asn Val Ser His Val Leu Trp Cys Cys Phe Val Pro
    50                  55                  60

Pro Asn His Thr His Thr Gly Gln Glu Arg Cys Arg Tyr Phe Ser Ser
65                  70                  75                  80

Gly Pro Asp Arg Thr Val Gln Phe Trp Glu Gln Asp Gly Ile Pro Val
                85                  90                  95

Leu Ser Lys Val Asn Phe Trp Val Glu Ser Arg Leu Gly Asn Arg Thr
            100                 105                 110

Met Lys Ser Gln Lys Ile Ser Gln Tyr Leu Tyr Asn Trp Thr Lys Thr
        115                 120                 125
```

Thr Pro Pro Leu Gly His Ile Lys Val Ser Gln Ser His Arg Gln Leu
130 135 140

Arg Met Asp Trp Asn Val Ser Glu Glu Ala Gly Ala Glu Val Gln Phe
145 150 155 160

Arg Arg Arg Met Pro Thr Thr Asn Trp Thr Leu Gly Asp Cys Gly Pro
165 170 175

Gln Val Asn Ser Gly Ser Gly Val Leu Gly Asp Ile Arg Gly Ser Met
180 185 190

Ser Glu Ser Cys Leu Cys Pro Ser Glu Asn Met Ala Gln Glu Ile Gln
195 200 205

Ile Arg Arg Arg Arg Arg Leu Ser Ser Gly Ala Pro Gly Gly Pro Trp
210 215 220

Ser Asp Trp Ser Met Pro Val Cys Val Pro Pro Glu Val Leu Pro Gln
225 230 235 240

Ala His Pro Val Gly Leu Leu Ala Arg Val Pro Leu Ser Tyr Ser Gly
245 250 255

His Pro Val Gly Leu Leu Ala Arg Val Pro Leu Ser Tyr Ser Gly Ser
260 265 270

Gly Leu Leu Ser Gly Arg Ser Asp Asn His Pro Leu Gly Val Arg Gly
275 280 285

Lys Pro Leu Gly Val Arg Gly Lys Gly Gly Gly Ser Gly Gly Gly Ser
290 295 300

Arg Val Ile Pro Val Ser Gly Pro Ala Arg Cys Leu Ser Gln Ser Arg
305 310 315 320

Asn Leu Leu Lys Thr Thr Asp Asp Met Val Lys Thr Ala Arg Glu Lys
325 330 335

Leu Lys His Tyr Ser Cys Thr Ala Glu Asp Ile Asp His Glu Asp Ile
340 345 350

Thr Arg Asp Gln Thr Ser Thr Leu Lys Thr Cys Leu Pro Leu Glu Leu
355 360 365

His Lys Asn Glu Ser Cys Leu Ala Thr Arg Glu Thr Ser Ser Thr Thr
370 375 380

Arg Gly Ser Cys Leu Pro Pro Gln Lys Thr Ser Leu Met Met Thr Leu
385 390 395 400

Cys Leu Gly Ser Ile Tyr Glu Asp Leu Lys Met Tyr Gln Thr Glu Phe
405 410 415

Gln Ala Ile Asn Ala Ala Leu Gln Asn His Asn His Gln Gln Ile Ile
420 425 430

Leu Asp Lys Gly Met Leu Val Ala Ile Asp Glu Leu Met Gln Ser Leu
435 440 445

Asn His Asn Gly Glu Thr Leu Arg Gln Lys Pro Pro Val Gly Glu Ala
450 455 460

Asp Pro Tyr Arg Val Lys Met Lys Leu Cys Ile Leu Leu His Ala Phe
465 470 475 480

Ser Thr Arg Val Val Thr Ile Asn Arg Val Met Gly Tyr Leu Ser Ser
485 490 495

Ala

<210> SEQ ID NO 203
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 203

```
Gln Leu Gly Ala Ser Gly Pro Gly Asp Cys Cys Val Glu Lys Thr Ser
1               5                   10                  15

Phe Pro Glu Gly Ala Ser Gly Ser Pro Leu Gly Pro Arg Asn Leu Ser
            20                  25                  30

Cys Tyr Arg Val Ser Lys Thr Asp Tyr Glu Cys Ser Trp Gln Tyr Asp
        35                  40                  45

Gly Pro Glu Asp Asn Val Ser His Val Leu Trp Cys Cys Phe Val Pro
    50                  55                  60

Pro Asn His Thr His Thr Gly Gln Glu Arg Cys Arg Tyr Phe Ser Ser
65                  70                  75                  80

Gly Pro Asp Arg Thr Val Gln Phe Trp Glu Gln Asp Gly Ile Pro Val
                85                  90                  95

Leu Ser Lys Val Asn Phe Trp Val Glu Ser Arg Leu Gly Asn Arg Thr
            100                 105                 110

Met Lys Ser Gln Lys Ile Ser Gln Tyr Leu Tyr Asn Trp Thr Lys Thr
        115                 120                 125

Thr Pro Pro Leu Gly His Ile Lys Val Ser Gln Ser His Arg Gln Leu
    130                 135                 140

Arg Met Asp Trp Asn Val Ser Glu Glu Ala Gly Ala Glu Val Gln Phe
145                 150                 155                 160

Arg Arg Arg Met Pro Thr Thr Asn Trp Thr Leu Gly Asp Cys Gly Pro
                165                 170                 175

Gln Val Asn Ser Gly Ser Gly Val Leu Gly Asp Ile Arg Gly Ser Met
            180                 185                 190

Ser Glu Ser Cys Leu Cys Pro Ser Glu Asn Met Ala Gln Glu Ile Gln
        195                 200                 205

Ile Arg Arg Arg Arg Arg Leu Ser Ser Gly Ala Pro Gly Gly Pro Trp
    210                 215                 220

Ser Asp Trp Ser Met Pro Val Cys Val Pro Pro Glu Val Leu Pro Gln
225                 230                 235                 240

Ala His Pro Val Gly Leu Leu Ala Arg Val Pro Leu Ser Tyr Ser Gly
                245                 250                 255

His Pro Val Gly Leu Leu Ala Arg Val Pro Leu Ser Tyr Ser Gly Ser
            260                 265                 270

Gly Leu Leu Ser Gly Arg Ser Asp Asn His Pro Leu Gly Val Arg Gly
        275                 280                 285

Lys Pro Leu Gly Val Arg Gly Lys Gly Glu Arg Gly Pro Pro Gly Pro
    290                 295                 300

Gln Gly Ala Ala Arg Gly Phe Pro Gly Thr Pro Gly Leu Gly Glu Arg
305                 310                 315                 320

Gly Pro Pro Gly Pro Gln Gly Ala Ala Arg Gly Phe Pro Gly Thr Pro
                325                 330                 335

Gly Leu Gly Gly Gly Ser Gly Gly Gly Ser Arg Val Ile Pro Val Ser
            340                 345                 350

Gly Pro Ala Arg Cys Leu Ser Gln Ser Arg Asn Leu Leu Lys Thr Thr
        355                 360                 365

Asp Asp Met Val Lys Thr Ala Arg Glu Lys Leu Lys His Tyr Ser Cys
    370                 375                 380

Thr Ala Glu Asp Ile Asp His Glu Asp Ile Thr Arg Asp Gln Thr Ser
385                 390                 395                 400

Thr Leu Lys Thr Cys Leu Pro Leu Glu Leu His Lys Asn Glu Ser Cys
                405                 410                 415
```

```
Leu Ala Thr Arg Glu Thr Ser Ser Thr Thr Arg Gly Ser Cys Leu Pro
            420                 425                 430

Pro Gln Lys Thr Ser Leu Met Met Thr Leu Cys Leu Gly Ser Ile Tyr
        435                 440                 445

Glu Asp Leu Lys Met Tyr Gln Thr Glu Phe Gln Ala Ile Asn Ala Ala
    450                 455                 460

Leu Gln Asn His Asn His Gln Gln Ile Ile Leu Asp Lys Gly Met Leu
465                 470                 475                 480

Val Ala Ile Asp Glu Leu Met Gln Ser Leu Asn His Asn Gly Glu Thr
                485                 490                 495

Leu Arg Gln Lys Pro Pro Val Gly Glu Ala Asp Pro Tyr Arg Val Lys
            500                 505                 510

Met Lys Leu Cys Ile Leu Leu His Ala Phe Ser Thr Arg Val Val Thr
        515                 520                 525

Ile Asn Arg Val Met Gly Tyr Leu Ser Ser Ala
    530                 535


<210> SEQ ID NO 204
<211> LENGTH: 660
<212> TYPE: PRT
<213> ORGANISM: Artificial Sequence
<220> FEATURE:
<223> OTHER INFORMATION: Synthetic Polypeptide

<400> SEQUENCE: 204

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile Gly Gly Gly Ser Gly Gly Gly Ser Cys Cys Val Glu Lys Thr Ser
        195                 200                 205

Phe Pro Glu Gly Ala Ser Gly Ser Pro Leu Gly Pro Arg Asn Leu Ser
    210                 215                 220

Cys Tyr Arg Val Ser Lys Thr Asp Tyr Glu Cys Ser Trp Gln Tyr Asp
225                 230                 235                 240
```

```
Gly Pro Glu Asp Asn Val Ser His Val Leu Trp Cys Cys Phe Val Pro
                245                 250                 255

Pro Asn His Thr His Thr Gly Gln Glu Arg Cys Arg Tyr Phe Ser Ser
            260                 265                 270

Gly Pro Asp Arg Thr Val Gln Phe Trp Glu Gln Asp Gly Ile Pro Val
        275                 280                 285

Leu Ser Lys Val Asn Phe Trp Val Glu Ser Arg Leu Gly Asn Arg Thr
    290                 295                 300

Met Lys Ser Gln Lys Ile Ser Gln Tyr Leu Tyr Asn Trp Thr Lys Thr
305                 310                 315                 320

Thr Pro Pro Leu Gly His Ile Lys Val Ser Gln Ser His Arg Gln Leu
                325                 330                 335

Arg Met Asp Trp Asn Val Ser Glu Glu Ala Gly Ala Glu Val Gln Phe
            340                 345                 350

Arg Arg Arg Met Pro Thr Thr Asn Trp Thr Leu Gly Asp Cys Gly Pro
        355                 360                 365

Gln Val Asn Ser Gly Ser Gly Val Leu Gly Asp Ile Arg Gly Ser Met
    370                 375                 380

Ser Glu Ser Cys Leu Cys Pro Ser Glu Asn Met Ala Gln Glu Ile Gln
385                 390                 395                 400

Ile Arg Arg Arg Arg Arg Leu Ser Ser Gly Ala Pro Gly Gly Pro Trp
                405                 410                 415

Ser Asp Trp Ser Met Pro Val Cys Val Pro Pro Glu Val Leu Pro Gln
            420                 425                 430

Ala His Pro Val Gly Leu Leu Ala Arg Val Pro Leu Ser Tyr Ser Gly
        435                 440                 445

Ser Gly Leu Leu Ser Gly Arg Ser Asp Asn His Gly Gly Gly Ser Gly
    450                 455                 460

Gly Gly Ser Arg Val Ile Pro Val Ser Gly Pro Ala Arg Cys Leu Ser
465                 470                 475                 480

Gln Ser Arg Asn Leu Leu Lys Thr Thr Asp Asp Met Val Lys Thr Ala
                485                 490                 495

Arg Glu Lys Leu Lys His Tyr Ser Cys Thr Ala Glu Asp Ile Asp His
            500                 505                 510

Glu Asp Ile Thr Arg Asp Gln Thr Ser Thr Leu Lys Thr Cys Leu Pro
        515                 520                 525

Leu Glu Leu His Lys Asn Glu Ser Cys Leu Ala Thr Arg Glu Thr Ser
    530                 535                 540

Ser Thr Thr Arg Gly Ser Cys Leu Pro Pro Gln Lys Thr Ser Leu Met
545                 550                 555                 560

Met Thr Leu Cys Leu Gly Ser Ile Tyr Glu Asp Leu Lys Met Tyr Gln
                565                 570                 575

Thr Glu Phe Gln Ala Ile Asn Ala Ala Leu Gln Asn His Asn His Gln
            580                 585                 590

Gln Ile Ile Leu Asp Lys Gly Met Leu Val Ala Ile Asp Glu Leu Met
        595                 600                 605

Gln Ser Leu Asn His Asn Gly Glu Thr Leu Arg Gln Lys Pro Pro Val
    610                 615                 620

Gly Glu Ala Asp Pro Tyr Arg Val Lys Met Lys Leu Cys Ile Leu Leu
625                 630                 635                 640

His Ala Phe Ser Thr Arg Val Val Thr Ile Asn Arg Val Met Gly Tyr
                645                 650                 655
```

```
Leu Ser Ser Ala
            660


<210> SEQ ID NO 205
<211> LENGTH: 675
<212> TYPE: PRT
<213> ORGANISM: Artificial Sequence
<220> FEATURE:
<223> OTHER INFORMATION: Synthetic Polypeptide

<400> SEQUENCE: 205

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile Gly Gly Gly Ser Gly Gly Gly Ser Cys Cys Val Glu Lys Thr Ser
        195                 200                 205

Phe Pro Glu Gly Ala Ser Gly Ser Pro Leu Gly Pro Arg Asn Leu Ser
    210                 215                 220

Cys Tyr Arg Val Ser Lys Thr Asp Tyr Glu Cys Ser Trp Gln Tyr Asp
225                 230                 235                 240

Gly Pro Glu Asp Asn Val Ser His Val Leu Trp Cys Cys Phe Val Pro
                245                 250                 255

Pro Asn His Thr His Thr Gly Gln Glu Arg Cys Arg Tyr Phe Ser Ser
            260                 265                 270

Gly Pro Asp Arg Thr Val Gln Phe Trp Glu Gln Asp Gly Ile Pro Val
        275                 280                 285

Leu Ser Lys Val Asn Phe Trp Val Glu Ser Arg Leu Gly Asn Arg Thr
    290                 295                 300

Met Lys Ser Gln Lys Ile Ser Gln Tyr Leu Tyr Asn Trp Thr Lys Thr
305                 310                 315                 320

Thr Pro Pro Leu Gly His Ile Lys Val Ser Gln Ser His Arg Gln Leu
                325                 330                 335

Arg Met Asp Trp Asn Val Ser Glu Glu Ala Gly Ala Glu Val Gln Phe
            340                 345                 350
```

Arg Arg Arg Met Pro Thr Thr Asn Trp Thr Leu Gly Asp Cys Gly Pro
355 360 365

Gln Val Asn Ser Gly Ser Gly Val Leu Gly Asp Ile Arg Gly Ser Met
370 375 380

Ser Glu Ser Cys Leu Cys Pro Ser Glu Asn Met Ala Gln Glu Ile Gln
385 390 395 400

Ile Arg Arg Arg Arg Arg Leu Ser Ser Gly Ala Pro Gly Gly Pro Trp
405 410 415

Ser Asp Trp Ser Met Pro Val Cys Val Pro Pro Glu Val Leu Pro Gln
420 425 430

Ala His Pro Val Gly Leu Leu Ala Arg Val Pro Leu Ser Tyr Ser Gly
435 440 445

His Pro Val Gly Leu Leu Ala Arg Val Pro Leu Ser Tyr Ser Gly Ser
450 455 460

Gly Leu Leu Ser Gly Arg Ser Asp Asn His Gly Gly Gly Ser Gly Gly
465 470 475 480

Gly Ser Arg Val Ile Pro Val Ser Gly Pro Ala Arg Cys Leu Ser Gln
485 490 495

Ser Arg Asn Leu Leu Lys Thr Thr Asp Asp Met Val Lys Thr Ala Arg
500 505 510

Glu Lys Leu Lys His Tyr Ser Cys Thr Ala Glu Asp Ile Asp His Glu
515 520 525

Asp Ile Thr Arg Asp Gln Thr Ser Thr Leu Lys Thr Cys Leu Pro Leu
530 535 540

Glu Leu His Lys Asn Glu Ser Cys Leu Ala Thr Arg Glu Thr Ser Ser
545 550 555 560

Thr Thr Arg Gly Ser Cys Leu Pro Pro Gln Lys Thr Ser Leu Met Met
565 570 575

Thr Leu Cys Leu Gly Ser Ile Tyr Glu Asp Leu Lys Met Tyr Gln Thr
580 585 590

Glu Phe Gln Ala Ile Asn Ala Ala Leu Gln Asn His Asn His Gln Gln
595 600 605

Ile Ile Leu Asp Lys Gly Met Leu Val Ala Ile Asp Glu Leu Met Gln
610 615 620

Ser Leu Asn His Asn Gly Glu Thr Leu Arg Gln Lys Pro Pro Val Gly
625 630 635 640

Glu Ala Asp Pro Tyr Arg Val Lys Met Lys Leu Cys Ile Leu Leu His
645 650 655

Ala Phe Ser Thr Arg Val Val Thr Ile Asn Arg Val Met Gly Tyr Leu
660 665 670

Ser Ser Ala
675

<210> SEQ ID NO 206
<211> LENGTH: 509
<212> TYPE: PRT
<213> ORGANISM: Artificial Sequence
<220> FEATURE:
<223> OTHER INFORMATION: Synthetic Polypeptide

<400> SEQUENCE: 206

Gln Leu Gly Ala Ser Gly Pro Gly Asp Cys Cys Val Glu Lys Thr Ser
1 5 10 15

Phe Pro Glu Gly Ala Ser Gly Ser Pro Leu Gly Pro Arg Asn Leu Ser
20 25 30

```
Cys Tyr Arg Val Ser Lys Thr Asp Tyr Glu Cys Ser Trp Gln Tyr Asp
        35                  40                  45

Gly Pro Glu Asp Asn Val Ser His Val Leu Trp Cys Cys Phe Val Pro
    50                  55                  60

Pro Asn His Thr His Thr Gly Gln Glu Arg Cys Arg Tyr Phe Ser Ser
65                  70                  75                  80

Gly Pro Asp Arg Thr Val Gln Phe Trp Glu Gln Asp Gly Ile Pro Val
                85                  90                  95

Leu Ser Lys Val Asn Phe Trp Val Glu Ser Arg Leu Gly Asn Arg Thr
            100                 105                 110

Met Lys Ser Gln Lys Ile Ser Gln Tyr Leu Tyr Asn Trp Thr Lys Thr
        115                 120                 125

Thr Pro Pro Leu Gly His Ile Lys Val Ser Gln Ser His Arg Gln Leu
    130                 135                 140

Arg Met Asp Trp Asn Val Ser Glu Glu Ala Gly Ala Glu Val Gln Phe
145                 150                 155                 160

Arg Arg Arg Met Pro Thr Thr Asn Trp Thr Leu Gly Asp Cys Gly Pro
                165                 170                 175

Gln Val Asn Ser Gly Ser Gly Val Leu Gly Asp Ile Arg Gly Ser Met
            180                 185                 190

Ser Glu Ser Cys Leu Cys Pro Ser Glu Asn Met Ala Gln Glu Ile Gln
        195                 200                 205

Ile Arg Arg Arg Arg Arg Leu Ser Ser Gly Ala Pro Gly Gly Pro Trp
    210                 215                 220

Ser Asp Trp Ser Met Pro Val Cys Val Pro Pro Glu Val Leu Pro Gln
225                 230                 235                 240

Ala His Pro Val Gly Leu Leu Ala Arg Val Pro Leu Ser Tyr Ser Gly
                245                 250                 255

His Pro Val Gly Leu Leu Ala Arg Val Pro Leu Ser Tyr Ser Gly Ser
            260                 265                 270

Gly Leu Leu Ser Gly Arg Ser Asp Asn His Ile Ser Ser Gly Leu Leu
        275                 280                 285

Ser Gly Arg Ser Asp Asn His Ile Ser Ser Gly Leu Leu Ser Gly Arg
    290                 295                 300

Ser Asp Asn His Gly Gly Gly Ser Gly Gly Gly Ser Arg Val Ile Pro
305                 310                 315                 320

Val Ser Gly Pro Ala Arg Cys Leu Ser Gln Ser Arg Asn Leu Leu Lys
                325                 330                 335

Thr Thr Asp Asp Met Val Lys Thr Ala Arg Glu Lys Leu Lys His Tyr
            340                 345                 350

Ser Cys Thr Ala Glu Asp Ile Asp His Glu Asp Ile Thr Arg Asp Gln
        355                 360                 365

Thr Ser Thr Leu Lys Thr Cys Leu Pro Leu Glu Leu His Lys Asn Glu
    370                 375                 380

Ser Cys Leu Ala Thr Arg Glu Thr Ser Ser Thr Thr Arg Gly Ser Cys
385                 390                 395                 400

Leu Pro Pro Gln Lys Thr Ser Leu Met Met Thr Leu Cys Leu Gly Ser
                405                 410                 415

Ile Tyr Glu Asp Leu Lys Met Tyr Gln Thr Glu Phe Gln Ala Ile Asn
            420                 425                 430

Ala Ala Leu Gln Asn His Asn His Gln Gln Ile Ile Leu Asp Lys Gly
        435                 440                 445
```

Met Leu Val Ala Ile Asp Glu Leu Met Gln Ser Leu Asn His Asn Gly
    450                 455                 460

Glu Thr Leu Arg Gln Lys Pro Pro Val Gly Glu Ala Asp Pro Tyr Arg
465                 470                 475                 480

Val Lys Met Lys Leu Cys Ile Leu Leu His Ala Phe Ser Thr Arg Val
                485                 490                 495

Val Thr Ile Asn Arg Val Met Gly Tyr Leu Ser Ser Ala
            500                 505

<210> SEQ ID NO 207
<211> LENGTH: 482
<212> TYPE: PRT
<213> ORGANISM: Artificial Sequence
<220> FEATURE:
<223> OTHER INFORMATION: Synthetic Polypeptide

<400> SEQUENCE: 207

Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
            20                  25                  30

Ser Cys Tyr Arg Val Ser Lys Thr Asp Tyr Glu Cys Ser Trp Gln Tyr
        35                  40                  45

Asp Gly Pro Glu Asp Asn Val Ser His Val Leu Trp Cys Cys Phe Val
    50                  55                  60

Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95

Val Leu Ser Lys Val Asn Phe Trp Val Glu Ser Arg Leu Gly Asn Arg
            100                 105                 110

Thr Met Lys Ser Gln Lys Ile Ser Gln Tyr Leu Tyr Asn Trp Thr Lys
        115                 120                 125

Thr Thr Pro Pro Leu Gly His Ile Lys Val Ser Gln Ser His Arg Gln
    130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Gly Gly Gly Ser Gly Gly Gly Ser Gly Gly Gly Ser Gly Gly
                245                 250                 255

Gly Ser Pro Leu Gly Val Arg Gly Lys Gly Gly Gly Ser Gly Gly Gly
            260                 265                 270

Ser Gly Gly Gly Ser Gly Gly Gly Ser Gly Gly Gly Ser Gly Gly Gly
        275                 280                 285

Ser Arg Val Ile Pro Val Ser Gly Pro Ala Arg Cys Leu Ser Gln Ser
    290                 295                 300

Arg Asn Leu Leu Lys Thr Thr Asp Asp Met Val Lys Thr Ala Arg Glu
305 310 315 320

Lys Leu Lys His Tyr Ser Cys Thr Ala Glu Asp Ile Asp His Glu Asp
325 330 335

Ile Thr Arg Asp Gln Thr Ser Thr Leu Lys Thr Cys Leu Pro Leu Glu
340 345 350

Leu His Lys Asn Glu Ser Cys Leu Ala Thr Arg Glu Thr Ser Ser Thr
355 360 365

Thr Arg Gly Ser Cys Leu Pro Pro Gln Lys Thr Ser Leu Met Met Thr
370 375 380

Leu Cys Leu Gly Ser Ile Tyr Glu Asp Leu Lys Met Tyr Gln Thr Glu
385 390 395 400

Phe Gln Ala Ile Asn Ala Ala Leu Gln Asn His Asn His Gln Gln Ile
405 410 415

Ile Leu Asp Lys Gly Met Leu Val Ala Ile Asp Glu Leu Met Gln Ser
420 425 430

Leu Asn His Asn Gly Glu Thr Leu Arg Gln Lys Pro Pro Val Gly Glu
435 440 445

Ala Asp Pro Tyr Arg Val Lys Met Lys Leu Cys Ile Leu Leu His Ala
450 455 460

Phe Ser Thr Arg Val Val Thr Ile Asn Arg Val Met Gly Tyr Leu Ser
465 470 475 480

Ser Ala

<210> SEQ ID NO 208
<211> LENGTH: 475
<212> TYPE: PRT
<213> ORGANISM: Artificial Sequence
<220> FEATURE:
<223> OTHER INFORMATION: Synthetic Polypeptide

<400> SEQUENCE: 208

Gln Leu Gly Ala Ser Gly Pro Gly Asp Gly Cys Cys Val Glu Lys Thr
1 5 10 15

Ser Phe Pro Glu Gly Ala Ser Gly Ser Pro Leu Gly Pro Arg Asn Leu
20 25 30

Ser Cys Tyr Arg Val Ser Lys Thr Asp Tyr Glu Cys Ser Trp Gln Tyr
35 40 45

Asp Gly Pro Glu Asp Asn Val Ser His Val Leu Trp Cys Cys Phe Val
50 55 60

Pro Pro Asn His Thr His Thr Gly Gln Glu Arg Cys Arg Tyr Phe Ser
65 70 75 80

Ser Gly Pro Asp Arg Thr Val Gln Phe Trp Glu Gln Asp Gly Ile Pro
85 90 95

Val Leu Ser Lys Val Asn Phe Trp Val Glu Ser Arg Leu Gly Asn Arg
100 105 110

Thr Met Lys Ser Gln Lys Ile Ser Gln Tyr Leu Tyr Asn Trp Thr Lys
115 120 125

Thr Thr Pro Pro Leu Gly His Ile Lys Val Ser Gln Ser His Arg Gln
130 135 140

Leu Arg Met Asp Trp Asn Val Ser Glu Glu Ala Gly Ala Glu Val Gln
145 150 155 160

Phe Arg Arg Arg Met Pro Thr Thr Asn Trp Thr Leu Gly Asp Cys Gly
165 170 175

```
Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Gly Gly Gly Ser Gly Gly Gly Ser His Pro Val Gly Leu Leu
                245                 250                 255

Ala Arg His Pro Val Gly Leu Leu Ala Arg His Pro Val Gly Leu Leu
            260                 265                 270

Ala Arg Gly Gly Gly Ser Gly Gly Gly Ser Arg Val Ile Pro Val Ser
        275                 280                 285

Gly Pro Ala Arg Cys Leu Ser Gln Ser Arg Asn Leu Leu Lys Thr Thr
    290                 295                 300

Asp Asp Met Val Lys Thr Ala Arg Glu Lys Leu Lys His Tyr Ser Cys
305                 310                 315                 320

Thr Ala Glu Asp Ile Asp His Glu Asp Ile Thr Arg Asp Gln Thr Ser
                325                 330                 335

Thr Leu Lys Thr Cys Leu Pro Leu Glu Leu His Lys Asn Glu Ser Cys
            340                 345                 350

Leu Ala Thr Arg Glu Thr Ser Ser Thr Thr Arg Gly Ser Cys Leu Pro
        355                 360                 365

Pro Gln Lys Thr Ser Leu Met Met Thr Leu Cys Leu Gly Ser Ile Tyr
    370                 375                 380

Glu Asp Leu Lys Met Tyr Gln Thr Glu Phe Gln Ala Ile Asn Ala Ala
385                 390                 395                 400

Leu Gln Asn His Asn His Gln Gln Ile Ile Leu Asp Lys Gly Met Leu
                405                 410                 415

Val Ala Ile Asp Glu Leu Met Gln Ser Leu Asn His Asn Gly Glu Thr
            420                 425                 430

Leu Arg Gln Lys Pro Pro Val Gly Glu Ala Asp Pro Tyr Arg Val Lys
        435                 440                 445

Met Lys Leu Cys Ile Leu Leu His Ala Phe Ser Thr Arg Val Val Thr
    450                 455                 460

Ile Asn Arg Val Met Gly Tyr Leu Ser Ser Ala
465                 470                 475


<210> SEQ ID NO 209
<211> LENGTH: 484
<212> TYPE: PRT
<213> ORGANISM: Artificial Sequence
<220> FEATURE:
<223> OTHER INFORMATION: Synthetic Polypeptide

<400> SEQUENCE: 209

Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
            20                  25                  30

Ser Cys Tyr Arg Val Ser Lys Thr Asp Tyr Glu Cys Ser Trp Gln Tyr
        35                  40                  45

Asp Gly Pro Glu Asp Asn Val Ser His Val Leu Trp Cys Cys Phe Val
    50                  55                  60
```

```
Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95

Val Leu Ser Lys Val Asn Phe Trp Val Glu Ser Arg Leu Gly Asn Arg
            100                 105                 110

Thr Met Lys Ser Gln Lys Ile Ser Gln Tyr Leu Tyr Asn Trp Thr Lys
        115                 120                 125

Thr Thr Pro Pro Leu Gly His Ile Lys Val Ser Gln Ser His Arg Gln
    130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Gly Gly Gly Ser Gly Gly Gly Ser Ser Gly Leu Leu Ser Gly
                245                 250                 255

Arg Ser Asp Asn His Ser Gly Leu Leu Ser Gly Arg Ser Asp Asn His
            260                 265                 270

Ser Gly Leu Leu Ser Gly Arg Ser Asp Asn His Gly Gly Gly Ser Gly
        275                 280                 285

Gly Gly Ser Arg Val Ile Pro Val Ser Gly Pro Ala Arg Cys Leu Ser
    290                 295                 300

Gln Ser Arg Asn Leu Leu Lys Thr Thr Asp Asp Met Val Lys Thr Ala
305                 310                 315                 320

Arg Glu Lys Leu Lys His Tyr Ser Cys Thr Ala Glu Asp Ile Asp His
                325                 330                 335

Glu Asp Ile Thr Arg Asp Gln Thr Ser Thr Leu Lys Thr Cys Leu Pro
            340                 345                 350

Leu Glu Leu His Lys Asn Glu Ser Cys Leu Ala Thr Arg Glu Thr Ser
        355                 360                 365

Ser Thr Thr Arg Gly Ser Cys Leu Pro Pro Gln Lys Thr Ser Leu Met
    370                 375                 380

Met Thr Leu Cys Leu Gly Ser Ile Tyr Glu Asp Leu Lys Met Tyr Gln
385                 390                 395                 400

Thr Glu Phe Gln Ala Ile Asn Ala Ala Leu Gln Asn His Asn His Gln
                405                 410                 415

Gln Ile Ile Leu Asp Lys Gly Met Leu Val Ala Ile Asp Glu Leu Met
            420                 425                 430

Gln Ser Leu Asn His Asn Gly Glu Thr Leu Arg Gln Lys Pro Pro Val
        435                 440                 445

Gly Glu Ala Asp Pro Tyr Arg Val Lys Met Lys Leu Cys Ile Leu Leu
    450                 455                 460
```

His Ala Phe Ser Thr Arg Val Val Thr Ile Asn Arg Val Met Gly Tyr
465 470 475 480

Leu Ser Ser Ala

<210> SEQ ID NO 210
<211> LENGTH: 478
<212> TYPE: PRT
<213> ORGANISM: Artificial Sequence
<220> FEATURE:
<223> OTHER INFORMATION: Synthetic Polypeptide

<400> SEQUENCE: 210

Gln Leu Gly Ala Ser Gly Pro Gly Asp Gly Cys Cys Val Glu Lys Thr
1 5 10 15

Ser Phe Pro Glu Gly Ala Ser Gly Ser Pro Leu Gly Pro Arg Asn Leu
20 25 30

Ser Cys Tyr Arg Val Ser Lys Thr Asp Tyr Glu Cys Ser Trp Gln Tyr
35 40 45

Asp Gly Pro Glu Asp Asn Val Ser His Val Leu Trp Cys Cys Phe Val
50 55 60

Pro Pro Asn His Thr His Thr Gly Gln Glu Arg Cys Arg Tyr Phe Ser
65 70 75 80

Ser Gly Pro Asp Arg Thr Val Gln Phe Trp Glu Gln Asp Gly Ile Pro
85 90 95

Val Leu Ser Lys Val Asn Phe Trp Val Glu Ser Arg Leu Gly Asn Arg
100 105 110

Thr Met Lys Ser Gln Lys Ile Ser Gln Tyr Leu Tyr Asn Trp Thr Lys
115 120 125

Thr Thr Pro Pro Leu Gly His Ile Lys Val Ser Gln Ser His Arg Gln
130 135 140

Leu Arg Met Asp Trp Asn Val Ser Glu Glu Ala Gly Ala Glu Val Gln
145 150 155 160

Phe Arg Arg Arg Met Pro Thr Thr Asn Trp Thr Leu Gly Asp Cys Gly
165 170 175

Pro Gln Val Asn Ser Gly Ser Gly Val Leu Gly Asp Ile Arg Gly Ser
180 185 190

Met Ser Glu Ser Cys Leu Cys Pro Ser Glu Asn Met Ala Gln Glu Ile
195 200 205

Gln Ile Arg Arg Arg Arg Arg Leu Ser Ser Gly Ala Pro Gly Gly Pro
210 215 220

Trp Ser Asp Trp Ser Met Pro Val Cys Val Pro Pro Glu Val Leu Pro
225 230 235 240

Gln Ala Gly Gly Gly Ser Gly Gly Gly Ser His Pro Val Gly Leu Leu
245 250 255

Ala Arg Val Pro Leu Ser Leu Tyr Ser Gly Ser Gly Leu Leu Ser Gly
260 265 270

Arg Ser Asp Asn His Gly Gly Gly Ser Gly Gly Gly Ser Arg Val Ile
275 280 285

Pro Val Ser Gly Pro Ala Arg Cys Leu Ser Gln Ser Arg Asn Leu Leu
290 295 300

Lys Thr Thr Asp Asp Met Val Lys Thr Ala Arg Glu Lys Leu Lys His
305 310 315 320

Tyr Ser Cys Thr Ala Glu Asp Ile Asp His Glu Asp Ile Thr Arg Asp
325 330 335

```
Gln Thr Ser Thr Leu Lys Thr Cys Leu Pro Leu Glu Leu His Lys Asn
            340                 345                 350

Glu Ser Cys Leu Ala Thr Arg Glu Thr Ser Ser Thr Thr Arg Gly Ser
        355                 360                 365

Cys Leu Pro Pro Gln Lys Thr Ser Leu Met Met Thr Leu Cys Leu Gly
    370                 375                 380

Ser Ile Tyr Glu Asp Leu Lys Met Tyr Gln Thr Glu Phe Gln Ala Ile
385                 390                 395                 400

Asn Ala Ala Leu Gln Asn His Asn His Gln Gln Ile Ile Leu Asp Lys
                405                 410                 415

Gly Met Leu Val Ala Ile Asp Glu Leu Met Gln Ser Leu Asn His Asn
            420                 425                 430

Gly Glu Thr Leu Arg Gln Lys Pro Pro Val Gly Glu Ala Asp Pro Tyr
        435                 440                 445

Arg Val Lys Met Lys Leu Cys Ile Leu Leu His Ala Phe Ser Thr Arg
    450                 455                 460

Val Val Thr Ile Asn Arg Val Met Gly Tyr Leu Ser Ser Ala
465                 470                 475


<210> SEQ ID NO 211
<211> LENGTH: 486
<212> TYPE: PRT
<213> ORGANISM: Artificial Sequence
<220> FEATURE:
<223> OTHER INFORMATION: Synthetic Polypeptide

<400> SEQUENCE: 211

Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
            20                  25                  30

Ser Cys Tyr Arg Val Ser Lys Thr Asp Tyr Glu Cys Ser Trp Gln Tyr
        35                  40                  45

Asp Gly Pro Glu Asp Asn Val Ser His Val Leu Trp Cys Cys Phe Val
    50                  55                  60

Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95

Val Leu Ser Lys Val Asn Phe Trp Val Glu Ser Arg Leu Gly Asn Arg
            100                 105                 110

Thr Met Lys Ser Gln Lys Ile Ser Gln Tyr Leu Tyr Asn Trp Thr Lys
        115                 120                 125

Thr Thr Pro Pro Leu Gly His Ile Lys Val Ser Gln Ser His Arg Gln
    130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220
```

```
Trp Ser Asp Trp Ser Met Pro Val Cys Val Pro Pro Glu Val Leu Pro
225                 230                 235                 240

Gln Ala His Pro Val Gly Leu Leu Ala Arg Val Pro Leu Ser Leu Tyr
                245                 250                 255

Ser Gly His Pro Val Gly Leu Leu Ala Arg Val Pro Leu Ser Leu Tyr
            260                 265                 270

Ser Gly Ser Gly Leu Leu Ser Gly Arg Ser Asp Asn His Gly Gly Gly
        275                 280                 285

Ser Gly Gly Gly Ser Arg Val Ile Pro Val Ser Gly Pro Ala Arg Cys
    290                 295                 300

Leu Ser Gln Ser Arg Asn Leu Leu Lys Thr Thr Asp Asp Met Val Lys
305                 310                 315                 320

Thr Ala Arg Glu Lys Leu Lys His Tyr Ser Cys Thr Ala Glu Asp Ile
                325                 330                 335

Asp His Glu Asp Ile Thr Arg Asp Gln Thr Ser Thr Leu Lys Thr Cys
            340                 345                 350

Leu Pro Leu Glu Leu His Lys Asn Glu Ser Cys Leu Ala Thr Arg Glu
        355                 360                 365

Thr Ser Ser Thr Thr Arg Gly Ser Cys Leu Pro Pro Gln Lys Thr Ser
    370                 375                 380

Leu Met Met Thr Leu Cys Leu Gly Ser Ile Tyr Glu Asp Leu Lys Met
385                 390                 395                 400

Tyr Gln Thr Glu Phe Gln Ala Ile Asn Ala Ala Leu Gln Asn His Asn
                405                 410                 415

His Gln Gln Ile Ile Leu Asp Lys Gly Met Leu Val Ala Ile Asp Glu
            420                 425                 430

Leu Met Gln Ser Leu Asn His Asn Gly Glu Thr Leu Arg Gln Lys Pro
        435                 440                 445

Pro Val Gly Glu Ala Asp Pro Tyr Arg Val Lys Met Lys Leu Cys Ile
    450                 455                 460

Leu Leu His Ala Phe Ser Thr Arg Val Val Thr Ile Asn Arg Val Met
465                 470                 475                 480

Gly Tyr Leu Ser Ser Ala
                485


<210> SEQ ID NO 212
<211> LENGTH: 479
<212> TYPE: PRT
<213> ORGANISM: Artificial Sequence
<220> FEATURE:
<223> OTHER INFORMATION: Synthetic Polypeptide

<400> SEQUENCE: 212

Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
            20                  25                  30

Ser Cys Tyr Arg Val Ser Lys Thr Asp Tyr Glu Cys Ser Trp Gln Tyr
        35                  40                  45

Asp Gly Pro Glu Asp Asn Val Ser His Val Leu Trp Cys Cys Phe Val
    50                  55                  60

Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95
```

```
Val Leu Ser Lys Val Asn Phe Trp Val Glu Ser Arg Leu Gly Asn Arg
            100                 105                 110

Thr Met Lys Ser Gln Lys Ile Ser Gln Tyr Leu Tyr Asn Trp Thr Lys
        115                 120                 125

Thr Thr Pro Pro Leu Gly His Ile Lys Val Ser Gln Ser His Arg Gln
    130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Gly Gly Gly Ser Gly Gly Gly Ser Val Pro Leu Ser Leu Tyr
                245                 250                 255

Ser Gly Val Pro Leu Ser Leu Tyr Ser Gly Val Pro Leu Ser Leu Tyr
            260                 265                 270

Ser Gly Gly Gly Gly Ser Gly Gly Gly Ser Gly Gly Gly Ser Arg Val
        275                 280                 285

Ile Pro Val Ser Gly Pro Ala Arg Cys Leu Ser Gln Ser Arg Asn Leu
    290                 295                 300

Leu Lys Thr Thr Asp Asp Met Val Lys Thr Ala Arg Glu Lys Leu Lys
305                 310                 315                 320

His Tyr Ser Cys Thr Ala Glu Asp Ile Asp His Glu Asp Ile Thr Arg
                325                 330                 335

Asp Gln Thr Ser Thr Leu Lys Thr Cys Leu Pro Leu Glu Leu His Lys
            340                 345                 350

Asn Glu Ser Cys Leu Ala Thr Arg Glu Thr Ser Ser Thr Thr Arg Gly
        355                 360                 365

Ser Cys Leu Pro Pro Gln Lys Thr Ser Leu Met Met Thr Leu Cys Leu
    370                 375                 380

Gly Ser Ile Tyr Glu Asp Leu Lys Met Tyr Gln Thr Glu Phe Gln Ala
385                 390                 395                 400

Ile Asn Ala Ala Leu Gln Asn His Asn His Gln Gln Ile Ile Leu Asp
                405                 410                 415

Lys Gly Met Leu Val Ala Ile Asp Glu Leu Met Gln Ser Leu Asn His
            420                 425                 430

Asn Gly Glu Thr Leu Arg Gln Lys Pro Pro Val Gly Glu Ala Asp Pro
        435                 440                 445

Tyr Arg Val Lys Met Lys Leu Cys Ile Leu Leu His Ala Phe Ser Thr
    450                 455                 460

Arg Val Val Thr Ile Asn Arg Val Met Gly Tyr Leu Ser Ser Ala
465                 470                 475
```

```
<210> SEQ ID NO 213
<211> LENGTH: 483
<212> TYPE: PRT
<213> ORGANISM: Artificial Sequence
<220> FEATURE:
<223> OTHER INFORMATION: Synthetic Polypeptide
```

<400> SEQUENCE: 213

Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
            20                  25                  30

Ser Cys Tyr Arg Val Ser Lys Thr Asp Tyr Glu Cys Ser Trp Gln Tyr
        35                  40                  45

Asp Gly Pro Glu Asp Asn Val Ser His Val Leu Trp Cys Cys Phe Val
    50                  55                  60

Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95

Val Leu Ser Lys Val Asn Phe Trp Val Glu Ser Arg Leu Gly Asn Arg
            100                 105                 110

Thr Met Lys Ser Gln Lys Ile Ser Gln Tyr Leu Tyr Asn Trp Thr Lys
        115                 120                 125

Thr Thr Pro Pro Leu Gly His Ile Lys Val Ser Gln Ser His Arg Gln
    130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
            180                 185                 190

Met Ser Glu Ser Cys Leu Cys Pro Ser Glu Asn Met Ala Gln Glu Ile
        195                 200                 205

Gln Ile Arg Arg Arg Arg Arg Leu Ser Ser Gly Ala Pro Gly Gly Pro
    210                 215                 220

Trp Ser Asp Trp Ser Met Pro Val Cys Val Pro Pro Glu Val Leu Pro
225                 230                 235                 240

Gln Ala Gly Gly Gly Ser Gly Gly Gly Ser Val Pro Leu Ser Leu Tyr
                245                 250                 255

Ser Gly Gly Gly Gly Ser Gly Gly Gly Ser Leu Ser Gly Arg Ser Asp
            260                 265                 270

Asn His Leu Ser Gly Arg Ser Asp Asn His Gly Gly Gly Ser Gly Gly
        275                 280                 285

Gly Ser Arg Val Ile Pro Val Ser Gly Pro Ala Arg Cys Leu Ser Gln
    290                 295                 300

Ser Arg Asn Leu Leu Lys Thr Thr Asp Asp Met Val Lys Thr Ala Arg
305                 310                 315                 320

Glu Lys Leu Lys His Tyr Ser Cys Thr Ala Glu Asp Ile Asp His Glu
                325                 330                 335

Asp Ile Thr Arg Asp Gln Thr Ser Thr Leu Lys Thr Cys Leu Pro Leu
            340                 345                 350

Glu Leu His Lys Asn Glu Ser Cys Leu Ala Thr Arg Glu Thr Ser Ser
        355                 360                 365

Thr Thr Arg Gly Ser Cys Leu Pro Pro Gln Lys Thr Ser Leu Met Met
    370                 375                 380

Thr Leu Cys Leu Gly Ser Ile Tyr Glu Asp Leu Lys Met Tyr Gln Thr
385                 390                 395                 400

```
Glu Phe Gln Ala Ile Asn Ala Ala Leu Gln Asn His Asn His Gln Gln
                405                 410                 415

Ile Ile Leu Asp Lys Gly Met Leu Val Ala Ile Asp Glu Leu Met Gln
            420                 425                 430

Ser Leu Asn His Asn Gly Glu Thr Leu Arg Gln Lys Pro Pro Val Gly
        435                 440                 445

Glu Ala Asp Pro Tyr Arg Val Lys Met Lys Leu Cys Ile Leu Leu His
    450                 455                 460

Ala Phe Ser Thr Arg Val Val Thr Ile Asn Arg Val Met Gly Tyr Leu
465                 470                 475                 480

Ser Ser Ala


<210> SEQ ID NO 214
<211> LENGTH: 457
<212> TYPE: PRT
<213> ORGANISM: Artificial Sequence
<220> FEATURE:
<223> OTHER INFORMATION: Synthetic Polypeptide

<400> SEQUENCE: 214

Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
            100                 105                 110

Ser Val Lys Tyr Glu Pro Pro Leu Gly Asp Ile Lys Val Ser Lys Leu
        115                 120                 125

Ala Gly Gln Leu Arg Met Glu Trp Glu Thr Pro Asp Asn Gln Val Gly
    130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Asp Thr Glu Ser Cys Leu Cys Pro
                165                 170                 175

Leu Glu Met Asn Val Ala Gln Glu Phe Gln Leu Arg Arg Arg Gln Leu
            180                 185                 190

Gly Ser Gln Gly Ser Ser Trp Ser Lys Trp Ser Ser Pro Val Cys Val
        195                 200                 205

Pro Pro Glu Gly Gly Gly Ser Gly Gly Gly Ser Val Pro Leu Ser Leu
    210                 215                 220

Tyr Ser Gly Gly Gly Gly Ser Gly Gly Gly Ser Leu Ser Gly Arg Ser
225                 230                 235                 240

Asp Asn His Leu Ser Gly Arg Ser Asp Asn His Gly Gly Gly Ser Gly
                245                 250                 255

Gly Gly Ser Gly Arg Asn Leu Pro Val Ala Thr Pro Asp Pro Gly Met
            260                 265                 270
```

```
Phe Pro Cys Leu His His Ser Gln Asn Leu Leu Arg Ala Val Ser Asn
        275                 280                 285

Met Leu Gln Lys Ala Arg Gln Thr Leu Glu Phe Tyr Pro Cys Thr Ser
    290                 295                 300

Glu Glu Ile Asp His Glu Asp Ile Thr Lys Asp Lys Thr Ser Thr Val
305                 310                 315                 320

Glu Ala Cys Leu Pro Leu Glu Leu Thr Lys Asn Glu Ser Cys Leu Asn
                325                 330                 335

Ser Arg Glu Thr Ser Phe Ile Thr Asn Gly Ser Cys Leu Ala Ser Arg
            340                 345                 350

Lys Thr Ser Phe Met Met Ala Leu Cys Leu Ser Ser Ile Tyr Glu Asp
        355                 360                 365

Leu Lys Met Tyr Gln Val Glu Phe Lys Thr Met Asn Ala Lys Leu Leu
    370                 375                 380

Met Asp Pro Lys Arg Gln Ile Phe Leu Asp Gln Asn Met Leu Ala Val
385                 390                 395                 400

Ile Asp Glu Leu Met Gln Ala Leu Asn Phe Asn Ser Glu Thr Val Pro
                405                 410                 415

Gln Lys Ser Ser Leu Glu Glu Pro Asp Phe Tyr Lys Thr Lys Ile Lys
            420                 425                 430

Leu Cys Ile Leu Leu His Ala Phe Arg Ile Arg Ala Val Thr Ile Asp
        435                 440                 445

Arg Val Met Ser Tyr Leu Asn Ala Ser
    450                 455
```

<210> SEQ ID NO 215
<211> LENGTH: 452
<212> TYPE: PRT
<213> ORGANISM: Artificial Sequence
<220> FEATURE:
<223> OTHER INFORMATION: Synthetic Polypeptide

<400> SEQUENCE: 215

```
Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
            100                 105                 110

Ser Val Lys Tyr Glu Pro Pro Leu Gly Asp Ile Lys Val Ser Lys Leu
        115                 120                 125

Ala Gly Gln Leu Arg Met Glu Trp Glu Thr Pro Asp Asn Gln Val Gly
    130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Asp Thr Glu Ser Cys Leu Cys Pro
                165                 170                 175
```

```
Leu Glu Met Asn Val Ala Gln Glu Phe Gln Leu Arg Arg Arg Gln Leu
            180                 185                 190

Gly Ser Gln Gly Ser Ser Trp Ser Lys Trp Ser Ser Pro Val Cys Val
        195                 200                 205

Pro Pro Glu Gly Gly Gly Ser Gly Gly Gly Ser Val Pro Leu Ser Leu
    210                 215                 220

Tyr Ser Gly Val Pro Leu Ser Leu Tyr Ser Gly Val Pro Leu Ser Leu
225                 230                 235                 240

Tyr Ser Gly Gly Gly Gly Ser Gly Gly Gly Ser Gly Gly Gly Ser Arg
                245                 250                 255

Asn Leu Pro Val Ala Thr Pro Asp Pro Gly Met Phe Pro Cys Leu His
            260                 265                 270

His Ser Gln Asn Leu Leu Arg Ala Val Ser Asn Met Leu Gln Lys Ala
        275                 280                 285

Arg Gln Thr Leu Glu Phe Tyr Pro Cys Thr Ser Glu Glu Ile Asp His
    290                 295                 300

Glu Asp Ile Thr Lys Asp Lys Thr Ser Thr Val Glu Ala Cys Leu Pro
305                 310                 315                 320

Leu Glu Leu Thr Lys Asn Glu Ser Cys Leu Asn Ser Arg Glu Thr Ser
                325                 330                 335

Phe Ile Thr Asn Gly Ser Cys Leu Ala Ser Arg Lys Thr Ser Phe Met
            340                 345                 350

Met Ala Leu Cys Leu Ser Ser Ile Tyr Glu Asp Leu Lys Met Tyr Gln
        355                 360                 365

Val Glu Phe Lys Thr Met Asn Ala Lys Leu Leu Met Asp Pro Lys Arg
    370                 375                 380

Gln Ile Phe Leu Asp Gln Asn Met Leu Ala Val Ile Asp Glu Leu Met
385                 390                 395                 400

Gln Ala Leu Asn Phe Asn Ser Glu Thr Val Pro Gln Lys Ser Ser Leu
                405                 410                 415

Glu Glu Pro Asp Phe Tyr Lys Thr Lys Ile Lys Leu Cys Ile Leu Leu
            420                 425                 430

His Ala Phe Arg Ile Arg Ala Val Thr Ile Asp Arg Val Met Ser Tyr
        435                 440                 445

Leu Asn Ala Ser
    450


<210> SEQ ID NO 216
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 216

Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80
```

-continued

```
Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
            100                 105                 110

Ser Val Lys Tyr Glu Pro Pro Leu Gly Asp Ile Lys Val Ser Lys Leu
        115                 120                 125

Ala Gly Gln Leu Arg Met Glu Trp Glu Thr Pro Asp Asn Gln Val Gly
    130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Asp Thr Glu Ser Cys Leu Cys Pro
                165                 170                 175

Leu Glu Met Asn Val Ala Gln Glu Phe Gln Leu Arg Arg Arg Gln Leu
            180                 185                 190

Gly Ser Gln Gly Ser Ser Trp Ser Lys Trp Ser Ser Pro Val Cys Val
        195                 200                 205

Pro Pro Glu Gly Gly Gly Ser Gly Gly Gly Ser His Pro Val Gly Leu
    210                 215                 220

Leu Ala Arg Val Pro Leu Ser Leu Tyr Ser Gly Ser Gly Leu Leu Ser
225                 230                 235                 240

Gly Arg Ser Asp Asn His Gly Gly Gly Ser Gly Gly Gly Ser Arg Asn
                245                 250                 255

Leu Pro Val Ala Thr Pro Asp Pro Gly Met Phe Pro Cys Leu His His
            260                 265                 270

Ser Gln Asn Leu Leu Arg Ala Val Ser Asn Met Leu Gln Lys Ala Arg
        275                 280                 285

Gln Thr Leu Glu Phe Tyr Pro Cys Thr Ser Glu Glu Ile Asp His Glu
    290                 295                 300

Asp Ile Thr Lys Asp Lys Thr Ser Thr Val Glu Ala Cys Leu Pro Leu
305                 310                 315                 320

Glu Leu Thr Lys Asn Glu Ser Cys Leu Asn Ser Arg Glu Thr Ser Phe
                325                 330                 335

Ile Thr Asn Gly Ser Cys Leu Ala Ser Arg Lys Thr Ser Phe Met Met
            340                 345                 350

Ala Leu Cys Leu Ser Ser Ile Tyr Glu Asp Leu Lys Met Tyr Gln Val
        355                 360                 365

Glu Phe Lys Thr Met Asn Ala Lys Leu Leu Met Asp Pro Lys Arg Gln
    370                 375                 380

Ile Phe Leu Asp Gln Asn Met Leu Ala Val Ile Asp Glu Leu Met Gln
385                 390                 395                 400

Ala Leu Asn Phe Asn Ser Glu Thr Val Pro Gln Lys Ser Ser Leu Glu
                405                 410                 415

Glu Pro Asp Phe Tyr Lys Thr Lys Ile Lys Leu Cys Ile Leu Leu His
            420                 425                 430

Ala Phe Arg Ile Arg Ala Val Thr Ile Asp Arg Val Met Ser Tyr Leu
        435                 440                 445

Asn Ala Ser
    450
```

<210> SEQ ID NO 217
<211> LENGTH: 472
<212> TYPE: PRT
<213> ORGANISM: Artificial Sequence
<220> FEATURE:
<223> OTHER INFORMATION: Synthetic Polypeptide

<400> SEQUENCE: 217

Cys Arg Thr Ser Glu Cys Cys Phe Gln Asp Pro Pro Tyr Pro Asp Ala
1 5 10 15

Asp Ser Gly Ser Ala Ser Gly Pro Arg Asp Leu Arg Cys Tyr Arg Ile
20 25 30

Ser Ser Asp Arg Tyr Glu Cys Ser Trp Gln Tyr Glu Gly Pro Thr Ala
35 40 45

Gly Val Ser His Phe Leu Arg Cys Cys Leu Ser Ser Gly Arg Cys Cys
50 55 60

Tyr Phe Ala Ala Gly Ser Ala Thr Arg Leu Gln Phe Ser Asp Gln Ala
65 70 75 80

Gly Val Ser Val Leu Tyr Thr Val Thr Leu Trp Val Glu Ser Trp Ala
85 90 95

Arg Asn Gln Thr Glu Lys Ser Pro Glu Val Thr Leu Gln Leu Tyr Asn
100 105 110

Ser Val Lys Tyr Glu Pro Pro Leu Gly Asp Ile Lys Val Ser Lys Leu
115 120 125

Ala Gly Gln Leu Arg Met Glu Trp Glu Thr Pro Asp Asn Gln Val Gly
130 135 140

Ala Glu Val Gln Phe Arg His Arg Thr Pro Ser Ser Pro Trp Lys Leu
145 150 155 160

Gly Asp Cys Gly Pro Gln Asp Asp Asp Thr Glu Ser Cys Leu Cys Pro
165 170 175

Leu Glu Met Asn Val Ala Gln Glu Phe Gln Leu Arg Arg Arg Gln Leu
180 185 190

Gly Ser Gln Gly Ser Ser Trp Ser Lys Trp Ser Ser Pro Val Cys Val
195 200 205

Pro Pro Glu Pro Leu Gly Val Arg Gly Lys Pro Leu Gly Val Arg Gly
210 215 220

Lys Gly Glu Arg Gly Pro Pro Gly Pro Gln Gly Ala Ala Arg Gly Phe
225 230 235 240

Pro Gly Thr Pro Gly Leu Gly Glu Arg Gly Pro Pro Gly Pro Gln Gly
245 250 255

Ala Ala Arg Gly Phe Pro Gly Thr Pro Gly Leu Gly Gly Gly Ser Gly
260 265 270

Gly Gly Ser Arg Asn Leu Pro Val Ala Thr Pro Asp Pro Gly Met Phe
275 280 285

Pro Cys Leu His His Ser Gln Asn Leu Leu Arg Ala Val Ser Asn Met
290 295 300

Leu Gln Lys Ala Arg Gln Thr Leu Glu Phe Tyr Pro Cys Thr Ser Glu
305 310 315 320

Glu Ile Asp His Glu Asp Ile Thr Lys Asp Lys Thr Ser Thr Val Glu
325 330 335

Ala Cys Leu Pro Leu Glu Leu Thr Lys Asn Glu Ser Cys Leu Asn Ser
340 345 350

Arg Glu Thr Ser Phe Ile Thr Asn Gly Ser Cys Leu Ala Ser Arg Lys
355 360 365

Thr Ser Phe Met Met Ala Leu Cys Leu Ser Ser Ile Tyr Glu Asp Leu
370 375 380

Lys Met Tyr Gln Val Glu Phe Lys Thr Met Asn Ala Lys Leu Leu Met
385 390 395 400

Asp Pro Lys Arg Gln Ile Phe Leu Asp Gln Asn Met Leu Ala Val Ile
405 410 415

Asp Glu Leu Met Gln Ala Leu Asn Phe Asn Ser Glu Thr Val Pro Gln
420 425 430

Lys Ser Ser Leu Glu Glu Pro Asp Phe Tyr Lys Thr Lys Ile Lys Leu
435 440 445

Cys Ile Leu Leu His Ala Phe Arg Ile Arg Ala Val Thr Ile Asp Arg
450 455 460

Val Met Ser Tyr Leu Asn Ala Ser
465 470

<210> SEQ ID NO 218
<211> LENGTH: 471
<212> TYPE: PRT
<213> ORGANISM: Artificial Sequence
<220> FEATURE:
<223> OTHER INFORMATION: Synthetic Polypeptide

<400> SEQUENCE: 218

Cys Arg Thr Ser Glu Cys Cys Phe Gln Asp Pro Pro Tyr Pro Asp Ala
1 5 10 15

Asp Ser Gly Ser Ala Ser Gly Pro Arg Asp Leu Arg Cys Tyr Arg Ile
20 25 30

Ser Ser Asp Arg Tyr Glu Cys Ser Trp Gln Tyr Glu Gly Pro Thr Ala
35 40 45

Gly Val Ser His Phe Leu Arg Cys Cys Leu Ser Ser Gly Arg Cys Cys
50 55 60

Tyr Phe Ala Ala Gly Ser Ala Thr Arg Leu Gln Phe Ser Asp Gln Ala
65 70 75 80

Gly Val Ser Val Leu Tyr Thr Val Thr Leu Trp Val Glu Ser Trp Ala
85 90 95

Arg Asn Gln Thr Glu Lys Ser Pro Glu Val Thr Leu Gln Leu Tyr Asn
100 105 110

Ser Val Lys Tyr Glu Pro Pro Leu Gly Asp Ile Lys Val Ser Lys Leu
115 120 125

Ala Gly Gln Leu Arg Met Glu Trp Glu Thr Pro Asp Asn Gln Val Gly
130 135 140

Ala Glu Val Gln Phe Arg His Arg Thr Pro Ser Ser Pro Trp Lys Leu
145 150 155 160

Gly Asp Cys Gly Pro Gln Asp Asp Asp Thr Glu Ser Cys Leu Cys Pro
165 170 175

Leu Glu Met Asn Val Ala Gln Glu Phe Gln Leu Arg Arg Arg Gln Leu
180 185 190

Gly Ser Gln Gly Ser Ser Trp Ser Lys Trp Ser Ser Pro Val Cys Val
195 200 205

Pro Pro Glu His Pro Val Gly Leu Leu Ala Arg Val Pro Leu Ser Tyr
210 215 220

Ser Gly His Pro Val Gly Leu Leu Ala Arg Val Pro Leu Ser Tyr Ser
225 230 235 240

Gly Ser Gly Leu Leu Ser Gly Arg Ser Asp Asn His Pro Leu Gly Val
245 250 255

Arg Gly Lys Pro Leu Gly Val Arg Gly Lys Gly Gly Gly Ser Gly Gly
260 265 270

Gly Ser Arg Asn Leu Pro Val Ala Thr Pro Asp Pro Gly Met Phe Pro
275 280 285

Cys Leu His His Ser Gln Asn Leu Leu Arg Ala Val Ser Asn Met Leu
    290                 295                 300

Gln Lys Ala Arg Gln Thr Leu Glu Phe Tyr Pro Cys Thr Ser Glu Glu
305                 310                 315                 320

Ile Asp His Glu Asp Ile Thr Lys Asp Lys Thr Ser Thr Val Glu Ala
                325                 330                 335

Cys Leu Pro Leu Glu Leu Thr Lys Asn Glu Ser Cys Leu Asn Ser Arg
            340                 345                 350

Glu Thr Ser Phe Ile Thr Asn Gly Ser Cys Leu Ala Ser Arg Lys Thr
        355                 360                 365

Ser Phe Met Met Ala Leu Cys Leu Ser Ser Ile Tyr Glu Asp Leu Lys
    370                 375                 380

Met Tyr Gln Val Glu Phe Lys Thr Met Asn Ala Lys Leu Leu Met Asp
385                 390                 395                 400

Pro Lys Arg Gln Ile Phe Leu Asp Gln Asn Met Leu Ala Val Ile Asp
                405                 410                 415

Glu Leu Met Gln Ala Leu Asn Phe Asn Ser Glu Thr Val Pro Gln Lys
            420                 425                 430

Ser Ser Leu Glu Glu Pro Asp Phe Tyr Lys Thr Lys Ile Lys Leu Cys
        435                 440                 445

Ile Leu Leu His Ala Phe Arg Ile Arg Ala Val Thr Ile Asp Arg Val
    450                 455                 460

Met Ser Tyr Leu Asn Ala Ser
465                 470

<210> SEQ ID NO 219
<211> LENGTH: 43
<212> TYPE: PRT
<213> ORGANISM: Artificial Sequence
<220> FEATURE:
<223> OTHER INFORMATION: Synthetic Polypeptide

<400> SEQUENCE: 219

His Pro Val Gly Leu Leu Ala Arg Val Pro Leu Ser Leu Tyr Ser Gly
1               5                   10                  15

His Pro Val Gly Leu Leu Ala Arg Val Pro Leu Ser Leu Tyr Ser Gly
            20                  25                  30

Ser Gly Leu Leu Ser Gly Arg Ser Asp Asn His
        35                  40

<210> SEQ ID NO 220
<211> LENGTH: 51
<212> TYPE: PRT
<213> ORGANISM: Artificial Sequence
<220> FEATURE:
<223> OTHER INFORMATION: Synthetic Polypeptide

<400> SEQUENCE: 220

His Pro Val Gly Leu Leu Ala Arg Val Pro Leu Ser Leu Tyr Ser Gly
1               5                   10                  15

His Pro Val Gly Leu Leu Ala Arg Val Pro Leu Ser Leu Tyr Ser Gly
            20                  25                  30

Ser Gly Leu Leu Ser Gly Arg Ser Asp Asn His Gly Gly Gly Ser Gly
        35                  40                  45

Gly Gly Ser
    50

<210> SEQ ID NO 221
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 221

His Pro Val Gly Leu Leu Ala Arg Val Pro Leu Ser Tyr Ser Gly Ser
1 5 10 15

Gly Leu Leu Ser Gly Arg Ser Asp Asn His
20 25

<210> SEQ ID NO 222
<211> LENGTH: 67
<212> TYPE: PRT
<213> ORGANISM: Artificial Sequence
<220> FEATURE:
<223> OTHER INFORMATION: Synthetic Polypeptide

<400> SEQUENCE: 222

His Pro Val Gly Leu Leu Ala Arg Val Pro Leu Ser Tyr Ser Gly His
1 5 10 15

Pro Val Gly Leu Leu Ala Arg Val Pro Leu Ser Tyr Ser Gly Ser Gly
20 25 30

Leu Leu Ser Gly Arg Ser Asp Asn His Ile Ser Ser Gly Leu Leu Ser
35 40 45

Gly Arg Ser Asp Asn His Ile Ser Ser Gly Leu Leu Ser Gly Arg Ser
50 55 60

Asp Asn His
65

<210> SEQ ID NO 223
<211> LENGTH: 47
<212> TYPE: PRT
<213> ORGANISM: Artificial Sequence
<220> FEATURE:
<223> OTHER INFORMATION: Synthetic Polypeptide

<400> SEQUENCE: 223

Gly Gly Gly Ser Gly Gly Gly Ser Gly Gly Gly Ser Gly Gly Gly Ser
1 5 10 15

Pro Leu Gly Val Arg Gly Lys Gly Gly Gly Ser Gly Gly Gly Ser Gly
20 25 30

Gly Gly Ser Gly Gly Gly Ser Gly Gly Gly Ser Gly Gly Gly Ser
35 40 45

<210> SEQ ID NO 224
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 224

His Pro Val Gly Leu Leu Ala Arg His Pro Val Gly Leu Leu Ala Arg
1 5 10 15

His Pro Val Gly Leu Leu Ala Arg
20

<210> SEQ ID NO 225
<211> LENGTH: 49
<212> TYPE: PRT

<213> ORGANISM: Artificial Sequence
<220> FEATURE:
<223> OTHER INFORMATION: Synthetic Polypeptide

<400> SEQUENCE: 225

His Pro Val Gly Leu Leu Ala Arg Val Pro Leu Ser Tyr Ser Gly His
1 5 10 15

Pro Val Gly Leu Leu Ala Arg Val Pro Leu Ser Tyr Ser Gly Ser Gly
20 25 30

Leu Leu Ser Gly Arg Ser Asp Asn His Gly Gly Gly Ser Gly Gly Gly
35 40 45

Ser

<210> SEQ ID NO 226
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 226

Pro Leu Gly Val Arg Gly Lys Pro Leu Gly Val Arg Gly Lys Pro Leu
1 5 10 15

Gly Val Arg Gly Lys Gly Gly Gly Ser Gly Gly Gly Ser
20 25

<210> SEQ ID NO 227
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 227

Gly Glu Arg Gly Pro Pro Gly Pro Gln Gly Ala Ala Arg Gly Phe Pro
1 5 10 15

Gly Thr Pro Gly Leu Gly Glu Arg Gly Pro Pro Gly Pro Gln Gly Ala
20 25 30

Ala Arg Gly Phe Pro Gly Thr Pro Gly Leu Gly Gly Gly Ser Gly Gly
35 40 45

Gly Ser
50

<210> SEQ ID NO 228
<211> LENGTH: 71
<212> TYPE: PRT
<213> ORGANISM: Artificial Sequence
<220> FEATURE:
<223> OTHER INFORMATION: Synthetic Polypeptide

<400> SEQUENCE: 228

Pro Leu Gly Val Arg Gly Lys Pro Leu Gly Val Arg Gly Lys Pro Leu
1 5 10 15

Gly Val Arg Gly Lys Gly Glu Arg Gly Pro Pro Gly Pro Gln Gly Ala
20 25 30

Ala Arg Gly Phe Pro Gly Thr Pro Gly Leu Gly Glu Arg Gly Pro Pro
35 40 45

Gly Pro Gln Gly Ala Ala Arg Gly Phe Pro Gly Thr Pro Gly Leu Gly
50 55 60

Gly Gly Ser Gly Gly Gly Ser
65 70

<210> SEQ ID NO 229
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 229

```
Pro Leu Gly Val Arg Gly Lys Pro Leu Gly Val Arg Gly Lys Gly Gly
1               5                   10                  15

Gly Ser Gly Gly Gly Ser
            20
```

<210> SEQ ID NO 230
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 230

```
His Pro Val Gly Leu Leu Ala Arg Val Pro Leu Ser Tyr Ser Gly His
1               5                   10                  15

Pro Val Gly Leu Leu Ala Arg Val Pro Leu Ser Tyr Ser Gly Ser Gly
            20                  25                  30

Leu Leu Ser Gly Arg Ser Asp Asn His Pro Leu Gly Val Arg Gly Lys
        35                  40                  45

Pro Leu Gly Val Arg Gly Lys Gly Glu Arg Gly Pro Pro Gly Pro Gln
    50                  55                  60

Gly Ala Ala Arg Gly Phe Pro Gly Thr Pro Gly Leu Gly Glu Arg Gly
65                  70                  75                  80

Pro Pro Gly Pro Gln Gly Ala Ala Arg Gly Phe Pro Gly Thr Pro Gly
                85                  90                  95

Leu Gly Gly Gly Ser Gly Gly Gly Ser
            100                 105
```

<210> SEQ ID NO 231
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 231

```
His Pro Val Gly Leu Leu Ala Arg Val Pro Leu Ser Tyr Ser Gly Ser
1               5                   10                  15

Gly Leu Leu Ser Gly Arg Ser Asp Asn His Gly Gly Gly Ser Gly Gly
            20                  25                  30

Gly Ser
```

<210> SEQ ID NO 232
<211> LENGTH: 75
<212> TYPE: PRT
<213> ORGANISM: Artificial Sequence
<220> FEATURE:
<223> OTHER INFORMATION: Synthetic Polypeptide

<400> SEQUENCE: 232

```
His Pro Val Gly Leu Leu Ala Arg Val Pro Leu Ser Tyr Ser Gly His
1               5                   10                  15
```

-continued

```
Pro Val Gly Leu Leu Ala Arg Val Pro Leu Ser Tyr Ser Gly Ser Gly
            20                  25                  30

Leu Leu Ser Gly Arg Ser Asp Asn His Ile Ser Ser Gly Leu Leu Ser
        35                  40                  45

Gly Arg Ser Asp Asn His Ile Ser Ser Gly Leu Leu Ser Gly Arg Ser
    50                  55                  60

Asp Asn His Gly Gly Gly Ser Gly Gly Gly Ser
65                  70                  75


<210> SEQ ID NO 233
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 233

Gly Gly Gly Ser Gly Gly Gly Ser His Pro Val Gly Leu Leu Ala Arg
1               5                   10                  15

His Pro Val Gly Leu Leu Ala Arg His Pro Val Gly Leu Leu Ala Arg
            20                  25                  30

Gly Gly Gly Ser Gly Gly Gly Ser
        35                  40


<210> SEQ ID NO 234
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 234

Ser Gly Leu Leu Ser Gly Arg Ser Asp Asn His Ser Gly Leu Leu Ser
1               5                   10                  15

Gly Arg Ser Asp Asn His Ser Gly Leu Leu Ser Gly Arg Ser Asp Asn
            20                  25                  30

His


<210> SEQ ID NO 235
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 235

Gly Gly Gly Ser Gly Gly Gly Ser Ser Gly Leu Leu Ser Gly Arg Ser
1               5                   10                  15

Asp Asn His Ser Gly Leu Leu Ser Gly Arg Ser Asp Asn His Ser Gly
            20                  25                  30

Leu Leu Ser Gly Arg Ser Asp Asn His Gly Gly Gly Ser Gly Gly Gly
        35                  40                  45

Ser


<210> SEQ ID NO 236
<211> LENGTH: 27
<212> TYPE: PRT
<213> ORGANISM: Artificial Sequence
<220> FEATURE:
<223> OTHER INFORMATION: Synthetic Polypeptide
```

<400> SEQUENCE: 236

His Pro Val Gly Leu Leu Ala Arg Val Pro Leu Ser Leu Tyr Ser Gly
1               5                   10                  15

Ser Gly Leu Leu Ser Gly Arg Ser Asp Asn His
            20                  25

<210> SEQ ID NO 237
<211> LENGTH: 43
<212> TYPE: PRT
<213> ORGANISM: Artificial Sequence
<220> FEATURE:
<223> OTHER INFORMATION: Synthetic Polypeptide

<400> SEQUENCE: 237

Gly Gly Gly Ser Gly Gly Gly Ser His Pro Val Gly Leu Leu Ala Arg
1               5                   10                  15

Val Pro Leu Ser Leu Tyr Ser Gly Ser Gly Leu Leu Ser Gly Arg Ser
            20                  25                  30

Asp Asn His Gly Gly Gly Ser Gly Gly Gly Ser
        35                  40

<210> SEQ ID NO 238
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 238

Val Pro Leu Ser Leu Tyr Ser Gly Val Pro Leu Ser Leu Tyr Ser Gly
1               5                   10                  15

Val Pro Leu Ser Leu Tyr Ser
            20

<210> SEQ ID NO 239
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 239

Gly Gly Gly Ser Gly Gly Gly Ser Val Pro Leu Ser Leu Tyr Ser Gly
1               5                   10                  15

Val Pro Leu Ser Leu Tyr Ser Gly Val Pro Leu Ser Leu Tyr Ser Gly
            20                  25                  30

Gly Gly Gly Ser Gly Gly Gly Ser Gly Gly Gly Ser
        35                  40

<210> SEQ ID NO 240
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 240

Val Pro Leu Ser Leu Tyr Ser Gly Gly Gly Gly Ser Gly Gly Gly Ser
1               5                   10                  15

Leu Ser Gly Arg Ser Asp Asn His Leu Ser Gly Arg Ser Asp Asn His
            20                  25                  30

<210> SEQ ID NO 241
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 241

```
Gly Gly Gly Ser Gly Gly Gly Ser Val Pro Leu Ser Leu Tyr Ser Gly
1               5                   10                  15

Gly Gly Gly Ser Gly Gly Gly Ser Leu Ser Gly Arg Ser Asp Asn His
            20                  25                  30

Leu Ser Gly Arg Ser Asp Asn His Gly Gly Gly Ser Gly Gly Gly Ser
        35                  40                  45
```

<210> SEQ ID NO 242
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 242

```
Gly Gly Gly Ser Gly Gly Gly Ser Val Pro Leu Ser Leu Tyr Ser Gly
1               5                   10                  15

Gly Gly Gly Ser Gly Gly Gly Ser Leu Ser Gly Arg Ser Asp Asn His
            20                  25                  30

Leu Ser Gly Arg Ser Asp Asn His Gly Gly Gly Ser Gly Gly Gly Ser
        35                  40                  45

Gly
```

<210> SEQ ID NO 243
<211> LENGTH: 56
<212> TYPE: PRT
<213> ORGANISM: Artificial Sequence
<220> FEATURE:
<223> OTHER INFORMATION: Synthetic Polypeptide

<400> SEQUENCE: 243

```
Pro Leu Gly Val Arg Gly Lys Pro Leu Gly Val Arg Gly Lys Gly Glu
1               5                   10                  15

Arg Gly Pro Pro Gly Pro Gln Gly Ala Ala Arg Gly Phe Pro Gly Thr
            20                  25                  30

Pro Gly Leu Gly Glu Arg Gly Pro Pro Gly Pro Gln Gly Ala Ala Arg
        35                  40                  45

Gly Phe Pro Gly Thr Pro Gly Leu
    50                  55
```

<210> SEQ ID NO 244
<211> LENGTH: 64
<212> TYPE: PRT
<213> ORGANISM: Artificial Sequence
<220> FEATURE:
<223> OTHER INFORMATION: Synthetic Polypeptide

<400> SEQUENCE: 244

```
Pro Leu Gly Val Arg Gly Lys Pro Leu Gly Val Arg Gly Lys Gly Glu
1               5                   10                  15

Arg Gly Pro Pro Gly Pro Gln Gly Ala Ala Arg Gly Phe Pro Gly Thr
            20                  25                  30
```

Pro Gly Leu Gly Glu Arg Gly Pro Pro Gly Pro Gln Gly Ala Ala Arg
35 40 45

Gly Phe Pro Gly Thr Pro Gly Leu Gly Gly Gly Ser Gly Gly Gly Ser
50 55 60

<210> SEQ ID NO 245
<211> LENGTH: 55
<212> TYPE: PRT
<213> ORGANISM: Artificial Sequence
<220> FEATURE:
<223> OTHER INFORMATION: Synthetic Polypeptide

<400> SEQUENCE: 245

His Pro Val Gly Leu Leu Ala Arg Val Pro Leu Ser Tyr Ser Gly His
1 5 10 15

Pro Val Gly Leu Leu Ala Arg Val Pro Leu Ser Tyr Ser Gly Ser Gly
20 25 30

Leu Leu Ser Gly Arg Ser Asp Asn His Pro Leu Gly Val Arg Gly Lys
35 40 45

Pro Leu Gly Val Arg Gly Lys
50 55

<210> SEQ ID NO 246
<211> LENGTH: 63
<212> TYPE: PRT
<213> ORGANISM: Artificial Sequence
<220> FEATURE:
<223> OTHER INFORMATION: Synthetic Polypeptide

<400> SEQUENCE: 246

His Pro Val Gly Leu Leu Ala Arg Val Pro Leu Ser Tyr Ser Gly His
1 5 10 15

Pro Val Gly Leu Leu Ala Arg Val Pro Leu Ser Tyr Ser Gly Ser Gly
20 25 30

Leu Leu Ser Gly Arg Ser Asp Asn His Pro Leu Gly Val Arg Gly Lys
35 40 45

Pro Leu Gly Val Arg Gly Lys Gly Gly Gly Ser Gly Gly Gly Ser
50 55 60

<210> SEQ ID NO 247
<211> LENGTH: 484
<212> TYPE: PRT
<213> ORGANISM: Artificial Sequence
<220> FEATURE:
<223> OTHER INFORMATION: Synthetic Polypeptide

<400> SEQUENCE: 247

Gln Leu Gly Ala Ser Gly Pro Gly Asp Cys Cys Val Glu Lys Thr Ser
1 5 10 15

Phe Pro Glu Gly Ala Ser Gly Ser Pro Leu Gly Pro Arg Asn Leu Ser
20 25 30

Cys Tyr Arg Val Ser Lys Thr Asp Tyr Glu Cys Ser Trp Gln Tyr Asp
35 40 45

Gly Pro Glu Asp Asn Val Ser His Val Leu Trp Cys Cys Phe Val Pro
50 55 60

Pro Asn His Thr His Thr Gly Gln Glu Arg Cys Arg Tyr Phe Ser Ser
65 70 75 80

Gly Pro Asp Arg Thr Val Gln Phe Trp Glu Gln Asp Gly Ile Pro Val
85 90 95

```
Leu Ser Lys Val Asn Phe Trp Val Glu Ser Arg Leu Gly Asn Arg Thr
            100                 105                 110

Met Lys Ser Gln Lys Ile Ser Gln Tyr Leu Tyr Asn Trp Thr Lys Thr
        115                 120                 125

Thr Pro Pro Leu Gly His Ile Lys Val Ser Gln Ser His Arg Gln Leu
    130                 135                 140

Arg Met Asp Trp Asn Val Ser Glu Glu Ala Gly Ala Glu Val Gln Phe
145                 150                 155                 160

Arg Arg Arg Met Pro Thr Thr Asn Trp Thr Leu Gly Asp Cys Gly Pro
                165                 170                 175

Gln Val Asn Ser Gly Ser Gly Val Leu Gly Asp Ile Arg Gly Ser Met
            180                 185                 190

Ser Glu Ser Cys Leu Cys Pro Ser Glu Asn Met Ala Gln Glu Ile Gln
        195                 200                 205

Ile Arg Arg Arg Arg Arg Leu Ser Ser Gly Ala Pro Gly Gly Pro Trp
    210                 215                 220

Ser Asp Trp Ser Met Pro Val Cys Val Pro Pro Glu Val Leu Pro Gln
225                 230                 235                 240

Ala Gly Gly Gly Ser Gly Gly Gly Ser Gly Gly Gly Ser Gly Gly Gly
                245                 250                 255

Ser Gly Gly Gly Ser Gly Gly Gly Ser Gly Gly Gly Ser Gly Gly Gly
            260                 265                 270

Ser Gly Gly Gly Ser Gly Gly Gly Ser Gly Gly Gly Ser Arg Val Ile
        275                 280                 285

Pro Val Ser Gly Pro Ala Arg Cys Leu Ser Gln Ser Arg Asn Leu Leu
    290                 295                 300

Lys Thr Thr Asp Asp Met Val Lys Thr Ala Arg Glu Lys Leu Lys His
305                 310                 315                 320

Tyr Ser Cys Thr Ala Glu Asp Ile Asp His Glu Asp Ile Thr Arg Asp
                325                 330                 335

Gln Thr Ser Thr Leu Lys Thr Cys Leu Pro Leu Glu Leu His Lys Asn
            340                 345                 350

Glu Ser Cys Leu Ala Thr Arg Glu Thr Ser Ser Thr Thr Arg Gly Ser
        355                 360                 365

Cys Leu Pro Pro Gln Lys Thr Ser Leu Met Met Thr Leu Cys Leu Gly
    370                 375                 380

Ser Ile Tyr Glu Asp Leu Lys Met Tyr Gln Thr Glu Phe Gln Ala Ile
385                 390                 395                 400

Asn Ala Ala Leu Gln Asn His Asn His Gln Gln Ile Ile Leu Asp Lys
                405                 410                 415

Gly Met Leu Val Ala Ile Asp Glu Leu Met Gln Ser Leu Asn His Asn
            420                 425                 430

Gly Glu Thr Leu Arg Gln Lys Pro Pro Val Gly Glu Ala Asp Pro Tyr
        435                 440                 445

Arg Val Lys Met Lys Leu Cys Ile Leu Leu His Ala Phe Ser Thr Arg
    450                 455                 460

Val Val Thr Ile Asn Arg Val Met Gly Tyr Leu Ser Ser Ala His His
465                 470                 475                 480

His His His His
```

<210> SEQ ID NO 248
<211> LENGTH: 459
<212> TYPE: PRT
<213> ORGANISM: Artificial Sequence
<220> FEATURE:
<223> OTHER INFORMATION: Synthetic Polypeptide

<400> SEQUENCE: 248

Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
            100                 105                 110

Ser Val Lys Tyr Glu Pro Pro Leu Gly Asp Ile Lys Val Ser Lys Leu
        115                 120                 125

Ala Gly Gln Leu Arg Met Glu Trp Glu Thr Pro Asp Asn Gln Val Gly
    130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Asp Thr Glu Ser Cys Leu Cys Pro
                165                 170                 175

Leu Glu Met Asn Val Ala Gln Glu Phe Gln Leu Arg Arg Arg Gln Leu
            180                 185                 190

Gly Ser Gln Gly Ser Ser Trp Ser Lys Trp Ser Ser Pro Val Cys Val
        195                 200                 205

Pro Pro Glu Gly Gly Gly Ser Gly Gly Gly Ser Gly Gly Gly Ser Gly
    210                 215                 220

Gly Gly Ser Gly Gly Gly Ser Gly Gly Gly Ser Gly Gly Gly Ser Gly
225                 230                 235                 240

Gly Gly Ser Gly Gly Gly Ser Gly Gly Gly Ser Gly Gly Gly Ser Gly
                245                 250                 255

Arg Asn Leu Pro Val Ala Thr Pro Asp Pro Gly Met Phe Pro Cys Leu
            260                 265                 270

His His Ser Gln Asn Leu Leu Arg Ala Val Ser Asn Met Leu Gln Lys
        275                 280                 285

Ala Arg Gln Thr Leu Glu Phe Tyr Pro Cys Thr Ser Glu Glu Ile Asp
    290                 295                 300

His Glu Asp Ile Thr Lys Asp Lys Thr Ser Thr Val Glu Ala Cys Leu
305                 310                 315                 320

Pro Leu Glu Leu Thr Lys Asn Glu Ser Cys Leu Asn Ser Arg Glu Thr
                325                 330                 335

Ser Phe Ile Thr Asn Gly Ser Cys Leu Ala Ser Arg Lys Thr Ser Phe
            340                 345                 350

Met Met Ala Leu Cys Leu Ser Ser Ile Tyr Glu Asp Leu Lys Met Tyr
        355                 360                 365

Gln Val Glu Phe Lys Thr Met Asn Ala Lys Leu Leu Met Asp Pro Lys
    370                 375                 380

Arg Gln Ile Phe Leu Asp Gln Asn Met Leu Ala Val Ile Asp Glu Leu
385                 390                 395                 400

-continued

```
Met Gln Ala Leu Asn Phe Asn Ser Glu Thr Val Pro Gln Lys Ser Ser
                405                 410                 415

Leu Glu Glu Pro Asp Phe Tyr Lys Thr Lys Ile Lys Leu Cys Ile Leu
            420                 425                 430

Leu His Ala Phe Arg Ile Arg Ala Val Thr Ile Asp Arg Val Met Ser
        435                 440                 445

Tyr Leu Asn Ala Ser His His His His His His
    450                 455


<210> SEQ ID NO 249
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: X is alanine, arginine, asparagine, aspartic
      acid, cysteine, glutamine, glutamic acid, glycine, histidine,
      isoleucine, leucine, lysine, methionine, phenylalanine, proline,
      serine, threonine, tryptophan, tyrosine, or valine
<220> FEATURE:
<221> NAME/KEY: misc_feature
<222> LOCATION: (2)..(2)
<223> OTHER INFORMATION: X is alanine, arginine, asparagine, aspartic
      acid, cysteine, glutamine, glutamic acid, glycine, histidine,
      isoleucine, leucine, lysine, methionine, phenylalanine, proline,
      serine, threonine, tryptophan, tyrosine, or valine
<220> FEATURE:
<221> NAME/KEY: misc_feature
<222> LOCATION: (7)..(7)
<223> OTHER INFORMATION: X is alanine, arginine, asparagine, aspartic
      acid, cysteine, glutamine, glutamic acid, glycine, histidine,
      isoleucine, leucine, lysine, methionine, phenylalanine, proline,
      serine, threonine, tryptophan, tyrosine, or valine

<400> SEQUENCE: 249

Xaa Xaa Gln Ala Arg Val Xaa
1               5
```